United States Patent
Freimoser-Grundschober et al.

(10) Patent No.: US 11,672,858 B2
(45) Date of Patent: Jun. 13, 2023

(54) BISPECIFIC ANTIBODY MOLECULES BINDING TO CD3 AND TYRP-1

(71) Applicant: Hoffmann-La Roche Inc., Little Falls, NJ (US)

(72) Inventors: Anne Freimoser-Grundschober, Schlieren (CH); Thomas Hofer, Schlieren (CH); Ralf Hosse, Schlieren (CH); Ekkehard Moessner, Schlieren (CH); Valeria G. Nicolini, Schlieren (CH); Pablo Umaña, Schlieren (CH); Inja Waldhauer, Schlieren (CH); Wolfgang Richter, Basel (CH); Alexander Knaupp, Penzberg (DE); Halina Trochanowska, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 52 days.

(21) Appl. No.: 16/721,254

(22) Filed: Dec. 19, 2019

(65) Prior Publication Data

US 2020/0270347 A1    Aug. 27, 2020

(30) Foreign Application Priority Data

Dec. 21, 2018 (EP) .................................. 18214994

(51) Int. Cl.
| | |
|---|---|
| *A61K 39/395* | (2006.01) |
| *C07K 16/30* | (2006.01) |
| *C07K 16/28* | (2006.01) |
| *A61P 35/00* | (2006.01) |
| *A61K 39/00* | (2006.01) |

(52) U.S. Cl.
CPC ........ *A61K 39/39558* (2013.01); *A61P 35/00* (2018.01); *C07K 16/2809* (2013.01); *C07K 16/2863* (2013.01); *C07K 16/3053* (2013.01); *A61K 2039/505* (2013.01); *C07K 2317/31* (2013.01); *C07K 2317/55* (2013.01); *C07K 2317/565* (2013.01)

(58) Field of Classification Search
CPC .................................................... C07K 16/30
See application file for complete search history.

(56) References Cited

U.S. PATENT DOCUMENTS

| | | |
|---|---|---|
| 2013/0078249 A1 | 3/2013 | Ast et al. |
| 2016/0075785 A1 | 3/2016 | Ast et al. |
| 2016/0145354 A1 | 5/2016 | Bacac et al. |
| 2020/0199234 A1 | 6/2020 | Georges et al. |
| 2021/0403562 A1 | 12/2021 | Freimoser-Grundschober et al. |
| 2022/0010014 A1 | 1/2022 | Freimoser-Grundschober et al. |
| 2022/0213199 A1 | 7/2022 | Bujotzek et al. |
| 2022/0259318 A1 | 8/2022 | Bujotzek et al. |

FOREIGN PATENT DOCUMENTS

| | | |
|---|---|---|
| CL | 2015001988 A1 | 11/2015 |
| CL | 2017000954 A1 | 12/2017 |
| CL | 2018000263 A1 | 10/2018 |
| WO | WO-2014/131712 A1 | 9/2014 |
| WO | WO-2016/079076 A1 | 5/2016 |
| WO | WO-2017/021370 A1 | 2/2017 |
| WO | WO-2020/127618 A1 | 6/2020 |
| WO | WO-2021/018859 A2 | 2/2021 |
| WO | WO-2021/255138 A1 | 12/2021 |
| WO | WO-2021/255143 A1 | 12/2021 |
| WO | WO-2021/255146 A1 | 12/2021 |

OTHER PUBLICATIONS

Paul (Fundamental Immunology, 3rd Edition, 1993, pp. 292-295) (Year: 1993).*
Rudikoff et al. (Proceedings of the National Academy of Sciences USA, vol. 79, p. 1979-1983, 1982) (Year: 1982).*
Polyak et al. (Blood, vol. 99, No. 9, p. 3256-3262, 2002) (Year: 2002).*
Munodzana et al. (Infection and Immunity, vol. 66 No. 6, p. 2619-2624, 1998) (Year: 1998).*
Komenaka et al. (Clinics in Dermatology, 2004, vol. 22, p. 251-265) (Year: 2004).*
Evans et al. (Q. J. Med 1999: 92: 299-307) (Year: 1999).*
Schiffman et al. (The New England Journal of Medicine, Vo. 353, No. 20, p. 2101-2104, 2005) (Year: 2005).*
Cuzick et al. (The Lancet, vol. 361, p. 296-300, 2003) (Year: 2003).*
Hernandez-Ledesma (Peptides, vol. 30, p. 426-430, 2009) (Year: 2009).*
Haberger et al. "Assessment of chemical modifications of sites in the CDRs of recombinant antibodies: Susceptibility vs. functionality of critical quality attributes," MAbs. 6(2):327-39 (2014).
Lu et al. "Deamidation and isomerization liability analysis of 131 clinical-stage antibodies," MAbs. 11(1):45-57 (2019).
Sydow et al. "Structure-based prediction of asparagine and aspartate degradation sites in antibody variable regions," PLoS One. 9(6):e100736 (2014) (13 pages).
International Search Report and Written Opinion for International Application No. PCT/EP2019/086144, dated Apr. 9, 2020 (17 pages).
Kearns et al., "Enhanced Targeting of the EGFR Network with MM-151, an Oligoclonal Anti-EGFR Antibody Therapeutic," Mol Cancer Ther. 14(7):1625-36 (2015).
Haberger et al., "Assessment of chemical modifications of sites in the CDRs of recombinant antibodies: Susceptability vs. functionality of critical quality attributes," MAbs. 6(2):327-39 (2014) (24 pages).

(Continued)

*Primary Examiner* — Michael Allen
(74) *Attorney, Agent, or Firm* — Clark & Elbing, LLP; Karen L. Elbing

(57) ABSTRACT

The present invention generally relates to antibodies that bind to CD3, including multispecific antibodies e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

16 Claims, 51 Drawing Sheets

Specification includes a Sequence Listing.

(56) References Cited

OTHER PUBLICATIONS

Lu et al., "Deamidation and isomerization liability analysis of 131 clinical-stage antibodies," MAbs. 11(1):45-57 (Dec. 10, 2018) (14 pages).

Sydow et al., "Structure-Based Prediction of Asparagine and Aspartate Degradation Sites in Antibody Variable Regions," PLoS One. 9(6):e100736 (2014) (16 pages).

* cited by examiner

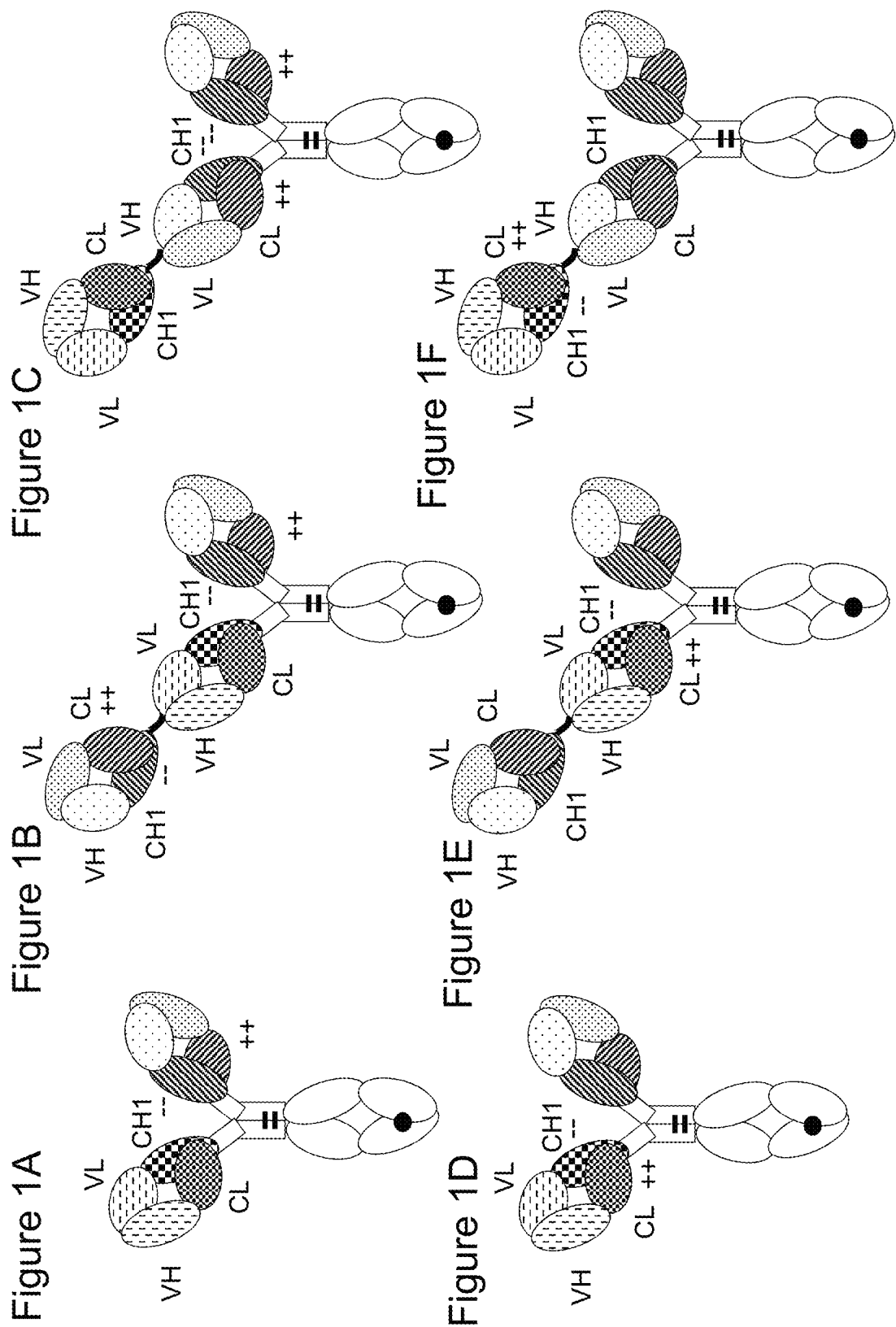

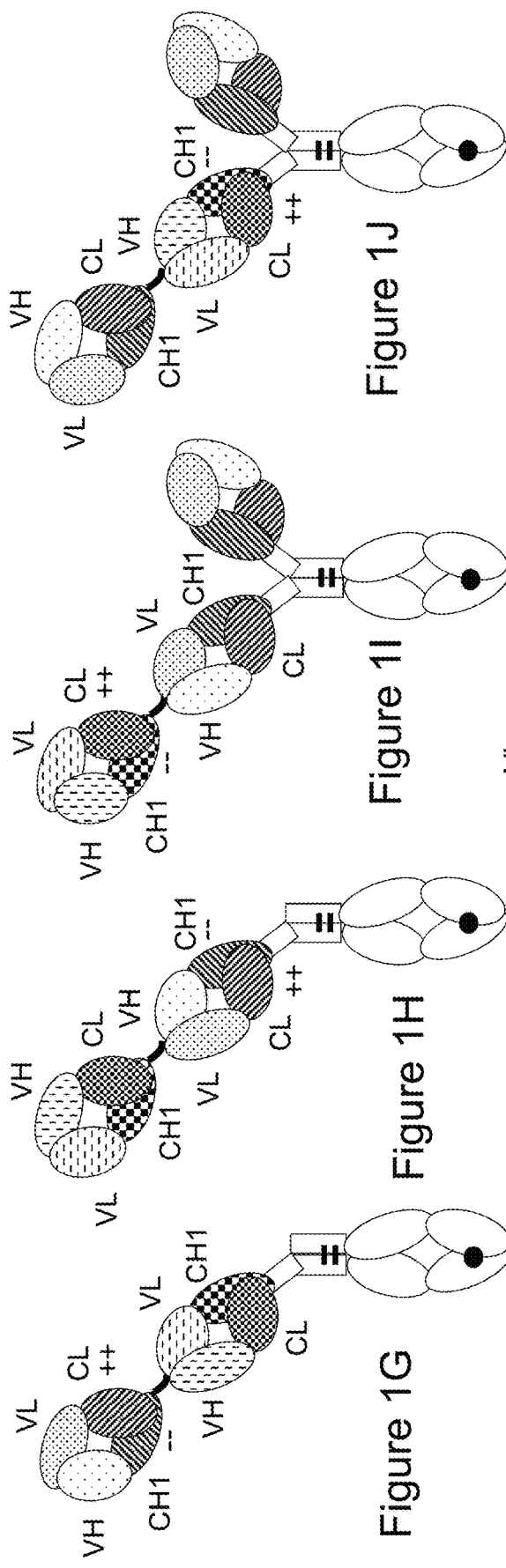
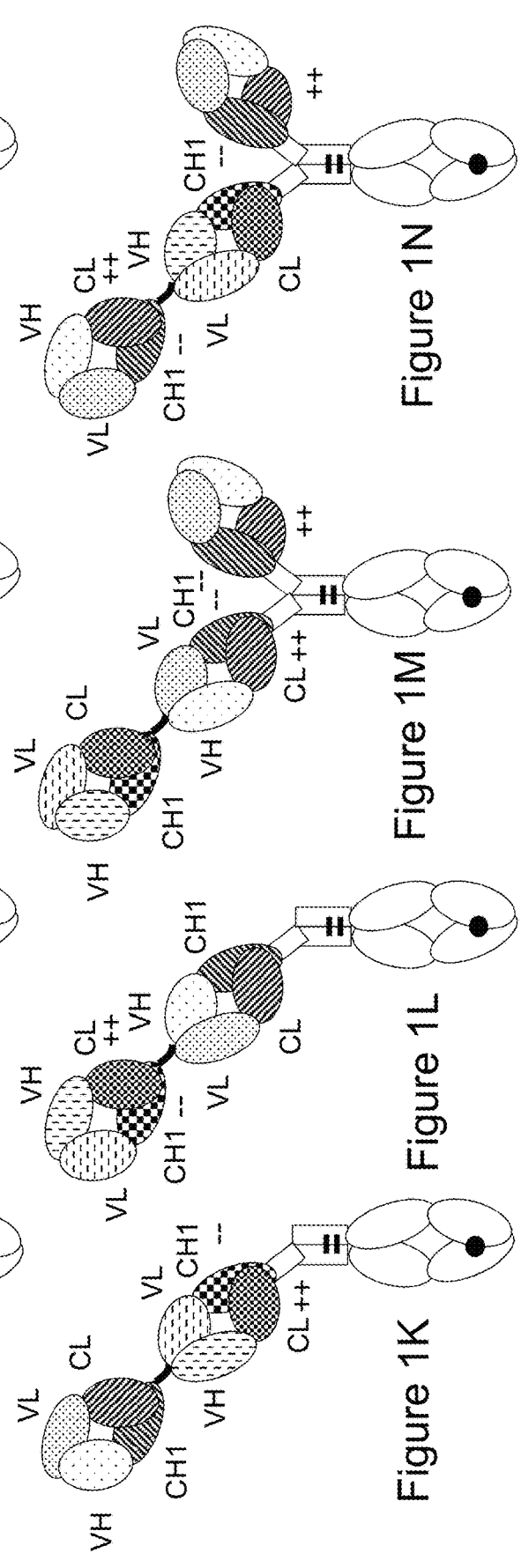
Figure 1G
Figure 1H
Figure 1I
Figure 1J
Figure 1K
Figure 1L
Figure 1M
Figure 1N

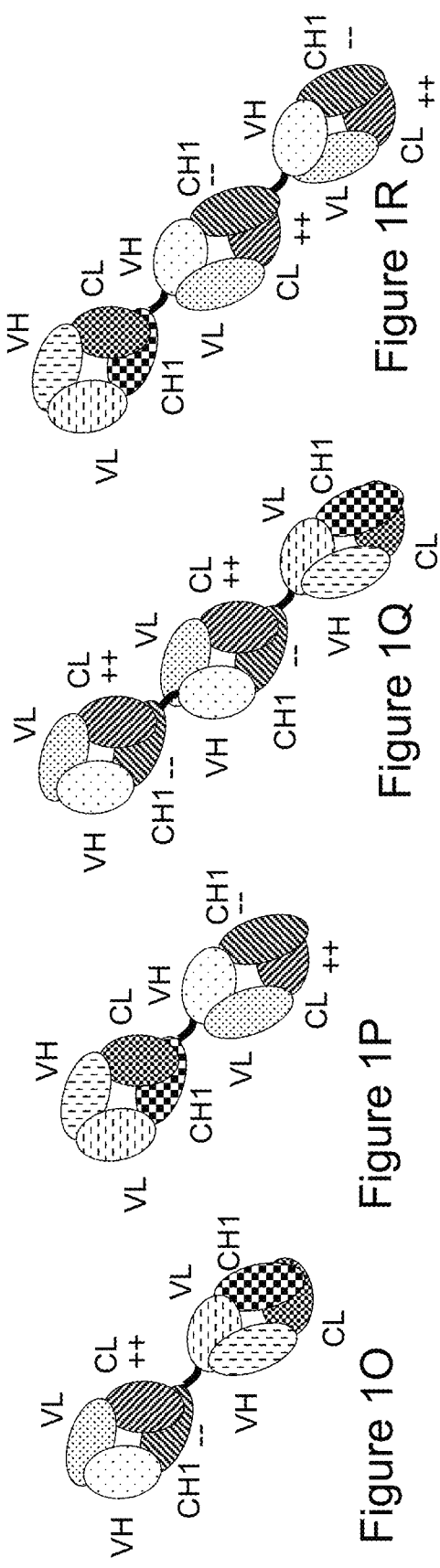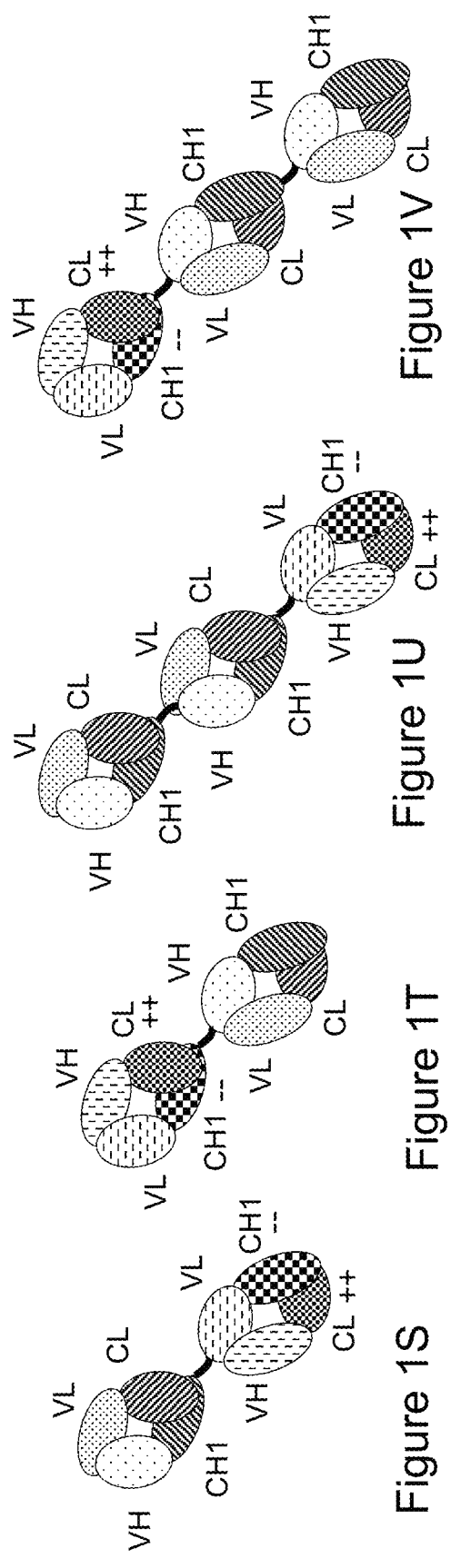

TYRP1 TCB CD3$_{opt}$  TYRP1 TCB CD3$_{orig}$

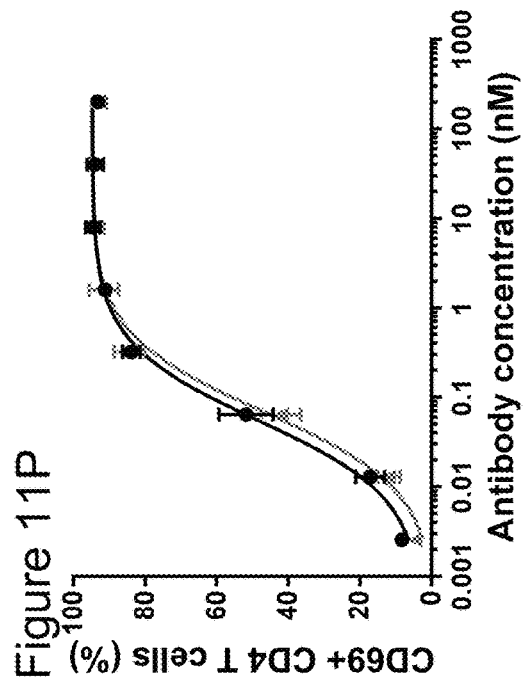
Figure 11O
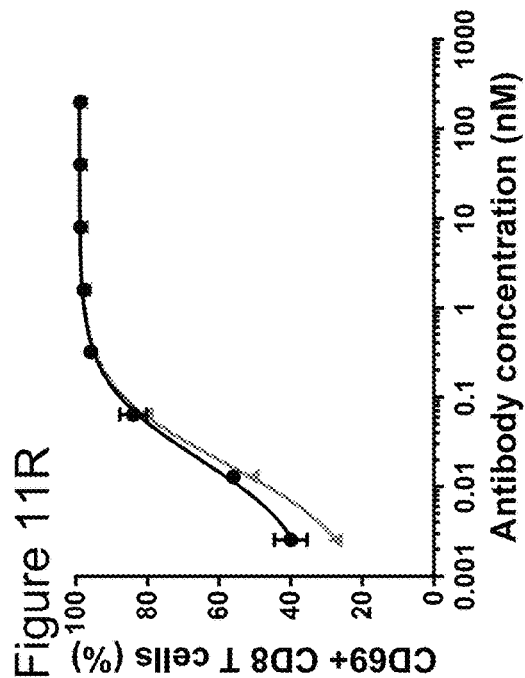
Figure 11P
Figure 11Q
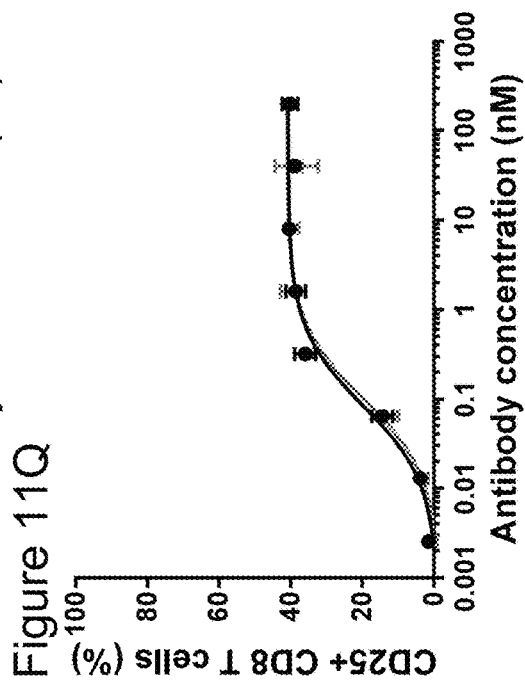
Figure 11R

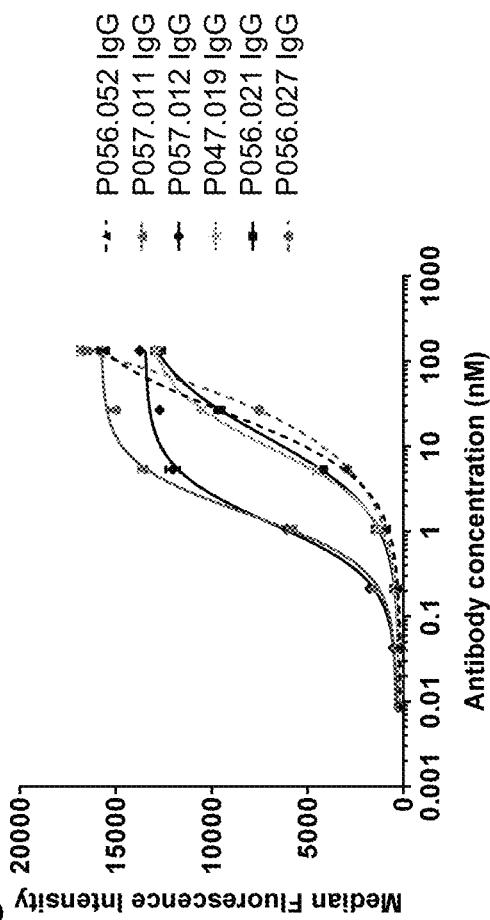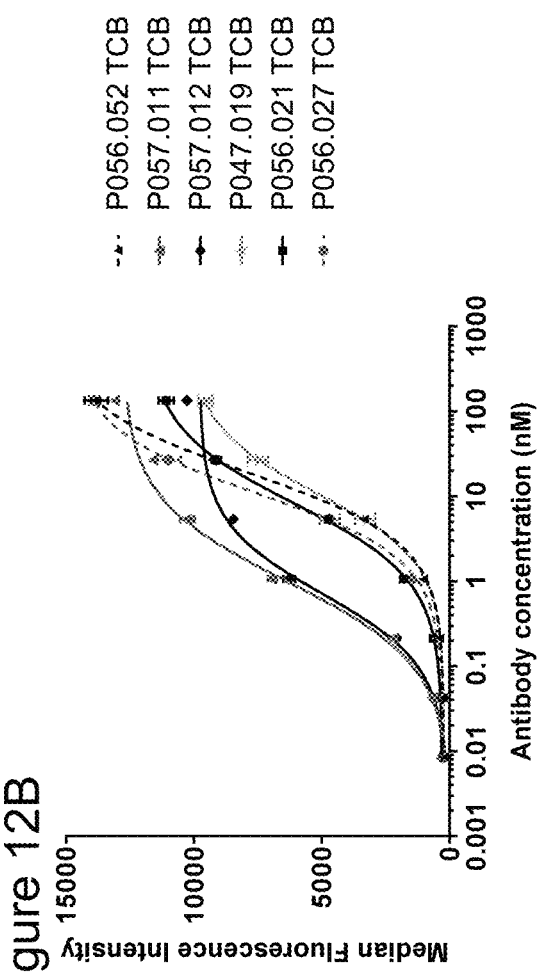

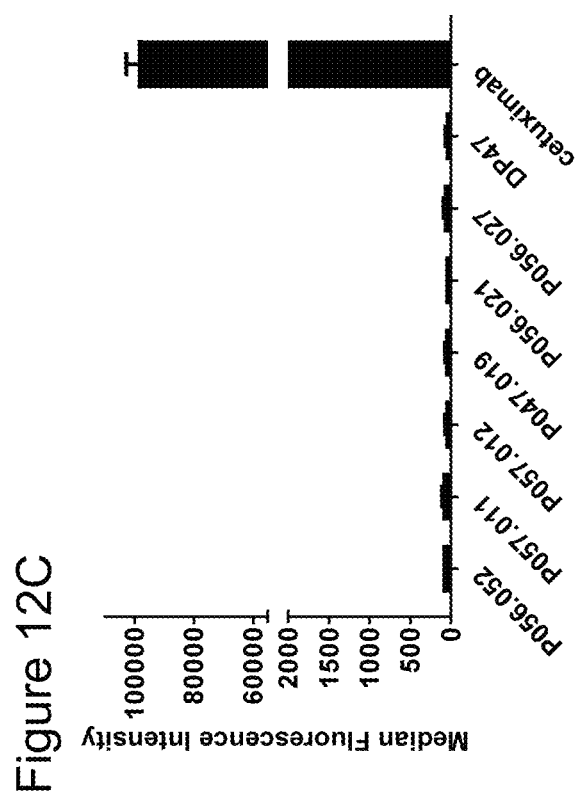

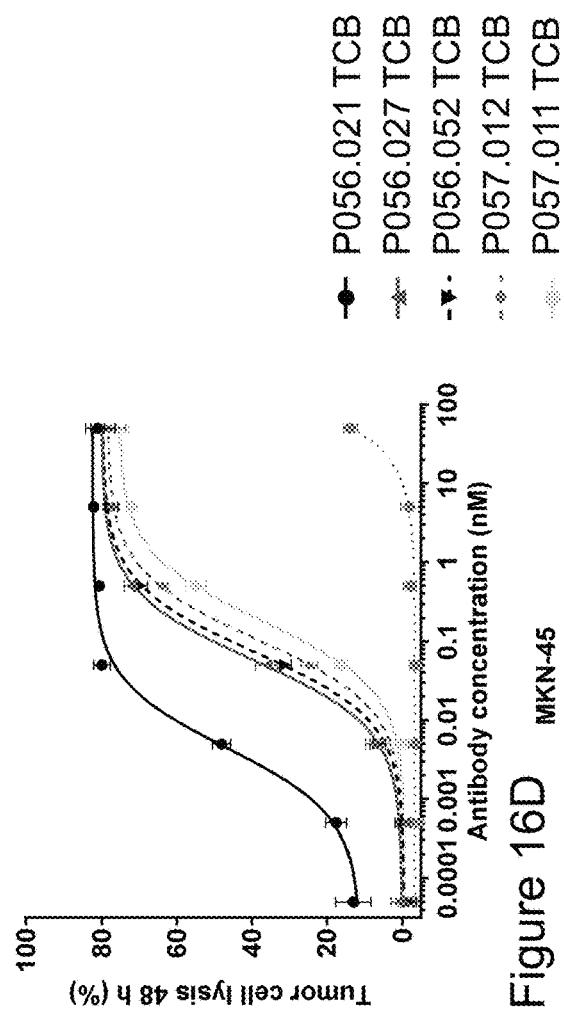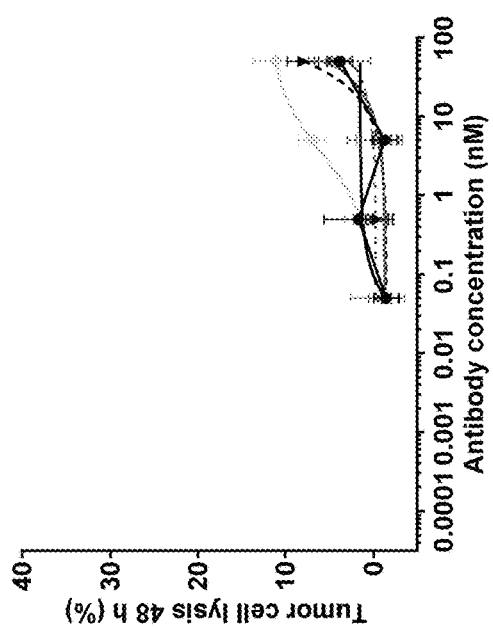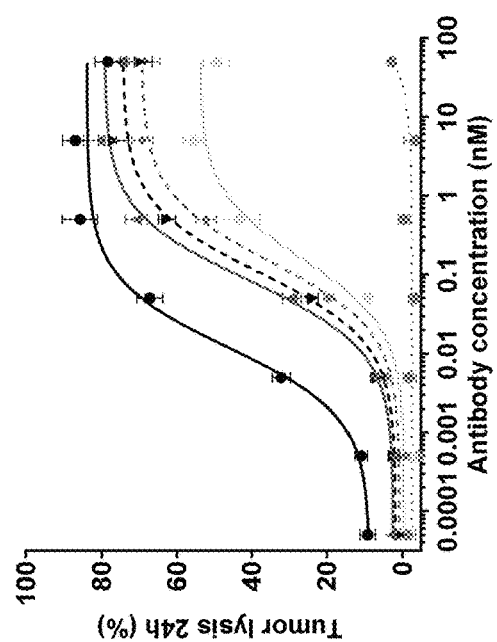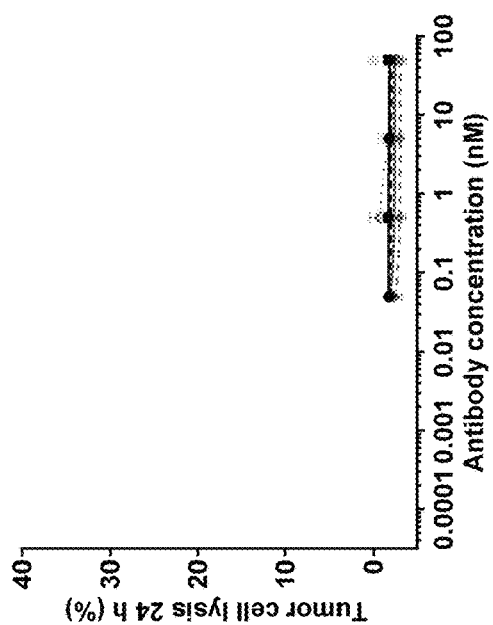

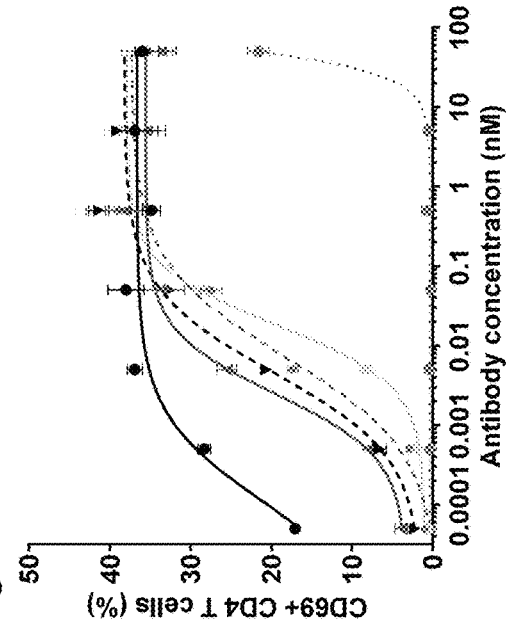
Figure 17A / Figure 17B
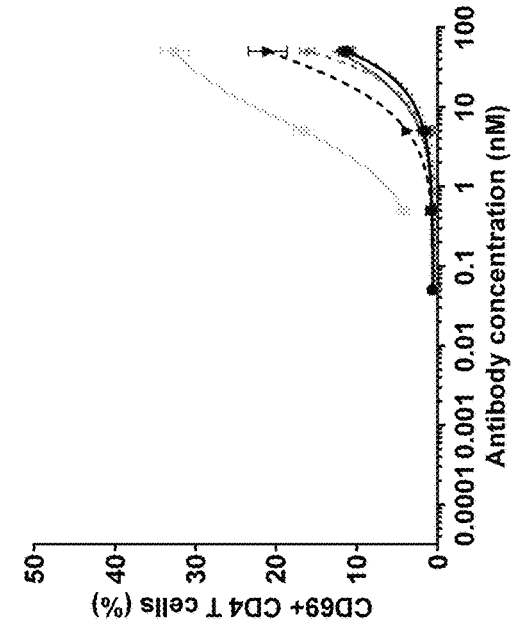
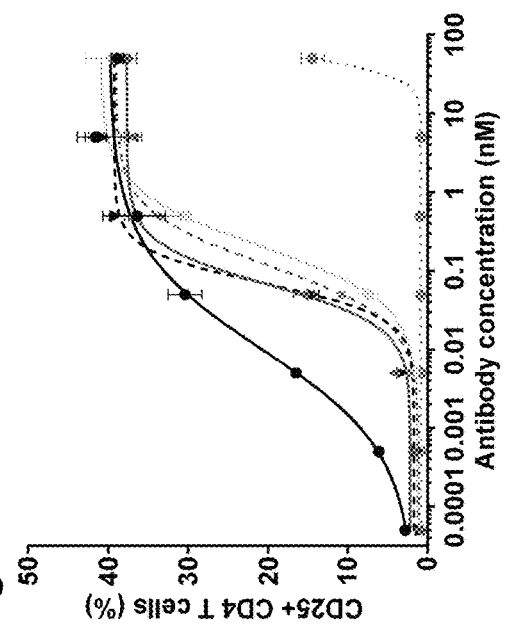
Figure 17C / Figure 17D
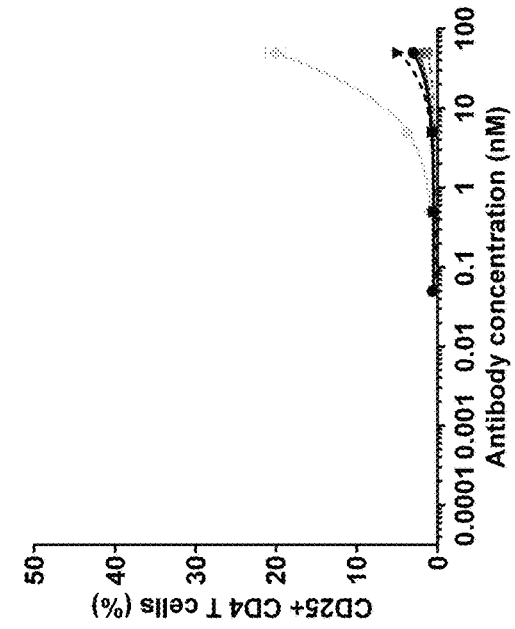

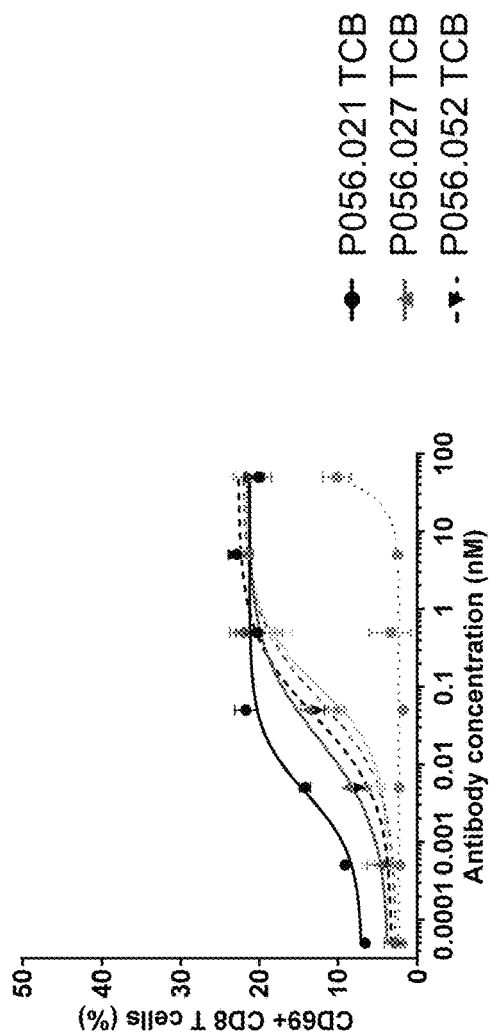
Figure 17E DK-MG
Figure 17F DK-MG
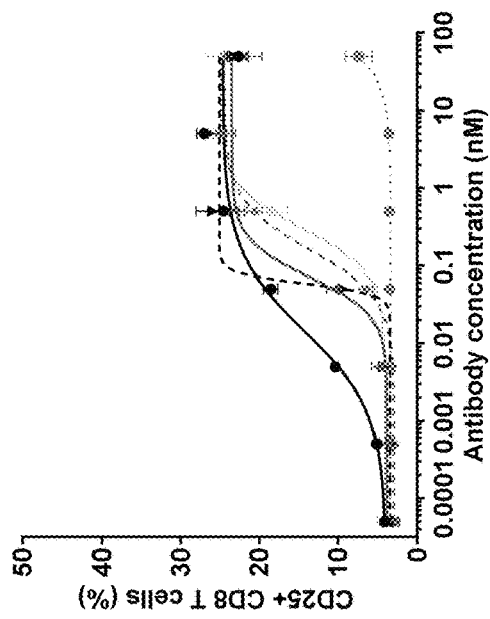
Figure 17G MKN-45
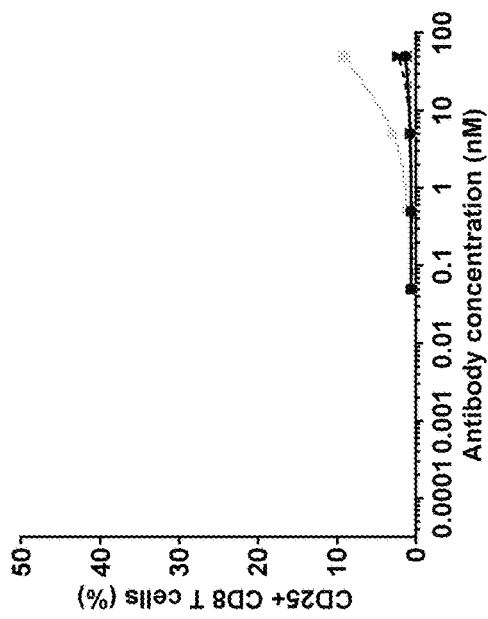
Figure 17H MKN-45

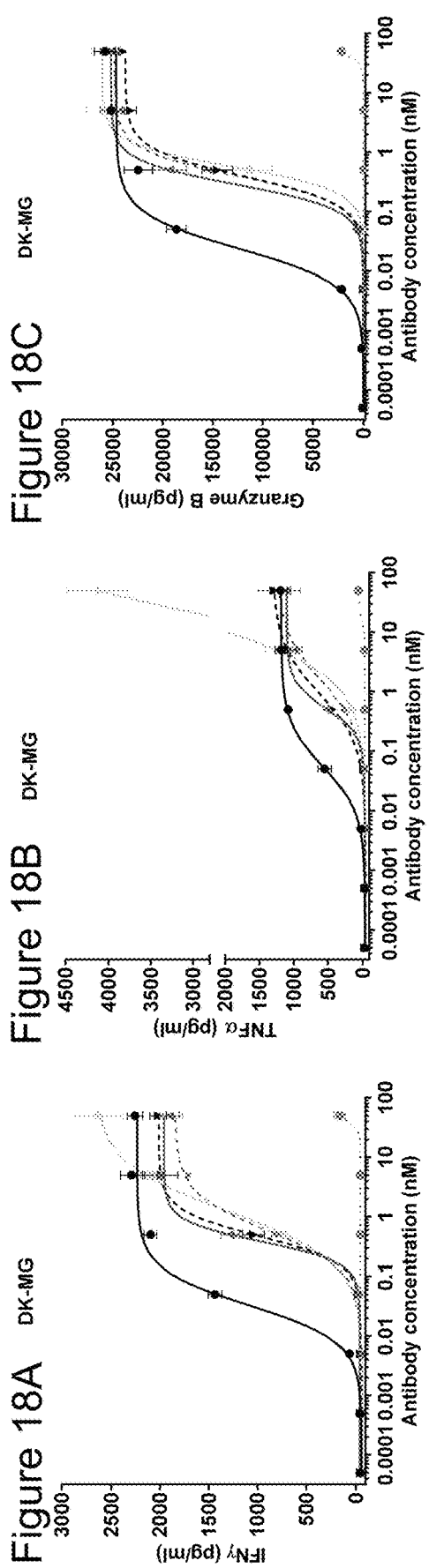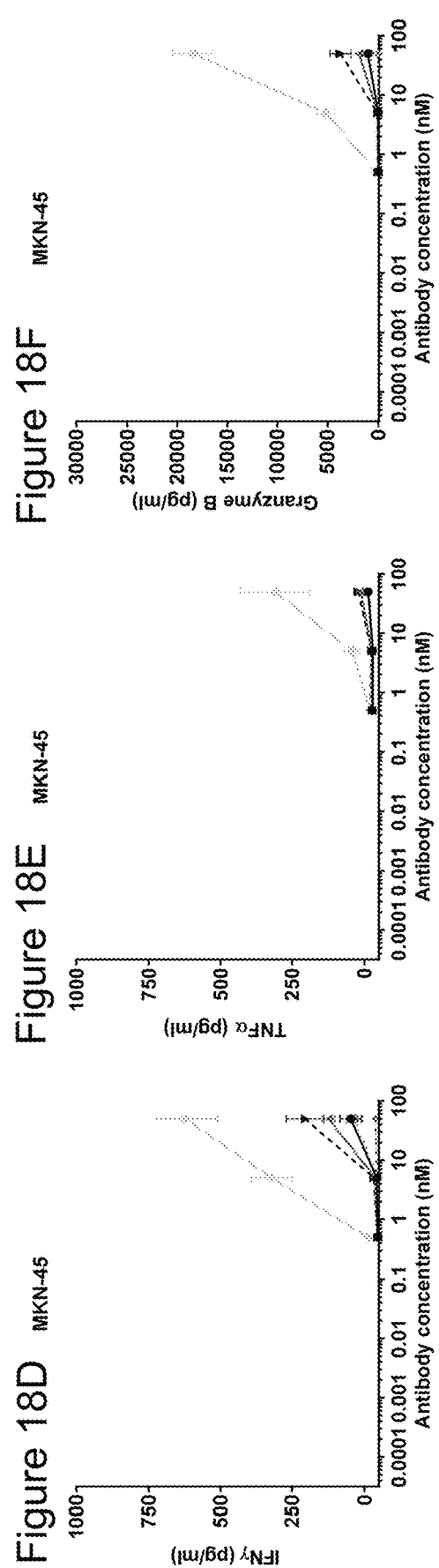

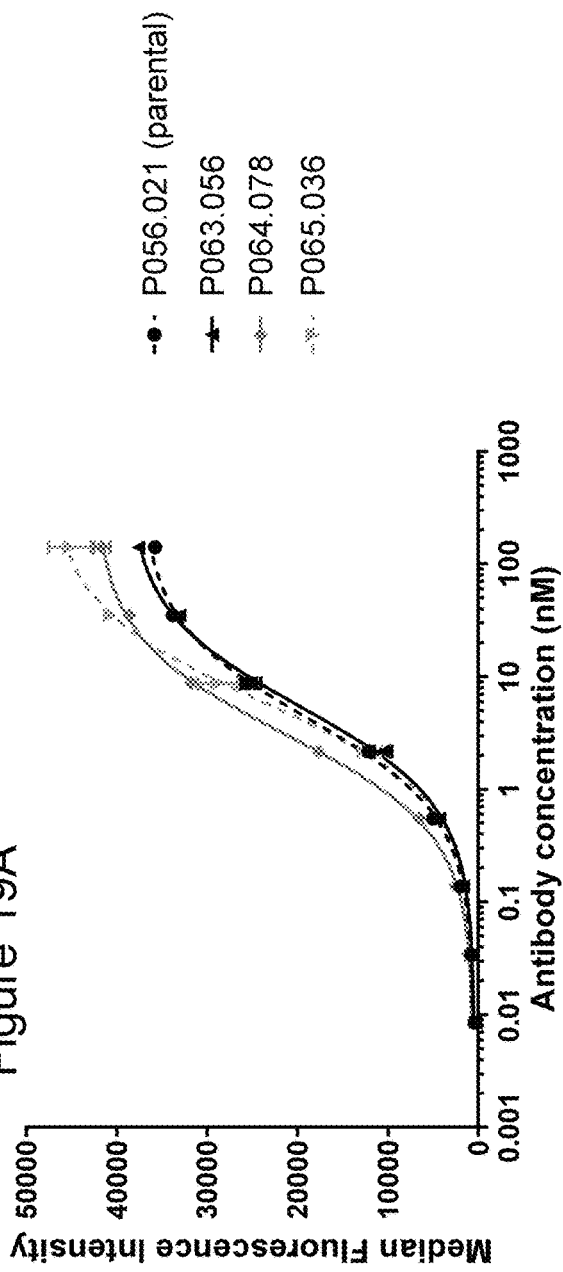
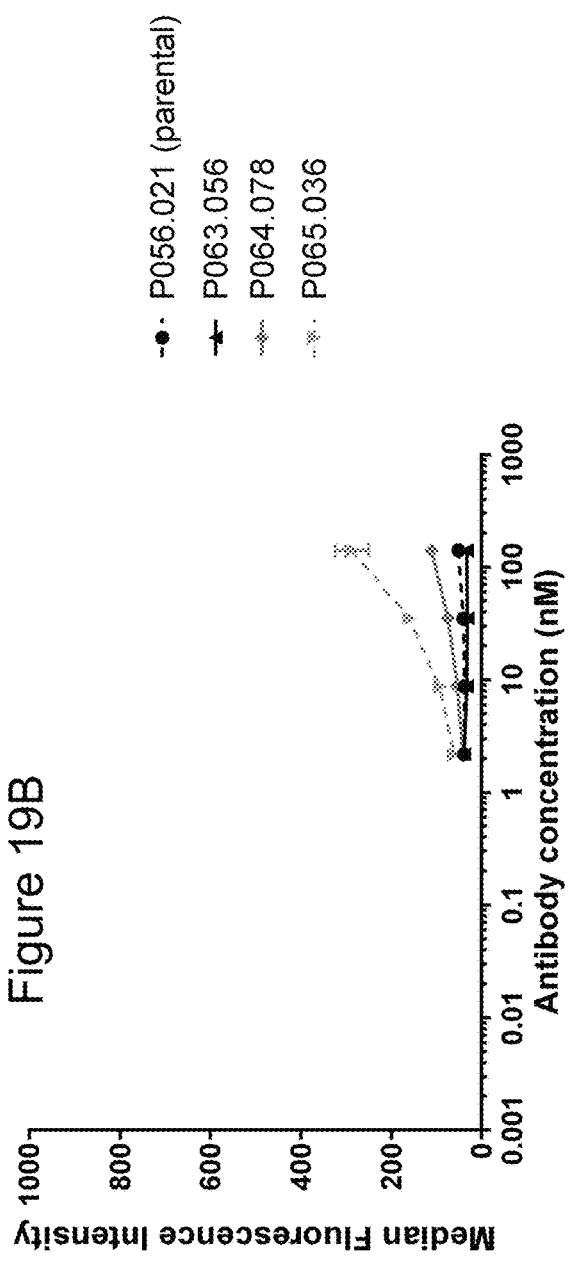

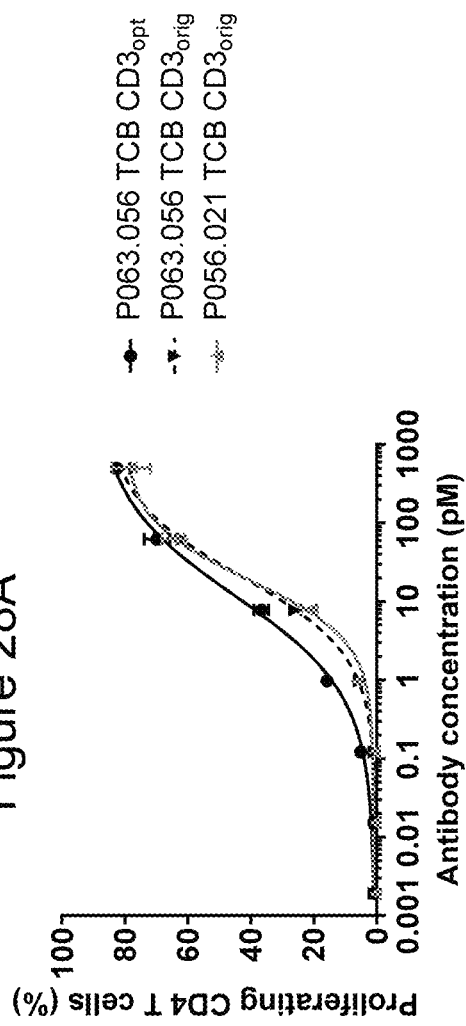
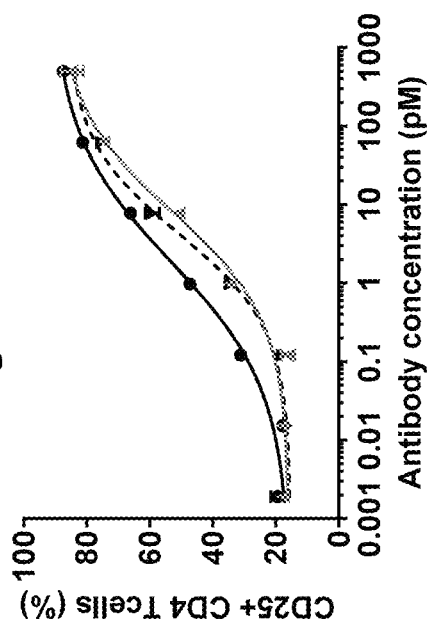
Figure 28A
Figure 28B

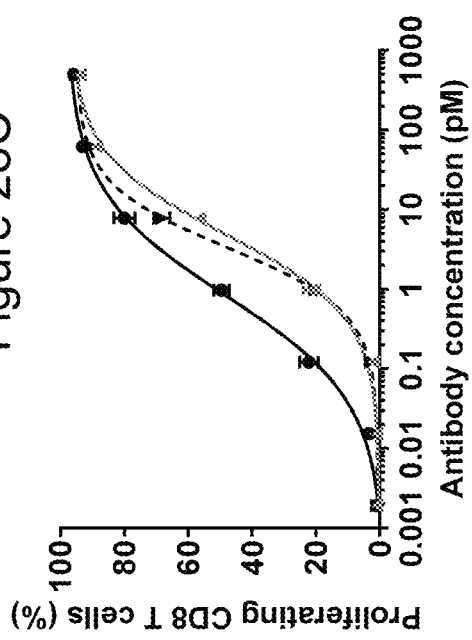
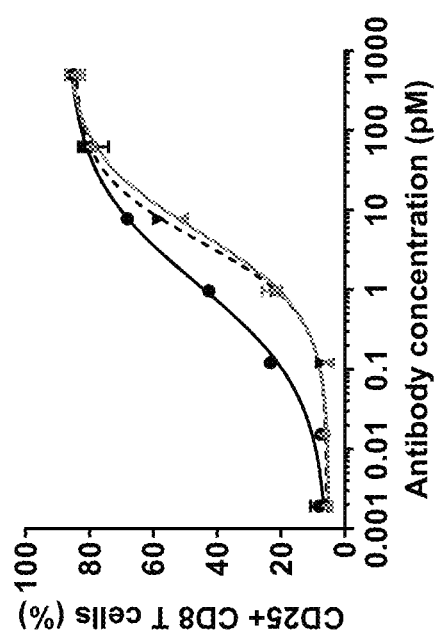
Figure 28C
Figure 28D

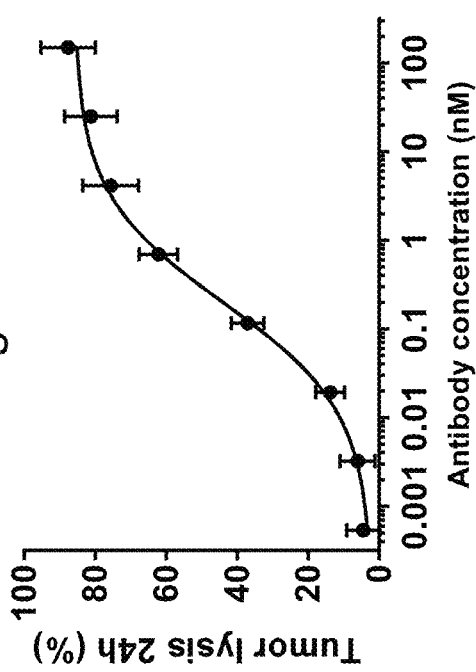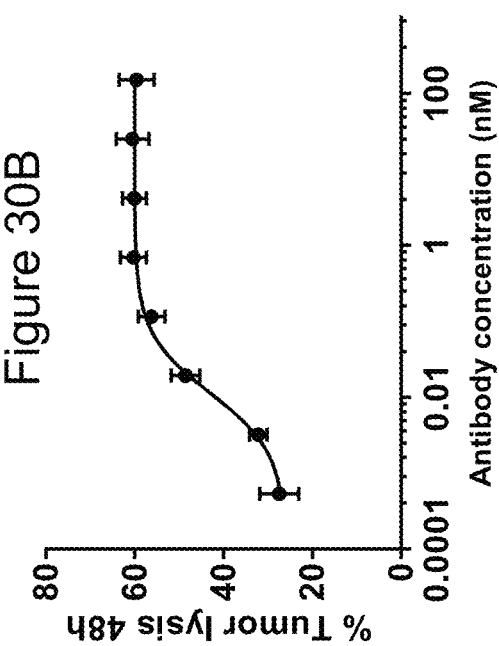

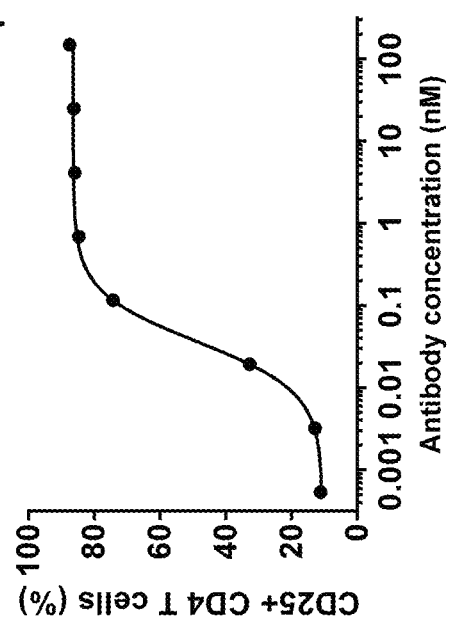
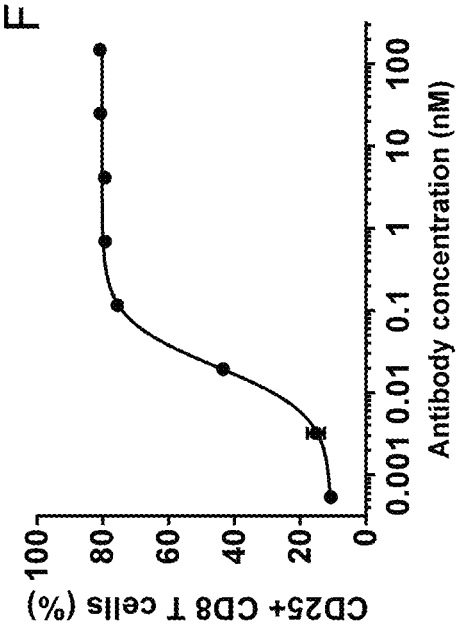

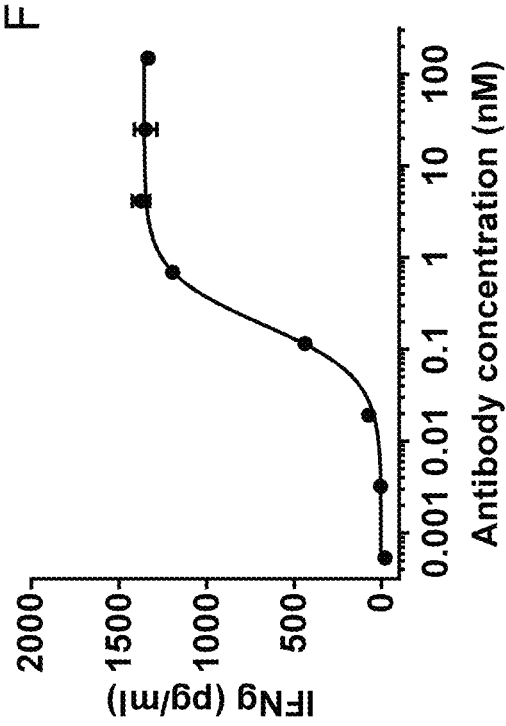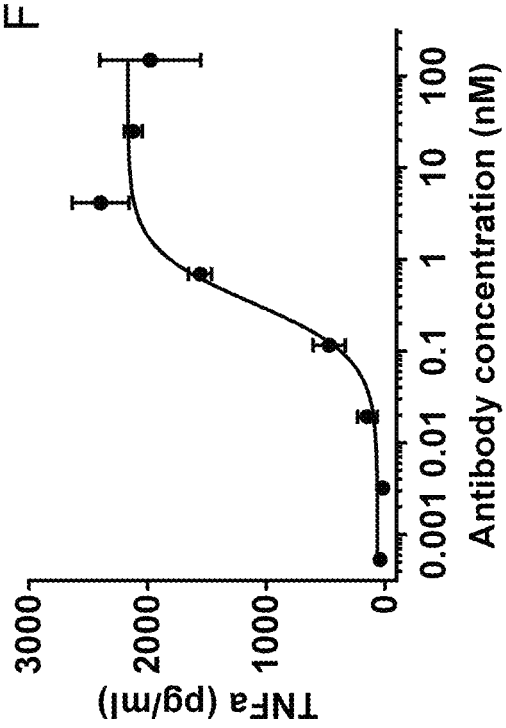

SEQUENCE LISTING

```
<160> NUMBER OF SEQ ID NOS: 158

<210> SEQ ID NO 1
<211> LENGTH: 5
<212> TYPE: PRT
<213> ORGANISM: Artificial Sequence
<220> FEATURE:
<223> OTHER INFORMATION: CD3orig HCDR1

<400> SEQUENCE: 1

Thr Tyr Ala Met Asn
1               5

<210> SEQ ID NO 2
<211> LENGTH: 5
<212> TYPE: PRT
<213> ORGANISM: Artificial Sequence
<220> FEATURE:
<223> OTHER INFORMATION: CD3opt HCDR1

<400> SEQUENCE: 2
```

```
Ser Tyr Ala Met Asn
1               5

<210> SEQ ID NO 3
<211> LENGTH: 19
<212> TYPE: PRT
<213> ORGANISM: Artificial Sequence
<220> FEATURE:
<223> OTHER INFORMATION: CD3orig / CD3opt HCDR2

<400> SEQUENCE: 3

Arg Ile Arg Ser Lys Tyr Asn Asn Tyr Ala Thr Tyr Tyr Ala Asp Ser
1               5                   10                  15

Val Lys Gly

<210> SEQ ID NO 4
<211> LENGTH: 14
<212> TYPE: PRT
<213> ORGANISM: Artificial Sequence
<220> FEATURE:
<223> OTHER INFORMATION: CD3orig HCDR3

<400> SEQUENCE: 4

His Gly Asn Phe Gly Asn Ser Tyr Val Ser Trp Phe Ala Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: CD3opt HCDR3

<400> SEQUENCE: 5

His Thr Thr Phe Pro Ser Ser Tyr Val Ser Tyr Tyr Gly Tyr
1               5                   10

<210> SEQ ID NO 6
<211> LENGTH: 125
<212> TYPE: PRT
<213> ORGANISM: Artificial Sequence
<220> FEATURE:
<223> OTHER INFORMATION: CD3orig VH

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 7
<211> LENGTH: 125
<212> TYPE: PRT
<213> ORGANISM: Artificial Sequence
<220> FEATURE:
<223> OTHER INFORMATION: CD3opt VH

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser
        115                 120                 125
```

<210> SEQ ID NO 8
<211> LENGTH: 14
<212> TYPE: PRT
<213> ORGANISM: Artificial Sequence
<220> FEATURE:
<223> OTHER INFORMATION: CD3orig / CD3opt LCDR1

<400> SEQUENCE: 8

```
Gly Ser Ser Thr Gly Ala Val Thr Thr Ser Asn Tyr Ala Asn
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: CD3orig / CD3opt LCDR2

<400> SEQUENCE: 9

```
Gly Thr Asn Lys Arg Ala Pro
1               5
```

<210> SEQ ID NO 10
<211> LENGTH: 9
<212> TYPE: PRT
<213> ORGANISM: Artificial Sequence
<220> FEATURE:
<223> OTHER INFORMATION: CD3orig / CD3opt LCDR3

<400> SEQUENCE: 10

```
Ala Leu Trp Tyr Ser Asn Leu Trp Val
1               5
```

<210> SEQ ID NO 11
<211> LENGTH: 109
<212> TYPE: PRT
<213> ORGANISM: Artificial Sequence
<220> FEATURE:
<223> OTHER INFORMATION: CD3orig / CD3opt VL

<400> SEQUENCE: 11

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 12
<211> LENGTH: 453
<212> TYPE: PRT
<213> ORGANISM: Artificial Sequence
<220> FEATURE:
<223> OTHER INFORMATION: CD3orig IgG HC

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

```
Glu Leu Leu Gly Gly Pro Ser Val Phe Leu Phe Pro Lys Pro Lys
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro
    450

<210> SEQ ID NO 13
<211> LENGTH: 453
<212> TYPE: PRT
<213> ORGANISM: Artificial Sequence
<220> FEATURE:
<223> OTHER INFORMATION: CD3opt IgG HC

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140
```

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450

<210> SEQ ID NO 14
<211> LENGTH: 216
<212> TYPE: PRT
<213> ORGANISM: Artificial Sequence
<220> FEATURE:
<223> OTHER INFORMATION: CD3orig / CD3opt IgG LC

<400> SEQUENCE: 14

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45
```

Leu Ile Gly Gly Thr Asn Lys Arg Ala Pro Gly Thr Pro Ala Arg Phe
            50                  55                  60

Ser Gly Ser Leu Leu Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
                210                 215

<210> SEQ ID NO 15
<211> LENGTH: 5
<212> TYPE: PRT
<213> ORGANISM: Artificial Sequence
<220> FEATURE:
<223> OTHER INFORMATION: TYRP1 HCDR1

<400> SEQUENCE: 15

Asp Tyr Phe Leu His
1               5

<210> SEQ ID NO 16
<211> LENGTH: 17
<212> TYPE: PRT
<213> ORGANISM: Artificial Sequence
<220> FEATURE:
<223> OTHER INFORMATION: TYRP1 HCDR2

<400> SEQUENCE: 16

Trp Ile Asn Pro Asp Asn Gly Asn Thr Val Tyr Ala Gln Lys Phe Gln
1               5                   10                  15

Gly

<210> SEQ ID NO 17
<211> LENGTH: 12
<212> TYPE: PRT
<213> ORGANISM: Artificial Sequence
<220> FEATURE:
<223> OTHER INFORMATION: TYRP1 HCDR3

<400> SEQUENCE: 17

Arg Asp Tyr Thr Tyr Glu Lys Ala Ala Leu Asp Tyr
1               5                   10

<210> SEQ ID NO 18
<211> LENGTH: 121
<212> TYPE: PRT
<213> ORGANISM: Artificial Sequence

<220> FEATURE:
<223> OTHER INFORMATION: TYRP1 VH

<400> SEQUENCE: 18

Gln Val Gln Leu Val Gln Ser Gly Ala Glu Lys Lys Pro Gly Ala
1               5                   10                  15

Ser Val Lys Val Ser Cys Lys Ala Ser Gly Phe Asn Ile Lys Asp Tyr
            20                  25                  30

Phe Leu His Trp Val Arg Gln Ala Pro Gly Gln Gly Leu Glu Trp Met
        35                  40                  45

Gly Trp Ile Asn Pro Asp Asn Gly Asn Thr Val Tyr Ala Gln Lys Phe
    50                  55                  60

Gln Gly Arg Val Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Asp Tyr Thr Tyr Glu Lys Ala Ala Leu Asp Tyr Trp Gly
            100                 105                 110

Gln Gly Thr Leu Val Thr Val Ser Ser
        115                 120

<210> SEQ ID NO 19
<211> LENGTH: 11
<212> TYPE: PRT
<213> ORGANISM: Artificial Sequence
<220> FEATURE:
<223> OTHER INFORMATION: TYRP1 LCDR1

<400> SEQUENCE: 19

Arg Ala Ser Gly Asn Ile Tyr Asn Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: TYRP1 LCDR2

<400> SEQUENCE: 20

Asp Ala Lys Thr Leu Ala Asp
1               5

<210> SEQ ID NO 21
<211> LENGTH: 9
<212> TYPE: PRT
<213> ORGANISM: Artificial Sequence
<220> FEATURE:
<223> OTHER INFORMATION: TYRP1 LCDR3

<400> SEQUENCE: 21

Gln His Phe Trp Ser Leu Pro Phe Thr
1               5

<210> SEQ ID NO 22
<211> LENGTH: 107
<212> TYPE: PRT
<213> ORGANISM: Artificial Sequence
<220> FEATURE:
<223> OTHER INFORMATION: TYRP1 VL

<400> SEQUENCE: 22

Asp Ile Gln Met Thr Gln Ser Pro Ser Ser Leu Ser Ala Ser Val Gly

```
                1               5              10              15
        Asp Arg Val Thr Ile Thr Cys Arg Ala Ser Gly Asn Ile Tyr Asn Tyr
                           20              25              30

Leu Ala Trp Tyr Gln Gln Lys Pro Gly Lys Val Pro Lys Leu Leu Ile
                       35              40              45

Tyr Asp Ala Lys Thr Leu Ala Asp Gly Val Pro Ser Arg Phe Ser Gly
           50              55              60

Ser Gly Ser Gly Thr Asp Phe Thr Leu Thr Ile Ser Ser Leu Gln Pro
        65              70              75              80

Glu Asp Val Ala Thr Tyr Tyr Cys Gln His Phe Trp Ser Leu Pro Phe
                       85              90              95

Thr Phe Gly Gln Gly Thr Lys Leu Glu Ile Lys
                       100             105

<210> SEQ ID NO 23
        <211> LENGTH: 674
        <212> TYPE: PRT
        <213> ORGANISM: Artificial Sequence
        <220> FEATURE:
        <223> OTHER INFORMATION: TYRP1 VH-CH1(EE) - CD3orig/CD3opt VL-CH1 - Fc
              (knob, PGLALA)

<400> SEQUENCE: 23

Gln Val Gln Leu Val Gln Ser Gly Ala Glu Val Lys Lys Pro Gly Ala
        1               5              10              15

Ser Val Lys Val Ser Cys Lys Ala Ser Gly Phe Asn Ile Lys Asp Tyr
                       20              25              30

Phe Leu His Trp Val Arg Gln Ala Pro Gly Gln Gly Leu Glu Trp Met
                       35              40              45

Gly Trp Ile Asn Pro Asp Asn Gly Asn Thr Val Tyr Ala Gln Lys Phe
           50              55              60

Gln Gly Arg Val Thr Met Thr Ala Asp Thr Ser Thr Ser Thr Val Tyr
        65              70              75              80

Met Glu Leu Ser Ser Leu Arg Ser Glu Asp Thr Ala Val Tyr Tyr Cys
                       85              90              95

Thr Arg Arg Asp Tyr Thr Tyr Glu Lys Ala Ala Leu Asp Tyr Trp Gly
                       100             105             110

Gln Gly Thr Leu Val Thr Val Ser Ser Ala Ser Thr Lys Gly Pro Ser
                       115             120             125

Val Phe Pro Leu Ala Pro Ser Ser Lys Ser Thr Ser Gly Gly Thr Ala
           130             135             140

Ala Leu Gly Cys Leu Val Glu Asp Tyr Phe Pro Glu Pro Val Thr Val
        145             150             155             160

Ser Trp Asn Ser Gly Ala Leu Thr Ser Gly Val His Thr Phe Pro Ala
                       165             170             175

Val Leu Gln Ser Ser Gly Leu Tyr Ser Leu Ser Ser Val Val Thr Val
                       180             185             190

Pro Ser Ser Ser Leu Gly Thr Gln Thr Tyr Ile Cys Asn Val Asn His
                       195             200             205

Lys Pro Ser Asn Thr Lys Val Asp Glu Lys Val Glu Pro Lys Ser Cys
                   210             215             220

Asp Gly Gly Gly Gly Ser Gly Gly Gly Ser Gln Ala Val Val Thr
        225             230             235             240

Gln Glu Pro Ser Leu Thr Val Ser Pro Gly Gly Thr Val Thr Leu Thr
                       245             250             255
```

```
Cys Gly Ser Ser Thr Gly Ala Val Thr Thr Ser Asn Tyr Ala Asn Trp
            260                 265                 270

Val Gln Glu Lys Pro Gly Gln Ala Phe Arg Gly Leu Ile Gly Gly Thr
        275                 280                 285

Asn Lys Arg Ala Pro Gly Thr Pro Ala Arg Phe Ser Gly Ser Leu Leu
        290                 295                 300

Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
            340                 345                 350

Ser Val Phe Pro Leu Ala Pro Ser Ser Lys Ser Thr Ser Gly Gly Thr
            355                 360                 365

Ala Ala Leu Gly Cys Leu Val Lys Asp Tyr Phe Pro Glu Pro Val Thr
        370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Lys Val Glu Pro Lys Ser
        435                 440                 445

Cys Asp Lys Thr His Thr Cys Pro Pro Cys Pro Ala Pro Glu Ala Ala
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
    530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro
```

<210> SEQ ID NO 24
<211> LENGTH: 449
<212> TYPE: PRT
<213> ORGANISM: Artificial Sequence
<220> FEATURE:
<223> OTHER INFORMATION: TYRP1 VH-CH1(EE)-Fc (hole, PGLALA)

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Phe Leu His Trp Val Arg Gln Ala Pro Gly Gln Gly Leu Glu Trp Met
        35                  40                  45

Gly Trp Ile Asn Pro Asp Asn Gly Asn Thr Val Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Asp Tyr Thr Tyr Glu Lys Ala Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365
```

```
Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 25
<211> LENGTH: 214
<212> TYPE: PRT
<213> ORGANISM: Artificial Sequence
<220> FEATURE:
<223> OTHER INFORMATION: TYRP1 VL-CL(RK)

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile Tyr Asn Tyr
            20                  25                  30

Leu Ala Trp Tyr Gln Gln Lys Pro Gly Lys Val Pro Lys Leu Leu Ile
        35                  40                  45

Tyr Asp Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 232
<212> TYPE: PRT
<213> ORGANISM: Artificial Sequence
<220> FEATURE:
<223> OTHER INFORMATION: CD3orig VH-CL

<400> SEQUENCE: 26
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 27
<211> LENGTH: 232
<212> TYPE: PRT
<213> ORGANISM: Artificial Sequence
<220> FEATURE:
<223> OTHER INFORMATION: CD3opt VH-CL

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Tyr Val Ser Tyr Tyr
            100                 105                 110

Gly Tyr Trp Gly Gln Gly Thr Leu Val Thr Val Ser Ser Ala Ser Val
        115                 120                 125

```
Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230
```

<210> SEQ ID NO 28
<211> LENGTH: 360
<212> TYPE: PRT
<213> ORGANISM: Artificial Sequence
<220> FEATURE:
<223> OTHER INFORMATION: Human CD3 epsilon stalk - Fc(knob) - Avi

<400> SEQUENCE: 28

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
        50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Ser Glu Asn Cys Val Asp Glu Gln Leu Tyr Phe Gln Gly Gly Ser
            100                 105                 110

Pro Lys Ser Ala Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Asp Glu Leu Thr Lys
                245                 250                 255
```

```
Asn Gln Val Ser Leu Trp Cys Leu Val Lys Gly Phe Tyr Pro Ser Asp
            260                 265                 270
Ile Ala Val Glu Trp Glu Ser Asn Gly Gln Pro Glu Asn Asn Tyr Lys
            275                 280                 285
Thr Thr Pro Pro Val Leu Asp Ser Asp Gly Ser Phe Phe Leu Tyr Ser
            290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
            325                 330                 335
Leu Ser Leu Ser Pro Gly Lys Ser Gly Gly Leu Asn Asp Ile Phe Glu
            340                 345                 350
Ala Gln Lys Ile Glu Trp His Glu
            355                 360

<210> SEQ ID NO 29
<211> LENGTH: 325
<212> TYPE: PRT
<213> ORGANISM: Artificial Sequence
<220> FEATURE:
<223> OTHER INFORMATION: Human CD3 delta stalk - Fc (hole) - Avi

<400> SEQUENCE: 29

Phe Lys Ile Pro Ile Glu Glu Leu Glu Asp Arg Val Phe Val Asn Cys
1               5                   10                  15
Asn Thr Ser Ile Thr Trp Val Glu Gly Thr Val Gly Thr Leu Leu Ser
            20                  25                  30
Asp Ile Thr Arg Leu Asp Leu Gly Lys Arg Ile Leu Asp Pro Arg Gly
            35                  40                  45
Ile Tyr Arg Cys Asn Gly Thr Asp Ile Tyr Lys Asp Lys Glu Ser Thr
        50                  55                  60
Val Gln Val His Tyr Arg Met Cys Arg Ser Glu Gln Leu Tyr Phe Gln
65              70                  75                  80
Gly Asp Lys Thr His Thr Cys Pro Pro Cys Pro Ala Pro Glu Leu Leu
            85                  90                  95
Gly Gly Pro Ser Val Phe Leu Phe Pro Pro Lys Pro Lys Asp Thr Leu
            100                 105                 110
Met Ile Ser Arg Thr Pro Glu Val Thr Cys Val Val Val Asp Val Ser
            115                 120                 125
His Glu Asp Pro Glu Val Lys Phe Asn Trp Tyr Val Asp Gly Val Glu
        130                 135                 140
Val His Asn Ala Lys Thr Lys Pro Arg Glu Glu Gln Tyr Asn Ser Thr
145                 150                 155                 160
Tyr Arg Val Val Ser Val Leu Thr Val Leu His Gln Asp Trp Leu Asn
            165                 170                 175
Gly Lys Glu Tyr Lys Cys Lys Val Ser Asn Lys Ala Leu Pro Ala Pro
            180                 185                 190
Ile Glu Lys Thr Ile Ser Lys Ala Lys Gly Gln Pro Arg Glu Pro Gln
            195                 200                 205
Val Cys Thr Leu Pro Pro Ser Arg Asp Glu Leu Thr Lys Asn Gln Val
        210                 215                 220
Ser Leu Ser Cys Ala Val Lys Gly Phe Tyr Pro Ser Asp Ile Ala Val
225                 230                 235                 240
Glu Trp Glu Ser Asn Gly Gln Pro Glu Asn Asn Tyr Lys Thr Thr Pro
            245                 250                 255
```

```
Pro Val Leu Asp Ser Asp Gly Ser Phe Phe Leu Val Ser Lys Leu Thr
            260                 265                 270

Val Asp Lys Ser Arg Trp Gln Gln Gly Asn Val Phe Ser Cys Ser Val
        275                 280                 285

Met His Glu Ala Leu His Asn His Tyr Thr Gln Lys Ser Leu Ser Leu
    290                 295                 300

Ser Pro Gly Lys Ser Gly Gly Leu Asn Asp Ile Phe Glu Ala Gln Lys
305                 310                 315                 320

Ile Glu Trp His Glu
                325

<210> SEQ ID NO 30
<211> LENGTH: 351
<212> TYPE: PRT
<213> ORGANISM: Artificial Sequence
<220> FEATURE:
<223> OTHER INFORMATION: Cynomolgus CD3 epsilon stalk - Fc (knob) - Avi

<400> SEQUENCE: 30

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Ser Glu Asn Cys Val Asp Glu Gln
                85                  90                  95

Leu Tyr Phe Gln Gly Gly Ser Pro Lys Ser Ala Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Cys Arg Asp Glu Leu Thr Lys Asn Gln Val Ser Leu Trp Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285
```

```
Gly Ser Phe Leu Tyr Ser Lys Leu Thr Val Asp Lys Ser Arg Trp
        290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys Ser Gly
                325                 330                 335

Gly Leu Asn Asp Ile Phe Glu Ala Gln Lys Ile Glu Trp His Glu
            340                 345                 350

<210> SEQ ID NO 31
<211> LENGTH: 334
<212> TYPE: PRT
<213> ORGANISM: Artificial Sequence
<220> FEATURE:
<223> OTHER INFORMATION: Cynomolgus CD3 delta stalk - Fc (hole) - Avi

<400> SEQUENCE: 31

Phe Lys Ile Pro Val Glu Glu Leu Glu Asp Arg Val Phe Val Lys Cys
1               5                   10                  15

Asn Thr Ser Val Thr Trp Val Glu Gly Thr Val Gly Thr Leu Leu Thr
            20                  25                  30

Asn Asn Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Ala
    50                  55                  60

Val Gln Val His Tyr Arg Met Ser Gln Asn Cys Val Asp Glu Gln Leu
65                  70                  75                  80

Tyr Phe Gln Gly Gly Ser Pro Lys Ser Ala Asp Lys Thr His Thr Cys
                85                  90                  95

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
    130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Cys Thr Leu Pro Pro Ser
    210                 215                 220

Arg Asp Glu Leu Thr Lys Asn Gln Val Ser Leu Ser Cys Ala Val Lys
225                 230                 235                 240

Gly Phe Tyr Pro Ser Asp Ile Ala Val Glu Trp Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Val Ser Lys Leu Thr Val Asp Lys Ser Arg Trp Gln
        275                 280                 285

Gln Gly Asn Val Phe Ser Cys Ser Val Met His Glu Ala Leu His Asn
    290                 295                 300
```

```
His Tyr Thr Gln Lys Ser Leu Ser Leu Ser Pro Gly Lys Ser Gly Gly
305                 310                 315                 320

Leu Asn Asp Ile Phe Glu Ala Gln Lys Ile Glu Trp His Glu
                325                 330

<210> SEQ ID NO 32
<211> LENGTH: 699
<212> TYPE: PRT
<213> ORGANISM: Artificial Sequence
<220> FEATURE:
<223> OTHER INFORMATION: Human TYRP1 ECD - Fc (knob) - Avi

<400> SEQUENCE: 32

Gln Phe Pro Arg Gln Cys Ala Thr Val Glu Ala Leu Arg Ser Gly Met
1               5                   10                  15

Cys Cys Pro Asp Leu Ser Pro Val Ser Gly Pro Gly Thr Asp Arg Cys
                20                  25                  30

Gly Ser Ser Ser Gly Arg Gly Arg Cys Glu Ala Val Thr Ala Asp Ser
            35                  40                  45

Arg Pro His Ser Pro Gln Tyr Pro His Asp Gly Arg Asp Asp Arg Glu
        50                  55                  60

Val Trp Pro Leu Arg Phe Phe Asn Arg Thr Cys His Cys Asn Gly Asn
65                  70                  75                  80

Phe Ser Gly His Asn Cys Gly Thr Cys Arg Pro Gly Trp Arg Gly Ala
                85                  90                  95

Ala Cys Asp Gln Arg Val Leu Ile Val Arg Arg Asn Leu Leu Asp Leu
            100                 105                 110

Ser Lys Glu Glu Lys Asn His Phe Val Arg Ala Leu Asp Met Ala Lys
        115                 120                 125

Arg Thr Thr His Pro Leu Phe Val Ile Ala Thr Arg Arg Ser Glu Glu
130                 135                 140

Ile Leu Gly Pro Asp Gly Asn Thr Pro Gln Phe Glu Asn Ile Ser Ile
145                 150                 155                 160

Tyr Asn Tyr Phe Val Trp Thr His Tyr Tyr Ser Val Lys Lys Thr Phe
                165                 170                 175

Leu Gly Val Gly Gln Glu Ser Phe Gly Glu Val Asp Phe Ser His Glu
            180                 185                 190

Gly Pro Ala Phe Leu Thr Trp His Arg Tyr His Leu Leu Arg Leu Glu
        195                 200                 205

Lys Asp Met Gln Glu Met Leu Gln Glu Pro Ser Phe Ser Leu Pro Tyr
210                 215                 220

Trp Asn Phe Ala Thr Gly Lys Asn Val Cys Asp Ile Cys Thr Asp Asp
225                 230                 235                 240

Leu Met Gly Ser Arg Ser Asn Phe Asp Ser Thr Leu Ile Ser Pro Asn
                245                 250                 255

Ser Val Phe Ser Gln Trp Arg Val Val Cys Asp Ser Leu Glu Asp Tyr
            260                 265                 270

Asp Thr Leu Gly Thr Leu Cys Asn Ser Thr Glu Asp Gly Pro Ile Arg
        275                 280                 285

Arg Asn Pro Ala Gly Asn Val Ala Arg Pro Met Val Gln Arg Leu Pro
290                 295                 300

Glu Pro Gln Asp Val Ala Gln Cys Leu Glu Val Gly Leu Phe Asp Thr
305                 310                 315                 320

Pro Pro Phe Tyr Ser Asn Ser Thr Asn Ser Phe Arg Asn Thr Val Glu
                325                 330                 335
```

Gly Tyr Ser Asp Pro Thr Gly Lys Tyr Asp Pro Ala Val Arg Ser Leu
            340                 345                 350

His Asn Leu Ala His Leu Phe Leu Asn Gly Thr Gly Gly Gln Thr His
            355                 360                 365

Leu Ser Pro Asn Asp Pro Ile Phe Val Leu His Thr Phe Thr Asp
370                 375                 380

Ala Val Phe Asp Glu Trp Leu Arg Arg Tyr Asn Ala Asp Ile Ser Thr
385                 390                 395                 400

Phe Pro Leu Glu Asn Ala Pro Ile Gly His Asn Arg Gln Tyr Asn Met
                405                 410                 415

Val Pro Phe Trp Pro Pro Val Thr Asn Thr Glu Met Phe Val Thr Ala
            420                 425                 430

Pro Asp Asn Leu Gly Tyr Thr Tyr Glu Ile Gln Trp Pro Ser Arg Glu
            435                 440                 445

Phe Ser Val Pro Glu Gly Ser Asp Lys Thr His Thr Cys Pro Pro Cys
            450                 455                 460

Pro Ala Pro Glu Ala Ala Gly Gly Pro Ser Val Phe Leu Phe Pro Pro
465                 470                 475                 480

Lys Pro Lys Asp Thr Leu Met Ile Ser Arg Thr Pro Glu Val Thr Cys
                485                 490                 495

Val Val Val Asp Val Ser His Glu Asp Pro Glu Val Lys Phe Asn Trp
            500                 505                 510

Tyr Val Asp Gly Val Glu Val His Asn Ala Lys Thr Lys Pro Arg Glu
            515                 520                 525

Glu Gln Tyr Asn Ser Thr Tyr Arg Val Val Ser Val Leu Thr Val Leu
530                 535                 540

His Gln Asp Trp Leu Asn Gly Lys Glu Tyr Lys Cys Lys Val Ser Asn
545                 550                 555                 560

Lys Ala Leu Gly Ala Pro Ile Glu Lys Thr Ile Ser Lys Ala Lys Gly
                565                 570                 575

Gln Pro Arg Glu Pro Gln Val Tyr Thr Leu Pro Pro Cys Arg Asp Glu
            580                 585                 590

Leu Thr Lys Asn Gln Val Ser Leu Trp Cys Leu Val Lys Gly Phe Tyr
            595                 600                 605

Pro Ser Asp Ile Ala Val Glu Trp Glu Ser Asn Gly Gln Pro Glu Asn
            610                 615                 620

Asn Tyr Lys Thr Thr Pro Pro Val Leu Asp Ser Asp Gly Ser Phe Phe
625                 630                 635                 640

Leu Tyr Ser Lys Leu Thr Val Asp Lys Ser Arg Trp Gln Gln Gly Asn
                645                 650                 655

Val Phe Ser Cys Ser Val Met His Glu Ala Leu His Asn His Tyr Thr
            660                 665                 670

Gln Lys Ser Leu Ser Leu Ser Pro Gly Lys Ser Gly Gly Leu Asn Asp
            675                 680                 685

Ile Phe Glu Ala Gln Lys Ile Glu Trp His Glu
    690                 695

<210> SEQ ID NO 33
<211> LENGTH: 698
<212> TYPE: PRT
<213> ORGANISM: Artificial Sequence
<220> FEATURE:
<223> OTHER INFORMATION: Cynomolgus TYRP1 ECD - Fc (knob) - Avi

<400> SEQUENCE: 33

-continued

```
Gln Phe Pro Arg Glu Cys Ala Thr Val Glu Ala Leu Arg Ser Gly Met
1               5                   10                  15
Cys Cys Pro Asp Leu Ser Pro Met Ser Gly Pro Gly Thr Asp Arg Cys
                20                  25                  30
Gly Ser Ser Ser Gly Arg Gly Arg Cys Glu Ala Val Thr Ala Asp Ser
            35                  40                  45
Arg Pro His Ser Pro Arg Tyr Pro His Asp Gly Arg Asp Asp Arg Glu
        50                  55                  60
Val Trp Pro Leu Arg Phe Phe Asn Arg Thr Cys His Cys Asn Gly Asn
65                  70                  75                  80
Phe Ser Gly His Asn Cys Gly Thr Cys Arg Pro Gly Trp Arg Gly Ala
                85                  90                  95
Ala Cys Asp Gln Arg Val Leu Val Arg Arg Asn Leu Leu Asp Leu
                100                 105                 110
Ser Lys Glu Glu Lys Asn His Phe Val Arg Ala Leu Asp Met Ala Lys
            115                 120                 125
Arg Thr Thr His Pro Leu Phe Val Ile Ala Thr Arg Arg Ser Glu Glu
        130                 135                 140
Ile Leu Gly Pro Asp Gly Asn Thr Pro Gln Phe Glu Asn Ile Ser Ile
145                 150                 155                 160
Tyr Asn Tyr Phe Val Trp Thr His Tyr Tyr Ser Val Lys Lys Thr Phe
                165                 170                 175
Leu Gly Ala Gly Gln Glu Ser Phe Gly Glu Val Asp Phe Ser His Glu
            180                 185                 190
Gly Pro Ala Phe Leu Thr Trp His Arg Tyr His Leu Leu Arg Leu Glu
        195                 200                 205
Lys Asp Met Gln Glu Met Leu Gln Glu Pro Ser Phe Ser Leu Pro Tyr
    210                 215                 220
Trp Asn Phe Ala Thr Gly Lys Asn Val Cys Asp Ile Cys Thr Asp Asp
225                 230                 235                 240
Leu Met Gly Ser Arg Ser Asn Phe Asp Ser Thr Leu Ile Ser Pro Asn
                245                 250                 255
Ser Val Phe Ser Gln Trp Arg Val Val Cys Asp Ser Leu Glu Asp Tyr
            260                 265                 270
Asp Thr Leu Gly Thr Leu Cys Asn Ser Thr Glu Ser Gly Pro Ile Arg
        275                 280                 285
Arg Asn Pro Ala Gly Asn Val Ala Arg Pro Met Val Gln Arg Leu Pro
    290                 295                 300
Glu Pro Gln Asp Val Ala Gln Cys Leu Glu Val Gly Leu Phe Asp Thr
305                 310                 315                 320
Pro Pro Phe Tyr Ser Asn Ser Thr Asn Ser Phe Arg Asn Thr Val Glu
                325                 330                 335
Gly Tyr Ser Asp Pro Thr Gly Lys Tyr Asp Pro Ala Val Arg Ser Leu
            340                 345                 350
His Asn Leu Ala His Leu Phe Leu Asn Gly Thr Gly Gln Thr His
        355                 360                 365
Leu Ser Pro Asn Asp Pro Ile Phe Val Leu Leu His Thr Phe Thr Asp
    370                 375                 380
Ala Val Phe Asp Glu Trp Leu Arg Arg Tyr Asn Ala Asp Ile Ser Thr
385                 390                 395                 400
Phe Pro Leu Glu Asn Ala Pro Ile Gly His Asn Arg Gln Tyr Asn Met
                405                 410                 415
```

```
Val Pro Phe Trp Pro Pro Val Thr Asn Thr Glu Met Phe Val Thr Ala
            420                 425                 430

Pro Asp Asn Leu Gly Tyr Thr Tyr Glu Val Gln Trp Pro Ser Arg Glu
            435                 440                 445

Phe Ser Val Pro Gly Ser Asp Lys Thr His Thr Cys Pro Pro Cys Pro
            450                 455                 460

Ala Pro Glu Ala Ala Gly Gly Pro Ser Val Phe Leu Phe Pro Pro Lys
465                 470                 475                 480

Pro Lys Asp Thr Leu Met Ile Ser Arg Thr Pro Glu Val Thr Cys Val
            485                 490                 495

Val Val Asp Val Ser His Glu Asp Pro Glu Val Lys Phe Asn Trp Tyr
            500                 505                 510

Val Asp Gly Val Glu Val His Asn Ala Lys Thr Lys Pro Arg Glu Glu
            515                 520                 525

Gln Tyr Asn Ser Thr Tyr Arg Val Val Ser Val Leu Thr Val Leu His
            530                 535                 540

Gln Asp Trp Leu Asn Gly Lys Glu Tyr Lys Cys Lys Val Ser Asn Lys
545                 550                 555                 560

Ala Leu Gly Ala Pro Ile Glu Lys Thr Ile Ser Lys Ala Lys Gly Gln
            565                 570                 575

Pro Arg Glu Pro Gln Val Tyr Thr Leu Pro Pro Cys Arg Asp Glu Leu
            580                 585                 590

Thr Lys Asn Gln Val Ser Leu Trp Cys Leu Val Lys Gly Phe Tyr Pro
            595                 600                 605

Ser Asp Ile Ala Val Glu Trp Glu Ser Asn Gly Gln Pro Glu Asn Asn
610                 615                 620

Tyr Lys Thr Thr Pro Pro Val Leu Asp Ser Asp Gly Ser Phe Phe Leu
625                 630                 635                 640

Tyr Ser Lys Leu Thr Val Asp Lys Ser Arg Trp Gln Gln Gly Asn Val
            645                 650                 655

Phe Ser Cys Ser Val Met His Glu Ala Leu His Asn His Tyr Thr Gln
            660                 665                 670

Lys Ser Leu Ser Leu Ser Pro Gly Lys Ser Gly Gly Leu Asn Asp Ile
            675                 680                 685

Phe Glu Ala Gln Lys Ile Glu Trp His Glu
        690                 695

<210> SEQ ID NO 34
<211> LENGTH: 699
<212> TYPE: PRT
<213> ORGANISM: Artificial Sequence
<220> FEATURE:
<223> OTHER INFORMATION: Mouse TYRP1 ECD - Fc (knob) - Avi

<400> SEQUENCE: 34

Gln Phe Pro Arg Glu Cys Ala Asn Ile Glu Ala Leu Arg Arg Gly Val
1               5                   10                  15

Cys Cys Pro Asp Leu Leu Pro Ser Ser Gly Pro Gly Thr Asp Pro Cys
            20                  25                  30

Gly Ser Ser Ser Gly Arg Gly Arg Cys Val Ala Val Ile Ala Asp Ser
            35                  40                  45

Arg Pro His Ser Arg His Tyr Pro His Asp Gly Lys Asp Asp Arg Glu
            50                  55                  60

Ala Trp Pro Leu Arg Phe Phe Asn Arg Thr Cys Gln Cys Asn Asp Asn
65                  70                  75                  80
```

```
Phe Ser Gly His Asn Cys Gly Thr Cys Arg Pro Gly Trp Arg Gly Ala
                 85                  90                  95

Ala Cys Asn Gln Lys Ile Leu Thr Val Arg Arg Asn Leu Leu Asp Leu
            100                 105                 110

Ser Pro Glu Glu Lys Ser His Phe Val Arg Ala Leu Asp Met Ala Lys
            115                 120                 125

Arg Thr Thr His Pro Gln Phe Val Ile Ala Thr Arg Arg Leu Glu Asp
            130                 135                 140

Ile Leu Gly Pro Asp Gly Asn Thr Pro Gln Phe Glu Asn Ile Ser Val
145                 150                 155                 160

Tyr Asn Tyr Phe Val Trp Thr His Tyr Tyr Ser Val Lys Lys Thr Phe
                165                 170                 175

Leu Gly Thr Gly Gln Glu Ser Phe Gly Asp Val Asp Phe Ser His Glu
            180                 185                 190

Gly Pro Ala Phe Leu Thr Trp His Arg Tyr His Leu Leu Gln Leu Glu
            195                 200                 205

Arg Asp Met Gln Glu Met Leu Gln Glu Pro Ser Phe Ser Leu Pro Tyr
            210                 215                 220

Trp Asn Phe Ala Thr Gly Lys Asn Val Cys Asp Val Cys Thr Asp Asp
225                 230                 235                 240

Leu Met Gly Ser Arg Ser Asn Phe Asp Ser Thr Leu Ile Ser Pro Asn
                245                 250                 255

Ser Val Phe Ser Gln Trp Arg Val Val Cys Glu Ser Leu Glu Glu Tyr
            260                 265                 270

Asp Thr Leu Gly Thr Leu Cys Asn Ser Thr Glu Gly Gly Pro Ile Arg
            275                 280                 285

Arg Asn Pro Ala Gly Asn Val Gly Arg Pro Ala Val Gln Arg Leu Pro
290                 295                 300

Glu Pro Gln Asp Val Thr Gln Cys Leu Glu Val Arg Val Phe Asp Thr
305                 310                 315                 320

Pro Pro Phe Tyr Ser Asn Ser Thr Asp Ser Phe Arg Asn Thr Val Glu
                325                 330                 335

Gly Tyr Ser Ala Pro Thr Gly Lys Tyr Asp Pro Ala Val Arg Ser Leu
            340                 345                 350

His Asn Leu Ala His Leu Phe Leu Asn Gly Thr Gly Gly Gln Thr His
            355                 360                 365

Leu Ser Pro Asn Asp Pro Ile Phe Val Leu Leu His Thr Phe Thr Asp
            370                 375                 380

Ala Val Phe Asp Glu Trp Leu Arg Arg Tyr Asn Ala Asp Ile Ser Thr
385                 390                 395                 400

Phe Pro Leu Glu Asn Ala Pro Ile Gly His Asn Arg Gln Tyr Asn Met
                405                 410                 415

Val Pro Phe Trp Pro Pro Val Thr Asn Thr Glu Met Phe Val Thr Ala
            420                 425                 430

Pro Asp Asn Leu Gly Tyr Ala Tyr Glu Val Gln Trp Pro Gly Gln Glu
            435                 440                 445

Phe Thr Val Ser Glu Gly Ser Asp Lys Thr His Thr Cys Pro Pro Cys
            450                 455                 460

Pro Ala Pro Glu Ala Ala Gly Gly Pro Ser Val Phe Leu Phe Pro Pro
465                 470                 475                 480

Lys Pro Lys Asp Thr Leu Met Ile Ser Arg Thr Pro Glu Val Thr Cys
                485                 490                 495

Val Val Val Asp Val Ser His Glu Asp Pro Glu Val Lys Phe Asn Trp
```

```
              500                 505                 510
Tyr Val Asp Gly Val Glu Val His Asn Ala Lys Thr Lys Pro Arg Glu
            515                 520                 525

Glu Gln Tyr Asn Ser Thr Tyr Arg Val Val Ser Val Leu Thr Val Leu
        530                 535                 540

His Gln Asp Trp Leu Asn Gly Lys Glu Tyr Lys Cys Lys Val Ser Asn
545                 550                 555                 560

Lys Ala Leu Gly Ala Pro Ile Glu Lys Thr Ile Ser Lys Ala Lys Gly
                565                 570                 575

Gln Pro Arg Glu Pro Gln Val Tyr Thr Leu Pro Pro Cys Arg Asp Glu
            580                 585                 590

Leu Thr Lys Asn Gln Val Ser Leu Trp Cys Leu Val Lys Gly Phe Tyr
        595                 600                 605

Pro Ser Asp Ile Ala Val Glu Trp Glu Ser Asn Gly Gln Pro Glu Asn
            610                 615                 620

Asn Tyr Lys Thr Thr Pro Pro Val Leu Asp Ser Asp Gly Ser Phe Phe
625                 630                 635                 640

Leu Tyr Ser Lys Leu Thr Val Asp Lys Ser Arg Trp Gln Gln Gly Asn
                645                 650                 655

Val Phe Ser Cys Ser Val Met His Glu Ala Leu His Asn His Tyr Thr
            660                 665                 670

Gln Lys Ser Leu Ser Leu Ser Pro Gly Lys Ser Gly Gly Leu Asn Asp
        675                 680                 685

Ile Phe Glu Ala Gln Lys Ile Glu Trp His Glu
    690                 695

<210> SEQ ID NO 35
<211> LENGTH: 225
<212> TYPE: PRT
<213> ORGANISM: Artificial Sequence
<220> FEATURE:
<223> OTHER INFORMATION: Fc (hole)

<400> SEQUENCE: 35

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
```

```
                165                 170                 175
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro
225

<210> SEQ ID NO 36
<211> LENGTH: 393
<212> TYPE: PRT
<213> ORGANISM: Artificial Sequence
<220> FEATURE:
<223> OTHER INFORMATION: EGFRvIII ECD - Avi - His

<400> SEQUENCE: 36

Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
        35                  40                  45

Ile Gly Ile Gly Glu Phe Lys Asp Ser Leu Ser Ile Asn Ala Thr Asn
    50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
        115                 120                 125

Phe Glu Asn Leu Glu Ile Ile Arg Gly Arg Thr Lys Gln His Gly Gln
    130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205

Lys Ala Thr Gly Gln Val Cys His Ala Leu Cys Ser Pro Glu Gly Cys
    210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
                245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
        275                 280                 285

Ile Gln Cys Ala His Tyr Ile Asp Gly Pro His Cys Val Lys Thr Cys
```

```
                290                 295                 300
Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
                325                 330                 335

Cys Thr Gly Pro Gly Leu Glu Gly Cys Pro Thr Asn Gly Pro Lys Ile
            340                 345                 350

Pro Ser Val Asp Gly Gly Ser Pro Thr Pro Thr Pro Gly Gly Gly
        355                 360                 365

Ser Gly Leu Asn Asp Ile Phe Glu Ala Gln Lys Ile Glu Trp His Glu
    370                 375                 380

Ala Arg Ala His His His His His His
385                 390

<210> SEQ ID NO 37
<211> LENGTH: 5
<212> TYPE: PRT
<213> ORGANISM: Artificial Sequence
<220> FEATURE:
<223> OTHER INFORMATION: EGFRvIII P056.021 HCDR1

<400> SEQUENCE: 37

Ser Tyr Trp Ile Ala
1               5

<210> SEQ ID NO 38
<211> LENGTH: 17
<212> TYPE: PRT
<213> ORGANISM: Artificial Sequence
<220> FEATURE:
<223> OTHER INFORMATION: EGFRvIII P056.021 HCDR2

<400> SEQUENCE: 38

Val Ile His Pro Tyr Asp Ser Asp Thr Arg Tyr Ser Pro Ser Phe Gln
1               5                   10                  15

Gly

<210> SEQ ID NO 39
<211> LENGTH: 10
<212> TYPE: PRT
<213> ORGANISM: Artificial Sequence
<220> FEATURE:
<223> OTHER INFORMATION: EGFRvIII P056.021 HCDR3

<400> SEQUENCE: 39

Val Ser Arg Ser Ser Tyr Ala Phe Asp Tyr
1               5                   10

<210> SEQ ID NO 40
<211> LENGTH: 119
<212> TYPE: PRT
<213> ORGANISM: Artificial Sequence
<220> FEATURE:
<223> OTHER INFORMATION: EGFRvIII P056.021 VH

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30

Trp Ile Ala Trp Val Arg Gln Met Pro Gly Lys Gly Leu Glu Trp Met
        35                  40                  45
```

```
Gly Val Ile His Pro Tyr Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Val Ser Arg Ser Ser Tyr Ala Phe Asp Tyr Trp Gly Gln Gly
            100                 105                 110

Thr Leu Val Thr Val Ser Ser
        115

<210> SEQ ID NO 41
<211> LENGTH: 17
<212> TYPE: PRT
<213> ORGANISM: Artificial Sequence
<220> FEATURE:
<223> OTHER INFORMATION: EGFRvIII P056.021 LCDR1

<400> SEQUENCE: 41

Lys Ser Ser Gln Ser Val Leu Tyr Ser Ser Asn Asn Lys Asn Tyr Leu
 1               5                  10                  15

Ala

<210> SEQ ID NO 42
<211> LENGTH: 7
<212> TYPE: PRT
<213> ORGANISM: Artificial Sequence
<220> FEATURE:
<223> OTHER INFORMATION: EGFRvIII P056.021 LCDR2

<400> SEQUENCE: 42

Trp Ala Ser Thr Arg Glu Ser
 1               5

<210> SEQ ID NO 43
<211> LENGTH: 10
<212> TYPE: PRT
<213> ORGANISM: Artificial Sequence
<220> FEATURE:
<223> OTHER INFORMATION: EGFRvIII P056.021 LCDR3

<400> SEQUENCE: 43

Gln Gln Val His Ser Gly Pro Pro Val Thr
 1               5                  10

<210> SEQ ID NO 44
<211> LENGTH: 114
<212> TYPE: PRT
<213> ORGANISM: Artificial Sequence
<220> FEATURE:
<223> OTHER INFORMATION: EGFRvIII P056.021 VL

<400> SEQUENCE: 44

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Val His Ser Gly Pro Pro Val Thr Phe Gly Gln Gly Thr Lys Val Glu
            100                 105                 110

Ile Lys

<210> SEQ ID NO 45
<211> LENGTH: 5
<212> TYPE: PRT
<213> ORGANISM: Artificial Sequence
<220> FEATURE:
<223> OTHER INFORMATION: EGFRvIII P056.052 HCDR1

<400> SEQUENCE: 45

Asn Tyr Trp Ile Gly
1               5

<210> SEQ ID NO 46
<211> LENGTH: 17
<212> TYPE: PRT
<213> ORGANISM: Artificial Sequence
<220> FEATURE:
<223> OTHER INFORMATION: EGFRvIII P056.052 HCDR2

<400> SEQUENCE: 46

Thr Ile Tyr Pro Gly Asp Ser Asp Arg Arg Tyr Ser Pro Ser Phe Gln
1               5                   10                  15

Gly

<210> SEQ ID NO 47
<211> LENGTH: 10
<212> TYPE: PRT
<213> ORGANISM: Artificial Sequence
<220> FEATURE:
<223> OTHER INFORMATION: EGFRvIII P056.052 HCDR3

<400> SEQUENCE: 47

Val Ser Arg Ser Ser Tyr Ala Phe Asp Tyr
1               5                   10

<210> SEQ ID NO 48
<211> LENGTH: 119
<212> TYPE: PRT
<213> ORGANISM: Artificial Sequence
<220> FEATURE:
<223> OTHER INFORMATION: EGFRvIII P056.052 VH

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Met Asn Tyr
                20                  25                  30

Trp Ile Gly Trp Val Arg Gln Met Pro Gly Lys Gly Leu Glu Trp Met
            35                  40                  45

Gly Thr Ile Tyr Pro Gly Asp Ser Asp Arg Arg Tyr Ser Pro Ser Phe
        50                  55                  60

Gln Gly Gln Val Thr Leu Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Val Ser Arg Ser Ser Tyr Ala Phe Asp Tyr Trp Gly Gln Gly
            100                 105                 110

Thr Leu Val Thr Val Ser Ser
        115

<210> SEQ ID NO 49
<211> LENGTH: 17
<212> TYPE: PRT
<213> ORGANISM: Artificial Sequence
<220> FEATURE:
<223> OTHER INFORMATION: EGFRvIII P056.052 LCDR1

<400> SEQUENCE: 49

Lys Ser Ser Gln Ser Val Leu Tyr Ser Ser Asn Asn Lys Asn Tyr Leu
1               5                   10                  15

Ala

<210> SEQ ID NO 50
<211> LENGTH: 7
<212> TYPE: PRT
<213> ORGANISM: Artificial Sequence
<220> FEATURE:
<223> OTHER INFORMATION: EGFRvIII P056.052 LCDR2

<400> SEQUENCE: 50

Trp Ala Ser Thr Arg Glu Ser
1               5

<210> SEQ ID NO 51
<211> LENGTH: 10
<212> TYPE: PRT
<213> ORGANISM: Artificial Sequence
<220> FEATURE:
<223> OTHER INFORMATION: EGFRvIII P056.052 LCDR3

<400> SEQUENCE: 51

Gln Gln Val His Ser Gly Pro Pro Val Thr
1               5                   10

<210> SEQ ID NO 52
<211> LENGTH: 114
<212> TYPE: PRT
<213> ORGANISM: Artificial Sequence
<220> FEATURE:
<223> OTHER INFORMATION: EGFRvIII P056.052 VL

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Val His Ser Gly Pro Pro Val Thr Phe Gly Gln Gly Thr Lys Val Glu
            100                 105                 110
```

Ile Lys

<210> SEQ ID NO 53
<211> LENGTH: 5
<212> TYPE: PRT
<213> ORGANISM: Artificial Sequence
<220> FEATURE:
<223> OTHER INFORMATION: EGFRvIII P047.019 HCDR1

<400> SEQUENCE: 53

Ser Ile Trp Ile His
1               5

<210> SEQ ID NO 54
<211> LENGTH: 17
<212> TYPE: PRT
<213> ORGANISM: Artificial Sequence
<220> FEATURE:
<223> OTHER INFORMATION: EGFRvIII P047.019 HCDR2

<400> SEQUENCE: 54

Thr Ile Tyr Pro Gly Asp Ser Asp Thr Arg Tyr Ser Pro Ser Phe Gln
1               5                   10                  15

Gly

<210> SEQ ID NO 55
<211> LENGTH: 9
<212> TYPE: PRT
<213> ORGANISM: Artificial Sequence
<220> FEATURE:
<223> OTHER INFORMATION: EGFRvIII P047.019 HCDR3

<400> SEQUENCE: 55

Thr Gly Pro Gly Leu Ala Phe Asp Tyr
1               5

<210> SEQ ID NO 56
<211> LENGTH: 118
<212> TYPE: PRT
<213> ORGANISM: Artificial Sequence
<220> FEATURE:
<223> OTHER INFORMATION: EGFRvIII P047.019 VH

<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Pro Ser Ile
            20                  25                  30

Trp Ile His Trp Val Arg Gln Met Pro Gly Lys Gly Leu Glu Trp Met
        35                  40                  45

Gly Thr Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Gly Pro Gly Leu Ala Phe Asp Tyr Trp Gly Gln Gly Thr
            100                 105                 110

Leu Val Thr Val Ser Ser
        115

<210> SEQ ID NO 57

```
<211> LENGTH: 17
<212> TYPE: PRT
<213> ORGANISM: Artificial Sequence
<220> FEATURE:
<223> OTHER INFORMATION: EGFRvIII P047.019 LCDR1

<400> SEQUENCE: 57

Lys Ser Ser Gln Ser Val Leu Tyr Ser Ser Asn Asn Lys Asn Tyr Leu
1               5                   10                  15
Ala

<210> SEQ ID NO 58
<211> LENGTH: 7
<212> TYPE: PRT
<213> ORGANISM: Artificial Sequence
<220> FEATURE:
<223> OTHER INFORMATION: EGFRvIII P047.019 LCDR2

<400> SEQUENCE: 58

Trp Ala Ser Thr Arg Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: EGFRvIII P047.019 LCDR3

<400> SEQUENCE: 59

Gln Gln Ser Tyr Ser Thr Pro Ile Thr
1               5

<210> SEQ ID NO 60
<211> LENGTH: 113
<212> TYPE: PRT
<213> ORGANISM: Artificial Sequence
<220> FEATURE:
<223> OTHER INFORMATION: EGFRvIII P047.019 VL

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Thr Pro Ile Thr Phe Gly Gln Gly Thr Lys Val Glu Ile
            100                 105                 110
Lys

<210> SEQ ID NO 61
<211> LENGTH: 5
<212> TYPE: PRT
<213> ORGANISM: Artificial Sequence
<220> FEATURE:
<223> OTHER INFORMATION: EGFRvIII P057.012 HCDR1
```

<400> SEQUENCE: 61

Asn Tyr Trp Ile Ala
1               5

<210> SEQ ID NO 62
<211> LENGTH: 17
<212> TYPE: PRT
<213> ORGANISM: Artificial Sequence
<220> FEATURE:
<223> OTHER INFORMATION: EGFRvIII P057.012 HCDR2

<400> SEQUENCE: 62

Ile Ile Tyr Pro Asp Asp Ser Asp Thr Arg Tyr Ser Pro Ser Phe Gln
1               5                   10                  15
Gly

<210> SEQ ID NO 63
<211> LENGTH: 12
<212> TYPE: PRT
<213> ORGANISM: Artificial Sequence
<220> FEATURE:
<223> OTHER INFORMATION: EGFRvIII P057.012 HCDR3

<400> SEQUENCE: 63

Ala Thr Asn Ile Ala Ser Gly Gly Tyr Phe Asp Tyr
1               5                   10

<210> SEQ ID NO 64
<211> LENGTH: 121
<212> TYPE: PRT
<213> ORGANISM: Artificial Sequence
<220> FEATURE:
<223> OTHER INFORMATION: EGFRvIII P057.012 VH

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ala Asn Tyr
            20                  25                  30

Trp Ile Ala Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Thr Asn Ile Ala Ser Gly Gly Tyr Phe Asp Tyr Trp Gly
            100                 105                 110

Gln Gly Thr Leu Val Thr Val Ser Ser
        115                 120

<210> SEQ ID NO 65
<211> LENGTH: 17
<212> TYPE: PRT
<213> ORGANISM: Artificial Sequence
<220> FEATURE:
<223> OTHER INFORMATION: EGFRvIII P057.012 LCDR1

<400> SEQUENCE: 65

Lys Ser Ser Gln Ser Val Leu Trp Asn Ser Asn Asn Lys Asn Tyr Leu

```
1               5                   10                  15
Ala

<210> SEQ ID NO 66
<211> LENGTH: 7
<212> TYPE: PRT
<213> ORGANISM: Artificial Sequence
<220> FEATURE:
<223> OTHER INFORMATION: EGFRvIII P057.012 LCDR2

<400> SEQUENCE: 66

Trp Ala Ser Lys Arg Glu Ser
1               5

<210> SEQ ID NO 67
<211> LENGTH: 9
<212> TYPE: PRT
<213> ORGANISM: Artificial Sequence
<220> FEATURE:
<223> OTHER INFORMATION: EGFRvIII P057.012 LCDR3

<400> SEQUENCE: 67

Gln Gln Ser Tyr Ser Ala Pro Ile Thr
1               5

<210> SEQ ID NO 68
<211> LENGTH: 113
<212> TYPE: PRT
<213> ORGANISM: Artificial Sequence
<220> FEATURE:
<223> OTHER INFORMATION: EGFRvIII P057.012 VL

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Trp Asn
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Lys Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Ile Thr Phe Gly Gln Gly Thr Lys Val Glu Ile
            100                 105                 110

Lys

<210> SEQ ID NO 69
<211> LENGTH: 5
<212> TYPE: PRT
<213> ORGANISM: Artificial Sequence
<220> FEATURE:
<223> OTHER INFORMATION: EGFRvIII P057.011 HCDR1

<400> SEQUENCE: 69

Arg Arg Trp Ile Ala
1               5

<210> SEQ ID NO 70
<211> LENGTH: 17
```

```
<212> TYPE: PRT
<213> ORGANISM: Artificial Sequence
<220> FEATURE:
<223> OTHER INFORMATION: EGFRvIII P057.011 HCDR2

<400> SEQUENCE: 70

Ile Ile Tyr Pro Gly Asp Ser Asp Thr Arg Tyr Ser Pro Ser Phe Gln
1               5                   10                  15
Gly

<210> SEQ ID NO 71
<211> LENGTH: 12
<212> TYPE: PRT
<213> ORGANISM: Artificial Sequence
<220> FEATURE:
<223> OTHER INFORMATION: EGFRvIII P057.011 HCDR3

<400> SEQUENCE: 71

Ala Thr Asn Ile Ala Ser Gly Gly Tyr Phe Asp Tyr
1               5                   10

<210> SEQ ID NO 72
<211> LENGTH: 121
<212> TYPE: PRT
<213> ORGANISM: Artificial Sequence
<220> FEATURE:
<223> OTHER INFORMATION: EGFRvIII P057.011 VH

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Gly Arg Arg
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Thr Asn Ile Ala Ser Gly Gly Tyr Phe Asp Tyr Trp Gly
            100                 105                 110

Gln Gly Thr Leu Val Thr Val Ser Ser
        115                 120

<210> SEQ ID NO 73
<211> LENGTH: 17
<212> TYPE: PRT
<213> ORGANISM: Artificial Sequence
<220> FEATURE:
<223> OTHER INFORMATION: EGFRvIII P057.011 LCDR1

<400> SEQUENCE: 73

Lys Ser Ser Gln Ser Val Leu Trp Asn Ser Asn Asn Lys Asn Tyr Leu
1               5                   10                  15
Ala

<210> SEQ ID NO 74
<211> LENGTH: 7
<212> TYPE: PRT
<213> ORGANISM: Artificial Sequence
```

<220> FEATURE:
<223> OTHER INFORMATION: EGFRvIII P057.011 LCDR2

<400> SEQUENCE: 74

Trp Ala Ser Lys Arg Glu Ser
1               5

<210> SEQ ID NO 75
<211> LENGTH: 9
<212> TYPE: PRT
<213> ORGANISM: Artificial Sequence
<220> FEATURE:
<223> OTHER INFORMATION: EGFRvIII P057.011 LCDR3

<400> SEQUENCE: 75

Gln Gln Ser Tyr Ser Ala Pro Ile Thr
1               5

<210> SEQ ID NO 76
<211> LENGTH: 113
<212> TYPE: PRT
<213> ORGANISM: Artificial Sequence
<220> FEATURE:
<223> OTHER INFORMATION: EGFRvIII P057.011 VL

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Trp Asn
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Lys Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Ile Thr Phe Gly Gln Gly Thr Lys Val Glu Ile
            100                 105                 110

Lys

<210> SEQ ID NO 77
<211> LENGTH: 5
<212> TYPE: PRT
<213> ORGANISM: Artificial Sequence
<220> FEATURE:
<223> OTHER INFORMATION: EGFRvIII P056.027 HCDR1

<400> SEQUENCE: 77

Asn Asn Trp Ile Ala
1               5

<210> SEQ ID NO 78
<211> LENGTH: 17
<212> TYPE: PRT
<213> ORGANISM: Artificial Sequence
<220> FEATURE:
<223> OTHER INFORMATION: EGFRvIII P056.027 HCDR2

<400> SEQUENCE: 78

Val Ile Tyr Pro Gly Asp Ser Asp Lys Arg Tyr Ser Pro Ser Phe Gln
1               5                   10                  15

-continued

Gly

<210> SEQ ID NO 79
<211> LENGTH: 10
<212> TYPE: PRT
<213> ORGANISM: Artificial Sequence
<220> FEATURE:
<223> OTHER INFORMATION: EGFRvIII P056.027 HCDR3

<400> SEQUENCE: 79

Val Ser Arg Ser Ser Tyr Ala Phe Asp Tyr
1               5                   10

<210> SEQ ID NO 80
<211> LENGTH: 119
<212> TYPE: PRT
<213> ORGANISM: Artificial Sequence
<220> FEATURE:
<223> OTHER INFORMATION: EGFRvIII P056.027 VH

<400> SEQUENCE: 80

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Gly Asn Asn
            20                  25                  30

Trp Ile Ala Trp Val Arg Gln Met Pro Gly Lys Gly Leu Glu Trp Met
        35                  40                  45

Gly Val Ile Tyr Pro Gly Asp Ser Asp Lys Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Ser Ser Tyr Ala Phe Asp Tyr Trp Gly Gln Gly
            100                 105                 110

Thr Leu Val Thr Val Ser Ser
        115

<210> SEQ ID NO 81
<211> LENGTH: 17
<212> TYPE: PRT
<213> ORGANISM: Artificial Sequence
<220> FEATURE:
<223> OTHER INFORMATION: EGFRvIII P056.027 LCDR1

<400> SEQUENCE: 81

Lys Ser Ser Gln Ser Val Leu Tyr Ser Ser Asn Asn Lys Asn Tyr Leu
1               5                   10                  15

Ala

<210> SEQ ID NO 82
<211> LENGTH: 7
<212> TYPE: PRT
<213> ORGANISM: Artificial Sequence
<220> FEATURE:
<223> OTHER INFORMATION: EGFRvIII P056.027 LCDR2

<400> SEQUENCE: 82

Trp Ala Ser Thr Arg Glu Ser
1               5

```
<210> SEQ ID NO 83
<211> LENGTH: 10
<212> TYPE: PRT
<213> ORGANISM: Artificial Sequence
<220> FEATURE:
<223> OTHER INFORMATION: EGFRvIII P056.027 LCDR3

<400> SEQUENCE: 83

Gln Gln Val His Ser Gly Pro Pro Val Thr
1               5                   10

<210> SEQ ID NO 84
<211> LENGTH: 114
<212> TYPE: PRT
<213> ORGANISM: Artificial Sequence
<220> FEATURE:
<223> OTHER INFORMATION: EGFRvIII P056.027 VL

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Val His Ser Gly Pro Pro Val Thr Phe Gly Gln Gly Thr Lys Val Glu
                100                 105                 110

Ile Lys

<210> SEQ ID NO 85
<211> LENGTH: 5
<212> TYPE: PRT
<213> ORGANISM: Artificial Sequence
<220> FEATURE:
<223> OTHER INFORMATION: EGFRvIII P063.056 HCDR1

<400> SEQUENCE: 85

Ser Tyr Trp Ile Ala
1               5

<210> SEQ ID NO 86
<211> LENGTH: 17
<212> TYPE: PRT
<213> ORGANISM: Artificial Sequence
<220> FEATURE:
<223> OTHER INFORMATION: EGFRvIII P063.056 HCDR2

<400> SEQUENCE: 86

Val Ile His Pro Tyr Asp Ser Asp Thr Arg Tyr Ser Pro Ser Phe Gln
1               5                   10                  15

Gly

<210> SEQ ID NO 87
<211> LENGTH: 10
<212> TYPE: PRT
<213> ORGANISM: Artificial Sequence
<220> FEATURE:
```

<223> OTHER INFORMATION: EGFRvIII P063.056 HCDR3

<400> SEQUENCE: 87

Val Ser Arg Ser Ser Tyr Ala Phe Asp Tyr
1               5                   10

<210> SEQ ID NO 88
<211> LENGTH: 119
<212> TYPE: PRT
<213> ORGANISM: Artificial Sequence
<220> FEATURE:
<223> OTHER INFORMATION: EGFRvIII P063.056 VH

<400> SEQUENCE: 88

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30

Trp Ile Ala Trp Val Arg Gln Met Pro Gly Lys Gly Leu Glu Trp Met
        35                  40                  45

Gly Val Ile His Pro Tyr Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Ser Ser Tyr Ala Phe Asp Tyr Trp Gly Gln Gly
            100                 105                 110

Thr Leu Val Thr Val Ser Ser
        115

<210> SEQ ID NO 89
<211> LENGTH: 17
<212> TYPE: PRT
<213> ORGANISM: Artificial Sequence
<220> FEATURE:
<223> OTHER INFORMATION: EGFRvIII P063.056 LCDR1

<400> SEQUENCE: 89

Lys Ser Ser Gln Ser Val Leu Tyr Ser Ser Asn Asn Lys Asn Tyr Leu
1               5                   10                  15

Ala

<210> SEQ ID NO 90
<211> LENGTH: 7
<212> TYPE: PRT
<213> ORGANISM: Artificial Sequence
<220> FEATURE:
<223> OTHER INFORMATION: EGFRvIII P063.056 LCDR2

<400> SEQUENCE: 90

Trp Ala Ser Thr Arg Glu Ser
1               5

<210> SEQ ID NO 91
<211> LENGTH: 10
<212> TYPE: PRT
<213> ORGANISM: Artificial Sequence
<220> FEATURE:
<223> OTHER INFORMATION: EGFRvIII P063.056 LCDR3

<400> SEQUENCE: 91

```
Gln Gln Gln Arg Asp Gly Pro Pro Val Thr
 1               5                  10
```

<210> SEQ ID NO 92
<211> LENGTH: 114
<212> TYPE: PRT
<213> ORGANISM: Artificial Sequence
<220> FEATURE:
<223> OTHER INFORMATION: EGFRvIII P063.056 VL

<400> SEQUENCE: 92

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Gln Arg Asp Gly Pro Pro Val Thr Phe Gly Gln Gly Thr Lys Val Glu
            100                 105                 110

Ile Lys
```

<210> SEQ ID NO 93
<211> LENGTH: 5
<212> TYPE: PRT
<213> ORGANISM: Artificial Sequence
<220> FEATURE:
<223> OTHER INFORMATION: EGFRvIII P064.078 HCDR1

<400> SEQUENCE: 93

```
Ser Tyr Trp Ile Ala
 1               5
```

<210> SEQ ID NO 94
<211> LENGTH: 17
<212> TYPE: PRT
<213> ORGANISM: Artificial Sequence
<220> FEATURE:
<223> OTHER INFORMATION: EGFRvIII P064.078 HCDR2

<400> SEQUENCE: 94

```
Val Ile His Pro Tyr Asp Ser Asp Thr Arg Tyr Ser Pro Ser Phe Gln
 1               5                  10                  15

Gly
```

<210> SEQ ID NO 95
<211> LENGTH: 10
<212> TYPE: PRT
<213> ORGANISM: Artificial Sequence
<220> FEATURE:
<223> OTHER INFORMATION: EGFRvIII P064.078 HCDR3

<400> SEQUENCE: 95

```
Val Ser Arg Leu Ser Tyr Ala Leu Asp Tyr
 1               5                  10
```

<210> SEQ ID NO 96

```
<211> LENGTH: 119
<212> TYPE: PRT
<213> ORGANISM: Artificial Sequence
<220> FEATURE:
<223> OTHER INFORMATION: EGFRvIII P064.078 VH

<400> SEQUENCE: 96

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30

Trp Ile Ala Trp Val Arg Gln Met Pro Gly Lys Gly Leu Glu Trp Met
        35                  40                  45

Gly Val Ile His Pro Tyr Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Leu Ser Tyr Ala Leu Asp Tyr Trp Gly Gln Gly
            100                 105                 110

Thr Leu Val Thr Val Ser Ser
        115

<210> SEQ ID NO 97
<211> LENGTH: 17
<212> TYPE: PRT
<213> ORGANISM: Artificial Sequence
<220> FEATURE:
<223> OTHER INFORMATION: EGFRvIII P064.078 LCDR1

<400> SEQUENCE: 97

Lys Ser Ser Gln Ser Val Leu Tyr Ser Ser Asn Asn Lys Asn Tyr Leu
1               5                   10                  15

Ala

<210> SEQ ID NO 98
<211> LENGTH: 7
<212> TYPE: PRT
<213> ORGANISM: Artificial Sequence
<220> FEATURE:
<223> OTHER INFORMATION: EGFRvIII P064.078 LCDR2

<400> SEQUENCE: 98

Trp Ala Ser Thr Arg Glu Ser
1               5

<210> SEQ ID NO 99
<211> LENGTH: 10
<212> TYPE: PRT
<213> ORGANISM: Artificial Sequence
<220> FEATURE:
<223> OTHER INFORMATION: EGFRvIII P064.078 LCDR3

<400> SEQUENCE: 99

Gln Gln Val His Ser Gly Pro Pro Val Thr
1               5                   10

<210> SEQ ID NO 100
<211> LENGTH: 114
<212> TYPE: PRT
<213> ORGANISM: Artificial Sequence
<220> FEATURE:
```

<223> OTHER INFORMATION: EGFRvIII P064.078 VL

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Val His Ser Gly Pro Pro Val Thr Phe Gly Gln Gly Thr Lys Val Glu
            100                 105                 110

Ile Lys

<210> SEQ ID NO 101
<211> LENGTH: 5
<212> TYPE: PRT
<213> ORGANISM: Artificial Sequence
<220> FEATURE:
<223> OTHER INFORMATION: EGFRvIII P065.036 HCDR1

<400> SEQUENCE: 101

Ser Tyr Trp Ile Ala
1               5

<210> SEQ ID NO 102
<211> LENGTH: 17
<212> TYPE: PRT
<213> ORGANISM: Artificial Sequence
<220> FEATURE:
<223> OTHER INFORMATION: EGFRvIII P065.036 HCDR2

<400> SEQUENCE: 102

Val Ile His Pro Tyr Asp Ser Asp Thr Arg Tyr Ser Pro Ser Phe Gln
1               5                   10                  15

Gly

<210> SEQ ID NO 103
<211> LENGTH: 10
<212> TYPE: PRT
<213> ORGANISM: Artificial Sequence
<220> FEATURE:
<223> OTHER INFORMATION: EGFRvIII P065.036 HCDR3

<400> SEQUENCE: 103

Val Ser Arg Ser Ser Tyr Ala Leu Asp Tyr
1               5                   10

<210> SEQ ID NO 104
<211> LENGTH: 119
<212> TYPE: PRT
<213> ORGANISM: Artificial Sequence
<220> FEATURE:
<223> OTHER INFORMATION: EGFRvIII P065.036 VH

<400> SEQUENCE: 104

Glu Val Gln Leu Val Gln Ser Gly Ala Glu Val Lys Lys Pro Gly Glu

```
                1               5                   10                  15
            Ser Leu Lys Ile Ser Cys Lys Gly Ser Gly Tyr Ser Phe Asp Ser Tyr
                            20                  25                  30

Trp Ile Ala Trp Val Arg Gln Met Pro Gly Lys Gly Leu Glu Trp Met
                        35                  40                  45

Gly Val Ile His Pro Tyr Asp Ser Asp Thr Arg Tyr Ser Pro Ser Phe
                    50                  55                  60

Gln Gly Gln Val Thr Ile Ser Ala Asp Lys Ser Ile Ser Thr Ala Tyr
            65                  70                  75                  80

Leu Gln Trp Ser Ser Leu Lys Ala Ser Asp Thr Ala Met Tyr Tyr Cys
                            85                  90                  95

Ala Arg Val Ser Arg Ser Ser Tyr Ala Leu Asp Tyr Trp Gly Gln Gly
                        100                 105                 110

Thr Leu Val Thr Val Ser Ser
                    115
```

<210> SEQ ID NO 105
<211> LENGTH: 17
<212> TYPE: PRT
<213> ORGANISM: Artificial Sequence
<220> FEATURE:
<223> OTHER INFORMATION: EGFRvIII P065.036 LCDR1

<400> SEQUENCE: 105

```
Lys Ser Ser Gln Ser Val Leu Tyr Ser Ser Asn Asn Lys Asn Tyr Leu
1               5                   10                  15

Ala
```

<210> SEQ ID NO 106
<211> LENGTH: 7
<212> TYPE: PRT
<213> ORGANISM: Artificial Sequence
<220> FEATURE:
<223> OTHER INFORMATION: EGFRvIII P065.036 LCDR2

<400> SEQUENCE: 106

```
Trp Ala Ser Thr Arg Glu Ser
1               5
```

<210> SEQ ID NO 107
<211> LENGTH: 10
<212> TYPE: PRT
<213> ORGANISM: Artificial Sequence
<220> FEATURE:
<223> OTHER INFORMATION: EGFRvIII P065.036 LCDR3

<400> SEQUENCE: 107

```
Gln Gln Val Tyr Ser Gly Pro Pro Val Thr
1               5                   10
```

<210> SEQ ID NO 108
<211> LENGTH: 114
<212> TYPE: PRT
<213> ORGANISM: Artificial Sequence
<220> FEATURE:
<223> OTHER INFORMATION: EGFRvIII P065.036 VL

<400> SEQUENCE: 108

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30
```

```
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Val Tyr Ser Gly Pro Pro Val Thr Phe Gly Gln Gly Thr Lys Val Glu
                100                 105                 110

Ile Lys

<210> SEQ ID NO 109
<211> LENGTH: 672
<212> TYPE: PRT
<213> ORGANISM: Artificial Sequence
<220> FEATURE:
<223> OTHER INFORMATION: EGFRvIII VH-CH1(EE) - CD3orig/CD3opt VL-CH1 -
      Fc (knob, PGLALA)

<400> SEQUENCE: 109

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Asp Ser Tyr
             20                  25                  30

Trp Ile Ala Trp Val Arg Gln Met Pro Gly Lys Gly Leu Glu Trp Met
         35                  40                  45

Gly Val Ile His Pro Tyr Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Val Ser Arg Ser Ser Tyr Ala Phe Asp Tyr Trp Gly Gln Gly
                100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Ser Asn Tyr Ala Asn Trp Val Gln
            260                 265                 270
```

```
Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
    370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

<210> SEQ ID NO 110
<211> LENGTH: 447
```

<212> TYPE: PRT
<213> ORGANISM: Artificial Sequence
<220> FEATURE:
<223> OTHER INFORMATION: EGFRvIII VH-CH1(EE)-Fc (hole, PGLALA)

<400> SEQUENCE: 110

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30

Trp Ile Ala Trp Val Arg Gln Met Pro Gly Lys Gly Leu Glu Trp Met
        35                  40                  45

Gly Val Ile His Pro Tyr Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Ser Ser Tyr Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 111
<211> LENGTH: 221
<212> TYPE: PRT
<213> ORGANISM: Artificial Sequence
<220> FEATURE:
<223> OTHER INFORMATION: EGFRvIII VL-CL(RK)

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Gln Arg Asp Gly Pro Pro Val Thr Phe Gly Gln Gly Thr Lys Val Glu
            100                 105                 110

Ile Lys Arg Thr Val Ala Ala Pro Ser Val Phe Ile Phe Pro Pro Ser
        115                 120                 125

Asp Arg Lys Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 112
<211> LENGTH: 186
<212> TYPE: PRT
<213> ORGANISM: Homo sapiens

<400> SEQUENCE: 112

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
```

```
            35                  40                  45
Glu Asp Asp Lys Asn Ile Gly Ser Asp Glu Asp His Leu Ser Leu Lys
 50                  55                  60

Glu Phe Ser Glu Leu Glu Gln Ser Gly Tyr Tyr Val Cys Tyr Pro Arg
 65                  70                  75                  80

Gly Ser Lys Pro Glu Asp Ala Asn Phe Tyr Leu Tyr Leu Arg Ala Arg
                 85                  90                  95

Val Cys Glu Asn Cys Met Glu Met Asp Val Met Ser Val Ala Thr Ile
                100                 105                 110

Val Ile Val Asp Ile Cys Ile Thr Gly Leu Leu Leu Leu Val Tyr
            115                 120                 125

Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
                180                 185

<210> SEQ ID NO 113
<211> LENGTH: 177
<212> TYPE: PRT
<213> ORGANISM: Macaca fascicularis

<400> SEQUENCE: 113

Gln Asp Gly Asn Glu Glu Met Gly Ser Ile Thr Gln Thr Pro Tyr Gln
  1               5                  10                  15

Val Ser Ile Ser Gly Thr Thr Val Ile Leu Thr Cys Ser Gln His Leu
                 20                  25                  30

Gly Ser Glu Ala Gln Trp Gln His Asn Gly Lys Asn Lys Glu Asp Ser
             35                  40                  45

Gly Asp Arg Leu Phe Leu Pro Glu Phe Ser Glu Met Glu Gln Ser Gly
 50                  55                  60

Tyr Tyr Val Cys Tyr Pro Arg Gly Ser Asn Pro Glu Asp Ala Ser His
 65                  70                  75                  80

His Leu Tyr Leu Lys Ala Arg Val Cys Glu Asn Cys Met Glu Met Asp
                 85                  90                  95

Val Met Ala Val Ala Thr Ile Val Ile Val Asp Ile Cys Ile Thr Leu
                100                 105                 110

Gly Leu Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
        130                 135                 140

Gln Asn Lys Glu Arg Pro Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 114
<211> LENGTH: 513
<212> TYPE: PRT
<213> ORGANISM: Homo sapiens

<400> SEQUENCE: 114
```

```
Gln Phe Pro Arg Gln Cys Ala Thr Val Glu Ala Leu Arg Ser Gly Met
1               5                   10                  15
Cys Cys Pro Asp Leu Ser Pro Val Ser Gly Pro Gly Thr Asp Arg Cys
            20                  25                  30
Gly Ser Ser Ser Gly Arg Gly Arg Cys Glu Ala Val Thr Ala Asp Ser
        35                  40                  45
Arg Pro His Ser Pro Gln Tyr Pro His Asp Gly Arg Asp Asp Arg Glu
    50                  55                  60
Val Trp Pro Leu Arg Phe Phe Asn Arg Thr Cys His Cys Asn Gly Asn
65                  70                  75                  80
Phe Ser Gly His Asn Cys Gly Thr Cys Arg Pro Gly Trp Arg Gly Ala
                85                  90                  95
Ala Cys Asp Gln Arg Val Leu Ile Val Arg Arg Asn Leu Leu Asp Leu
            100                 105                 110
Ser Lys Glu Glu Lys Asn His Phe Val Arg Ala Leu Asp Met Ala Lys
        115                 120                 125
Arg Thr Thr His Pro Leu Phe Val Ile Ala Thr Arg Arg Ser Glu Glu
    130                 135                 140
Ile Leu Gly Pro Asp Gly Asn Thr Pro Gln Phe Glu Asn Ile Ser Ile
145                 150                 155                 160
Tyr Asn Tyr Phe Val Trp Thr His Tyr Ser Val Lys Lys Thr Phe
                165                 170                 175
Leu Gly Val Gly Gln Ser Phe Gly Glu Val Asp Phe Ser His Glu
            180                 185                 190
Gly Pro Ala Phe Leu Thr Trp His Arg Tyr His Leu Leu Arg Leu Glu
        195                 200                 205
Lys Asp Met Gln Glu Met Leu Gln Glu Pro Ser Phe Ser Leu Pro Tyr
    210                 215                 220
Trp Asn Phe Ala Thr Gly Lys Asn Val Cys Asp Ile Cys Thr Asp Asp
225                 230                 235                 240
Leu Met Gly Ser Arg Ser Asn Phe Asp Ser Thr Leu Ile Ser Pro Asn
                245                 250                 255
Ser Val Phe Ser Gln Trp Arg Val Val Cys Asp Ser Leu Glu Asp Tyr
            260                 265                 270
Asp Thr Leu Gly Thr Leu Cys Asn Ser Thr Glu Asp Gly Pro Ile Arg
        275                 280                 285
Arg Asn Pro Ala Gly Asn Val Ala Arg Pro Met Val Gln Arg Leu Pro
    290                 295                 300
Glu Pro Gln Asp Val Ala Gln Cys Leu Glu Val Gly Leu Phe Asp Thr
305                 310                 315                 320
Pro Pro Phe Tyr Ser Asn Ser Thr Asn Ser Phe Arg Asn Thr Val Glu
                325                 330                 335
Gly Tyr Ser Asp Pro Thr Gly Lys Tyr Asp Pro Ala Val Arg Ser Leu
            340                 345                 350
His Asn Leu Ala His Leu Phe Leu Asn Gly Thr Gly Gly Gln Thr His
        355                 360                 365
Leu Ser Pro Asn Asp Pro Ile Phe Val Leu Leu His Thr Phe Thr Asp
    370                 375                 380
Ala Val Phe Asp Glu Trp Leu Arg Arg Tyr Asn Ala Asp Ile Ser Thr
385                 390                 395                 400
Phe Pro Leu Glu Asn Ala Pro Ile Gly His Asn Arg Gln Tyr Asn Met
                405                 410                 415
```

-continued

```
Val Pro Phe Trp Pro Pro Val Thr Asn Thr Glu Met Phe Val Thr Ala
                420             425                 430

Pro Asp Asn Leu Gly Tyr Thr Tyr Glu Ile Gln Trp Pro Ser Arg Glu
            435                 440                 445

Phe Ser Val Pro Glu Ile Ile Ala Ile Ala Val Gly Ala Leu Leu
450                 455                 460

Leu Val Ala Leu Ile Phe Gly Thr Ala Ser Tyr Leu Ile Arg Ala Arg
465                 470                 475                 480

Arg Ser Met Asp Glu Ala Asn Gln Pro Leu Leu Thr Asp Gln Tyr Gln
                485                 490                 495

Cys Tyr Ala Glu Glu Tyr Glu Lys Leu Gln Asn Pro Asn Gln Ser Val
                500                 505                 510

Val
```

<210> SEQ ID NO 115
<211> LENGTH: 919
<212> TYPE: PRT
<213> ORGANISM: Homo sapiens

<400> SEQUENCE: 115

```
Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
                20                  25                  30

Arg Lys Cys Lys Lys Cys Glu Gly Pro Cys Arg Lys Val Cys Asn Gly
            35                  40                  45

Ile Gly Ile Gly Glu Phe Lys Asp Ser Leu Ser Ile Asn Ala Thr Asn
50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
        115                 120                 125

Phe Glu Asn Leu Glu Ile Ile Arg Gly Arg Thr Lys Gln His Gly Gln
130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205

Lys Ala Thr Gly Gln Val Cys His Ala Leu Cys Ser Pro Glu Gly Cys
210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
                245                 250                 255

Glu Phe Val Glu Asn Ser Glu Cys Ile Gln Cys His Pro Glu Cys Leu
            260                 265                 270
```

```
Pro Gln Ala Met Asn Ile Thr Cys Thr Gly Arg Gly Pro Asp Asn Cys
            275                 280                 285

Ile Gln Cys Ala His Tyr Ile Asp Gly Pro His Cys Val Lys Thr Cys
290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
                325                 330                 335

Cys Thr Gly Pro Gly Leu Glu Gly Cys Pro Thr Asn Gly Pro Lys Ile
            340                 345                 350

Pro Ser Ile Ala Thr Gly Met Val Gly Ala Leu Leu Leu Leu Leu Val
        355                 360                 365

Val Ala Leu Gly Ile Gly Leu Phe Met Arg Arg Arg His Ile Val Arg
370                 375                 380

Lys Arg Thr Leu Arg Arg Leu Leu Gln Glu Arg Glu Leu Val Glu Pro
385                 390                 395                 400

Leu Thr Pro Ser Gly Glu Ala Pro Asn Gln Ala Leu Leu Arg Ile Leu
                405                 410                 415

Lys Glu Thr Glu Phe Lys Lys Ile Lys Val Leu Gly Ser Gly Ala Phe
            420                 425                 430

Gly Thr Val Tyr Lys Gly Leu Trp Ile Pro Glu Gly Glu Lys Val Lys
        435                 440                 445

Ile Pro Val Ala Ile Lys Glu Leu Arg Glu Ala Thr Ser Pro Lys Ala
    450                 455                 460

Asn Lys Glu Ile Leu Asp Glu Ala Tyr Val Met Ala Ser Val Asp Asn
465                 470                 475                 480

Pro His Val Cys Arg Leu Leu Gly Ile Cys Leu Thr Ser Thr Val Gln
                485                 490                 495

Leu Ile Thr Gln Leu Met Pro Phe Gly Cys Leu Leu Asp Tyr Val Arg
            500                 505                 510

Glu His Lys Asp Asn Ile Gly Ser Gln Tyr Leu Leu Asn Trp Cys Val
        515                 520                 525

Gln Ile Ala Lys Gly Met Asn Tyr Leu Glu Asp Arg Arg Leu Val His
530                 535                 540

Arg Asp Leu Ala Ala Arg Asn Val Leu Val Lys Thr Pro Gln His Val
545                 550                 555                 560

Lys Ile Thr Asp Phe Gly Leu Ala Lys Leu Leu Gly Ala Glu Glu Lys
                565                 570                 575

Glu Tyr His Ala Glu Gly Gly Lys Val Pro Ile Lys Trp Met Ala Leu
            580                 585                 590

Glu Ser Ile Leu His Arg Ile Tyr Thr His Gln Ser Asp Val Trp Ser
        595                 600                 605

Tyr Gly Val Thr Val Trp Glu Leu Met Thr Phe Gly Ser Lys Pro Tyr
610                 615                 620

Asp Gly Ile Pro Ala Ser Glu Ile Ser Ser Ile Leu Glu Lys Gly Glu
625                 630                 635                 640

Arg Leu Pro Gln Pro Pro Ile Cys Thr Ile Asp Val Tyr Met Ile Met
                645                 650                 655

Val Lys Cys Trp Met Ile Asp Ala Asp Ser Arg Pro Lys Phe Arg Glu
            660                 665                 670

Leu Ile Ile Glu Phe Ser Lys Met Ala Arg Asp Pro Gln Arg Tyr Leu
        675                 680                 685

Val Ile Gln Gly Asp Glu Arg Met His Leu Pro Ser Pro Thr Asp Ser
```

```
                690                 695                 700
Asn Phe Tyr Arg Ala Leu Met Asp Glu Glu Asp Met Asp Val Val
705                 710                 715                 720

Asp Ala Asp Glu Tyr Leu Ile Pro Gln Gln Gly Phe Phe Ser Ser Pro
                725                 730                 735

Ser Thr Ser Arg Thr Pro Leu Leu Ser Ser Leu Ser Ala Thr Ser Asn
                740                 745                 750

Asn Ser Thr Val Ala Cys Ile Asp Arg Asn Gly Leu Gln Ser Cys Pro
            755                 760                 765

Ile Lys Glu Asp Ser Phe Leu Gln Arg Tyr Ser Ser Asp Pro Thr Gly
770                 775                 780

Ala Leu Thr Glu Asp Ser Ile Asp Asp Thr Phe Leu Pro Val Pro Glu
785                 790                 795                 800

Tyr Ile Asn Gln Ser Val Pro Lys Arg Pro Ala Gly Ser Val Gln Asn
                805                 810                 815

Pro Val Tyr His Asn Gln Pro Leu Asn Pro Ala Pro Ser Arg Asp Pro
            820                 825                 830

His Tyr Gln Asp Pro His Ser Thr Ala Val Gly Asn Pro Glu Tyr Leu
            835                 840                 845

Asn Thr Val Gln Pro Thr Cys Val Asn Ser Thr Phe Asp Ser Pro Ala
850                 855                 860

His Trp Ala Gln Lys Gly Ser His Gln Ile Ser Leu Asp Asn Pro Asp
865                 870                 875                 880

Tyr Gln Gln Asp Phe Phe Pro Lys Glu Ala Lys Pro Asn Gly Ile Phe
                885                 890                 895

Lys Gly Ser Thr Ala Glu Asn Ala Glu Tyr Leu Arg Val Ala Pro Gln
                900                 905                 910

Ser Ser Glu Phe Ile Gly Ala
            915

<210> SEQ ID NO 116
<211> LENGTH: 1186
<212> TYPE: PRT
<213> ORGANISM: Homo sapiens

<400> SEQUENCE: 116

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140
```

```
Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
        165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
            245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
            325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
            370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
            405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
        485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
```

-continued

```
            565                 570                 575
Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Thr
            610                 615                 620

Gly Met Val Gly Ala Leu Leu Leu Leu Val Val Ala Leu Gly Ile
625                 630                 635                 640

Gly Leu Phe Met Arg Arg Arg His Ile Val Arg Lys Arg Thr Leu Arg
                    645                 650                 655

Arg Leu Leu Gln Glu Arg Glu Leu Val Glu Pro Leu Thr Pro Ser Gly
                    660                 665                 670

Glu Ala Pro Asn Gln Ala Leu Leu Arg Ile Leu Lys Glu Thr Glu Phe
                    675                 680                 685

Lys Lys Ile Lys Val Leu Gly Ser Gly Ala Phe Gly Thr Val Tyr Lys
            690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
                    725                 730                 735

Asp Glu Ala Tyr Val Met Ala Ser Val Asp Asn Pro His Val Cys Arg
                    740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
                    805                 810                 815

Arg Asn Val Leu Val Lys Thr Pro Gln His Val Lys Ile Thr Asp Phe
                    820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                    885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
            930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                    965                 970                 975

Leu Met Asp Glu Glu Asp Met Asp Asp Val Val Asp Ala Asp Glu Tyr
            980                 985                 990
```

-continued

```
Leu Ile Pro Gln Gln Gly Phe Phe Ser Ser Pro Ser Thr Ser Arg Thr
        995                 1000                1005

Pro Leu Leu Ser Ser Leu Ser Ala Thr Ser Asn Asn Ser Thr Val
    1010                1015                1020

Ala Cys Ile Asp Arg Asn Gly Leu Gln Ser Cys Pro Ile Lys Glu
    1025                1030                1035

Asp Ser Phe Leu Gln Arg Tyr Ser Ser Asp Pro Thr Gly Ala Leu
    1040                1045                1050

Thr Glu Asp Ser Ile Asp Asp Thr Phe Leu Pro Val Pro Glu Tyr
    1055                1060                1065

Ile Asn Gln Ser Val Pro Lys Arg Pro Ala Gly Ser Val Gln Asn
    1070                1075                1080

Pro Val Tyr His Asn Gln Pro Leu Asn Pro Ala Pro Ser Arg Asp
    1085                1090                1095

Pro His Tyr Gln Asp Pro His Ser Thr Ala Val Gly Asn Pro Glu
    1100                1105                1110

Tyr Leu Asn Thr Val Gln Pro Thr Cys Val Asn Ser Thr Phe Asp
    1115                1120                1125

Ser Pro Ala His Trp Ala Gln Lys Gly Ser His Gln Ile Ser Leu
    1130                1135                1140

Asp Asn Pro Asp Tyr Gln Gln Asp Phe Phe Pro Lys Glu Ala Lys
    1145                1150                1155

Pro Asn Gly Ile Phe Lys Gly Ser Thr Ala Glu Asn Ala Glu Tyr
    1160                1165                1170

Leu Arg Val Ala Pro Gln Ser Ser Glu Phe Ile Gly Ala
    1175                1180                1185

<210> SEQ ID NO 117
<211> LENGTH: 225
<212> TYPE: PRT
<213> ORGANISM: Homo sapiens

<400> SEQUENCE: 117

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
```

```
                165                 170                 175
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 118
<211> LENGTH: 10
<212> TYPE: PRT
<213> ORGANISM: Artificial Sequence
<220> FEATURE:
<223> OTHER INFORMATION: linker

<400> SEQUENCE: 118

Gly Gly Gly Gly Ser Gly Gly Gly Gly Ser
1               5                   10

<210> SEQ ID NO 119
<211> LENGTH: 11
<212> TYPE: PRT
<213> ORGANISM: Artificial Sequence
<220> FEATURE:
<223> OTHER INFORMATION: linker

<400> SEQUENCE: 119

Asp Gly Gly Gly Gly Ser Gly Gly Gly Gly Ser
1               5                   10

<210> SEQ ID NO 120
<211> LENGTH: 107
<212> TYPE: PRT
<213> ORGANISM: Homo sapiens

<400> SEQUENCE: 120

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 121
<211> LENGTH: 105
<212> TYPE: PRT
<213> ORGANISM: Homo sapiens

<400> SEQUENCE: 121

Gln Pro Lys Ala Ala Pro Ser Val Thr Leu Phe Pro Pro Ser Ser Glu
1               5                   10                  15
```

```
Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105

<210> SEQ ID NO 122
<211> LENGTH: 328
<212> TYPE: PRT
<213> ORGANISM: Homo sapiens

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 123
<211> LENGTH: 5
<212> TYPE: PRT
<213> ORGANISM: Artificial Sequence
<220> FEATURE:
<223> OTHER INFORMATION: Synthetic Construct

<400> SEQUENCE: 123

Gly Gly Gly Gly Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic Construct

<400> SEQUENCE: 124

Ser Gly Gly Gly Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gly Gly Gly Gly Ser Gly Gly Gly Gly
1               5

<210> SEQ ID NO 126
<211> LENGTH: 20
<212> TYPE: PRT
<213> ORGANISM: Artificial Sequence
<220> FEATURE:
<223> OTHER INFORMATION: Synthetic Construct

<400> SEQUENCE: 126

Gly Gly Gly Gly Ser Gly Gly Gly Gly Ser Gly Gly Gly Gly Ser Gly
1               5                   10                  15

Gly Gly Gly Ser
            20

<210> SEQ ID NO 127
<211> LENGTH: 12
<212> TYPE: PRT
<213> ORGANISM: Artificial Sequence
<220> FEATURE:
<223> OTHER INFORMATION: Synthetic Construct

<400> SEQUENCE: 127

Gly Gly Gly Ser Gly Gly Gly Ser Gly Gly Gly Ser
1               5                   10
```

```
<210> SEQ ID NO 128
<211> LENGTH: 16
<212> TYPE: PRT
<213> ORGANISM: Artificial Sequence
<220> FEATURE:
<223> OTHER INFORMATION: Synthetic Construct

<400> SEQUENCE: 128

Gly Gly Gly Ser Gly Gly Gly Ser Gly Gly Gly Ser Gly Gly Gly Ser
1               5                   10                  15

<210> SEQ ID NO 129
<211> LENGTH: 20
<212> TYPE: PRT
<213> ORGANISM: Artificial Sequence
<220> FEATURE:
<223> OTHER INFORMATION: Synthetic Construct

<400> SEQUENCE: 129

Gly Gly Gly Ser Gly Gly Gly Ser Gly Gly Gly Ser Gly Gly Gly Ser
1               5                   10                  15

Gly Gly Gly Ser
            20

<210> SEQ ID NO 130
<211> LENGTH: 24
<212> TYPE: PRT
<213> ORGANISM: Artificial Sequence
<220> FEATURE:
<223> OTHER INFORMATION: Synthetic Construct

<400> SEQUENCE: 130

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Gly Gly Gly Gly Ser Gly Gly Gly Gly Ser
1               5                   10

<210> SEQ ID NO 132
<211> LENGTH: 15
<212> TYPE: PRT
<213> ORGANISM: Artificial Sequence
<220> FEATURE:
<223> OTHER INFORMATION: Synthetic Construct

<400> SEQUENCE: 132

Gly Gly Gly Gly Ser Gly Gly Gly Gly Ser Gly Gly Gly Gly Ser
1               5                   10                  15

<210> SEQ ID NO 133
<211> LENGTH: 20
<212> TYPE: PRT
<213> ORGANISM: Artificial Sequence
<220> FEATURE:
<223> OTHER INFORMATION: Synthetic Construct
```

```
<400> SEQUENCE: 133

Gly Gly Gly Gly Ser Gly Gly Gly Ser Gly Gly Gly Ser Gly
1               5                   10                  15

Gly Gly Gly Ser
            20

<210> SEQ ID NO 134
<211> LENGTH: 25
<212> TYPE: PRT
<213> ORGANISM: Artificial Sequence
<220> FEATURE:
<223> OTHER INFORMATION: Synthetic Construct

<400> SEQUENCE: 134

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 135
<211> LENGTH: 13
<212> TYPE: PRT
<213> ORGANISM: Artificial Sequence
<220> FEATURE:
<223> OTHER INFORMATION: Synthetic Construct

<400> SEQUENCE: 135

Gly Gly Gly Ser Gly Gly Gly Ser Gly Gly Gly Ser Gly
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Synthetic Construct

<400> SEQUENCE: 136

Gly Gly Gly Ser Gly Gly Gly Ser Gly Gly Gly Ser Gly Gly Gly Ser
1               5                   10                  15

Gly

<210> SEQ ID NO 137
<211> LENGTH: 21
<212> TYPE: PRT
<213> ORGANISM: Artificial Sequence
<220> FEATURE:
<223> OTHER INFORMATION: Synthetic Construct

<400> SEQUENCE: 137

Gly Gly Gly Ser Gly Gly Gly Ser Gly Gly Gly Ser Gly Gly Gly Ser
1               5                   10                  15

Gly Gly Gly Ser Gly
            20

<210> SEQ ID NO 138
<211> LENGTH: 25
<212> TYPE: PRT
<213> ORGANISM: Artificial Sequence
<220> FEATURE:
<223> OTHER INFORMATION: Synthetic Construct

<400> SEQUENCE: 138

Gly Gly Gly Ser Gly Gly Gly Ser Gly Gly Gly Ser Gly Gly Gly Ser
```

-continued

```
                1               5                  10                  15
Gly Gly Gly Ser Gly Gly Gly Ser Gly
            20                  25

<210> SEQ ID NO 139
<211> LENGTH: 11
<212> TYPE: PRT
<213> ORGANISM: Artificial Sequence
<220> FEATURE:
<223> OTHER INFORMATION: Synthetic Construct

<400> SEQUENCE: 139

Gly Gly Gly Gly Ser Gly Gly Gly Gly Ser Gly
1               5                  10

<210> SEQ ID NO 140
<211> LENGTH: 16
<212> TYPE: PRT
<213> ORGANISM: Artificial Sequence
<220> FEATURE:
<223> OTHER INFORMATION: Synthetic Construct

<400> SEQUENCE: 140

Gly Gly Gly Gly Ser Gly Gly Gly Gly Ser Gly Gly Gly Gly Ser Gly
1               5                  10                  15

<210> SEQ ID NO 141
<211> LENGTH: 21
<212> TYPE: PRT
<213> ORGANISM: Artificial Sequence
<220> FEATURE:
<223> OTHER INFORMATION: Synthetic Construct

<400> SEQUENCE: 141

Gly Gly Gly Gly Ser Gly Gly Gly Gly Ser Gly Gly Gly Gly Ser Gly
1               5                  10                  15
Gly Gly Gly Ser Gly
            20

<210> SEQ ID NO 142
<211> LENGTH: 26
<212> TYPE: PRT
<213> ORGANISM: Artificial Sequence
<220> FEATURE:
<223> OTHER INFORMATION: Synthetic Construct

<400> SEQUENCE: 142

Gly Gly Gly Gly Ser Gly Gly Gly Gly Ser Gly Gly Gly Gly Ser Gly
1               5                  10                  15
Gly Gly Gly Ser Gly Gly Gly Gly Ser Gly
            20                  25

<210> SEQ ID NO 143
<211> LENGTH: 14
<212> TYPE: PRT
<213> ORGANISM: Artificial Sequence
<220> FEATURE:
<223> OTHER INFORMATION: Synthetic Construct

<400> SEQUENCE: 143

Gly Gly Gly Ser Gly Gly Gly Ser Gly Gly Gly Ser Gly Gly
1               5                  10

<210> SEQ ID NO 144
<211> LENGTH: 18
```

```
<212> TYPE: PRT
<213> ORGANISM: Artificial Sequence
<220> FEATURE:
<223> OTHER INFORMATION: Synthetic Construct

<400> SEQUENCE: 144

Gly Gly Gly Ser Gly Gly Gly Ser Gly Gly Gly Ser Gly Gly Gly Ser
1               5                   10                  15
Gly Gly

<210> SEQ ID NO 145
<211> LENGTH: 22
<212> TYPE: PRT
<213> ORGANISM: Artificial Sequence
<220> FEATURE:
<223> OTHER INFORMATION: Synthetic Construct

<400> SEQUENCE: 145

Gly Gly Gly Ser Gly Gly Gly Ser Gly Gly Gly Ser Gly Gly Gly Ser
1               5                   10                  15
Gly Gly Gly Ser Gly Gly
            20

<210> SEQ ID NO 146
<211> LENGTH: 26
<212> TYPE: PRT
<213> ORGANISM: Artificial Sequence
<220> FEATURE:
<223> OTHER INFORMATION: Synthetic Construct

<400> SEQUENCE: 146

Gly Gly Gly Ser Gly Gly Gly Ser Gly Gly Gly Ser Gly Gly Gly Ser
1               5                   10                  15
Gly Gly Gly Ser Gly Gly Gly Ser Gly Gly
            20                  25

<210> SEQ ID NO 147
<211> LENGTH: 12
<212> TYPE: PRT
<213> ORGANISM: Artificial Sequence
<220> FEATURE:
<223> OTHER INFORMATION: Synthetic Construct

<400> SEQUENCE: 147

Gly Gly Gly Gly Ser Gly Gly Gly Gly Ser Gly Gly
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Synthetic Construct

<400> SEQUENCE: 148

Gly Gly Gly Gly Ser Gly Gly Gly Gly Ser Gly Gly Gly Gly Ser Gly
1               5                   10                  15
Gly

<210> SEQ ID NO 149
<211> LENGTH: 22
<212> TYPE: PRT
<213> ORGANISM: Artificial Sequence
<220> FEATURE:
<223> OTHER INFORMATION: Synthetic Construct
```

<400> SEQUENCE: 149

Gly Gly Gly Gly Ser Gly Gly Gly Ser Gly Gly Gly Gly Ser Gly
1               5                   10                  15

Gly Gly Gly Ser Gly Gly
            20

<210> SEQ ID NO 150
<211> LENGTH: 27
<212> TYPE: PRT
<213> ORGANISM: Artificial Sequence
<220> FEATURE:
<223> OTHER INFORMATION: Synthetic Construct

<400> SEQUENCE: 150

Gly Gly Gly Gly Ser Gly Gly Gly Ser Gly Gly Gly Gly Ser Gly
1               5                   10                  15

Gly Gly Gly Ser Gly Gly Gly Ser Gly Gly
            20                  25

<210> SEQ ID NO 151
<211> LENGTH: 15
<212> TYPE: PRT
<213> ORGANISM: Artificial Sequence
<220> FEATURE:
<223> OTHER INFORMATION: Synthetic Construct

<400> SEQUENCE: 151

Gly Gly Gly Ser Gly Gly Gly Ser Gly Gly Gly Ser Gly Gly Gly
1               5                   10                  15

<210> SEQ ID NO 152
<211> LENGTH: 19
<212> TYPE: PRT
<213> ORGANISM: Artificial Sequence
<220> FEATURE:
<223> OTHER INFORMATION: Synthetic Construct

<400> SEQUENCE: 152

Gly Gly Gly Ser Gly Gly Gly Ser Gly Gly Gly Ser Gly Gly Gly Ser
1               5                   10                  15

Gly Gly Gly

<210> SEQ ID NO 153
<211> LENGTH: 23
<212> TYPE: PRT
<213> ORGANISM: Artificial Sequence
<220> FEATURE:
<223> OTHER INFORMATION: Synthetic Construct

<400> SEQUENCE: 153

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 154
<211> LENGTH: 27
<212> TYPE: PRT
<213> ORGANISM: Artificial Sequence
<220> FEATURE:
<223> OTHER INFORMATION: Synthetic Construct

<400> SEQUENCE: 154

```
Gly Gly Gly Ser Gly Gly Gly Ser Gly Gly Ser Gly Gly Ser
1               5              10              15
Gly Gly Gly Ser Gly Gly Gly Ser Gly Gly Gly
            20              25

<210> SEQ ID NO 155
<211> LENGTH: 13
<212> TYPE: PRT
<213> ORGANISM: Artificial Sequence
<220> FEATURE:
<223> OTHER INFORMATION: Synthetic Construct

<400> SEQUENCE: 155

Gly Gly Gly Gly Ser Gly Gly Gly Gly Ser Gly Gly Gly
1               5                  10

<210> SEQ ID NO 156
<211> LENGTH: 18
<212> TYPE: PRT
<213> ORGANISM: Artificial Sequence
<220> FEATURE:
<223> OTHER INFORMATION: Synthetic Construct

<400> SEQUENCE: 156

Gly Gly Gly Gly Ser Gly Gly Gly Gly Ser Gly Gly Gly Gly Ser Gly
1               5                  10              15

Gly Gly

<210> SEQ ID NO 157
<211> LENGTH: 23
<212> TYPE: PRT
<213> ORGANISM: Artificial Sequence
<220> FEATURE:
<223> OTHER INFORMATION: Synthetic Construct

<400> SEQUENCE: 157

Gly Gly Gly Gly Ser Gly Gly Gly Gly Ser Gly Gly Gly Gly Ser Gly
1               5                  10              15

Gly Gly Gly Ser Gly Gly Gly
            20

<210> SEQ ID NO 158
<211> LENGTH: 28
<212> TYPE: PRT
<213> ORGANISM: Artificial Sequence
<220> FEATURE:
<223> OTHER INFORMATION: Synthetic Construct

<400> SEQUENCE: 158

Gly Gly Gly Gly Ser Gly Gly Gly Gly Ser Gly Gly Gly Gly Ser Gly
1               5                  10              15

Gly Gly Gly Ser Gly Gly Gly Gly Ser Gly Gly Gly
            20              25
```

BISPECIFIC ANTIBODY MOLECULES BINDING TO CD3 AND TYRP-1

CROSS-REFERENCE TO RELATED APPLICATIONS

This application claims benefit of priority to EP Application No. 18214994.8 filed Dec. 21, 2018, which is incorporated herein by reference in its entirety.

SEQUENCE LISTING

This application contains a Sequence Listing which has been submitted electronically in ASCII format and is hereby incorporated by reference in its entirety. Said ASCII copy, created on Mar. 29, 2022, is named 51177-032002_Sequence_Listing_3_29_22_ST25.txt and is 156,817 bytes in size.

FIELD OF THE INVENTION

The present invention generally relates to antibodies that bind to CD3, including multispecific antibodies e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

CD3 (cluster of differentiation 3) is a protein complex composed of four subunits, the CD3γ chain, the CD3δ chain, and two CD3ε chains. CD3 associates with the T-cell receptor and the ζ chain to generate an activation signal in T lymphocytes.

CD3 has been extensively explored as drug target. Monoclonal antibodies targeting CD3 have been used as immunosuppressant therapies in autoimmune diseases such as type I diabetes, or in the treatment of transplant rejection. The CD3 antibody muromonab-CD3 (OKT3) was the first monoclonal antibody ever approved for clinical use in humans, in 1985.

A more recent application of CD3 antibodies is in the form of bispecific antibodies, binding CD3 on the one hand and a tumor cell antigen on the other hand. The simultaneous binding of such an antibody to both of its targets will force a temporary interaction between target cell and T cell, causing activation of any cytotoxic T cell and subsequent lysis of the target cell.

For therapeutic purposes, an important requirement that antibodies have to fulfill is sufficient stability both in vitro (for storage of the drug) an in vivo (after administration to the patient). Modifications like asparagine deamidation are typical degradations for recombinant antibodies and can affect both in vitro stability and in vivo biological functions.

Given the tremendous therapeutic potential of antibodies, particularly bispecific antibodies for the activation of T cells, there is a need for CD3 antibodies with optimized properties.

SUMMARY OF THE INVENTION

The present invention provides antibodies, including multispecific (e.g. bispecific) antibodies, that bind to CD3 and are resistant to degradation by e.g. asparagine deamidation and thus particularly stable as required for therapeutic purposes. The (multispecific) antibodies provided further combine good efficacy and produceability with low toxicity and favorable pharmacokinetic properties.

As is shown herein, the antibodies, including multispecific antibodies, that bind to CD3, provided by the present invention, retain more than about 90% binding activity to CD3 after 2 weeks at pH 7.4, 37° C., relative to the binding activity after 2 weeks at pH 6, −80° C., as determined by surface plasmon resonance (SPR).

In one aspect, the invention provides an antibody that binds to CD3, wherein the antibody comprises a first antigen binding domain, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10. In one aspect, the VH comprises an amino acid sequence that is at least about 95%, 96%, 97%, 98%, 99% or 100% identical to the amino acid sequence of SEQ ID NO: 7, and/or the VL comprises an amino acid sequence that is at least about 95%, 96%, 97%, 98%, 99% or 100% identical to the amino acid sequence of SEQ ID NO: 11.

In a further aspect, the invention provides an antibody that binds to CD3, wherein the antibody comprises a first antigen binding domain comprising a VH sequence of SEQ ID NO: 7 and a VL sequence of SEQ ID NO: 11.

In one aspect, the first antigen binding domain is a Fab molecule.

In one aspect, the antibody comprises an Fc domain composed of a first and a second subunit.

In one aspect, the antibody comprises a second and optionally a third antigen binding domain which binds to a second antigen.

In one aspect the second and/or, where present, the third antigen binding domain is a Fab molecule.

In one aspect the first antigen binding domain is a Fab molecule wherein the variable domains VL and VH or the constant domains CL and CH1, particularly the variable domains VL and VH, of the Fab light chain and the Fab heavy chain are replaced by each other.

In one aspect the second and, where present, the third antigen binding domain is a conventional Fab molecule.

In one aspect, the second and, where present, the third antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, the first and the second antigen binding domain are fused to each other, optionally via a peptide linker.

In one aspect, the first and the second antigen binding domain are each a Fab molecule and either (i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.

In one aspect, the first, the second and, where present, the third antigen binding domain are each a Fab molecule and the antibody comprises an Fc domain composed of a first and a second subunit; and wherein either (i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and the third antigen binding domain, where present, is fused at the C-terminus of the Fab heavy chain to the N-terminus of the second subunit of the Fc domain.

In one aspect, the Fc domain is an IgG, particularly an $IgG_1$, Fc domain. In one aspect the Fc domain is a human Fc domain. In one aspect, the Fc comprises a modification promoting the association of the first and the second subunit of the Fc domain. In one aspect, the Fc domain comprises one or more amino acid substitution that reduces binding to an Fc receptor and/or effector function.

In one aspect, the second antigen is a target cell antigen, particularly a tumor cell antigen.

In one aspect, the second antigen is TYRP-1. In one aspect, the second and, where present, the third antigen binding domain comprises a VH comprising a HCDR 1 of SEQ ID NO: 15, a HCDR 2 of SEQ ID NO: 16, and a HCDR 3 of SEQ ID NO: 17, and a VL comprising a LCDR 1 of SEQ ID NO: 19, a LCDR 2 of SEQ ID NO: 20 and a LCDR 3 of SEQ ID NO: 21. In one aspect, the second and, where present, the third antigen binding domain comprises a VH comprising an amino acid sequence that is at least about 95%, 96%, 97%, 98%, 99% or 100% identical to the amino acid sequence of SEQ ID NO: 18, and/or a VL comprising an amino acid sequence that is at least about 95%, 96%, 97%, 98%, 99% or 100% identical to the amino acid sequence of SEQ ID NO: 22.

In one aspect, the second antigen is EGFRvIII. In one aspect, the second and, where present, the third antigen binding domain comprises a VH comprising a HCDR 1 of SEQ ID NO: 85, a HCDR 2 of SEQ ID NO: 86, and a HCDR 3 of SEQ ID NO: 87, and a VL comprising a LCDR 1 of SEQ ID NO: 89, a LCDR 2 of SEQ ID NO: 90 and a LCDR 3 of SEQ ID NO: 91. In one aspect, the second and, where present, the third antigen binding domain comprises a VH comprising an amino acid sequence that is at least about 95%, 96%, 97%, 98%, 99% or 100% identical to the amino acid sequence of SEQ ID NO: 88, and/or a VL comprising an amino acid sequence that is at least about 95%, 96%, 97%, 98%, 99% or 100% identical to the amino acid sequence of SEQ ID NO: 92.

According to a further aspect of the invention there is provided an isolated polynucleotide encoding an antibody of the invention, and a host cell comprising the isolated polynucleotide of the invention.

In another aspect is provided a method of producing an antibody that binds to CD3, comprising the steps of (a) culturing the host cell of the invention under conditions suitable for the expression of the antibody and optionally (b) recovering the antibody. The invention also encompasses an antibody that binds to CD3 produced by the method of the invention.

The invention further provides a pharmaceutical composition comprising the antibody of the invention and a pharmaceutically acceptable carrier.

Also encompassed by the invention are methods of using the antibody and pharmaceutical composition of the invention. In one aspect the invention provides an antibody or pharmaceutical composition according to the invention for use as a medicament. In one aspect is provided an antibody or pharmaceutical composition according to the invention for use in the treatment of a disease. In a specific aspect the disease is cancer.

Also provided is the use of an antibody or pharmaceutical composition according to the invention in the manufacture of a medicament, the use of an antibody or pharmaceutical composition according to the invention in the manufacture of a medicament for the treatment of a disease, particularly cancer. The invention also provides a method of treating a disease in an individual, comprising administering to said individual an effective amount of the antibody or pharmaceutical composition according to the invention.

BRIEF DESCRIPTION OF THE DRAWINGS

FIGS. 1A-1Z. Exemplary configurations of the (multispecific) antibodies of the invention. (FIG. 1A, FIG. 1D) Illustration of the "1+1 CrossMab" molecule. (FIG. 1B, FIG. 1E) Illustration of the "2+1 IgG Crossfab" molecule with alternative order of Crossfab and Fab components ("inverted"). (FIG. 1C, FIG. 1F) Illustration of the "2+1 IgG Crossfab" molecule. (FIG. 1G, FIG. 1K) Illustration of the "1+1 IgG Crossfab" molecule with alternative order of Crossfab and Fab components ("inverted"). (FIG. 1H, FIG. 1L) Illustration of the "1+1 IgG Crossfab" molecule. (FIG. 1I, FIG. 1M) Illustration of the "2+1 IgG Crossfab" molecule with two CrossFabs. (FIG. 1J, FIG. 1N) Illustration of the "2+1 IgG Crossfab" molecule with two CrossFabs and alternative order of Crossfab and Fab components ("inverted"). (FIG. 1O, FIG. 1S) Illustration of the "Fab-Crossfab" molecule. (FIG. 1P, FIG. 1T) Illustration of the "Crossfab-Fab" molecule. (FIG. 1Q, FIG. 1U) Illustration of the "(Fab)$_2$-Crossfab" molecule. (FIG. 1R, FIG. 1V) Illustration of the "Crossfab-(Fab)$_2$" molecule. (FIG. 1X, FIG. 1Z) Illustration of the "(Crossfab)$_2$-Fab" molecule. Black dot: optional modification in the Fc domain promoting heterodimerization. ++, −−: amino acids of opposite charges optionally introduced in the CH1 and CL domains. Crossfab molecules are depicted as comprising an exchange of VH and VL regions, but may—in aspects wherein no charge modifications are introduced in CH1 and CL domains—alternatively comprise an exchange of the CH1 and CL domains.

FIGS. 11A-11R. Tumor cell killing and T cell activation with TYRP1 TCBs comprising original or optimized CD3 binders. Killing of the melanoma cell line M150543 upon treatment with TYRP1 TCB $CD3_{orig}$ and TYRP1 TCB $CD3_{opt}$ by PBMCs from three different healthy donors (FIGS. 11A-11F: donor 1; FIGS. 11M-11R: donor 3) was determined by LDH release after 24 h (FIGS. 11A, 11G, 11M) and 48 h (FIGS. 11B, 11H, 11N). In parallel, CD25 (FIGS. 11C, 11E, 11I, 11K, 11O, 11Q) and CD69 (FIGS. 11D, 11F, 11J, 11L, 11P, 11R) upregulation on CD8 (FIGS. 11E, 11F, 11K, 11L, 11Q, 11R) and CD4 (FIGS. 11C, 11D, 11I, 11J, 11O, 11P) T cells within PBMCs was measured by flow cytometry as a marker for T cell activation after 48 h.

FIGS. 12A-12C. Specific binding of EGFRvIII IgG PGLALA. Specific binding of EGFRvIII IgG PGLALA antibodies to EGFRvIII without cross-reactivity to EGFRwt was tested by flow cytometry on CHO-EGFRvIII (FIG. 12A), EGFRvIII positive DK-MG (FIG. 12B) and EGFRwt expressing MKN-45 (FIG. 12C). Cetuximab was included as positive control for EGFRwt expression.

FIGS. 16A-16D. Tumor cell lysis with EGFRvIII TCBs. Induction of specific tumor cell lysis by EGFRvIII TCBs was determined upon co-culture with freshly isolated PBMCs and either EGFRvIII positive DK-MG cells (FIG. 16A, FIG. 16B) or EGFRwt positive MKN-45 cells (FIG. 16C, FIG. 16D) for 24 h (FIG. 16A, FIG. 16C) or 48 h (FIG. 16B, FIG. 16D).

FIGS. 17A-17H. T cell activation with EGFRvIII TCBs. Induction of T cell activation by EGFRvIII TCBs was determined upon co-culture with freshly isolated PBMCs and either EGFRvIII positive DK-MG cells (FIGS. 17A, 17B, 17E, 17F) or EGFRwt positive MKN-45 cells (FIGS. 17C, 17D, 17G, 17H) using activation markers CD25 (FIGS. 17A, 17C, 17E, 17G) or CD69 (FIGS. 17B, 17D, 17F, 17H) on CD4 T cells (FIGS. 17A-17D) or CD8 T cells (FIGS. 17E-17H).

FIGS. 18A-18F. Cytokine release with EGFRvIII TCBs. Induction of release of IFNγ (FIG. 18A, FIG. 18D), TNFα (FIG. 18B, FIG. 18E) and Granzyme B (FIG. 18C, FIG. 18F) by EGFRvIII TCBs was determined upon co-culture with freshly isolated PBMCs and either EGFRvIII positive DK-MG cells (FIGS. 18A-18C) or EGFRwt positive MKN-45 cells (FIGS. 18D-18F).

FIGS. 19A-19B. Specific binding of affinity matured EGFRvIII IgG PGLALA. Specific binding of affinity matured EGFRvIII antibodies to EGFRvIII was compared to the parental EGFRvIII binder on U87MG-EGFRvIII cells (FIG. 19A) and on the EGFRwt positive cell line MKN-45 (FIG. 19B).

FIGS. 28A-28D. T cell activation and proliferation with EGFRvIII TCBs. Induction of T cell proliferation (FIG. 28A, FIG. 28C) and T cell activation of CD4 T cells (FIG. 28A, FIG. 28B) and CD8 T cells (FIG. 28C, FIG. 28D) by EGFRvIII TCBs was determined upon co-culture of U87MG-EGFRvIII and PBMCs isolated from healthy donors.

FIGS. 30A-30F. Tumor cell lysis, T cell activation and cytokine release with TYRP-1 TCB. Induction of tumor cell lysis (FIG. 30A, FIG. 30B), T cell activation (FIG. 30C, FIG. 30D) and release of IFNγ and TNFα (FIG. 30E, FIG. 30F) by TYRP-1 TCB was determined upon co-culture with the patient derived melanoma cell line M150543 with PBMCs. Tumor cell lysis was measured after 24 h and 48 h of treatment, T cell activation and cytokine release was measured after 48 h.

DETAILED DESCRIPTION OF THE INVENTION

Definitions

Figure 1X:
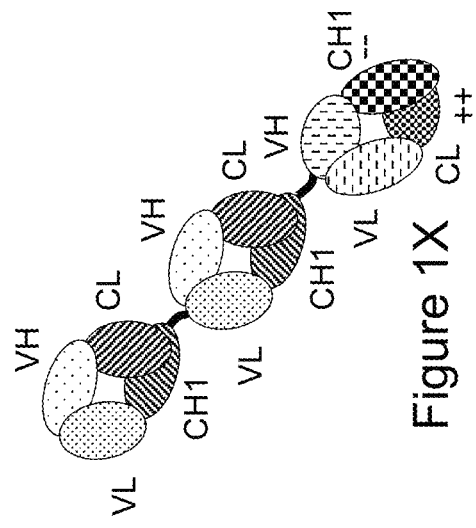
Figure 1Z:
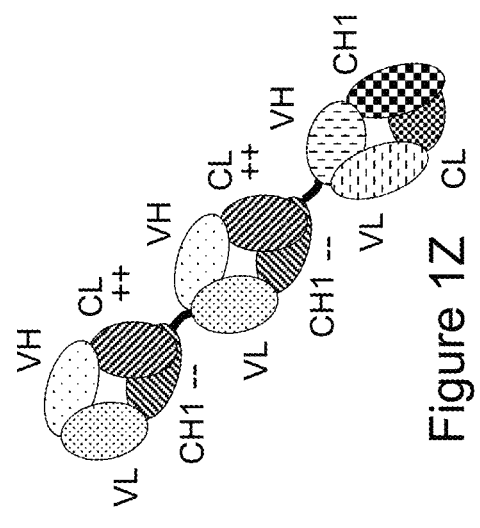
Figure 1W:
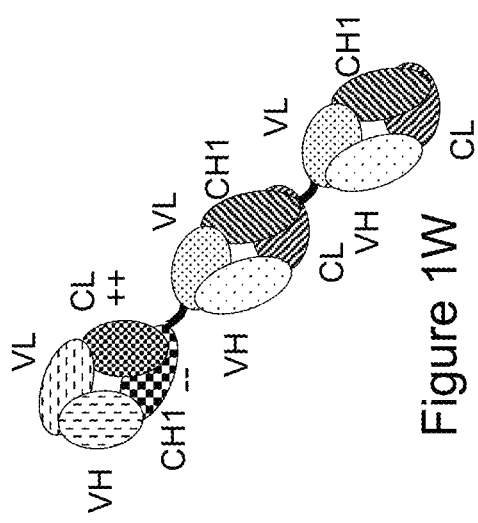
(FIG. 1W, FIG. 1Y) Illustration of the "Fab-(Crossfab)$_2$" molecule.
Figure 1Y:
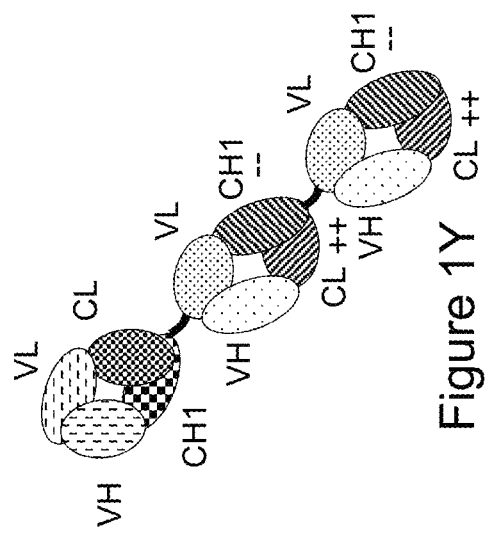

Terms are used herein as generally used in the art, unless otherwise defined in the following. As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one aspect, the extent of binding of an anti-CD3 antibody to an unrelated, non-CD3 protein is less than about 10% of the binding of the antibody to CD3 as measured, e.g., by surface plasmon resonance (SPR). In certain aspects, an antibody that binds to CD3 has a dissociation constant ($K_D$) of ≤1 μM, ≤500 nM, ≤200 nM, or ≤100 nM. An antibody is said to "specifically bind" to CD3 when the antibody has a $K_D$ of 1 μM or less, as measured, e.g., by SPR. In certain aspects, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv and scFab), single-domain antibodies, and multispecific antibodies formed from antibody fragments. For a review of certain antibody fragments, see Hollinger and Hudson, Nature Biotechnology 23:1126-1136 (2005). The terms "full-length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC, affinity chromatography, size exclusion chromatography) methods. For review of methods for assessment of antibody purity, see, e.g., Flatman et al., *J. Chromatogr. B* 848:79-87 (2007). In some aspects, the antibodies provided by the present invention are isolated antibodies.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some aspects, some FR residues in a humanized antibody are substituted with corresponding residues from a non-human antibody (e.g., the antibody from which the CDR residues are derived), e.g., to restore or improve antibody specificity or affinity. A "humanized form" of an antibody, e.g. of a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain aspects, a human antibody is derived from a non-human transgenic mammal, for example a mouse, a rat, or a rabbit. In certain aspects, a human antibody is derived from a hybridoma cell line. Antibodies or antibody fragments isolated from human antibody libraries are also considered human antibodies or human antibody fragments herein.

The term "antigen binding domain" refers to the part of an antibody that comprises the area which binds to and is complementary to part or all of an antigen. An antigen binding domain may be provided by, for example, one or more antibody variable domains (also called antibody variable regions). In preferred aspects, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and complementarity determining regions (CDRs). See, e.g., Kindt et al., *Kuby Immunology*, 6$^{th}$ ed., W.H. Freeman & Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, Md. (1991)) is used for the light chain constant domain CL of kappa and lambda isotype and the Kabat EU index numbering system (see pages 661-723) is used for the heavy chain constant domains (CH1, hinge, CH2 and CH3), which is herein further clarified by referring to "numbering according to Kabat EU index" or "Kabat EU index numbering" in this case.

The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991)); and
  (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementarity determining regions (CDRs). The FR of a variable domain generally consists of four FR domains: FR1, FR2, FR3, and FR4. Accordingly, the HVR and FR sequences generally appear in the following order in VH (or VL): FR1-HCDR1(LCDR1)-FR2-HCDR2 (LCDR2)-FR3-HCDR3(LCDR3)-FR4.

Unless otherwise indicated, CDR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes is 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3.

The term "immunoglobulin molecule" herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "Fc domain" or "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain.

Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region (or a subunit of an Fc domain as defined herein) are denoted herein without C-terminal glycine-lysine dipeptide if not indicated otherwise.

In one aspect, a heavy chain including an Fc region (subunit) as specified herein, comprised in an antibody according to the invention, comprises an additional C-terminal glycine-lysine dipeptide (G446 and K447, numbering according to Kabat EU index). In one aspect, a heavy chain including an Fc region (subunit) as specified herein, comprised in an antibody according to the invention, comprises an additional C-terminal glycine residue (G446, numbering according to Kabat EU index). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

By "fused" is meant that the components (e.g. a Fab molecule and an Fc domain subunit) are linked by peptide bonds, either directly or via one or more peptide linkers.

The term "multispecific" means that the antibody is able to specifically bind to at least two distinct antigenic determinants. A multispecific antibody can be, for example, a bispecific antibody. Typically, a bispecific antibody comprises two antigen binding sites, each of which is specific for a different antigenic determinant. In certain aspects the multispecific (e.g. bispecific) antibody is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigenic determinant" or "antigen" refers to a site (e.g. a contiguous stretch of amino acids or a conformational configuration made up of different regions of non-contiguous amino acids) on a polypeptide macromolecule to which an antigen binding domain binds, forming an antigen binding domain-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). In a preferred aspect, the antigen is a human protein.

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one aspect, CD3 is human CD3, particularly the epsilon subunit of human CD3 (CD3ε). The amino acid sequence of human CD3ε is shown in SEQ ID NO: 112 (without signal peptide). See also UNIPROT® (uniprot.org) accession no. P07766 (version 189), or NCBI (ncbi.nlm.nih.gov) RefSeq NP_000724.1. In another aspect, CD3 is cynomolgus (*Macaca fascicularis*) CD3, particularly cynomolgus CD3ε. The amino acid sequence of cynomolgus CD3ε is shown in SEQ ID NO: 113 (without signal peptide). See also NCBI GENBANK® no. BAB71849.1. In certain aspects the antibody of the invention binds to an epitope of CD3 that is conserved among the CD3 antigens from different species, particularly human and cynomolgus CD3. In preferred aspects, the antibody binds to human CD3.

A "target cell antigen" as used herein refers to an antigenic determinant presented on the surface of a target cell, for example a cell in a tumor such as a cancer cell or a cell of the tumor stroma (in that case a "tumor cell antigen"). Preferably, the target cell antigen is not CD3, and/or is expressed on a different cell than CD3. In a preferred aspect, the target cell antigen is TYRP-1, particularly human TYRP-1. In another preferred aspect, the target cell antigen is EGFRvIII, particularly human EGFRvIII.

"TYRP1" or "TYRP-1" stands for tyrosine-related protein 1, which is an enzyme involved in melanin synthesis. The mature form of TYRP1, also originally called gp75, is a 75 kDa transmembrane glycoprotein. The sequence of human TYRP1 is shown in SEQ ID NO: 114 (without signal peptide). See also UNIPROT® entry no. P17643 (version 185). "TYRP1" as used herein refers to any native TYRP1 from any vertebrate source, including mammals such as primates (e.g. humans), non-human primates (e.g. cynomolgus monkeys) and rodents (e.g. mice and rats), unless otherwise indicated. The term encompasses "full-length," unprocessed TYRP1 as well as any form of TYRP1 that results from processing in the cell. The term also encompasses naturally occurring variants of TYRP1, e.g., splice variants or allelic variants. In one aspect, TYRP1 is human TYRP1.

"EGFRvIII" stands for Epidermal Growth Factor Receptor Variant III, which is a mutant of EGFR, formed by an in-frame deletion of exons 2-7, leading to deletion of 267 amino acids with a glycine substitution at the junction. The sequence of human EGFRvIII is shown in SEQ ID NO: 115 (without signal peptide). The sequence of wild-type human EGFR is shown in SEQ ID NO: 116 (without signal peptide). See also UNIPROT® entry no. P00533 (version 258).

"EGFRvIII" as used herein refers to any native EGFRvIII from any vertebrate source, including mammals such as primates (e.g. humans), non-human primates (e.g. cynomolgus monkeys) and rodents (e.g. mice and rats), unless otherwise indicated. The term encompasses "full-length," unprocessed EGFRvIII (but not wild-type EGFR) as well as any form of EGFRvIII that results from processing in the cell (e.g. EGFRvIII without signal peptide). In one aspect, EGFRvIII is human EGFRvIII.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., an antibody and an antigen). The affinity of a molecule X for its partner Y can generally be represented by the dissociation constant ($K_D$). Affinity can be measured by well-established methods known in the art, including those described herein. A preferred method for measuring affinity is Surface Plasmon Resonance (SPR).

An "affinity matured" antibody refers to an antibody with one or more alterations in one or more complementarity determining regions (CDRs), compared to a parent antibody which does not possess such alterations, such alterations resulting in an improvement in the affinity of the antibody for antigen.

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein preferably includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which may be non-identical in the sense that further components fused to each of the subunits (e.g. antigen binding domains) are not the same. In some aspects, the modification promoting the association of the first and the second subunit of the Fc domain comprises an amino acid mutation in the Fc domain, specifically an amino acid substitution. In a preferred aspect, the modification promoting the association of the first and the second subunit of the Fc domain comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Preferred amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611. Unless otherwise indicated, for purposes herein, % amino acid sequence identity values are generated using the ggsearch program of the FASTA package version 36.3.8c or later with a BLOSUM50 comparison matrix. The FASTA program package was authored by W. R. Pearson and D. J. Lipman ("Improved Tools for Biological Sequence Analysis", PNAS 85 (1988) 2444-2448), W. R. Pearson ("Effective protein sequence comparison" Meth. Enzymol. 266 (1996) 227- 258), and Pearson et. al. (Genomics 46 (1997) 24-36) and is publicly available fromfasta.bioch.virginia.edu or ebi.ac.uk Alternatively, a public server accessible at fasta.bioch.virginia.edu can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" or "nucleic acid molecule" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

An "isolated" nucleic acid molecule refers to a nucleic acid molecule that has been separated from a component of its natural environment. An isolated nucleic acid molecule includes a nucleic acid molecule contained in cells that ordinarily contain the nucleic acid molecule, but the nucleic acid molecule is present extrachromosomally or at a chromosomal location that is different from its natural chromosomal location.

"Isolated polynucleotide (or nucleic acid) encoding an antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one aspect, the host cell of the invention is a eukaryotic cell, particularly a mammalian cell. In one aspect, the host cell is not a cell within a human body.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human.

An "effective amount" of an agent, e.g., a pharmaceutical composition, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

Compositions and Methods

The invention provides antibodies that bind CD3, including multispecific antibodies that bind CD3 and a second antigen. The antibodies show superior stability, combined with other favorable properties for therapeutic application, e.g. with respect to efficacy and safety, pharmacokinetics, as well as produceability. Antibodies of the invention as useful, e.g., for the treatment of diseases such as cancer.

A. Anti-CD3 Antibodies

In one aspect, the invention provides antibodies that bind to CD3. In one aspect, provided are isolated antibodies that bind to CD3. In one aspect, the invention provides antibodies that specifically bind to CD3. In certain aspects, the anti-CD3 antibodies retain more than about 90% binding activity to CD3 after 2 weeks at pH 7.4, 37° C., relative to the binding activity after 2 weeks at pH 6, −80° C., as determined by surface plasmon resonance (SPR).

In one aspect, the invention provides an antibody that binds to CD3, wherein the antibody comprises a first antigen binding domain, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10.

In one aspect, the antibody is a humanized antibody. In one aspect, the antigen binding domain is a humanized antigen binding domain (i.e. an antigen binding domain of a humanized antibody).

In one aspect, the VH and/or the VL is a humanized variable region.

In one aspect, the VH and/or the VL comprises an acceptor human framework, e.g. a human immunoglobulin framework or a human consensus framework.

In one aspect, the VH comprises one or more heavy chain framework sequence (i.e. the FR1, FR2, FR3 and/or FR4 sequence) of the heavy chain variable region sequence of SEQ ID NO: 7.

In one aspect, the VH comprises an amino acid sequence that is at least about 95%, 96%, 97%, 98%, or 99% identical to the amino acid sequence of SEQ ID NO: 7. In one aspect, the VH comprises an amino acid sequence that is at least about 95% identical to the amino acid sequence of SEQ ID NO: 7. In one aspect, the VH comprises an amino acid sequence that is at least about 98% identical to the amino acid sequence of SEQ ID NO: 7. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 7. In certain aspects, substitutions, insertions, or deletions occur in regions outside the CDRs (i.e., in the FRs). In one aspect, the VH comprises the amino acid sequence of SEQ ID NO: 7. Optionally, the VH comprises the amino acid sequence of SEQ ID NO: 7, including post-translational modifications of that sequence.

In one aspect, the VL comprises one or more light chain framework sequence (i.e. the FR1, FR2, FR3 and/or FR4 sequence) of the light chain variable region sequence of SEQ ID NO: 11. In one aspect, the VL comprises an amino acid sequence that is at least about 95%, 96%, 97%, 98%, or 99% identical to the amino acid sequence of SEQ ID NO: 11. In one aspect, the VL comprises an amino acid sequence that is at least about 95% identical to the amino acid sequence of SEQ ID NO: 11. In one aspect, the VL comprises an amino acid sequence that is at least about 98% identical to the amino acid sequence of SEQ ID NO: 11. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 11. In certain aspects, substitutions, insertions, or deletions occur in regions outside the CDRs (i.e., in the FRs). In one aspect, the VL comprises the amino acid sequence of SEQ ID NO: 11. Optionally, the VL comprises the amino acid sequence of SEQ ID NO: 11, including post-translational modifications of that sequence.

In one aspect, the VH comprises an amino acid sequence that is at least about 95%, 96%, 97%, 98%, or 99% identical to the amino acid sequence of SEQ ID NO: 7, and the VL comprises an amino acid sequence that is at least about 95%, 96%, 97%, 98%, or 99% identical to the amino acid sequence of SEQ ID NO: 11. In one aspect, the VH comprises the amino acid sequence of SEQ ID NO: 7 and the VL comprises the amino acid sequence of SEQ ID NO: 11.

In a further aspect, the invention provides an antibody that binds to CD3, wherein the antibody comprises a first antigen binding domain comprising a VH comprising the amino acid sequence of SEQ ID NO: 7 and a VL comprising the amino acid sequence of SEQ ID NO: 11.

In a further aspect, the invention provides an antibody that binds to CD3, wherein the antibody comprises a first antigen binding domain comprising a VH sequence of SEQ ID NO: 7 and a VL sequence of SEQ ID NO: 11.

In another aspect, the invention provides an antibody that binds to CD3, wherein the antibody comprises a first antigen binding domain comprising a VH comprising the heavy chain CDR sequences of the VH of SEQ ID NO: 7, and a VL comprising the light chain CDR sequences of the VL of SEQ ID NO: 11.

In a further aspect, the first antigen binding domain comprises the HCDR1, HCDR2 and HCDR3 amino acid sequences of the VH of SEQ ID NO: 7 and the LCDR1, LCDR2 and LCDR3 amino acid sequences of the VL of SEQ ID NO: 11.

In one aspect, the VH comprises the heavy chain CDR sequences of the VH of SEQ ID NO: 7 and a framework of at least 95%, 96%, 97%, 98% or 99% sequence identity to the framework sequence of the VH of SEQ ID NO: 7. In one aspect, the VH comprises the heavy chain CDR sequences of the VH of SEQ ID NO: 7 and a framework of at least 95% sequence identity to the framework sequence of the VH of SEQ ID NO: 7. In another aspect, the VH comprises the heavy chain CDR sequences of the VH of SEQ ID NO: 7 and a framework of at least 98% sequence identity to the framework sequence of the VH of SEQ ID NO: 7.

In one aspect, the VL comprises the light chain CDR sequences of the VL of SEQ ID NO: 11 and a framework of at least 95%, 96%, 97%, 98% or 99% sequence identity to the framework sequence of the VL of SEQ ID NO: 11. In one aspect, the VL comprises the light chain CDR sequences of the VL of SEQ ID NO: 11 and a framework of at least 95% sequence identity to the framework sequence of the VL of SEQ ID NO: 11. In another aspect, the VL comprises the light chain CDR sequences of the VL of SEQ ID NO: 11 and a framework of at least 98% sequence identity to the framework sequence of the VL of SEQ ID NO: 11.

In one aspect, the invention provides an antibody that binds to CD3, wherein the antibody comprises a first antigen binding domain comprising a VH sequence as in any of the aspects provided above, and a VL sequence as in any of the aspects provided above.

In one aspect, the antibody comprises a human constant region. In one aspect, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 120 and 121 (human kappa and lambda CL domains, respectively) and SEQ ID NO: 122 (human IgG1 heavy chain constant domains CH1-CH2-CH3). In one aspect, the antibody comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. In one aspect, the antibody comprises a heavy chain constant region comprising an amino acid sequence that is at least about 95%, 96%, 97%, 98%, 99% or 100% identical to the amino acid sequence of SEQ ID NO: 122. Particularly, the heavy chain constant region may comprise amino acid mutations in the Fc domain as described herein.

In one aspect, the first antigen binding domain comprises a human constant region. In one aspect, the first antigen binding moiety is a Fab molecule comprising a human constant region, particularly a human CH1 and/or CL domain. In one aspect, the first antigen binding domain comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the first antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 122. Particularly, the heavy chain constant region (specifically CH1 domain) may comprise amino acid mutations as described herein under "charge modifications".

In one aspect, the antibody is a monoclonal antibody.

In one aspect, the antibody is an IgG, particularly an $IgG_1$, antibody. In one aspect, the antibody is a full-length antibody.

In another aspect, the antibody is an antibody fragment selected from the group of an Fv molecule, a scFv molecule, a Fab molecule, and a F(ab')2 molecule; particularly a Fab molecule.

In another aspect, the antibody fragment is a diabody, a triabody or a tetrabody.

In one aspect, the first antigen binding domain is a Fab molecule. In a preferred aspect the first antigen binding domain is a Fab molecule wherein the variable domains VL and VH or the constant domains CL and CH1, particularly the variable domains VL and VH, of the Fab light chain and the Fab heavy chain are replaced by each other (i.e. the first antigen binding domain is a crossover Fab molecule).

In a further aspect, the antibody according to any of the above aspects may incorporate any of the features, singly or in combination, as described in sections II. A. 1.-8. below.

In a preferred aspect, the antibody comprises an Fc domain, particularly an IgG Fc domain, more particularly an IgG1 Fc domain. In one aspect the Fc domain is a human Fc domain. In one aspect, the Fc domain is a human $IgG_1$ Fc domain. The Fc domain is composed of a first and a second subunit and may incorporate any of the features, singly or in combination, described hereinbelow in relation to Fc domain variants (section II. A. 8.).

In another preferred aspect, the antibody comprises a second and optionally a third antigen binding domain which binds to a second antigen (i.e. the antibody is a multispecific antibody, as further described hereinbelow (section II. A. 7.).

1. Antibody Fragments

In certain aspects, an antibody provided herein is an antibody fragment.

In one aspect, the antibody fragment is a Fab, Fab', Fab'-SH, or F(ab')$_2$ molecule, in particular a Fab molecule as described herein. "Fab' molecule" differ from Fab molecules by the addition of residues at the carboxy terminus of the CH1 domain including one or more cysteines from the antibody hinge region. Fab'-SH are Fab' molecules in which the cysteine residue(s) of the constant domains bear a free thiol group. Pepsin treatment yields an F(ab')2 molecule that has two antigen-binding sites (two Fab molecules) and a part of the Fc region.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab molecule. A "single chain Fab molecule" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab molecules are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as recombinant production by recombinant host cells (e.g., *E. coli*), as described herein.

2. Humanized Antibodies

In certain aspects, an antibody provided herein is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region.

In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

3. Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87:614-622 (2004); Kanda, Y. et al., Biotechnol. Bioeng., 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc.

Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

4. Cysteine Engineered Antibody Variants

In certain aspects, it may be desirable to create cysteine engineered antibodies, e.g., THIOMAB™ antibodies, in which one or more residues of an antibody are substituted with cysteine residues. In preferred aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. No. 7,521,541, 8,30,930, 7,855,275, 9,000,130, or WO 2016040856.

5. Antibody Derivatives

In certain aspects, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

6. Immunoconjugates

The invention also provides immunoconjugates comprising an anti-CD3 antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody of the invention conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody of the invention conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as $I^{123}$, $I^{131}$, $In^{111}$, $F^{19}$, $C^{13}$, $N^{15}$, $O^{17}$, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane an, bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

7. Multispecific Antibodies

In certain aspects, an antibody provided herein is a multispecific antibody, particularly a bispecific antibody. Multispecific antibodies are monoclonal antibodies that have binding specificities for at least two different antigenic determinants (e.g., two different proteins, or two different epitopes on the same protein). In certain aspects, the multispecific antibody has three or more binding specificities. In certain aspects, one of the binding specificities is for CD3 and the other specificity is for any other antigen. In certain aspects, multispecific antibodies may bind to two (or more) different epitopes of CD3. Multispecific (e.g., bispecific) antibodies may also be used to localize cytotoxic agents or cells to cells which express CD3. Multispecific antibodies may be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The multispecific antibody or antigen binding fragment thereof also includes a "Dual Acting FAb" or "DAF" comprising an antigen binding site that binds to CD3 as well as another different antigen, or two different epitopes of CD3 (see, e.g., US 2008/0069820 and WO 2015/095539).

Multi-specific antibodies may also be provided in an asymmetric form with a domain crossover in one or more binding arms of the same antigen specificity (so-called "CrossMab" technology), i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

A particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells. Hence, in preferred aspects, an antibody provided herein is a multispecific antibody, particularly a bispecific antibody, wherein one of the binding specificities is for CD3 and the other is for target cell antigen.

Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bauerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

Preferred aspects of the multispecific antibodies of the present invention are described in the following.

In one aspect, the invention provides an antibody that binds to CD3, comprising a first antigen binding domain that binds to CD3, as described herein, and comprising a second and optionally a third antigen binding domain which binds to a second antigen.

According to preferred aspects of the invention, the antigen binding domains comprised in the antibody are Fab molecules (i.e. antigen binding domains composed of a heavy and a light chain, each comprising a variable and a constant domain). In one aspect, the first, the second and/or, where present, the third antigen binding domain is a Fab molecule. In one aspect, said Fab molecule is human. In a preferred aspect, said Fab molecule is humanized. In yet another aspect, said Fab molecule comprises human heavy and light chain constant domains.

Preferably, at least one of the antigen binding domains is a crossover Fab molecule. Such modification reduces mispairing of heavy and light chains from different Fab molecules, thereby improving the yield and purity of the (multispecific) antibody of the invention in recombinant production. In a preferred crossover Fab molecule useful for the (multispecific) antibody of the invention, the variable domains of the Fab light chain and the Fab heavy chain (VL and VH, respectively) are exchanged. Even with this domain exchange, however, the preparation of the (multispecific) antibody may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired (multispecific) antibody, charged amino acids with opposite charges may be introduced at specific amino acid positions in the CH1 and CL domains of either the Fab molecule binding to the first antigen (CD3), or the Fab molecule(s) binding to the second antigen (e.g. a target cell antigen such as TYRP-1 or EGFRvIII), as further described herein. Charge modifications are made either in the conventional Fab molecule(s) comprised in the (multispecific) antibody (such as shown e.g. in FIG. 1A-FIG. 1C, FIG. 1G-FIG. 1J), or in the VH/VL crossover Fab molecule(s) comprised in the (multispecific) antibody (such as shown e.g. in FIG. 1D-FIG. 1F, FIG. 1K-FIG. 1N) (but not in both). In preferred aspects, the charge modifications are made in the conventional Fab molecule(s) comprised in the (multispecific) antibody (which in preferred aspects bind(s) to the second antigen, e.g. a target cell antigen such as TYRP-1 or EGFRvIII). In a preferred aspect according to the invention, the (multispecific) antibody is capable of simultaneous binding to the first antigen (i.e. CD3), and the second antigen (e.g. a target antigen such as TYRP-1 or EGFRvIII). In one aspect, the (multispecific) antibody is capable of crosslinking a T cell and a target cell by simultaneous binding to CD3 and a target cell antigen.

In an even more preferred aspect, such simultaneous binding results in lysis of the target cell, particularly a target cell antigen (e.g. TYRP-1 or EGFRvIII)-expressing tumor cell. In one aspect, such simultaneous binding results in activation of the T cell. In other aspects, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one aspect, binding of the (multispecific) antibody to CD3 without simultaneous binding to the target cell antigen does not result in T cell activation.

In one aspect, the (multispecific) antibody is capable of re-directing cytotoxic activity of a T cell to a target cell. In a preferred aspect, said re-direction is independent of MHC-mediated peptide antigen presentation by the target cell and and/or specificity of the T cell.

Preferably, a T cell according to any of the aspects of the invention is a cytotoxic T cell. In some aspects the T cell is a $CD4^+$ or a $CD8^+$ T cell, particularly a $CD8^+$ T cell.

a) First Antigen Binding Domain

The (multispecific) antibody of the invention comprises at least one antigen binding domain (the first antigen binding domain) that binds to CD3. In preferred aspects, CD3 is human CD3 (SEQ ID NO: 112) or cynomolgus CD3 (SEQ ID NO: 113) most particularly human CD3. In one aspect the first antigen binding domain is cross-reactive for (i.e. specifically binds to) human and cynomolgus CD3. In some aspects, CD3 is the epsilon subunit of CD3 (CD3 epsilon).

In a preferred aspect, the (multispecific) antibody comprises not more than one antigen binding domain that binds to CD3. In one aspect the (multispecific) antibody provides monovalent binding to CD3.

In one aspect, the antigen binding domain that binds to CD3 is an antibody fragment selected from the group of an Fv molecule, a scFv molecule, a Fab molecule, and a F(ab')2 molecule. In a preferred aspect, the antigen binding domain that binds to CD3 is a Fab molecule.

In preferred aspects, the antigen binding domain that binds to CD3 is a crossover Fab molecule as described herein, i.e. a Fab molecule wherein the variable domains VH and VL or the constant domains CH1 and CL of the Fab heavy and light chains are exchanged/replaced by each other.

In such aspects, the antigen binding domain(s) that binds to the second antigen (e.g. a target cell antigen such as TYRP-1 or EGFRvIII) is preferably a conventional Fab molecule. In aspects where there is more than one antigen binding domain, particularly Fab molecule, that binds to a second antigen comprised in the (multispecific) antibody, the antigen binding domain that binds to CD3 preferably is a crossover Fab molecule and the antigen binding domain that bind to the second antigen are conventional Fab molecules.

In alternative aspects, the antigen binding domain that binds to CD3 is a conventional Fab molecule. In such aspects, the antigen binding domain(s) that binds to the second antigen (e.g. a target cell antigen such as TYRP-1 or EGFRvIII) is a crossover Fab molecule as described herein, i.e. a Fab molecule wherein the variable domains VH and VL or the constant domains CH1 and CL of the Fab heavy and light chains are exchanged/replaced by each other. In aspects where there is more than one antigen binding domain, particularly Fab molecule, that binds to CD3 comprised in the (multispecific) antibody, the antigen binding domain that binds to the second antigen preferably is a crossover Fab molecule and the antigen binding domains that bind to CD3 are conventional Fab molecules.

In preferred aspects, the first antigen binding domain is a Fab molecule wherein the variable domains VL and VH or the constant domains CL and CH1, particularly the variable domains VL and VH, of the Fab light chain and the Fab heavy chain are replaced by each other (i.e. according to such aspect, the first antigen binding domain is a crossover Fab molecule wherein the variable or constant domains of the Fab light chain and the Fab heavy chain are exchanged). In one such aspect, the second (and the third, if any) antigen binding domain is a conventional Fab molecule.

In one aspect, not more than one antigen binding domain that binds to CD3 is present in the (multispecific) antibody (i.e. the antibody provides monovalent binding to CD3).

b) Second (and Third) Antigen Binding Domain

In certain aspects, the (multispecific) antibody of the invention comprises at least one antigen binding domain, particularly a Fab molecule, that binds to a second antigen. The second antigen preferably is not CD3, i.e. different from CD3. In one aspect, the second antigen is an antigen expressed on a different cell than CD3 (e.g. expressed on a cell other than a T cell). In one aspect, the second antigen is a target cell antigen, particularly a tumor cell antigen. In a specific aspect, the second antigen is TYRP-1. In another specific aspect, the second antigen is EGFRvIII. The second antigen binding domain is able to direct the (multispecific) antibody to a target site, for example to a specific type of tumor cell that expresses the second antigen.

In one aspect, the antigen binding domain that binds to the second antigen is an antibody fragment selected from the group of an Fv molecule, a scFv molecule, a Fab molecule, and a F(ab')2 molecule. In a preferred aspect, the antigen binding domain that binds to the second antigen is a Fab molecule.

In certain aspects, the (multispecific) antibody comprises two antigen binding domains, particularly Fab molecules, that bind to the second antigen. In a preferred such aspect, each of these antigen binding domains binds to the same antigenic determinant. In an even more preferred aspect, all of these antigen binding domains are identical, i.e. they have the same molecular format (e.g. conventional or crossover Fab molecule) and comprise the same amino acid sequences including the same amino acid substitutions in the CH1 and CL domain as described herein (if any). In one aspect, the (multispecific) antibody comprises not more than two antigen binding domains, particularly Fab molecules, that bind to the second antigen.

In preferred aspects, the antigen binding domain(s) that bind to the second antigen is/are a conventional Fab molecule. In such aspects, the antigen binding domain(s) that binds to CD3 is a crossover Fab molecule as described herein, i.e. a Fab molecule wherein the variable domains VH and VL or the constant domains CH1 and CL of the Fab heavy and light chains are exchanged/replaced by each other.

In alternative aspects, the antigen binding domain(s) that bind to the second antigen is/are a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to CD3 is a conventional Fab molecule.

In one aspect, the second (and, where present, third) antigen binding domain comprises a human constant region. In one aspect, the second (and, where present, third) antigen binding domain is a Fab molecule comprising a human constant region, particularly a human CH1 and/or CL domain. Exemplary sequences of human constant regions are given in SEQ ID NOs 120 and 121 (human kappa and lambda CL domains, respectively) and SEQ ID NO: 122 (human IgG1 heavy chain constant domains CH1-CH2-CH3). In one aspect, the second (and, where present, third) antigen binding domain comprises a light chain constant region comprising an amino acid sequence that is at least about 95%, 96%, 97%, 98%, 99% or 100% identical to the amino acid sequence of SEQ ID NO: 120 or SEQ ID NO: 121, particularly the amino acid sequence of SEQ ID NO: 120. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the second (and, where present, third) antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 122. Particularly, the heavy chain constant region (specifically CH1 domain) may comprise amino acid mutations as described herein under "charge modifications".

TYRP-1

In preferred aspects, the second antigen is TYRP-1, particularly human TYRP-1 (SEQ ID NO: 114).

In one aspect, the second (and, where present, third) antigen binding domain comprises a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody). In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, third) antigen binding domain comprises one or more heavy chain framework sequence (i.e. the FR1, FR2, FR3 and/or FR4 sequence) of SEQ ID NO: 18. In one aspect, the VH comprises an amino acid sequence that is at least about 95%, 96%, 97%, 98%, or 99% identical to the amino acid sequence of SEQ ID NO: 18. In one aspect, the VH comprises an amino acid sequence that is at least about 95% identical to the amino acid sequence of SEQ ID NO: 18. In one aspect, the VH comprises an amino acid sequence that is at least about 98% identical to the amino acid sequence of SEQ ID NO: 18. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to TYRP-1. In certain aspects, a total of 1 to 10 amino acids have been substituted, inserted and/or deleted in the amino acid sequence of SEQ ID NO: 18. In certain aspects, substitutions, insertions, or deletions occur in regions outside the CDRs (i.e., in the FRs). In one aspect, the VH comprises the amino acid sequence of SEQ ID NO: 18. Optionally, the VH comprises the amino acid sequence of SEQ ID NO: 18, including post-translational modifications of that sequence.

In one aspect, the VL of the second (and, where present, third) antigen binding domain comprises one or more light chain framework sequence (i.e. the FR1, FR2, FR3 and/or FR4 sequence) of SEQ ID NO: 22. In one aspect, the VL comprises an amino acid sequence that is at least about 95%, 96%, 97%, 98%, or 99% identical to the amino acid sequence of SEQ ID NO:

22. In one aspect, the VL comprises an amino acid sequence that is at least about 95% identical to the amino acid sequence of SEQ ID NO: 22. In one aspect, the VL comprises an amino acid sequence that is at least about 98% identical to the amino acid sequence of SEQ ID NO: 22. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to TYRP-1. In certain aspects, a total of 1 to 10 amino acids have been substituted, inserted and/or deleted in the amino acid sequence of SEQ ID NO: 22. In certain aspects, substitutions, insertions, or deletions occur in regions outside the CDRs (i.e., in the FRs). In one aspect, the VL comprises the amino acid sequence of SEQ ID NO: 22. Optionally, the VL comprises the amino acid sequence of SEQ ID NO: 22, including post-translational modifications of that sequence.

In one aspect, the VH of the second (and, where present, third) antigen binding domain comprises an amino acid sequence that is at least about 95%, 96%, 97%, 98%, or 99% identical to the amino acid sequence of SEQ ID NO: 18, and the VL of the second (and, where present, third) antigen binding domain comprises an amino acid sequence that is at least about 95%, 96%, 97%, 98%, or 99% identical to the amino acid sequence of SEQ ID NO: 22. In one aspect, the VH comprises the amino acid sequence of SEQ ID NO: 18 and the VL comprises the amino acid sequence of SEQ ID NO: 22.

In a further aspect, the second (and, where present, third) antigen binding domain comprises a VH comprising the sequence of SEQ ID NO: 18 and a VL comprising the sequence of SEQ ID NO: 22.

In a further aspect, the second (and, where present, third) antigen binding domain comprises a VH sequence of SEQ ID NO: 18 and a VL sequence of SEQ ID NO: 22.

In another aspect, the second (and, where present, third) antigen binding domain comprises a VH comprising the heavy chain CDR sequences of the VH of SEQ ID NO: 18, and a VL comprising the light chain CDR sequences of the VL of SEQ ID NO: 22.

In a further aspect, the second (and, where present, third) antigen binding domain comprises the HCDR1, HCDR2 and HCDR3 amino acid sequences of the VH of SEQ ID NO: 18 and the LCDR1, LCDR2 and LCDR3 amino acid sequences of the VL of SEQ ID NO: 22.

In one aspect, the VH of the second (and, where present, third) antigen binding domain comprises the heavy chain CDR sequences of the VH of SEQ ID NO: 18 and a framework of at least 95%, 96%, 97%, 98% or 99% sequence identity to the framework sequence of the VH of SEQ ID NO: 18. In one aspect, the VH comprises the heavy chain CDR sequences of the VH of SEQ ID NO: 18 and a framework of at least 95% sequence identity to the framework sequence of the VH of SEQ ID NO: 18. In another aspect, the VH comprises the heavy chain CDR sequences of the VH of SEQ ID NO: 18 and a framework of at least 98% sequence identity to the framework sequence of the VH of SEQ ID NO: 18.

In one aspect, the VL of the second (and, where present, third) antigen binding domain comprises the light chain CDR sequences of the VL of SEQ ID NO: 22 and a framework of at least 95%, 96%, 97%, 98% or 99% sequence identity to the framework sequence of the VL of SEQ ID NO: 22. In one aspect, the VL comprises the light chain CDR sequences of the VL of SEQ ID NO: 22 and a framework of at least 95% sequence identity to the framework sequence of the VL of SEQ ID NO: 22. In another aspect, the VL comprises the light chain CDR sequences of the VL of SEQ ID NO: 22 and a framework of at least 98% sequence identity to the framework sequence of the VL of SEQ ID NO: 22.

EGFRvIII

In preferred aspects, the second antigen is EGFRvIII, particularly human EGFRvIII (SEQ ID NO: 115).

In one aspect, the second (and, where present, third) antigen binding domain comprises a heavy chain variable region (VH) comprising a heavy chain complementary determining region (HCDR) 1 of SEQ ID NO: 85, a HCDR 2 of SEQ ID NO: 86, and a HCDR 3 of SEQ ID NO: 87, and a light chain variable region (VL) comprising a light chain complementarity determining region (LCDR) 1 of SEQ ID NO: 89, a LCDR 2 of SEQ ID NO: 90 and a LCDR 3 of SEQ ID NO: 91.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody). In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, third) antigen binding domain comprises one or more heavy chain framework sequence (i.e. the FR1, FR2, FR3 and/or FR4 sequence) of SEQ ID NO: 88. In one aspect, the VH comprises an amino acid sequence that is at least about 95%, 96%, 97%, 98%, or 99% identical to the amino acid sequence of SEQ ID NO: 88. In one aspect, the VH comprises an amino acid sequence that is at least about 95% identical to the amino acid sequence of SEQ ID NO: 88. In one aspect, the VH comprises an amino acid sequence that is at least about 98% identical to the amino acid sequence of SEQ ID NO: 88. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to EGFRvIII. In certain aspects, a total of 1 to 10 amino acids have been substituted, inserted and/or deleted in the amino acid sequence of SEQ ID NO: 88. In certain aspects, substitutions, insertions, or deletions occur in regions outside the CDRs (i.e., in the FRs). In one aspect, the VH comprises the amino acid sequence of SEQ ID NO: 88. Optionally, the VH comprises the amino acid sequence of SEQ ID NO: 88, including post-translational modifications of that sequence.

In one aspect, the VL of the second (and, where present, third) antigen binding domain comprises one or more light chain framework sequence (i.e. the FR1, FR2, FR3 and/or FR4 sequence) of SEQ ID NO: 92. In one aspect, the VL comprises an amino acid sequence that is at least about 95%, 96%, 97%, 98%, or 99% identical to the amino acid sequence of SEQ ID NO: 92. In one aspect, the VL comprises an amino acid sequence that is at least about 95% identical to the amino acid sequence of SEQ ID NO: 92. In one aspect, the VL comprises an amino acid sequence that is at least about 98% identical to the amino acid sequence of SEQ ID NO: 92. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to EGFRvIII. In certain aspects, a total of 1 to 10 amino acids have been substituted, inserted and/or deleted in the amino acid sequence of SEQ ID NO: 92. In certain aspects, substitutions, insertions, or deletions occur in regions outside the CDRs (i.e., in the FRs). In one aspect, the VL comprises the amino acid sequence of SEQ ID NO: 92. Optionally, the VL comprises the amino acid sequence of SEQ ID NO: 92, including post-translational modifications of that sequence.

In one aspect, the VH of the second (and, where present, third) antigen binding domain comprises an amino acid sequence that is at least about 95%, 96%, 97%, 98%, or 99% identical to the amino acid sequence of SEQ ID NO: 88, and the VL of the second (and, where present, third) antigen binding domain comprises an amino acid sequence that is at least about 95%, 96%, 97%, 98%, or 99% identical to the amino acid sequence of SEQ ID NO: 92. In one aspect, the VH comprises the amino acid sequence of SEQ ID NO: 88 and the VL comprises the amino acid sequence of SEQ ID NO: 92.

In a further aspect, the second (and, where present, third) antigen binding domain comprises a VH comprising the sequence of SEQ ID NO: 88 and a VL comprising the sequence of SEQ ID NO: 92.

In a further aspect, the second (and, where present, third) antigen binding domain comprises a VH sequence of SEQ ID NO: 88 and a VL sequence of SEQ ID NO: 92.

In another aspect, the second (and, where present, third) antigen binding domain comprises a VH comprising the heavy chain CDR sequences of the VH of SEQ ID NO: 88, and a VL comprising the light chain CDR sequences of the VL of SEQ ID NO: 92.

In a further aspect, the second (and, where present, third) antigen binding domain comprises the HCDR1, HCDR2 and HCDR3 amino acid sequences of the VH of SEQ ID NO: 88 and the LCDR1, LCDR2 and LCDR3 amino acid sequences of the VL of SEQ ID NO: 92.

In one aspect, the VH of the second (and, where present, third) antigen binding domain comprises the heavy chain CDR sequences of the VH of SEQ ID NO: 88 and a framework of at least 95%, 96%, 97%, 98% or 99% sequence identity to the framework sequence of the VH of SEQ ID NO: 88. In one aspect, the VH comprises the heavy chain CDR sequences of the VH of SEQ ID NO: 88 and a framework of at least 95% sequence identity to the framework sequence of the VH of SEQ ID NO: 88. In another aspect, the VH comprises the heavy chain CDR sequences of the VH of SEQ ID NO: 88 and a framework of at least 98% sequence identity to the framework sequence of the VH of SEQ ID NO: 88.

In one aspect, the VL of the second (and, where present, third) antigen binding domain comprises the light chain CDR sequences of the VL of SEQ ID NO: 92 and a framework of at least 95%, 96%, 97%, 98% or 99% sequence identity to the framework sequence of the VL of SEQ ID NO: 92. In one aspect, the VL comprises the light chain CDR sequences of the VL of SEQ ID NO: 92 and a framework of at least 95% sequence identity to the framework sequence of the VL of SEQ ID NO: 92. In another aspect, the VL comprises the light chain CDR sequences of the VL of SEQ ID NO: 92 and a framework of at least 98% sequence identity to the framework sequence of the VL of SEQ ID NO: 92.

In alternative aspects, the second (and, where present, third) antigen binding domain comprises a VH sequence as in any of the aspects provided in this section above in relation to EGFRvIII, and a VL sequence as in any of the aspects provided in this section above in relation to EGFRvIII, but based on the following sequences (ordered in rows) instead of SEQ ID NOs 85 (HCDR1), 86 (HCDR2), 87 (HCDR3), 88 (VH), 89 (LCDR1), 90 (LCDR2), 91 (LCDR3) and 92 (VL):

| HCDR1 | HCDR2 | HCDR3 | VH | LCDR1 | LCDR2 | LCDR3 | VL |
|---|---|---|---|---|---|---|---|
| SEQ ID NO: 37 | SEQ ID NO: 38 | SEQ ID NO: 39 | SEQ ID NO: 40 | SEQ ID NO: 41 | SEQ ID NO: 42 | SEQ ID NO: 43 | SEQ ID NO: 44 |
| SEQ ID NO: 45 | SEQ ID NO: 46 | SEQ ID NO: 47 | SEQ ID NO: 48 | SEQ ID NO: 49 | SEQ ID NO: 50 | SEQ ID NO: 51 | SEQ ID NO: 52 |
| SEQ ID NO: 53 | SEQ ID NO: 54 | SEQ ID NO: 55 | SEQ ID NO: 56 | SEQ ID NO: 57 | SEQ ID NO: 58 | SEQ ID NO: 59 | SEQ ID NO: 60 |
| SEQ ID NO: 61 | SEQ ID NO: 62 | SEQ ID NO: 63 | SEQ ID NO: 64 | SEQ ID NO: 65 | SEQ ID NO: 66 | SEQ ID NO: 67 | SEQ ID NO: 68 |
| SEQ ID NO: 69 | SEQ ID NO: 70 | SEQ ID NO: 71 | SEQ ID NO: 72 | SEQ ID NO: 73 | SEQ ID NO: 74 | SEQ ID NO: 75 | SEQ ID NO: 76 |
| SEQ ID NO: 77 | SEQ ID NO: 78 | SEQ ID NO: 79 | SEQ ID NO: 80 | SEQ ID NO: 81 | SEQ ID NO: 82 | SEQ ID NO: 83 | SEQ ID NO: 84 |
| SEQ ID NO: 93 | SEQ ID NO: 94 | SEQ ID NO: 95 | SEQ ID NO: 96 | SEQ ID NO: 97 | SEQ ID NO: 98 | SEQ ID NO: 99 | SEQ ID NO: 100 |
| SEQ ID NO: 101 | SEQ ID NO: 102 | SEQ ID NO: 103 | SEQ ID NO: 104 | SEQ ID NO: 105 | SEQ ID NO: 106 | SEQ ID NO: 107 | SEQ ID NO: 108 |

In one aspect, the second (and, where present, third) antigen binding domain comprises a VH sequence as in any of the aspects provided in this section above, and a VL sequence as in any of the aspects provided in this section above.

Anti-TYRP-1 and Anti-EGFRvIII Antibodies

The invention also provides an antibody that binds to TYRP-1, comprising a VH sequence as in any of the aspects provided in this section above in relation to TYRP-1, and a VL sequence as in any of the aspects provided in this section above in relation to TYRP-1 (for example, an antibody that binds to TYRP-1 comprising a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21; or an antibody that binds to TYRP-1 comprising a VH comprising the sequence of SEQ ID NO: 18 and a VL comprising the sequence of SEQ ID NO: 22).

The invention also provides an antibody that binds to EGFRvIII, comprising a VH sequence as in any of the aspects provided in this section above in relation to EGFRvIII, and a VL sequence as in any of the aspects provided in this section above in relation to EGFRvIII (for example, an antibody that binds to EGFRvIII comprising a heavy chain variable region (VH) comprising a heavy chain complementary determining region (HCDR) 1 of SEQ ID NO: 85, a HCDR 2 of SEQ ID NO: 86, and a HCDR 3 of SEQ ID NO: 87, and a light chain variable region (VL) comprising a light chain complementarity determining region (LCDR) 1 of SEQ ID NO: 89, a LCDR 2 of SEQ ID NO: 90 and a LCDR 3 of SEQ ID NO: 91; or an antibody that binds to TYRP-1 comprising a VH comprising the sequence of SEQ ID NO: 88 and a VL comprising the sequence of SEQ ID NO: 92).

In a further aspect, the antibodies that bind to TYRP-1 or EGFRvIII according to any of the above aspects may incorporate any of the features, singly or in combination, as described in relation to the antibody that binds to CD3 (unless clearly specific to the anti-CD3 antibody, such as the binding sequences).

c) Charge Modifications

The (multispecific) antibody of the invention may comprise amino acid substitutions in Fab molecules comprised therein which are particularly efficient in reducing mispairing of light chains with non-matching heavy chains (Bence-Jones-type side products), which can occur in the production of Fab-based multispecific antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired (multispecific) antibody compared to undesired side products, in particular Bence Jones-type side products occurring in multispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some aspects wherein the first and the second (and, where present, third) antigen binding domain of the (multispecific) antibody are both Fab molecules, and in one of the antigen binding domains (particularly the first antigen binding domain) the variable domains VL and VH of the Fab light chain and the Fab heavy chain are replaced by each other, i) in the constant domain CL of the second (and, where present, third) antigen binding domain the amino acid at position 124 is substituted by a positively charged amino acid (numbering according to Kabat), and wherein in the constant domain CH1 of the second (and, where present, third) antigen binding domain the amino acid at position 147 or the amino acid at position 213 is substituted by a negatively charged amino acid (numbering according to Kabat EU index); or ii) in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index).

The (multispecific) antibody does not comprise both modifications mentioned under i) and ii). The constant domains CL and CH1 of the antigen binding domain having the VH/VL exchange are not replaced by each other (i.e. remain unexchanged).

In a more specific aspect, i) in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 or the amino acid at position 213 is substituted independently by glutamic acid (E), or aspartic acid (D) (numbering according to Kabat EU index); or ii) in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In one such aspect, in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 or the amino acid at position 213 is substituted independently by glutamic acid (E), or aspartic acid (D) (numbering according to Kabat EU index).

In a further aspect, in the constant domain CL of the second (and, where present, third) antigen binding domain the amino acid at position 124 is substituted independently by lysine (K), arginine (R) or histidine (H) (numbering according to Kabat), and in the constant domain CH1 of the second (and, where present, third) antigen binding domain the amino acid at position 147 is substituted independently by glutamic acid (E), or aspartic acid (D) (numbering according to Kabat EU index).

In a preferred aspect, in the constant domain CL of the second (and, where present, third) antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more preferred aspect, in the constant domain CL of the second (and, where present, third) antigen binding domain the amino acid at position 124 is substituted by lysine (K) (numbering according to Kabat) and the amino acid at position 123 is substituted by lysine (K) (numbering according to Kabat), and in the constant domain CH1 of the second (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In an even more preferred aspect, in the constant domain CL of the second (and, where present, third) antigen binding domain the amino acid at position 124 is substituted by lysine (K) (numbering according to Kabat) and the amino acid at position 123 is substituted by arginine (R) (numbering according to Kabat), and in the constant domain CH1 of the second (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In preferred aspects, if amino acid substitutions according to the above aspects are made in the constant domain CL and the constant domain CH1 of the second (and, where present, third) antigen binding domain, the constant domain CL of the second (and, where present, third) antigen binding domain is of kappa isotype.

Alternatively, the amino acid substitutions according to the above aspects may be made in the constant domain CL and the constant domain CH1 of the first antigen binding domain instead of in the constant domain CL and the constant domain CH1 of the second (and, where present, third) antigen binding domain. In preferred such aspects, the constant domain CL of the first antigen binding domain is of kappa isotype.

Accordingly, in one aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In a further aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index).

In still another aspect, in the constant domain CL of the first antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, in the constant domain CL of the first antigen binding domain the amino acid at position 124 is substituted by lysine (K) (numbering according to Kabat) and the amino acid at position 123 is substituted by lysine (K) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In another aspect, in the constant domain CL of the first antigen binding domain the amino acid at position 124 is substituted by lysine (K) (numbering according to Kabat) and the amino acid at position 123 is substituted by arginine (R) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In a preferred aspect, the (multispecific) antibody of the invention comprises (a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10, and (b) a second and optionally a third antigen binding domain that binds to a second antigen; wherein in the constant domain CL of the second (and, where present, third) antigen binding domain the amino acid at position 124 is substituted independently by lysine (K), arginine (R) or histidine (H) (numbering according to Kabat) (in a preferred aspect independently by lysine (K) or arginine (R)) and the amino acid at position 123 is substituted independently by lysine (K), arginine (R) or histidine (H) (numbering according to Kabat) (in a preferred aspect independently by lysine (K) or arginine (R)), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

d) Multispecific Antibody Formats

The (multispecific) antibody according to the present invention can have a variety of configurations. Exemplary configurations are depicted in FIG. 1.

In preferred aspects, the antigen binding domains comprised in the (multispecific) antibody are Fab molecules. In such aspects, the first, second, third etc. antigen binding domain may be referred to herein as first, second, third etc. Fab molecule, respectively.

In one aspect, the first and the second antigen binding domain of the (multispecific) antibody are fused to each other, optionally via a peptide linker. In preferred aspects, the first and the second antigen binding domain are each a Fab molecule. In one such aspect, the first antigen binding domain is fused at the C-terminus of the Fab heavy chain to the N-terminus of the Fab heavy chain of the second antigen binding domain. In another such aspect, the second antigen binding domain is fused at the C-terminus of the Fab heavy chain to the N-terminus of the Fab heavy chain of the first antigen binding domain. In aspects wherein either (i) the first antigen binding domain is fused at the C-terminus of the Fab heavy chain to the N-terminus of the Fab heavy chain of the second antigen binding domain or (ii) the second antigen binding domain is fused at the C-terminus of the Fab heavy chain to the N-terminus of the Fab heavy chain of the first antigen binding domain, additionally the Fab light chain of the first antigen binding domain and the Fab light chain of the second antigen binding domain may be fused to each other, optionally via a peptide linker.

A (multispecific) antibody with a single antigen binding domain (such as a Fab molecule) capable of specific binding to a second antigen, e.g. a target cell antigen such as TYRP-1 or EGFRvIII, (for example as shown in FIG. 1A, FIG. 1D, FIG. 1G, FIG. 1H, FIG. 1K, FIG. 1L) is useful, particularly in cases where internalization of the second antigen is to be expected following binding of a high affinity antigen binding domain. In such cases, the presence of more than one antigen binding domain specific for the second antigen may enhance internalization of the second antigen, thereby reducing its availability.

In other cases, however, it will be advantageous to have a (multispecific) antibody comprising two or more antigen binding domains (such as Fab molecules) specific for a second antigen, e.g. a target cell antigen (see examples shown in FIG. 1B, FIG. 1C, FIG. 1E, FIG. 1F, FIG. 1I, FIG. 1J, FIG. 1M or FIG. 1N), for example to optimize targeting to the target site or to allow crosslinking of target cell antigens.

Accordingly, in preferred aspects, the (multispecific) antibody according to the present invention comprises a third antigen binding domain.

In one aspect, the third antigen binding domain binds to the second antigen, e.g. a target cell antigen such as TYRP-1 or EGFRvIII. In one aspect, the third antigen binding domain is a Fab molecule.

In one aspect, the third antigen domain is identical to the second antigen binding domain.

In some aspects, the third and the second antigen binding domain are each a Fab molecule and the third antigen binding domain is identical to the second antigen binding domain. Thus, in these aspects, the second and the third antigen binding domain comprise the same heavy and light chain amino acid sequences and have the same arrangement of domains (i.e. conventional or crossover). Furthermore, in these aspects, the third antigen binding domain comprises the same amino acid substitutions, if any, as the second antigen binding domain. For example, the amino acid substitutions described herein as "charge modifications" will be made in the constant domain CL and the constant domain CH1 of each of the second antigen binding domain and the third antigen binding domain. Alternatively, said amino acid substitutions may be made in the constant domain CL and the constant domain CH1 of the first antigen binding domain (which in preferred aspects is also a Fab molecule), but not in the constant domain CL and the constant domain CH1 of the second antigen binding domain and the third antigen binding domain. Like the second antigen binding domain, the third antigen binding domain preferably is a conventional Fab molecule. Aspects wherein the second and the third antigen binding domains are crossover Fab molecules (and the first antigen binding domain is a conventional Fab molecule) are, however, also contemplated. Thus, in preferred aspects, the second and the third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other aspects, the second and the third antigen binding domains are each a crossover Fab molecule and the first antigen binding domain is a conventional Fab molecule.

If a third antigen binding domain is present, in a preferred aspect the first antigen domain binds to CD3, and the second and third antigen binding domain bind to a second antigen, particularly a target cell antigen, such as TYRP-1 or EGFRvIII.

In preferred aspects, the (multispecific) antibody of the invention comprises an Fc domain composed of a first and a second subunit. The first and the second subunit of the Fc domain are capable of stable association.

The (multispecific) antibody according to the invention can have different configurations, i.e. the first, second (and optionally third) antigen binding domain may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some aspects, the first and the second antigen binding domain are each a Fab molecule and the first antigen binding domain is fused at the C-terminus of the Fab heavy chain to the N-terminus of the first or the second subunit of the Fc domain. In such aspects, the second antigen binding domain may be fused at the C-terminus of the Fab heavy chain to the N-terminus of the Fab heavy chain of the first antigen binding domain or to the N-terminus of the other one of the subunits of the Fc domain. In preferred such aspects, the second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other.

In other such aspects, the second antigen binding domain is a crossover Fab molecule and the first antigen binding domain is a conventional Fab molecule.

In one aspect, the first and the second antigen binding domain are each a Fab molecule, the first antigen binding domain is fused at the C-terminus of the Fab heavy chain to the N-terminus of the first or the second subunit of the Fc domain, and the second antigen binding domain is fused at the C-terminus of the Fab heavy chain to the N-terminus of the Fab heavy chain of the first antigen binding domain. In a specific aspect, the (multispecific) antibody essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIG. 1G and FIG. 1K (with the first antigen binding domain in these examples being a VH/VL crossover Fab molecule). Optionally, the Fab light chain of the first Fab molecule and the Fab light chain of the second Fab molecule may additionally be fused to each other.

In another aspect, the first and the second antigen binding domain are each a Fab molecule and the first and the second antigen binding domain are each fused at the C-terminus of the Fab heavy chain to the N-terminus of one of the subunits of the Fc domain. In a specific aspect, the (multispecific) antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D (in these examples with the first antigen binding domain being a VH/VL crossover Fab molecule and the second antigen binding domain being a conventional Fab molecule). The first and the second Fab molecule may be fused to the Fc domain directly or through a peptide linker. In a preferred aspect the first and the second Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain.

In some aspects, the first and the second antigen binding domain are each a Fab molecule and the second antigen binding domain is fused at the C-terminus of the Fab heavy chain to the N-terminus of the first or the second subunit of the Fc domain. In such aspects, the first antigen binding domain may be fused at the C-terminus of the Fab heavy chain to the N-terminus of the Fab heavy chain of the first antigen binding domain or (as described above) to the N-terminus of the other one of the subunits of the Fc domain. In preferred such aspects, said second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said second antigen binding domain is a crossover Fab molecule and the first antigen binding domain is a conventional Fab molecule.

In one aspect, the first and the second antigen binding domain are each a Fab molecule, the second antigen binding domain is fused at the C-terminus of the Fab heavy chain to the N-terminus of the first or the second subunit of the Fc domain, and the first antigen binding domain is fused at the C-terminus of the Fab heavy chain to the N-terminus of the Fab heavy chain of the second antigen binding domain. In a specific aspect, the (multispecific) antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1H and FIG. 1L (in these examples with the first antigen binding domain being a VH/VL crossover Fab molecule and the second antigen binding domain being a conventional Fab molecule). Optionally, the Fab light chain of the first Fab molecule and the Fab light chain of the second Fab molecule may additionally be fused to each other.

In some aspects, a third antigen binding domain, particularly a third Fab molecule, is fused at the C-terminus of the Fab heavy chain to the N-terminus of the first or second subunit of the Fc domain. In preferred such aspects, said second and third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other.

In other such aspects, said second and third antigen binding domains are each a crossover Fab molecule and the first antigen binding domain is a conventional Fab molecule.

In a preferred such aspect, the first and the third antigen binding domain are each fused at the C-terminus of the Fab heavy chain to the N-terminus of one of the subunits of the Fc domain, and the second antigen binding domain is fused at the C-terminus of the Fab heavy chain to the N-terminus of the Fab heavy chain of the first Fab molecule. In a specific aspect, the (multispecific) antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1B and FIG. 1E (in these examples with the first antigen binding domain being a VH/VL crossover Fab molecule, and the second and the third antigen binding domain being a conventional Fab molecule), and FIG. 1J and FIG. 1N (in these examples with the first antigen binding domain being a conventional Fab molecule, and the second and the third antigen binding domain being a VH/VL crossover Fab molecule). The first and the third Fab molecule may be fused to the Fc domain directly or through a peptide linker. In a preferred aspect, the first and the third Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In another such aspect, the second and the third antigen binding domain are each fused at the C-terminus of the Fab heavy chain to the N-terminus of one of the subunits of the Fc domain, and the first antigen binding domain is fused at the C-terminus of the Fab heavy chain to the N-terminus of the Fab heavy chain of the second antigen binding domain. In a specific aspect, the (multispecific) antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1C and FIG. 1F (in these examples with the first antigen binding domain being a VH/VL crossover Fab molecule, and the second and the third antigen binding domain being a conventional Fab molecule) and in FIG. 1I and FIG. 1M (in these examples with the first antigen binding domain being a conventional Fab molecule, and the second and the third antigen binding domain being a VH/VL crossover Fab molecule). The second and the third Fab molecule may be fused to the Fc domain directly or through a peptide linker. In a preferred aspect the second and the third Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the (multispecific) antibody wherein a Fab molecule is fused at the C-terminus of the Fab heavy chain to the N-terminus of each of the subunits of the Fc domain through an immunoglobulin hinge region, the two Fab molecules, the hinge regions and the Fc domain essentially form an immunoglobulin molecule. In a preferred aspect the immunoglobulin molecule is an IgG class immunoglobulin. In an even more preferred aspect the immunoglobulin is an $IgG_1$ subclass immunoglobulin. In another aspect the immunoglobulin is an $IgG_4$ subclass immunoglobulin. In a further preferred aspect the immunoglobulin is a human immunoglobulin.

In other aspects the immunoglobulin is a chimeric immunoglobulin or a humanized immunoglobulin. In one aspect, the immunoglobulin comprises a human constant region, particularly a human Fc region.

In some of the (multispecific) antibodies of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the (multispecific) antibody of the invention.

The antigen binding domains may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 123), $(SG_4)_n$ (SEQ ID NO: 124), or $G_4(SG_4)_n$ (SEQ ID NO: 125) peptide linkers. "n" is generally an integer from 1 to 10, typically from 2 to 4. In one aspect said peptide linker has a length of at least 5 amino acids, in one aspect a length of 5 to 100, in a further aspect of 10 to 50 amino acids. In one aspect said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one aspect x=4 and n=2 or 3, in a further aspect x=4 and n=2 (SEQ ID NOs: 127-158). In one aspect said peptide linker is $(G_4S)_2$ (SEQ ID NO: 118). A particularly suitable peptide linker for fusing the Fab light chains of the first and the second Fab molecule to each other is $(G_4S)_2$ (SEQ ID NO: 118). An exemplary peptide linker suitable for connecting the Fab heavy chains of the first and the second Fab fragments comprises the sequence (D)-$(G_4S)_2$ (SEQ ID NOs 118 and 119). Another suitable such linker comprises the sequence $(G_4S)_4$ (SEQ ID NO: 126). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-CH2-CH3(-CH4)), and a polypeptide wherein the Fab heavy chain of the second Fab molecule shares a carboxy-terminal peptide bond with an Fc domain subunit ($VH_{(2)}$-$CH1_{(2)}$-CH2-CH3(-CH4)). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In certain aspects the polypeptides are covalently linked, e.g., by a disulfide bond.

In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-CH2-CH3(-CH4)), and a polypeptide wherein the Fab heavy chain of the second Fab molecule shares a carboxy-terminal peptide bond with an Fc domain subunit ($VH_{(2)}$-$CH1_{(2)}$-CH2-CH3(-CH4)). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In certain aspects the polypeptides are covalently linked, e.g., by a disulfide bond.

In some aspects, the (multispecific) antibody comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with an Fc domain subunit ($VL_{(1)}$-$CH1_{(1)}$-$VH_{(2)}$-$CH1_{(2)}$-CH2-CH3(-CH4)). In other aspects, the (multispecific) antibody comprises a polypeptide wherein the Fab heavy chain of the second Fab molecule shares a carboxy-terminal peptide bond with the Fab light chain variable region of the first Fab molecule which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with an Fc domain subunit ($VH_{(2)}$-$CH1_{(2)}$-$VL_{(1)}$-$CH1_{(1)}$-CH2-CH3(-CH4)). In some of these aspects the (multispecific) antibody further comprises a crossover Fab light chain polypeptide of the first Fab molecule, wherein the Fab heavy chain variable region of the first Fab molecule shares a carboxy-terminal peptide bond with the Fab light chain constant region of the first Fab molecule ($VH_{(1)}$-$CL_{(1)}$, and the Fab light chain polypeptide of the second Fab molecule ($VL_{(2)}$-$CL_{(2)}$). In others of these aspects the (multispecific) antibody further comprises a polypeptide wherein the Fab heavy chain variable region of the first Fab molecule shares a carboxy-terminal peptide bond with the Fab light chain constant region of the first Fab molecule which in turn shares a carboxy-terminal peptide bond with the Fab light chain polypeptide of the second Fab molecule ($VH_{(1)}$-$CL_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$, as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In some aspects, the (multispecific) antibody comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with an Fc domain subunit ($VH_{(1)}$-$CL_{(1)}$-$VH_{(2)}$-$CH1_{(2)}$-CH2-CH3(-CH4)). In other aspects, the (multispecific) antibody comprises a polypeptide wherein the Fab heavy chain of the second Fab molecule shares a carboxy-terminal peptide bond with the Fab heavy chain variable region of the first Fab molecule which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CH1_{(2)}$-$VH_{(1)}$-$CL_{(1)}$-CH2-CH3(-CH4)). In some of these aspects the (multispecific) antibody further comprises a crossover Fab light chain polypeptide of the first Fab molecule, wherein the Fab light chain variable region of the first Fab molecule shares a carboxy-terminal peptide bond with the Fab heavy chain constant region of the first Fab molecule ($VL_{(1)}$-$CH1_{(1)}$, and the Fab light chain polypeptide of the second Fab molecule ($VL_{(2)}$-$CL_{(2)}$). In others of these aspects the (multispecific) antibody further comprises a polypeptide wherein the Fab light chain variable region of the first Fab molecule shares a carboxy-terminal peptide bond with the Fab heavy chain constant region of the first Fab molecule which in turn shares a carboxy-terminal peptide bond with the Fab light chain polypeptide of the second Fab molecule ($VL_{(1)}$-$CH1_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$, as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In certain aspects, the (multispecific) antibody does not comprise an Fc domain. In preferred such aspects, said second and, if present, third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said second and, if present, third antigen binding domains are each a crossover Fab molecule and the first antigen binding domain is a conventional Fab molecule.

In one such aspect, the (multispecific) antibody essentially consists of the first and the second antigen binding domain, and optionally one or more peptide linkers, wherein the first and the second antigen binding domain are both Fab molecules and the second antigen binding domain is fused at the C-terminus of the Fab heavy chain to the N-terminus of the Fab heavy chain of the first antigen binding domain. Such a configuration is schematically depicted in FIG. 1O and FIG. 1S (in these examples with the first antigen binding domain being a VH/VL crossover Fab molecule and the second antigen binding domain being a conventional Fab molecule).

In another such aspect, the (multispecific) antibody essentially consists of the first and the second antigen binding domain, and optionally one or more peptide linkers, wherein the first and the second antigen binding domain are both Fab molecules and the first antigen binding domain is fused at the C-terminus of the Fab heavy chain to the N-terminus of the Fab heavy chain of the second antigen binding domain. Such a configuration is schematically depicted in FIG. 1P and FIG. 1T (in these examples with the first antigen binding domain being a VH/VL crossover Fab molecule and the second antigen binding domain being a conventional Fab molecule).

In some aspects, the second Fab molecule is fused at the C-terminus of the Fab heavy chain to the N-terminus of the Fab heavy chain of the first Fab molecule, and the (multispecific) antibody further comprises a third antigen binding domain, particularly a third Fab molecule, wherein said third Fab molecule is fused at the C-terminus of the Fab heavy chain to the N-terminus of the Fab heavy chain of the second Fab molecule. In certain such aspects, the (multispecific) antibody essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the C-terminus of the Fab heavy chain to the N-terminus of the Fab heavy chain of the second Fab molecule. Such a configuration is schematically depicted in FIG. 1Q and FIG. 1U (in these examples with the first antigen binding domain being a VH/VL crossover Fab molecule and the second and the third antigen binding domain each being a conventional Fab molecule), or FIG. 1X and FIG. 1Z (in these examples with the first antigen binding domain being a conventional Fab molecule and the second and the third antigen binding domain each being a VH/VL crossover Fab molecule).

In some aspects, the first Fab molecule is fused at the C-terminus of the Fab heavy chain to the N-terminus of the Fab heavy chain of the second Fab molecule, and the (multispecific) antibody further comprises a third antigen binding domain, particularly a third Fab molecule, wherein said third Fab molecule is fused at the N-terminus of the Fab heavy chain to the C-terminus of the Fab heavy chain of the second Fab molecule. In certain such aspects, the (multispecific) antibody essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the N-terminus of the Fab heavy chain to the C-terminus of the Fab heavy chain of the second Fab molecule. Such a configuration is schematically depicted in FIG. 1R and FIG. 1V (in these examples with the first antigen binding domain being a VH/VL crossover Fab molecule and the second and the third antigen binding domain each being a conventional Fab molecule), or FIG. 1W and FIG. 1Y (in these examples with the first antigen binding domain being a conventional Fab molecule and the second and the third antigen binding domain each being a VH/VL crossover Fab molecule).

In certain aspects the (multispecific) antibody according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region) ($VH_{(2)}$-$CH1_{(2)}$-$VL_{(1)}$-$CH1_{(1)}$. In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule ($VL_{(1)}$-$CH1_{(1)}$-$VH_{(2)}$-$CH1_{(2)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$ and the Fab light chain polypeptide of the second Fab molecule ($VL_{(2)}$-$CL_{(2)}$).

In certain aspects the (multispecific) antibody according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region) ($VH_{(2)}$-$CH1_{(2)}$-$VH_{(1)}$-$CL_{(1)}$. In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$ and the Fab light chain polypeptide of the second Fab molecule ($VL_{(2)}$-$CL_{(2)}$).

In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule ($VH_{(1)}$-$CL_{(1)}$-$VH_{(2)}$-$CH1_{(2)}$). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab heavy chain of a third Fab molecule shares a carboxy-terminal peptide bond with the Fab heavy chain of the second Fab molecule, which in turn shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region) ($VH_{(3)}$-$CH1_{(3)}$-$VH_{(2)}$-$CH1_{(2)}$-$VL_{(1)}$-$CH1_{(1)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$).

In certain aspects the (multispecific) antibody according to the invention comprises a polypeptide wherein the Fab heavy chain of a third Fab molecule shares a carboxy-terminal peptide bond with the Fab heavy chain of the second Fab molecule, which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region) ($VH_{(3)}$-$CH1_{(3)}$-$VH_{(2)}$-$CH1_{(2)}$-$VH_{(1)}$-$CL_{(0)}$. In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$).

In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with the Fab heavy chain of a third Fab molecule ($VL_{(1)}$-$CH1_{(1)}$-$VH_{(2)}$-$CH1_{(2)}$-$VH_{(3)}$-$CH1_{(3)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$).

In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with the Fab heavy chain of a third Fab molecule ($VH_{(1)}$-$CL_{(1)}$-$VH_{(2)}$-$CH1_{(2)}$-$VH_{(3)}$-$CH1_{(3)}$). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$).

In certain aspects the (multispecific) antibody according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1(i)$-$VL_{(2)}$-$CH1_{(2)}$-$VL_{(3)}$-$CH1_{(3)}$). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(0)}$). In some aspects the (multispecific) antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain aspects the (multispecific) antibody according to the invention comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$-$VH_{(3)}$-$CL_{(3)}$). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some aspects the (multispecific) antibody further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In certain aspects the (multispecific) antibody according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule (VL$_{(3)}$-CH1$_{(3)}$-VL$_{(2)}$-CH1$_{(2)}$-VH$_{(1)}$-CH1$_{(0)}$). In some aspects the (multispecific) antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(0)}$). In some aspects the (multispecific) antibody further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain aspects the (multispecific) antibody according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule (VH$_{(3)}$-CL$_{(3)}$-VH$_{(2)}$-CL$_{(2)}$-VH$_{(1)}$-CH1$_{(1)}$. In some aspects the (multispecific) antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$. In some aspects the (multispecific) antibody further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In one aspect, the invention provides a (multispecific) antibody comprising a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly TYRP-1 or EGFRvIII, wherein the second antigen binding domain is a (conventional) Fab molecule;

c) an Fc domain composed of a first and a second subunit; wherein (i) the first antigen binding domain under a) is fused at the C-terminus of the Fab heavy chain to the N-terminus of the Fab heavy chain of the second antigen binding domain under b), and the second antigen binding domain under b) is fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) is fused at the C-terminus of the Fab heavy chain to the N-terminus of one of the subunits of the Fc domain under c).

In a preferred aspect, the invention provides a (multispecific) antibody comprising a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second and a third antigen binding domain that bind to a second antigen, particularly a target cell antigen, more particularly TYRP-1 or EGFRvIII, wherein the second and the third antigen binding domain are each a (conventional) Fab molecule; and c) an Fc domain composed of a first and a second subunit; wherein (i) the first antigen binding domain under a) is fused at the C-terminus of the Fab heavy chain to the N-terminus of the Fab heavy chain of the second antigen binding domain under b), and the second antigen binding domain under b) and the third antigen binding domain under b) are each fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In another aspect, the invention provides a (multispecific) antibody comprising a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly TYRP-1 or EGFRvIII, wherein the second antigen binding domain is a (conventional) Fab molecule;

c) an Fc domain composed of a first and a second subunit; wherein (i) the first antigen binding domain under a) and the second antigen binding domain under b) are each fused at the C-terminus of the Fab heavy chain to the N-terminus of one of the subunits of the Fc domain under c).

In all of the different configurations of the (multispecific) antibody according to the invention, the amino acid substitutions ("charge modifications") described herein, if present, may either be in the CH1 and CL domains of the second and (if present) the third antigen binding domain/Fab molecule, or in the CH1 and CL domains of the first antigen binding domain/Fab molecule. Preferably, they are in the CH1 and CL domains of the second and (if present) the third antigen binding domain/Fab molecule. In accordance with the concept of the invention, if amino acid substitutions as described herein are made in the second (and, if present, the third) antigen binding domain/Fab molecule, no such amino acid substitutions are made in the first antigen binding domain/Fab molecule. Conversely, if amino acid substitutions as described herein are made in the first antigen binding domain/Fab molecule, no such amino acid substitutions are made in the second (and, if present, the third) antigen binding domain/Fab molecule. Amino acid substitutions are preferably made in (multispecific) antibodies comprising a Fab molecule wherein the variable domains VL and VH1 of the Fab light chain and the Fab heavy chain are replaced by each other.

In preferred aspects of the (multispecific) antibody according to the invention, particularly wherein amino acid substitutions as described herein are made in the second (and, if present, the third) antigen binding domain/Fab molecule, the constant domain CL of the second (and, if present, the third) Fab molecule is of kappa isotype. In other aspects of the (multispecific) antibody according to the invention, particularly wherein amino acid substitutions as described herein are made in the first antigen binding domain/Fab molecule, the constant domain CL of the first antigen binding domain/Fab molecule is of kappa isotype. In some aspects, the constant domain CL of the second (and, if present, the third) antigen binding domain/Fab molecule and the constant domain CL of the first antigen binding domain/Fab molecule are of kappa isotype.

In one aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly TYRP-1 or EGFRvIII, wherein the second antigen binding domain is a (conventional) Fab molecule;

c) an Fc domain composed of a first and a second subunit;

wherein in the constant domain CL of the second antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding domain under a) is fused at the C-terminus of the Fab heavy chain to the N-terminus of the Fab heavy chain of the second antigen binding domain under b), and the second antigen binding domain under b) is fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) is fused at the C-terminus of the Fab heavy chain to the N-terminus of one of the subunits of the Fc domain under c).

In a preferred aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second and a third antigen binding domain that bind to a second antigen, particularly a target cell antigen, more particularly TYRP-1 or EGFRvIII, wherein the second and third antigen binding domain are each a (conventional) Fab molecule; and c) an Fc domain composed of a first and a second subunit;

wherein in the constant domain CL of the second antigen binding domain under b) and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) and the third antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding domain under a) is fused at the C-terminus of the Fab heavy chain to the N-terminus of the Fab heavy chain of the second antigen binding domain under b), and the second antigen binding domain under b) and the third antigen binding domain under b) are each fused at the C-terminus of the Fab heavy chain to the N-terminus of one of the subunits of the Fc domain under c), or (ii) the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In another aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second antigen binding domain that binds to a second antigen, particularly a target cell antigen, more particularly TYRP-1 or EGFRvIII, wherein the second antigen binding domain is a (conventional) Fab molecule;

c) an Fc domain composed of a first and a second subunit;

wherein in the constant domain CL of the second antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein the first antigen binding domain under a) and the second antigen binding domain under b) are each fused at the C-terminus of the Fab heavy chain to the N-terminus of one of the subunits of the Fc domain under c).

According to any of the above aspects, components of the (multispecific) antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, (G4S)$_n$ (SEQ ID NO: 123), (SG$_4$)$_n$ (SEQ ID NO: 124), or G$_4$(SG$_4$)$_n$ (SEQ ID NO: 125) peptide linkers, wherein n is generally an integer from 1 to 10, typically from 2 to 4.

In a preferred aspect, the invention provides a (multispecific) antibody comprising a) a first antigen binding domain that binds CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second and a third antigen binding domain that bind to TYRP-1, wherein the second and the third antigen binding domain are each a (conventional) Fab molecule, and comprise a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21;

c) an Fc domain composed of a first and a second subunit;

wherein in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a further preferred aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region comprising the amino acid sequence of SEQ ID NO: 7 and a light chain variable region comprising the amino acid sequence of SEQ ID NO: 11;

b) a second and a third antigen binding domain that bind to TYRP-1, wherein the second and the third antigen binding domain are each a (conventional) Fab molecule, and comprise a heavy chain variable region comprising the amino acid sequence of SEQ ID NO: 18 and a light chain variable region comprising the amino acid sequence of SEQ ID NO: 22;

c) an Fc domain composed of a first and a second subunit;

wherein in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a preferred aspect, the invention provides a (multispecific) antibody comprising a) a first antigen binding domain that binds CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;

b) a second and a third antigen binding domain that bind to EGFRvIII, wherein the second and the third antigen binding domain are each a (conventional) Fab molecule, and comprise a heavy chain variable region (VH) comprising a heavy chain complementary determining region (HCDR) 1 of SEQ ID NO: 85, a HCDR 2 of SEQ ID NO:86, and a HCDR 3 of SEQ ID NO: 87, and a light chain variable region (VL) comprising a light chain complementarity determining region (LCDR) 1 of SEQ ID NO: 89, a LCDR 2 of SEQ ID NO: 90 and a LCDR 3 of SEQ ID NO: 91;

c) an Fc domain composed of a first and a second subunit; wherein in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a further preferred aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region comprising the amino acid sequence of SEQ ID NO: 7 and a light chain variable region comprising the amino acid sequence of SEQ ID NO: 11;

b) a second and a third antigen binding domain that bind to EGFRvIII, wherein the second and the third antigen binding domain are each a (conventional) Fab molecule, and comprise a heavy chain variable region comprising the amino acid sequence of SEQ ID NO: 88 and a light chain variable region comprising the amino acid sequence of SEQ ID NO: 92;

c) an Fc domain composed of a first and a second subunit; wherein in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In one aspect according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further aspect according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further aspect according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further aspect according to these aspects of the invention, the Fc domain is a human IgG$_1$ Fc domain.

In a preferred specific aspect, the (multispecific) antibody comprises a polypeptide comprising an amino acid sequence that is at least 95%, 96%, 97%, 98%, or 99% identical to the sequence of SEQ ID NO: 23, a polypeptide comprising an amino acid sequence that is at least 95%, 96%, 97%, 98%, or 99% identical to the sequence of SEQ ID NO: 24, a polypeptide (particularly two polypeptides) comprising an amino acid sequence that is at least 95%, 96%, 97%, 98%, or 99% identical to the sequence of SEQ ID NO: 25, and a polypeptide comprising an amino acid sequence that is at least 95%, 96%, 97%, 98%, or 99% identical to the sequence of SEQ ID NO: 27. In a further preferred specific aspect, the (multispecific) antibody comprises a polypeptide comprising the amino acid sequence of SEQ ID NO: 23, a polypeptide comprising the amino acid sequence of SEQ ID NO: 24, a polypeptide (particularly two polypeptides) comprising the amino acid sequence of SEQ ID NO: 25 and a polypeptide comprising the amino acid sequence of SEQ ID NO: 27.

In one aspect the invention provides a (multispecific) antibody that binds to CD3 and TYRP-1, comprising a polypeptide comprising an amino acid sequence that is at least 95%, 96%, 97%, 98%, or 99% identical to the sequence of SEQ ID NO: 23, a polypeptide comprising an amino acid sequence that is at least 95%, 96%, 97%, 98%, or 99% identical to the sequence of SEQ ID NO: 24, a polypeptide (particularly two polypeptides) comprising an amino acid sequence that is at least 95%, 96%, 97%, 98%, or 99% identical to the sequence of SEQ ID NO: 25, and a polypeptide comprising an amino acid sequence that is at least 95%, 96%, 97%, 98%, or 99% identical to the sequence of SEQ ID NO: 27. In one aspect the invention provides a (multispecific) antibody that binds to CD3 and TYRP-1, comprising a polypeptide comprising the amino acid sequence of SEQ ID NO: 23, a polypeptide comprising the amino acid sequence of SEQ ID NO: 24, a polypeptide (particularly two polypeptides) comprising the amino acid sequence of SEQ ID NO: 25 and a polypeptide comprising the amino acid sequence of SEQ ID NO: 27.

In a further preferred specific aspect, the (multispecific) antibody comprises a polypeptide comprising an amino acid sequence that is at least 95%, 96%, 97%, 98%, or 99% identical to the sequence of SEQ ID NO: 109, a polypeptide comprising an amino acid sequence that is at least 95%, 96%, 97%, 98%, or 99% identical to the sequence of SEQ ID NO: 110, a polypeptide (particularly two polypeptides) comprising an amino acid sequence that is at least 95%, 96%, 97%, 98%, or 99% identical to the sequence of SEQ ID NO: 111, and a polypeptide comprising an amino acid sequence that is at least 95%, 96%, 97%, 98%, or 99% identical to the sequence of SEQ ID NO: 27. In a further particular specific aspect, the (multispecific) antibody comprises a polypeptide comprising the amino acid sequence of SEQ ID NO: 109, a polypeptide comprising the amino acid sequence of SEQ ID NO: 110, a polypeptide (particularly two polypeptides) comprising the amino acid sequence of SEQ ID NO: 111, and a polypeptide comprising the amino acid sequence of SEQ ID NO: 27.

In one aspect the invention provides a (multispecific) antibody that binds to CD3 and EGFRvIII, comprising a polypeptide comprising an amino acid sequence that is at least 95%, 96%, 97%, 98%, or 99% identical to the sequence of SEQ ID NO: 109, a polypeptide comprising an amino acid sequence that is at least 95%, 96%, 97%, 98%, or 99% identical to the sequence of SEQ ID NO: 110, a polypeptide (particularly two polypeptides) comprising an amino acid sequence that is at least 95%, 96%, 97%, 98%, or 99% identical to the sequence of SEQ ID NO: 111, and a polypeptide comprising an amino acid sequence that is at least 95%, 96%, 97%, 98%, or 99% identical to the sequence of SEQ ID NO: 27. In one aspect the invention provides a (multispecific) antibody that binds to CD3 and EGFRvIII, comprising a polypeptide comprising the amino acid sequence of SEQ ID NO: 109, a polypeptide comprising the amino acid sequence of SEQ ID NO: 110, a polypeptide (particularly two polypeptides) comprising the amino acid sequence of SEQ ID NO: 111 and a polypeptide comprising the amino acid sequence of SEQ ID 8. Fc Domain Variants In preferred aspects, the (multispecific) antibody of the invention comprises an Fc domain composed of a first and a second subunit.

The Fc domain of the (multispecific) antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one aspect, the (multispecific) antibody of the invention comprises not more than one Fc domain.

In one aspect, the Fc domain of the (multispecific) antibody is an IgG Fc domain. In a preferred aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further preferred aspect, the Fc domain is a human Fc domain. In an even more preferred aspect, the Fc domain is a human $IgG_1$ Fc domain. An exemplary sequence of a human $IgG_1$ Fc region is given in SEQ ID NO: 117.

a) Fc Domain Modifications Promoting Heterodimerization (Multispecific) antibodies according to the invention comprise different antigen binding domains, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of (multispecific) antibodies in recombinant production, it will thus be advantageous to introduce in the Fc domain of the (multispecific) antibody a modification promoting the association of the desired polypeptides.

Accordingly, in preferred aspects, the Fc domain of the (multispecific) antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291.

Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the (multispecific) antibody which reduce heavy/light chain mispairing and Bence Jones-type side products.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a preferred aspect, in the CH3 domain of the first subunit of the Fc domain of the (multispecific) antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific aspect, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index). In a preferred aspect the antigen binding domain that binds to CD3 is fused (optionally via the second antigen binding domain, which binds to a second antigen, and/or a peptide linker) to the first subunit of the Fc domain (comprising the "knob" modification). Without wishing to be bound by theory, fusion of the antigen binding domain that binds CD3 to the knob-containing subunit of the Fc domain will (further) minimize the generation of antibodies comprising two antigen binding domains that bind to CD3 (steric clash of two knob-containing polypeptides). Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one aspect, the heterodimerization approach described in EP 1870459, is used alternatively. This approach is based on the introduction of charged amino acids with opposite charges at specific amino acid positions in the CH3/CH3 domain interface between the two subunits of the Fc domain. A particular aspect for the (multispecific) antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another aspect, the (multispecific) antibody of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another aspect, the (multispecific) antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said (multispecific) antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one aspect, the heterodimerization approach described in WO 2013/157953 is used alternatively. In one aspect, a first CH3 domain comprises amino acid mutation T366K and a second CH3 domain comprises amino acid mutation L351D (numberings according to Kabat EU index). In a further aspect, the first CH3 domain comprises further amino acid mutation L351K. In a further aspect, the second CH3 domain comprises further an amino acid mutation selected from Y349E, Y349D and L368E (particularly L368E) (numberings according to Kabat EU index).

In one aspect, the heterodimerization approach described in WO 2012/058768 is used alternatively. In one aspect a first CH3 domain comprises amino acid mutations L351Y, Y407A and a second CH3 domain comprises amino acid mutations T366A, K409F. In a further aspect the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further aspect a first CH3 domain comprises amino acid mutations L351Y, Y407A and a second CH3 domain comprises amino acid mutations T366V, K409F. In a further aspect, a first CH3 domain comprises amino acid mutation Y407A and a second CH3 domain comprises amino acid mutations T366A, K409F. In a further aspect, the second CH3 domain further comprises amino acid mutations K392E, T411E, D399R and S400R (numberings according to Kabat EU index). In one aspect, the heterodimerization approach described in WO 2011/143545 is used alternatively, e.g. with the amino acid modification at a position selected from the group consisting of 368 and 409 (numbering according to Kabat EU index).

In one aspect, the heterodimerization approach described in WO 2011/090762, which also uses the knobs-into-holes technology described above, is used alternatively. In one aspect a first CH3 domain comprises amino acid mutation T366W and a second CH3 domain comprises amino acid mutation Y407A. In one aspect, a first CH3 domain comprises amino acid mutation T366Y and a second CH3 domain comprises amino acid mutation Y407T (numberings according to Kabat EU index).

In one aspect, the (multispecific) antibody or its Fc domain is of IgG$_2$ subclass and the heterodimerization approach described in WO 2010/129304 is used alternatively.

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such aspect, a first CH3 domain comprises amino acid substitution of K392 or N392 with a negatively charged amino acid (e.g. glutamic acid (E), or aspartic acid (D), particularly K392D or N392D) and a second CH3 domain comprises amino acid substitution of D399, E356, D356, or E357 with a positively charged amino acid (e.g. lysine (K) or arginine (R), particularly D399K, E356K, D356K, or E357K, and more particularly D399K and E356K). In a further aspect, the first CH3 domain further comprises amino acid substitution of K409 or R409 with a negatively charged amino acid (e.g. glutamic acid (E), or aspartic acid (D), particularly K409D or R409D). In a further aspect the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further aspect, the heterodimerization approach described in WO 2007/147901 is used alternatively. In one aspect, a first CH3 domain comprises amino acid mutations K253E, D282K, and K322D and a second CH3 domain comprises amino acid mutations D239K, E240K, and K292D (numberings according to Kabat EU index).

In still another aspect, the heterodimerization approach described in WO 2007/110205 can be used alternatively.

In one aspect, the first subunit of the Fc domain comprises amino acid substitutions K392D and K409D, and the second subunit of the Fc domain comprises amino acid substitutions D356K and D399K (numbering according to Kabat EU index).

b) Fc Domain Modifications Reducing Fc Receptor Binding and/or Effector Function The Fc domain confers to the (multispecific) antibody favorable pharmacokinetic properties, including a long serum half-life which contributes to good accumulation in the target tissue and a favorable tissue-blood distribution ratio. At the same time it may, however, lead to undesirable targeting of the (multispecific) antibody to cells expressing Fc receptors rather than to the preferred antigen-bearing cells. Moreover, the co-activation of Fc receptor signaling pathways may lead to cytokine release which, in combination with the T cell activating properties and the long half-life of the (multispecific) antibody, results in excessive activation of cytokine receptors and severe side effects upon systemic administration. Activation of (Fc receptor-bearing) immune cells other than T cells may even reduce efficacy of the (multispecific) antibody due to the potential destruction of T cells e.g. by NK cells.

Accordingly, in preferred aspects, the Fc domain of the (multispecific) antibody according to the invention exhibits reduced binding affinity to an Fc receptor and/or reduced effector function, as compared to a native IgG$_1$ Fc domain. In one such aspect the Fc domain (or the (multispecific) antibody comprising said Fc domain) exhibits less than 50%, particularly less than 20%, more particularly less than 10% and most particularly less than 5% of the binding affinity to an Fc receptor, as compared to a native IgG$_1$ Fc domain (or a (multispecific) antibody comprising a native IgG$_1$ Fc domain), and/or less than 50%, particularly less than 20%, more particularly less than 10% and most particularly less than 5% of the effector function, as compared to a native IgG$_1$ Fc domain domain (or a (multispecific) antibody comprising a native IgG$_1$ Fc domain). In one aspect, the Fc domain domain (or the (multispecific) antibody comprising said Fc domain) does not substantially bind to an Fc receptor and/or induce effector function. In a preferred aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa. In one aspect the effector function is one or more selected from the group of CDC, ADCC, ADCP, and cytokine secretion. In a preferred aspect, the effector function is ADCC. In one aspect, the Fc domain domain exhibits substantially similar binding affinity to neonatal Fc receptor (FcRn), as compared to a native IgG$_1$ Fc domain domain. Substantially similar binding to FcRn is achieved when the Fc domain (or the (multispecific) antibody comprising said Fc domain) exhibits greater than about 70%, particularly greater than about 80%, more particularly greater than about 90% of the binding affinity of a native IgG$_1$ Fc domain (or the (multispecific) antibody comprising a native IgG$_1$ Fc domain) to FcRn.

In certain aspects the Fc domain is engineered to have reduced binding affinity to an Fc receptor and/or reduced effector function, as compared to a non-engineered Fc domain. In preferred aspects, the Fc domain of the (multispecific) antibody comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In one aspect, the amino acid mutation reduces the binding affinity of the Fc domain to an Fc receptor by at least 2-fold, at least 5-fold, or at least 10-fold. In aspects where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one aspect the (multispecific) antibody comprising an engineered Fc domain exhibits less than 20%, particularly less than 10%, more particularly less than 5% of the binding affinity to an Fc receptor as compared to a (multispecific) antibody comprising a non-engineered Fc domain. In a preferred aspect, the Fc receptor is an Fcγ receptor. In some aspects, the Fc receptor is a human Fc receptor. In some aspects, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the (multispecific) antibody comprising said Fc domain) exhibits greater than about 70% of the binding affinity of a non-engineered form of the Fc domain (or the (multispecific) antibody comprising said non-engineered form of the Fc domain) to FcRn. The Fc domain, or (multispecific) antibodies of the invention comprising said Fc domain, may exhibit greater than about 80% and even greater than about 90% of such affinity. In certain aspects, the Fc domain of the (multispecific) antibody is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one aspect, the reduced effector function is one or more selected from the group of reduced CDC, reduced ADCC, reduced ADCP, and reduced cytokine secretion. In a preferred aspect, the reduced effector function is reduced ADCC. In one aspect the reduced ADCC is less than 20% of the ADCC induced by a non-engineered Fc domain (or a (multispecific) antibody comprising a non-engineered Fc domain).

In one aspect, the amino acid mutation that reduces the binding affinity of the Fc domain to an Fc receptor and/or effector function is an amino acid substitution. In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an IgG$_1$ Fc domain, particularly a human IgG$_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In preferred aspects, the Fc domain comprises amino acid substitutions at positions P329, L234 and L235 (numberings according to Kabat EU index). In more preferred aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such aspect, the Fc domain is an IgG$_1$ Fc domain, particularly a human IgG$_1$ Fc domain.

The "P329G LALA" combination of amino acid substitutions almost completely abolishes Fcγ receptor (as well as complement) binding of a human IgG$_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some aspects, the Fc domain of the (multispecific) antibodies of the invention is an IgG$_4$ Fc domain, particularly a human IgG$_4$ Fc domain. In one aspect, the IgG$_4$ Fc domain comprises an amino acid substitution at position 5228, specifically the amino acid substitution S228P (numberings according to Kabat EU index). To further reduce its binding affinity to an Fc receptor and/or its effector function, in one aspect, the IgG$_4$ Fc domain comprises an amino acid substitution at position L235, specifically the amino acid substitution L235E (numberings according to Kabat EU index). In another aspect, the IgG$_4$ Fc domain comprises an amino acid substitution at position P329, specifically the amino acid substitution P329G (numberings according to Kabat EU index). In a preferred aspect, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a preferred aspect, the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain aspects, N-glycosylation of the Fc domain has been eliminated. In one such aspect, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or (multispecific) antibodies comprising an Fc domain for Fc receptors may be evaluated using cell lines known to express particular Fc receptors, such as human NK cells expressing FcγIIIa receptor.

Effector function of an Fc domain, or a (multispecific) antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the Fc domain, or the (multispecific) antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half life determinations can also be performed using methods known in the art (see, e.g., Petkova, S. B. et al., Int'l. Immunol. 18(12):1759-1769 (2006); WO 2013/120929).

B. Polynucleotides

The invention further provides an isolated polynucleotide encoding an antibody of the invention. Said isolated polynucleotide may be a single polynucleotide or a plurality of polynucleotides. The polynucleotides encoding (multispecific) antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the portion of the antibody comprising the heavy chain of the antibody.

When co-expressed, the heavy chain polypeptides will associate with the light chain polypeptides to form the antibody. In another example, the portion of the antibody comprising one of the two Fc domain subunits and optionally (part of) one or more Fab molecules could be encoded by a separate polynucleotide from the portion of the antibody comprising the other of the two Fc domain subunits and optionally (part of) a Fab molecule. When co-expressed, the Fc domain subunits will associate to form the Fc domain.

In some aspects, the isolated polynucleotide encodes the entire antibody molecule according to the invention as described herein. In other aspects, the isolated polynucleotide encodes a polypeptide comprised in the antibody according to the invention as described herein.

In certain aspects the polynucleotide or nucleic acid is DNA. In other aspects, a polynucleotide of the present invention is RNA, for example, in the form of messenger RNA (mRNA). RNA of the present invention may be single stranded or double stranded.

C. Recombinant Methods

Antibodies of the invention may be obtained, for example, by solid-state peptide synthesis (e.g. Merrifield solid phase synthesis) or recombinant production. For recombinant production one or more polynucleotide encoding the antibody, e.g., as described above, is isolated and inserted into one or more vectors for further cloning and/or expression in a host cell. Such polynucleotide may be readily isolated and sequenced using conventional procedures. In one aspect a vector, particularly an expression vector, comprising the polynucleotide (i.a. a single polynucleotide or a plurality of polynucleotides) of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antibody (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention, or variant or derivative thereof.

Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible by tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain aspects, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further aspect, a host cell comprising a polynucleotide (i.e. a single polynucleotide or a plurality of polynucleotides) of the invention is provided. In certain aspects a host cell comprising a vector of the invention is provided. The polynucleotides and vectors may incorporate any of the features, singly or in combination, described herein in relation to polynucleotides and vectors, respectively. In one such aspect a host cell comprises (e.g. has been transformed or transfected with) one or more vector comprising one or more polynucleotide that encodes (part of) an antibody of the invention. As used herein, the term "host cell" refers to any kind of cellular system which can be engineered to generate the antibody of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one aspect, the host cell is a eukaryotic cell, particularly a mammalian cell, such as a Chinese Hamster Ovary (CHO) cell, a human embryonic kidney (HEK) cell or a lymphoid cell (e.g., YO, NSO, Sp20 cell). In one aspect, the host cell is not a cell within a human body.

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain. In one aspect, a method of producing an antibody according to the invention is provided, wherein the method comprises culturing a host cell comprising a polynucleotide encoding the antibody, as provided herein, under conditions suitable for expression of the antibody, and optionally recovering the antibody from the host cell (or host cell culture medium).

The components of the (multispecific) antibody of the invention may be genetically fused to each other. The (multispecific) antibody can be designed such that its components are fused directly to each other or indirectly through a linker sequence. The composition and length of the linker may be determined in accordance with methods well known in the art and may be tested for efficacy. Examples of linker sequences between different components of (multispecific) antibodies are provided herein. Additional sequences may also be included to incorporate a cleavage site to separate the individual components of the fusion if desired, for example an endopeptidase recognition sequence.

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well-known analytical methods including gel electrophoresis, high pressure liquid chromatography, and the like.

D. Assays

Antibodies provided herein may be identified, screened for, or characterized for their physical/chemical properties and/or biological activities by various assays known in the art.

1. Binding Assays

The binding (affinity) of the antibody to an Fc receptor or a target antigen can be determined for example by surface plasmon resonance (SPR), using standard instrumentation such as a BIAcore instrument (GE Healthcare), and receptors or target proteins such as may be obtained by recombinant expression. Alternatively, binding of antibodies to different receptors or target antigens may be evaluated using cell lines expressing the particular receptor or target antigen, for example by flow cytometry (FACS). A specific illustrative and exemplary aspect for measuring binding activity to CD3 is described in the following.

In one aspect, the binding activity to CD3 is determined by SPR as follows: SPR is performed on a Biacore T200 instrument (GE Healthcare). Anti-Fab capturing antibody (GE Healthcare, #28958325) is immobilized on a Series S Sensor Chip CMS (GE Healthcare) using standard amine coupling chemistry, at a surface density of 4000-6000 resonance units (RU). As running and dilution buffer, HBS-P+ (10 mM HEPES, 150 mM NaCl pH 7.4, 0.05% Surfactant P20) is used. CD3 antibodies with a concentration of 2 µg/ml (in 20 mM His, 140 mM NaCl, pH 6.0) are injected for about 60 s at a flow rate of 5 µl/min. The CD3 antigen used is a heterodimer of CD3 delta and CD3 epsilon ectodomains fused to a human Fc domain with knob-into-hole modifications and a C-terminal AviTag™ tag (see SEQ ID NOs 28 and 29). CD3 antigen is injected at a concentration of 10 µg/ml for 120 s and dissociation is monitored at a flow rate of 5 µl/min for about 120 s. The chip surface is regenerated by two consecutive injections of 10 mM glycine pH 2.1 for about 60 s each. Bulk refractive index differences are corrected by subtracting blank injections and by subtracting the response obtained from the blank control flow cell. For evaluation, the binding response is taken 5 seconds after injection end. To normalize the binding signal, the CD3 binding is divided by the anti-Fab response (the signal (RU) obtained upon capture of the CD3 antibody on the immobilized anti-Fab antibody). The binding activity to CD3 of an antibody after a certain treatment, relative to the binding activity to CD3 of the antibody after a different treatment (also referred to as relative active concentration (RAC)) is calculated by referencing the binding activity of a sample of the antibody after the certain treatment to the binding activity of a corresponding sample of the antibody after the different treatment.

2. Activity Assays

Biological activity of the (multispecific) antibodies of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

E. Compositions, Formulations, and Routes of Administration

In a further aspect, the invention provides pharmaceutical compositions comprising any of the antibodies provided herein, e.g., for use in any of the below therapeutic methods. In one aspect, a pharmaceutical composition comprises an antibody according to the invention and a pharmaceutically acceptable carrier. In another aspect, a pharmaceutical composition comprises an antibody according to the invention and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise an effective amount of antibody dissolved or dispersed in a pharmaceutically acceptable carrier. The phrase "pharmaceutically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated. An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, particularly in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular aspects, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

F. Therapeutic Methods and Compositions

Any of the antibodies provided herein may be used in therapeutic methods. Antibodies of the invention may be used as immunotherapeutic agents, for example in the treatment of cancers. For use in therapeutic methods, antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies of the invention for use as a medicament are provided. In further aspects, antibodies of the invention for use in treating a disease are provided. In certain aspects, antibodies of the invention for use in a method of treatment are provided. In one aspect, the invention provides an antibody of the invention for use in the treatment of a disease in an individual in need thereof. In certain aspects, the invention provides an antibody for use in a method of treating an individual having a disease comprising administering to the individual an effective amount of the antibody. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. In further aspects, the invention provides an antibody of the invention for use in inducing lysis of a target cell, particularly a tumor cell. In certain aspects, the invention provides an antibody of the invention for use in a method of inducing lysis of a target cell, particularly a tumor cell, in an individual comprising administering to the individual an effective amount of the antibody to induce lysis of a target cell. An "individual" according to any of the above aspects is a mammal, preferably a human.

In a further aspect, the invention provides for the use of an antibody of the invention in the manufacture or preparation of a medicament. In one aspect the medicament is for the treatment of a disease in an individual in need thereof. In a further aspect, the medicament is for use in a method of treating a disease comprising administering to an individual having the disease an effective amount of the medicament. In certain aspects the disease to be treated is a proliferative disorder. In a preferred aspect the disease is cancer. In one aspect, the method further comprises administering to the individual an effective amount of at least one additional therapeutic agent, e.g., an anti-cancer agent if the disease to be treated is cancer. In a further aspect, the medicament is for inducing lysis of a target cell, particularly a tumor cell. In still a further aspect, the medicament is for use in a method of inducing lysis of a target cell, particularly a tumor cell, in an individual comprising administering to the individual an effective amount of the medicament to induce lysis of a target cell. An "individual" according to any of the above aspects may be a mammal, preferably a human.

In a further aspect, the invention provides a method for treating a disease. In one aspect, the method comprises administering to an individual having such disease an effective amount of an antibody of the invention. In one aspect a composition is administered to said individual, comprising the antibody of the invention in a pharmaceutically acceptable form. In certain aspects the disease to be treated is a proliferative disorder. In a preferred aspect the disease is cancer. In certain aspects the method further comprises administering to the individual an effective amount of at least one additional therapeutic agent, e.g., an anti-cancer agent if the disease to be treated is cancer. An "individual" according to any of the above aspects may be a mammal, preferably a human.

In a further aspect, the invention provides a method for inducing lysis of a target cell, particularly a tumor cell. In one aspect the method comprises contacting a target cell with an antibody of the invention in the presence of a T cell, particularly a cytotoxic T cell. In a further aspect, a method for inducing lysis of a target cell, particularly a tumor cell, in an individual is provided. In one such aspect, the method comprises administering to the individual an effective amount of an antibody of the invention to induce lysis of a target cell. In one aspect, an "individual" is a human.

In certain aspects, the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects the cancer is selected from the group consisting of kidney cancer, bladder cancer, skin cancer, lung cancer, colorectal cancer, breast cancer, brain cancer, head and neck cancer and prostate cancer. In one aspect, in particular wherein the antibody is a multispecific antibody binding to TYRP-1 as the second antigen, the cancer is a cancer expressing TYRP-1. In one aspect, in particular wherein the antibody is a multispecific antibody binding to TYRP-1 as the second antigen, the cancer is a skin cancer, in particular a melanoma. In one aspect, in particular wherein the antibody is a multispecific antibody binding to EGFRvIII as the second antigen, the cancer is a cancer expressing EGFRvIII. In one aspect, in particular wherein the antibody is a multispecific antibody binding to EGFRvIII as the second antigen, the cancer is a brain cancer, in particular a glioblastoma. A skilled artisan readily recognizes that in many cases the antibody may not provide a cure but may only provide partial benefit. In some aspects, a physiological change having some benefit is also considered therapeutically beneficial. Thus, in some aspects, an amount of antibody that provides a physiological change is considered an "effective amount". The subject, patient, or individual in need of treatment is typically a mammal, more specifically a human.

In some aspects, an effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various timepoints, bolus administration, and pulse infusion are contemplated herein.

The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in an effective amount. For systemic administration, an effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective dose of the antibodies of the invention will generally provide therapeutic benefit without causing substantial toxicity. Toxicity and therapeutic efficacy of an antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one aspect, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular disease being treated, preferably those with complementary activities that do not adversely affect each other. In certain aspects, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a preferred aspect, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody of the invention can occur prior to, simultaneously, and/or following, administration of the additional therapeutic agent and/or adjuvant. Antibodies of the invention may also be used in combination with radiation therapy.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

H. Methods and Compositions for Diagnostics and Detection

In certain aspects, any of the antibodies provided herein is useful for detecting the presence of its target (e.g. CD3, TYRP-1, EGFRvIII) in a biological sample. The term "detecting" as used herein encompasses quantitative or qualitative detection. In certain aspects, a biological sample comprises a cell or tissue, such as prostate tissue.

In one aspect, an antibody according to the invention for use in a method of diagnosis or detection is provided. In a further aspect, a method of detecting the presence of CD3, TYRP-1 or EGFRvIII in a biological sample is provided. In certain aspects, the method comprises contacting the biological sample with an antibody of the present invention under conditions permissive for binding of the antibody to CD3, TYRP-1 or EGFRvIII, and detecting whether a complex is formed between the antibody and CD3, TYRP-1 or EGFRvIII. Such method may be an in vitro or in vivo method. In one aspect, an antibody of the invention is used to select subjects eligible for therapy with an antibody that binds CD3, TYRP-1 and/or EGFRvIII, e.g. where CD3, TYRP-1 and/or EGFRvIII is a biomarker for selection of patients.

Exemplary disorders that may be diagnosed using an antibody of the invention include cancer, particularly skin cancer or brain cancer.

In certain aspects, an antibody according to the present invention is provided, wherein the antibody is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes and $^{32}P$, $^{14}C$, $^{125}I$, $^{3}H$, $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

SEQUENCES

|  | Amino Acid Sequence | SEQ ID NO |
|---|---|---|
| $CD3_{orig}$ HCDR1 | TYAMN | 1 |
| $CD3_{opt}$ HCDR1 | SYAMN | 2 |
| $CD3_{orig}$/ $CD3_{opt}$ HCDR2 | RIRSKYNNYATYYADSVKG | 3 |
| $CD3_{orig}$ HCDR3 | HGNFGNSYVSWFAY | 4 |
| $CD3_{opt}$ HCDR3 | HTTFPSSYVSYYGY | 5 |
| $CD3_{orig}$ VH | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSS | 6 |
| $CD3_{opt}$ VH | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSS | 7 |
| $CD3_{orig}$/ $CD3_{opt}$ LCDR1 | GSSTGAVTTSNYAN | 8 |
| $CD3_{orig}$/ $CD3_{opt}$ LCDR2 | GTNKRAP | 9 |
| $CD3_{orig}$/ $CD3_{opt}$ LCDR3 | ALWYSNLWV | 10 |
| $CD3_{orig}$/ $CD3_{opt}$ VL | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVL | 11 |
| $CD3_{orig}$ IgG HC | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASTKGPSVFPLAPSSKSTSGGTAALGCLVKDYFPE PVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPPS RDELTKNQVSLTCLVKGFYPSDIAVEWESNGQPENNYKTT PPVLDSDGSFFLYSKLTVDKSRWQQGNVFSCSVMHEALHN HYTQKSLSLSP | 12 |

| | Amino Acid Sequence | SEQ ID NO |
|---|---|---|
| CD3$_{opt}$ IgG HC | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSSASTKGPSVFPLAPSSKSTSGGTAALGCLVKDYFPEP VTVSWNSGALTSGVHTFPAVLQSSGLYSLSSVVTVPSSSLG TQTYICNVNHKPSNTKVDKKVEPKSCDKTHTCPPCPAPEA AGGPSVFLFPPKPKDTLMISRTPEVTCVVVDVSHEDPEVKF NWYVDGVEVHNAKTKPREEQYNSTYRVVSVLTVLHQDW LNGKEYKCKVSNKALGAPIEKTISKAKGQPREPQVYTLPPS RDELTKNQVSLTCLVKGFYPSDIAVEWESNGQPENNYKTT PPVLDSDGSFFLYSKLTVDKSRWQQGNVFSCSVMHEALHN HYTQKSLSLSP | 13 |
| CD3$_{orig}$/ CD3$_{opt}$ IgG LC | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVLRTVAAPSVFIFP PSDEQLKSGTASVVCLLNNFYPREAKVQWKVDNALQSGN SQESVTEQDSKDSTYSLSSTLTLSKADYEKHKVYACEVTH QGLSSPVTKSFNRGEC | 14 |
| TYRP1 HCDR1 | DYFLH | 15 |
| TYRP1 HCDR2 | WINPDNGNTVYAQKFQG | 16 |
| TYRP1 HCDR3 | RDYTYEKAALDY | 17 |
| TYRP1 VH | QVQLVQSGAEVKKPGASVKVSCKASGFNIKDYFLHWVRQ APGQGLEWMGWINPDNGNTVYAQKFQGRVTMTADTSTST VYMELSSLRSEDTAVYYCTRRDYTYEKAALDYWGQGTLV TVSS | 18 |
| TYRP1 LCDR1 | RASGNIYNYLA | 19 |
| TYRP1 LCDR2 | DAKTLAD | 20 |
| TYRP1 LCDR3 | QHFWSLPFT | 21 |
| TYRP1 VL | DIQMTQSPSSLSASVGDRVTITCRASGNIYNYLAWYQQKPG KVPKLLIYDAKTLADGVPSRFSGSGSGTDFTLTISSLQPEDV ATYYCQHFWSLPFTFGQGTKLEIK | 22 |
| TYRP1 VH-CH1(EE)- CD3$_{orig}$/ CD3$_{opt}$ VL-CH1-Fc(knob, PGLALA) | QVQLVQSGAEVKKPGASVKVSCKASGFNIKDYFLHWVRQ APGQGLEWMGWINPDNGNTVYAQKFQGRVTMTADTSTST VYMELSSLRSEDTAVYYCTRRDYTYEKAALDYWGQGTLV TVSSASTKGPSVFPLAPSSKSTSGGTAALGCLVEDYFPEPVT VSWNSGALTSGVHTFPAVLQSSGLYSLSSVVTVPSSSLGTQ TYICNVNHKPSNTKVDEKVEPKSCDGGGGSGGGGSQAVVT QEPSLTVSPGGTVTLTCGSSTGAVTTSNYANWVQEKPGQA FRGLIGGTNKRAPGTPARFSGSLLGGKAALTLSGAQPEDEA EYYCALWYSNLWVFGGGTKLTVLSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVDK KVEPKSCDKTHTCPPCPAPEAAGGPSVFLFPPKPKDTLMISR TPEVTCVVVDVSHEDPEVKFNWYVDGVEVHNAKTKPREE QYNSTYRVVSVLTVLHQDWLNGKEYKCKVSNKALGAPIE KTISKAKGQPREPQVYTLPPCRDELTKNQVSLWCLVKGFY PSDIAVEWESNGQPENNYKTTPPVLDSDGSFFLYSKLTVDK SRWQQGNVFSCSVMHEALHNHYTQKSLSLSP | 23 |
| TYRP1 VH-CH1(EE)- Fc(hole, PGLALA) | QVQLVQSGAEVKKPGASVKVSCKASGFNIKDYFLHWVRQ APGQGLEWMGWINPDNGNTVYAQKFQGRVTMTADTSTST VYMELSSLRSEDTAVYYCTRRDYTYEKAALDYWGQGTLV TVSSASTKGPSVFPLAPSSKSTSGGTAALGCLVEDYFPEPVT VSWNSGALTSGVHTFPAVLQSSGLYSLSSVVTVPSSSLGTQ TYICNVNHKPSNTKVDEKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLNG KEYKCKVSNKALGAPIEKTISKAKGQPREPQVCTLPPSRDE | 24 |

| | Amino Acid Sequence | SEQ ID NO |
|---|---|---|
| | LTKNQVSLSCAVKGFYPSDIAVEWESNGQPENNYKTTPPV LDSDGSFFLVSKLTVDKSRWQQGNVFSCSVMHEALHNHY TQKSLSLSP | |
| TYRP1 VL-CL(RK) | DIQMTQSPSSLSASVGDRVTITCRASGNIYNYLAWYQQKPG KVPKLLIYDAKTLADGVPSRFSGSGSGTDFTLTISSLQPEDV ATYYCQHFWSLPFTFGQGTKLEIKRTVAAPSVFIFPPSDRKL KSGTASVVCLLNNFYPREAKVQWKVDNALQSGNSQESVT EQDSKDSTYSLSSTLTLSKADYEKHKVYACEVTHQGLSSPV TKSFNRGEC | 25 |
| CD3$_{orig}$ VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 26 |
| CD3$_{opt}$ VH-CL | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSSASVAAPSVFIFPPSDEQLKSGTASVVCLLNNFYPRE AKVQWKVDNALQSGNSQESVTEQDSKDSTYSLSSTLTLSK ADYEKHKVYACEVTHQGLSSPVTKSFNRGEC | 27 |
| Human CD3 epsilon stalk-Fc(knob)-Avi | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVSENCDEQLYFQGGSPKSADKTHTC PPCPAPELLGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREPQ VYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPGKSGGLNDIFEAQKIEWHE | 28 |
| Human CD3 delta stalk-Fc(hole)-Avi | FKIPIEELEDRVFVNCNTSITWVEGTVGTLLSDITRLDLGKRI LDPRGIYRCNGTDIYKDKESTVQVHYRMCRSEQLYFQGDK THTCPPCPAPELLGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALPAPIEKTISKAKGQP REPQVCTLPPSRDELTKNQVSLSCAVKGFYPSDIAVEWESN GQPENNYKTTPPVLDSDGSFFLVSKLTVDKSRWQQGNVFS CSVMHEALHNHYTQKSLSLSPGKSGGLNDIFEAQKIEWHE | 29 |
| Cynomolgus CD3 epsilon stalk-Fc (knob)-Avi | QDGNEEMGSITQTPYQVSISGTTVILTCSQHLGSEAQWQHN GKNKEDSGDRLFLPEFSEMEQSGYYVCYPRGSNPEDASHH LYLKARVSENCDEQLYFQGGSPKSADKTHTCPPCPAPELL GGPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPCR DELTKNQVSLWCLVKGFYPSDIAVEWESNGQPENNYKTTP PVLDSDGSFFLYSKLTVDKSRWQQGNVFSCSVMHEALHNH YTQKSLSLSPGKSGGLNDIFEAQKIEWHE | 30 |
| Cynomolgus CD3 delta stalk-Fc (hole)-Avi | FKIPVEELEDRVFVKCNTSVTWVEGTVGTLLTNNTRLDLG KRILDPRGIYRCNGTDIYKDKESAVQVHYRMSQNCVDEQL YFQGGSPKSADKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVCTLPPSRDELTKNQVSLSCAVKG FYPSDIAVEWESNGQPENNYKTTPPVLDSDGSFFLVSKLTV DKSRWQQGNVFSCSVMHEALHNHYTQKSLSLSPGKSGGL NDIFEAQKIEWHE | 31 |
| Human TYRP1 ECD-Fc(knob)-Avi | QFPRQCATVEALRSGMCCPDLSPVSGPGTDRCGSSSGRGRC EAVTADSRPHSPQYPHDGRDDREVWPLRFFNRTCHCNGNF SGHNCGTCRPGWRGAACDQRVLIVRRNLLDLSKEEKNHFV RALDMAKRTTHPLFVIATRRSEEILGPDGNTPQFENISIYNY FVWTHYYSVKKTFLGVGQESFGEVDFSHEGPAFLTWHRY HLLRLEKDMQEMLQEPSFSLPYWNFATGKNVCDICTDDLM GSRSNFDSTLISPNSVFSQWRVVCDSLEDYDTLGTLCNSTE DGPIRRNPAGNVARPMVQRLPEPQDVAQCLEVGLFDTPPF YSNSTNSFRNTVEGYSDPTGKYDPAVRSLHNLAHLFLNGT GGQTHLSPNDPIFVLLHTFTDAVFDEWLRRYNADISTFPLE NAPIGHNRQYNMVPFWPPVTNTEMFVTAPDNLGYTYEIQ | 32 |

| Amino Acid Sequence | SEQ ID NO |
|---|---|
| | |

| | | |
|---|---|---|
| | WPSREFSVPEGSDKTHTCPPCPAPEAAGGPSVFLFPPKPKDT<br>LMISRTPEVTCVVVDVSHEDPEVKFNWYVDGVEVHNAKT<br>KPREEQYNSTYRVVSVLTVLHQDWLNGKEYKCKVSNKAL<br>GAPIEKTISKAKGQPREPQVYTLPPCRDELTKNQVSLWCLV<br>KGFYPSDIAVEWESNGQPENNYKTTPPVLDSDGSFFLYSKL<br>TVDKSRWQQGNVFSCSVMHEALHNHYTQKSLSLSPGKSG<br>GLNDIFEAQKIEWHE | |
| Cynomolgus TYRP1 ECD-Fc(knob)-Avi | QFPRECATVEALRSGMCCPDLSPMSGPGTDRCGSSSGRGR<br>CEAVTADSRPHSPRYPHDGRDDREVWPLRFFNRTCHCNGN<br>FSGHNCGTCRPGWRGAACDQRVLVVRRNLLDLSKEEKNH<br>FVRALDMAKRTTHPLFVIATRRSEEILGPDGNTPQFENISIY<br>NYFVWTHYYSVKKTFLGAGQESFGEVDFSHEGPAFLTWH<br>RYHLLRLEKDMQEMLQEPSFSLPYWNFATGKNVCDICTDD<br>LMGSRSNFDSTLISPNSVFSQWRVVCDSLEDYDTLGTLCNS<br>TESGPIRRNPAGNVARPMVQRLPEPQDVAQCLEVGLFDTPP<br>FYSNSTNSFRNTVEGYSDPTGKYDPAVRSLHNLAHLFLNGT<br>GGQTHLSPNDPIFVLLHTFTDAVFDEWLRRYNADISTFPLE<br>NAPIGHNRQYNMVPFWPPVTNTEMFVTAPDNLGYTYEVQ<br>WPSREFSVPGSDKTHTCPPCPAPEAAGGPSVFLFPPKPKDTL<br>MISRTPEVTCVVVDVSHEDPEVKFNWYVDGVEVHNAKTK<br>PREEQYNSTYRVVSVLTVLHQDWLNGKEYKCKVSNKALG<br>APIEKTISKAKGQPREPQVYTLPPCRDELTKNQVSLWCLVK<br>GFYPSDIAVEWESNGQPENNYKTTPPVLDSDGSFFLYSKLT<br>VDKSRWQQGNVFSCSVMHEALHNHYTQKSLSLSPGKSGG<br>LNDIFEAQKIEWHE | 33 |
| Mouse TYRP1 ECD-Fc(knob)-Avi | QFPRECANIEALRRGVCCPDLPSSGPGTDPCGSSSGRGRC<br>VAVIADSRPHSRHYPHDGKDDREAWPLRFFNRTCQCNDNF<br>SGHNCGTCRPGWRGAACNQKILTVRRNLLDLSPEEKSHFV<br>RALDMAKRTTHPQFVIATRRLEDILGPDGNTPQFENISVYN<br>YFVWTHYYSVKKTFLGTGQESFGDVDFSHEGPAFLTWHR<br>YHLLQLERDMQEMLQEPSFSLPYWNFATGKNVCDVCTDD<br>LMGSRSNFDSTLISPNSVFSQWRVVCESLEEYDTLGTLCNS<br>TEGGPIRRNPAGNVGRPAVQRLPEPQDVTQCLEVRVFDTPP<br>FYSNSTDSFRNTVEGYSAPTGKYDPAVRSLHNLAHLFLNGT<br>GGQTHLSPNDPIFVLLHTFTDAVFDEWLRRYNADISTFPLE<br>NAPIGHNRQYNMVPFWPPVTNTEMFVTAPDNLGYAYEVQ<br>WPGQEFTVSEGSDKTHTCPPCPAPEAAGGPSVFLFPPKPKD<br>TLMISRTPEVTCVVVDVSHEDPEVKFNWYVDGVEVHNAK<br>TKPREEQYNSTYRVVSVLTVLHQDWLNGKEYKCKVSNKA<br>LGAPIEKTISKAKGQPREPQVYTLPPCRDELTKNQVSLWCL<br>VKGFYPSDIAVEWESNGQPENNYKTTPPVLDSDGSFFLYSK<br>LTVDKSRWQQGNVFSCSVMHEALHNHYTQKSLSLSPGKS<br>GGLNDIFEAQKIEWHE | 34 |
| Fc(hole) | DKTHTCPPCPAPEAAGGPSVFLFPPKPKDTLMISRTPEVTCV<br>VVDVSHEDPEVKFNWYVDGVEVHNAKTKPREEQYNSTYR<br>VVSVLTVLHQDWLNGKEYKCKVSNKALGAPIEKTISKAKG<br>QPREPQVCTLPPSRDELTKNQVSLSCAVKGFYPSDIAVEWE<br>SNGQPENNYKTTPPVLDSDGSFFLVSKLTVDKSRWQQGNV<br>FSCSVMHEALHNRFTQKSLSLSP | 35 |
| EGFRvIII ECD-Avi-His | LEEKKGNYVVTDHGSCVRACGADSYEMEEDGVRKCKKCE<br>GPCRKVCNGIGIGEFKDSLSINATNIKHFKNCTSISGDLHILP<br>VAFRGDSFTHTPPLDPQELDILKTVKEITGFLLIQAWPENRT<br>DLHAFENLEIIRGRTKQHGQFSLAVVSLNITSLGLRSLKEISD<br>GDVIISGNKNLCYANTINWKKLFGTSGQKTKIISNRGENSC<br>KATGQVCHALCSPEGCWGPEPRDCVSCRNVSRGRECVDK<br>CNLLEGEPREFVENSECIQCHPECLPQAMNITCTGRGPDNCI<br>QCAHYIDGPHCVKTCPAGVMGENNTLVWKYADAGHVCH<br>LCHPNCTYGCTGPGLEGCPTNGPKIPSVDGGSPTPPTPGGGS<br>GLNDIFEAQKIEWHEARAHHHHHH | 36 |
| EGFRvIII P056.021 HCDR1 | SYWIA | 37 |
| EGFRvIII P056.021 HCDR2 | VIHPYDSDTRYSPSFQG | 38 |
| EGFRvIII P056.021 HCDR3 | VSRSSYAFDY | 39 |

| Amino Acid Sequence | SEQ ID NO |
|---|---|
| EGFRvIII P056.021 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSS | 40 |
| EGFRvIII P056.021 LCDR1 | KSSQSVLYSSNNKNYLA | 41 |
| EGFRvIII P056.021 LCDR2 | WASTRES | 42 |
| EGFRvIII P056.021 LCDR3 | QQVHSGPPVT | 43 |
| EGFRvIII P056.021 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 44 |
| EGFRvIII P056.052 HCDR1 | NYWIG | 45 |
| EGFRvIII P056.052 HCDR2 | TIYPGDSDRRYSPSFQG | 46 |
| EGFRvIII P056.052 HCDR3 | VSRSSYAFDY | 47 |
| EGFRvIII P056.052 VH | EVQLVQSGAEVKKPGESLKISCKGSGYTFMNYWIGWVRQ MPGKGLEWMGTIYPGDSDRRYSPSFQGQVTLSADKSISTA YLQWSSLKASDTAMYYCARVSRSSYAFDYWGQGTLVTVSS | 48 |
| EGFRvIII P056.052 LCDR1 | KSSQSVLYSSNNKNYLA | 49 |
| EGFRvIII P056.052 LCDR2 | WASTRES | 50 |
| EGFRvIII P056.052 LCDR3 | QQVHSGPPVT | 51 |
| EGFRvIII P056.052 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 52 |
| EGFRvIII P047.019 HCDR1 | SIWIH | 53 |
| EGFRvIII P047.019 HCDR2 | TIYPGDSDTRYSPSFQG | 54 |
| EGFRvIII P047.019 HCDR3 | TGPGLAFDY | 55 |
| EGFRvIII P047.019 VH | EVQLVQSGAEVKKPGESLKISCKGSGYSFPSIWIHWVRQMP GKGLEWMGTIYPGDSDTRYSPSFQGQVTISADKSISTAYLQ WSSLKASDTAMYYCARTGPGLAFDYWGQGTLVTVSS | 56 |
| EGFRvIII P047.019 LCDR1 | KSSQSVLYSSNNKNYLA | 57 |

-continued

| | Amino Acid Sequence | SEQ ID NO |
|---|---|---|
| EGFRvIII P047.019 LCDR2 | WASTRES | 58 |
| EGFRvIII P047.019 LCDR3 | QQSYSTPIT | 59 |
| EGFRvIII P047.019 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQSYSTPITFGQGTKVEIK | 60 |
| EGFRvIII P057.012 HCDR1 | NYWIA | 61 |
| EGFRvIII P057.012 HCDR2 | IIYPDDSDTRYSPSFQG | 62 |
| EGFRvIII P057.012 HCDR3 | ATNIASGGYFDY | 63 |
| EGFRvIII P057.012 VH | EVQLVQSGAEVKKPGESLKISCKGSGYSFANYWIAWVRQ MPGKGLEWMGIIYPDDSDTRYSPSFQGQVTISADKSISTAY LQWSSLKASDTAMYYCARATNIASGGYFDYWGQGTLVTV SS | 64 |
| EGFRvIII P057.012 LCDR1 | KSSQSVLWNSNNKNYLA | 65 |
| EGFRvIII P057.012 LCDR2 | WASKRES | 66 |
| EGFRvIII P057.012 LCDR3 | QQSYSAPIT | 67 |
| EGFRvIII P057.012 VL | DIVMTQSPDSLAVSLGERATINCKSSQSVLWNSNNKNYLA WYQQKPGQPPKLLIYWASKRESGVPDRFSGSGSGTDFTLTI SSLQAEDVAVYYCQQSYSAPITFGQGTKVEIK | 68 |
| EGFRvIII P057.011 HCDR1 | RRWIA | 69 |
| EGFRvIII P057.011 HCDR2 | IIYPGDSDTRYSPSFQG | 70 |
| EGFRvIII P057.011 HCDR3 | ATNIASGGYFDY | 71 |
| EGFRvIII P057.011 VH | EVQLVQSGAEVKKPGESLKISCKGSGYNFGRRWIAWVRQ MPGKGLEWMGIIYPGDSDTRYSPSFQGQVTISADKSISTAY LQWSSLKASDTAMYYCARATNIASGGYFDYWGQGTLVTV SS | 72 |
| EGFRvIII P057.011 LCDR1 | KSSQSVLWNSNNKNYLA | 73 |
| EGFRvIII P057.011 LCDR2 | WASKRES | 74 |
| EGFRvIII P057.011 LCDR3 | QQSYSAPIT | 75 |

|  | Amino Acid Sequence | SEQ ID NO |
|---|---|---|
| EGFRvIII P057.011 VL | DIVMTQSPDSLAVSLGERATINCKSSQSVLWNSNNKNYLA WYQQKPGQPPKLLIYWASKRESGVPDRFSGSGSGTDFTLTI SSLQAEDVAVYYCQQSYSAPITFGQGTKVEIK | 76 |
| EGFRvIII P056.027 HCDR1 | NNWIA | 77 |
| EGFRvIII P056.027 HCDR2 | VIYPGDSDKRYSPSFQG | 78 |
| EGFRvIII P056.027 HCDR3 | VSRSSYAFDY | 79 |
| EGFRvIII P056.027 VH | EVQLVQSGAEVKKPGESLKISCKGSGYTFGNNWIAWVRQ MPGKGLEWMGVIYPGDSDKRYSPSFQGQVTISADKSISTAY LQWSSLKASDTAMYYCARVSRSSYAFDYWGQGTLVTVSS | 80 |
| EGFRvIII P056.027 LCDR1 | KSSQSVLYSSNNKNYLA | 81 |
| EGFRvIII P056.027 LCDR2 | WASTRES | 82 |
| EGFRvIII P056.027 LCDR3 | QQVHSGPPVT | 83 |
| EGFRvIII P056.027 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 84 |
| EGFRvIII P063.056 HCDR1 | SYWIA | 85 |
| EGFRvIII P063.056 HCDR2 | VIHPYDSDTRYSPSFQG | 86 |
| EGFRvIII P063.056 HCDR3 | VSRSSYAFDY | 87 |
| EGFRvIII P063.056 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSS | 88 |
| EGFRvIII P063.056 LCDR1 | KSSQSVLYSSNNKNYLA | 89 |
| EGFRvIII P063.056 LCDR2 | WASTRES | 90 |
| EGFRvIII P063.056 LCDR3 | QQQRDGPPVT | 91 |
| EGFRvIII P063.056 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQQRDGPPVTFGQGTKVEIK | 92 |
| EGFRvIII P064.078 HCDR1 | SYWIA | 93 |
| EGFRvIII P064.078 HCDR2 | VIHPYDSDTRYSPSFQG | 94 |

| | Amino Acid Sequence | SEQ ID NO |
|---|---|---|
| EGFRvIII P064.078 HCDR3 | VSRLSYALDY | 95 |
| EGFRvIII P064.078 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRLSYALDYWGQGTLVTVSS | 96 |
| EGFRvIII P064.078 LCDR1 | KSSQSVLYSSNNKNYLA | 97 |
| EGFRvIII P064.078 LCDR2 | WASTRES | 98 |
| EGFRvIII P064.078 LCDR3 | QQVHSGPPVT | 99 |
| EGFRvIII P064.078 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVHSGPPVTFGQGTKVEIK | 100 |
| EGFRvIII P065.036 HCDR1 | SYWIA | 101 |
| EGFRvIII P065.036 HCDR2 | VIHPYDSDTRYSPSFQG | 102 |
| EGFRvIII P065.036 HCDR3 | VSRSSYALDY | 103 |
| EGFRvIII P065.036 VH | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYALDYWGQGTLVTVSS | 104 |
| EGFRvIII P065.036 LCDR1 | KSSQSVLYSSNNKNYLA | 105 |
| EGFRvIII P065.036 LCDR2 | WASTRES | 106 |
| EGFRvIII P065.036 LCDR3 | QQVYSGPPVT | 107 |
| EGFRvIII P065.036 VL | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQVYSGPPVTFGQGTKVEIK | 108 |
| EGFRvIII VH-CH1(EE)- CD3$_{orig}$/ CD3$_{opt}$ VL-CH1- Fc(knob, PGLALA) | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDGGGGSGGGGSQAVVTQEPSL TVSPGGTVTLTCGSSTGAVTTSNYANWVQEKPGQAFRGLI GGTNKRAPGTPARFSGSLLGGKAALTLSGAQPEDEAEYYC ALWYSNLWVFGGGTKLTVLSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEPK SCDKTHTCPPCPAPEAAGGPSVFLFPPKPKDTLMISRTPEVT CVVVDVSHEDPEVKFNWYVDGVEVHNAKTKPREEQYNST YRVVSVLTVLHQDWLNGKEYKCKVSNKALGAPIEKTISKA KGQPREPQVYTLPPCRDELTKNQVSLWCLVKGFYPSDIAV EWESNGQPENNYKTTPPVLDSDGSFFLYSKLTVDKSRWQQ GNVFSCSVMHEALHNHYTQKSLSLSP | 109 |

| | Amino Acid Sequence | SEQ ID NO |
|---|---|---|
| EGFRvIII VH-CH1(EE)-Fc(hole, PGLALA) | EVQLVQSGAEVKKPGESLKISCKGSGYSFDSYWIAWVRQM PGKGLEWMGVIHPYDSDTRYSPSFQGQVTISADKSISTAYL QWSSLKASDTAMYYCARVSRSSYAFDYWGQGTLVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKC KVSNKALGAPIEKTISKAKGQPREPQVCTLPPSRDELTKNQ VSLSCAVKGFYPSDIAVEWESNGQPENNYKTTPPVLDSDGS FFLVSKLTVDKSRWQQGNVFSCSVMHEALHNHYTQKSLSL SP | 110 |
| EGFRvIII VL-CL(RK) | DIVMTQSPDSLAVSLGERATINCKSSQSVLYSSNNKNYLAW YQQKPGQPPKLLIYWASTRESGVPDRFSGSGSGTDFTLTISS LQAEDVAVYYCQQQRDGPPVTFGQGTKVEIKRTVAAPSVF IFPPSDRKLKSGTASVVCLLNNFYPREAKVQWKVDNALQS GNSQESVTEQDSKDSTYSLSSTLTLSKADYEKHKVYACEV THQGLSSPVTKSFNRGEC | 111 |
| CD3$_{orig}$ VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 26 |
| CD3$_{opt}$ VH-CL | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYWGQGT LVTVSSASVAAPSVFIFPPSDEQLKSGTASVVCLLNNFYPRE AKVQWKVDNALQSGNSQESVTEQDSKDSTYSLSSTLTLSK ADYEKHKVYACEVTHQGLSSPVTKSFNRGEC | 27 |
| Human CD3 | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGG LLLLVYYWSKNRKAKAKPVTRGAGAGGRQRGQNKERPPP VPNPDYEPIRKGQRDLYSGLNQRRI | 112 |
| Cynomolgus CD3 | QDGNEEMGSITQTPYQVSISGTTVILTCSQHLGSEAQWQHN GKNKEDSGDRLFLPEFSEMEQSGYYVCYPRGSNPEDASHH LYLKARVCENCMEMDVMAVATIVIVDICITLGLLLLVYYW SKNRKAKAKPVTRGAGAGGRQRGQNKERPPPVPNPDYEPI RKGQQDLYSGLNQRRI | 113 |
| Human TYRP1 | QFPRQCATVEALRSGMCCPDLSPVSGPGTDRCGSSSGRGRC EAVTADSRPHSPQYPHDGRDDREVWPLRFFNRTCHCNGNF SGHNCGTCRPGWRGAACDQRVLIVRRNLLDLSKEEKNHFV RALDMAKRTTHPLFVIATRRSEEILGPDGNTPQFENISIYNY FVWTHYYSVKKTFLGVGQESFGEVDFSHEGPAFLTWHRY HLLRLEKDMQEMLQEPSFSLPYWNFATGKNVCDICTDDLM GSRSNFDSTLISPNSVFSQWRVVCDSLEDYDTLGTLCNSTE DGPIRRNPAGNVARPMVQRLPEPQDVAQCLEVGLFDTPPF YSNSTNSFRNTVEGYSDPTGKYDPAVRSLHNLAHLFLNGT GGQTHLSPNDPIFVLLHTFTDAVFDEWLRRYNADISTFPLE NAPIGHNRQYNMVPFWPPVTNTEMFVTAPDNLGYTYEIQ WPSREFSVPEIIAIAVVGALLLVALIFGTASYLIRARRSMDE ANQPLLTDQYQCYAEEYEKLQNPNQSVV | 114 |
| Human EGFRvIII | LEEKKGNYVVTDHGSCVRACGADSYEMEEDGVRKCKKCE GPCRKVCNGIGIGEFKDSLSINATNIKHFKNCTSISGDLHILP VAFRGDSFTHTPPLDPQELDILKTVKEITGFLLIQAWPENRT DLHAFENLEIIRGRTKQHGQFSLAVVSLNITSLGLRSLKEISD GDVIISGNKNLCYANTINWKKLFGTSGQKTKIISNRGENSC KATGQVCHALCSPEGCWGPEPRDCVSCRNVSRGRECVDK CNLLEGEPREFVENSECIQCHPECLPQAMNITCTGRGPDNCI QCAHYIDGPHCVKTCPAGVMGENNTLVWKYADAGHVCH LCHPNCTYGCTGPGLEGCPTNGPKIPSIATGMVGALLLLLV VALGIGLFMRRRHIVRKRTLRRLLQERELVEPLTPSGEAPN QALLRILKETEFKKIKVLGSGAFGTVYKGLWIPEGEKVKIP VAIKELREATSPKANKEILDEAYVMASVDNPHVCRLLGICL TSTVQLITQLMPFGCLLDYVREHKDNIGSQYLLNWCVQIA KGMNYLEDRRLVHRDLAARNVLVKTPQHVKITDFGLAKL LGAEEKEYHAEGGKVPIKWMALESILHRIYTHQSDVWSYG | 115 |

-continued

| | Amino Acid Sequence | SEQ ID NO |
|---|---|---|
| | VTVWELMTFGSKPYDGIPASEISSILEKGERLPQPPICTIDVY MIMVKCWMIDADSRPKFRELIIEFSKMARDPQRYLVIQGDE RMHLPSPTDSNFYRALMDEEDMDDVVDADEYLIPQQGFFS SPSTSRTPLLSSLSATSNNSTVACIDRNGLQSCPIKEDSFLQR YSSDPTGALTEDSIDDTFLPVPEYINQSVPKRPAGSVQNPVY HNQPLNPAPSRDPHYQDPHSTAVGNPEYLNTVQPTCVNST FDSPAHWAQKGSHQISLDNPDYQQDFFPKEAKPNGIFKGST AENAEYLRVAPQSSEFIGA | |
| Human EGFR | LEEKKVCQGTSNKLTQLGTFEDHFLSLQRMFNNCEVVLGN LEITYVQRNYDLSFLKTIQEVAGYVLIALNTVERIPLENLQII RGNMYYENSYALAVLSNYDANKTGLKELPMRNLQEILHG AVRFSNNPALCNVESIQWRDIVSSDFLSNMSMDFQNHLGS CQKCDPSCPNGSCWGAGEENCQKLTKIICAQQCSGRCRGK SPSDCCHNQCAAGCTGPRESDCLVCRKFRDEATCKDTCPP LMLYNPTTYQMDVNPEGKYSFGATCVKKCPRNYVVTDHG SCVRACGADSYEMEEDGVRKCKKCEGPCRKVCNGIGIGEF KDSLSINATNIKHFKNCTSISGDLHILPVAFRGDSFTHTPPLD PQELDILKTVKEITGFLLIQAWPENRTDLHAFENLEIIRGRTK QHGQFSLAVVSLNITSLGLRSLKEISDGDVIISGNKNLCYAN TINWKKLFGTSGQKTKIISNRGENSCKATGQVCHALCSPEG CWGPEPRDCVSCRNVSRGRECVDKCNLLEGEPREFVENSE CIQCHPECLPQAMNITCTGRGPDNCIQCAHYIDGPHCVKTC PAGVMGENNTLVWKYADAGHVCHLCHPNCTYGCTGPGL EGCPTNGPKIPSIATGMVGALLLLLVVALGIGLFMRRRHIV RKRTLRRLLQERELVEPLTPSGEAPNQALLRILKETEFKKIK VLGSGAFGTVYKGLWIPEGEKVKIPVAIKELREATSPKANK EILDEAYVMASVDNPHVCRLLGICLTSTVQLITQLMPFGCL LDYVREHKDNIGSQYLLNWCVQIAKGMNYLEDRRLVHRD LAARNVLVKTPQHVKITDFGLAKLLGAEEKEYHAEGGKVP IKWMALESILHRIYTHQSDVWSYGVTVWELMTFGSKPYDG IPASEISSILEKGERLPQPPICTIDVYMIMVKCWMIDADSRPK FRELIIEFSKMARDPQRYLVIQGDERMHLPSPTDSNFYRAL MDEEDMDDVVDADEYLIPQQGFFSSPSTSRTPLLSSLSATS NNSTVACIDRNGLQSCPIKEDSFLQRYSSDPTGALTEDSIDD TFLPVPEYINQSVPKRPAGSVQNPVYHNQPLNPAPSRDPHY QDPHSTAVGNPEYLNTVQPTCVNSTFDSPAHWAQKGSHQI SLDNPDYQQDFFPKEAKPNGIFKGSTAENAEYLRVAPQSSE FIGA | 116 |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 117 |
| linker | GGGGSGGGGS | 118 |
| linker | DGGGGSGGGGS | 119 |
| Human kappa CL domain | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 120 |
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 121 |
| Human IgG1 heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 122 |
| linker | GGGGS | 123 |
| linker | SGGGG | 124 |

| Amino Acid Sequence | SEQ ID NO |
|---|---|
| linker GGGGSGGGG | 125 |
| linker GGGGSGGGGSGGGGSGGGGS | 126 |

EXAMPLES

The following are examples of methods and compositions of the invention. It is understood that various other aspects may be practiced, given the general description provided above.

Example 1—Generation of Optimized CD3 Binder

Starting from a previously described (see e.g. WO 2014/131712, incorporated herein by reference) CD3 binder, termed "CD3$_{orig}$" herein and comprising the VH and VL sequences of SEQ ID NOs 6 and 11, respectively, we aimed at optimizing properties of this binder by removal of two asparagine deamidation sequence motifs at Kabat positions 97 and 100 of the heavy chain CDR3.

To this aim, we generated an antibody library, suitable for phage display, of the heavy chain with both asparagines at Kabat position 97 and 100 removed, and in addition the CDRs H1, H2, and H3 randomized in order to compensate for loss of affinity caused by replacing Asn97 and Asn100 through an affinity-maturation process.

This library was put on a filamentous phage via fusion to minor coat protein p3 (Marks et al. (1991) *J Mol Biol* 222, 581-597) and selected for binding to recombinant CD3ε.

10 candidate clones were identified in the initial screening, showing acceptable binding on recombinant antigen as measured by SPR as Fab fragments (produced in *E. coli*).

Only one of these clones, however, showed acceptable binding activity to CD3 expressing cells as measured by flow cytometry after conversion to IgG format.

The selected clone, termed "CD3$_{opt}$" herein and comprising the VH and VL sequences of SEQ ID NOs 7 and 11, respectively, was further evaluated and converted into bispecific format as described in the following.

Example 2—Binding of Optimized CD3 Binder to CD3

Binding to Recombinant CD3

Binding to recombinant CD3 was determined by surface plasmon resonance (SPR) for the optimized CD3 binder "CD3$_{opt}$" and the original CD3 binder "CD3$_{orig}$", both in human IgG1 format with P329G L234A L235A ("PGLALA", EU numbering) mutations in the Fc region (SEQ ID NOs 12 and 14 (CD3$_{orig}$) 1 and SEQ ID NOs 13 and 14 (CD3$_{opt}$)).

In order to assess the effect of the deamidation site removal and its effect on the stability of the antibodies, binding of the original and the optimized CD3 binder to recombinant CD3 was tested after temperature stress for 14 days at 37° C. or 40° C. Samples stored at −80° C. were used as reference. The reference samples and the samples stressed at 40° C. were in 20 mM His, 140 mM NaCl, pH 6.0, and the samples stressed at 37° C. in PBS, pH 7.4, all at a concentration of 1.2-1.3 mg/ml. After the stress period (14 days) samples in PBS were dialyzed back to 20 mM His, 140 mM NaCl, pH 6.0 for further analysis.

Relative Active Concentration (RAC) of the samples was determined by SPR as follows.

SPR was performed on a Biacore T200 instrument (GE Healthcare). Anti-Fab capturing antibody (GE Healthcare, #28958325) was immobilized on a Series S Sensor Chip CM5 (GE Healthcare) using standard amine coupling chemistry, resulting in a surface density of 4000-6000 resonance units (RU). As running and dilution buffer, HBS-P+(10 mM HEPES, 150 mM NaCl pH 7.4, 0.05% Surfactant P20) was used. CD3 antibodies with a concentration of 2 μg/ml were injected for 60 s at a flow rate of 5 CD3 antigen (see below) was injected at a concentration of 10 μg/ml for 120 s and dissociation was monitored at a flow rate of 5 μl/min for 120 s. The chip surface was regenerated by two consecutive injections of 10 mM glycine pH 2.1 for 60 s each. Bulk refractive index differences were corrected by subtracting blank injections and by subtracting the response obtained from the blank control flow cell. For evaluation, the binding response was taken 5 seconds after injection end. To normalize the binding signal, the CD3 binding was divided by the anti-Fab response (the signal (RU) obtained upon capture of the CD3 antibody on the immobilized anti-Fab antibody). The relative active concentration was calculated by referencing each temperature stressed sample to the corresponding, non-stressed sample.

The antigen used was a heterodimer of CD3 delta and CD3 epsilon ectodomains fused to a human Fc domain with knob-into-hole modifications and a C-terminal AviTag™ tag (see SEQ ID NOs 28 and 29).

Figure 2:
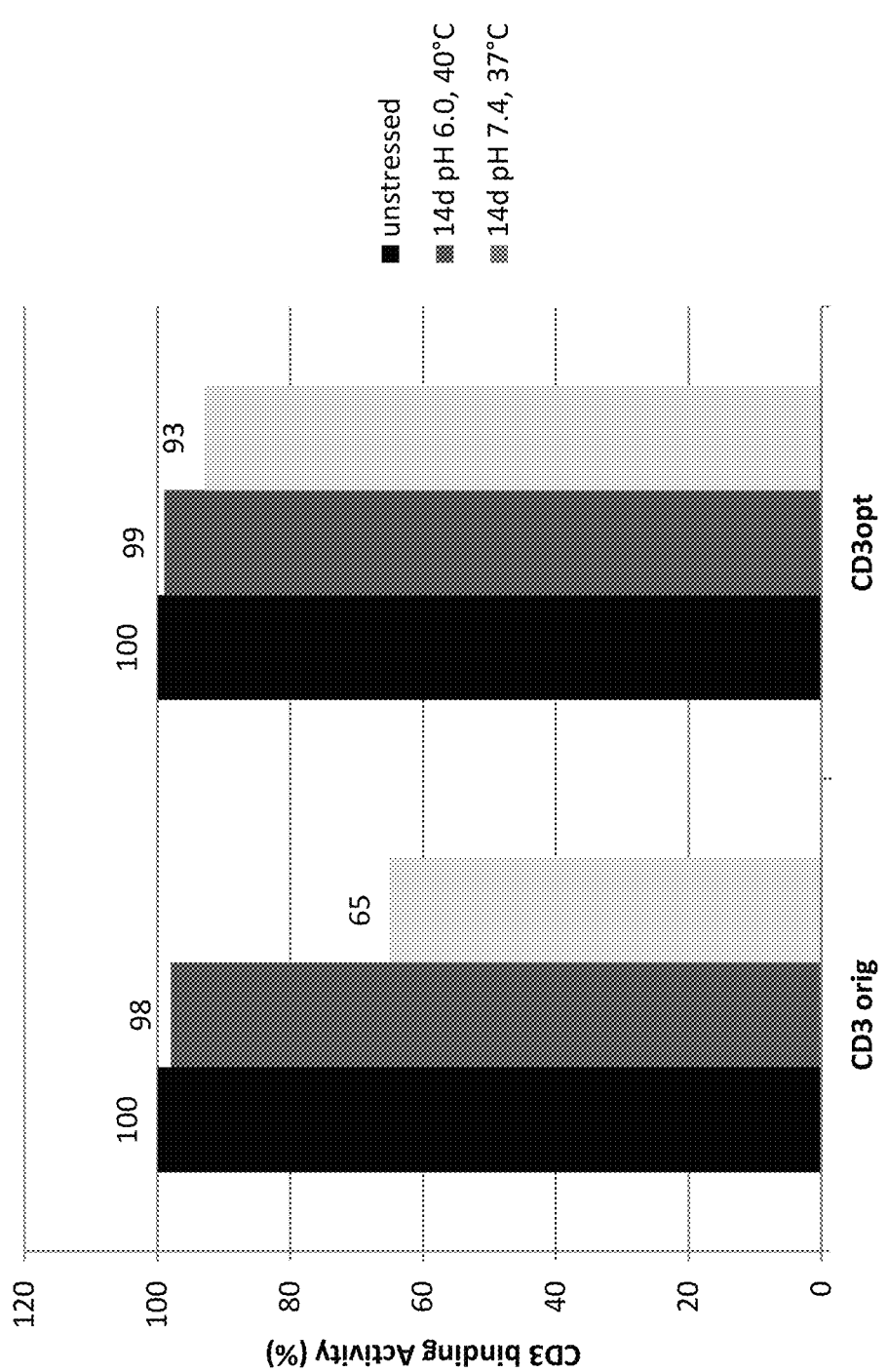
FIG. 2. Relative binding activity of original and optimized CD3 binders, $CD3_{orig}$ and $CD3_{opt}$, to recombinant CD3 as measured by SPR in unstressed condition, after 14 d at 40° C. pH 6, or after 14 d at 37° C. pH 7.4 (IgG format).

The results of this experiment are shown in FIG. 2. As can be seen, the optimized CD3 binder CD3$_{opt}$ showed strongly improved binding to CD3 after temperature stress (2 weeks at 37° C., pH 7.4) as compared to the original CD3 binder CD3$_{orig}$. This result demonstrates that the deamidation site removal was successful, and has yielded an antibody with superior stability properties, relevant for in vivo half-life, as well as formulation of the antibody at neutral pH.

Binding to CD3 on Jurkat Cells

Binding to CD3 on the human reporter T-cell line Jurkat NFAT was determined by FACS for the optimized CD3 binder "CD3$_{opt}$" and the original CD3 binder "CD3$_{orig}$", both in human IgG1 format with P329G L234A L235A ("PGLALA", EU numbering) mutations in the Fc region (SEQ ID NOs 12 and 14 (CD3$_{orig}$) 1 and SEQ ID NOs 13 and 14 (CD3$_{opt}$)).

Jurkat-NFAT reporter cells (GloResponse Jurkat NFAT-RE-luc2P; Promega #CS176501) are a human acute lymphatic leukemia reporter cell line with a NFAT promoter, expressing human CD3. The cells were cultured in RPMI1640, 2 g/l glucose, 2 g/l NaHCO$_3$, 10% FCS, 25 mM HEPES, 2 mM L-glutamine, 1×NEAA, 1× sodium-pyruvate at 0.1-0.5 mio cells per ml. A final concentration of 200 μg per ml hygromycin B was added whenever cells were passaged. For the binding assay, Jurkat NFAT cells were harvested, washed with PBS and resuspended in FACS buffer. The antibody staining was performed in a 96-well round bottom plate. Therefore 100'000 to 200'000 cells were seeded per well. The plate was centrifuged for 4 min at 400 x g and the supernatant was removed. The test antibodies were diluted in FACS buffer and 20 µl of the antibody solution were added to the cells for 30 min at 4° C. To remove unbound antibody, the cells were washed twice with FACS buffer before addition of the diluted secondary antibody (PE-conjugated AffiniPure F(ab')2 Fragment goat anti-human IgG Fcg Fragment Specific; Jackson ImmunoResearch #109-116-170). After 30 min incubation at 4° C. unbound secondary antibody was washed away. Before measurement the cells were resuspended in 200 µl FACS buffer and then analyzed by flow cytometry using a BD FACSCanto™ II device.

Figure 3:
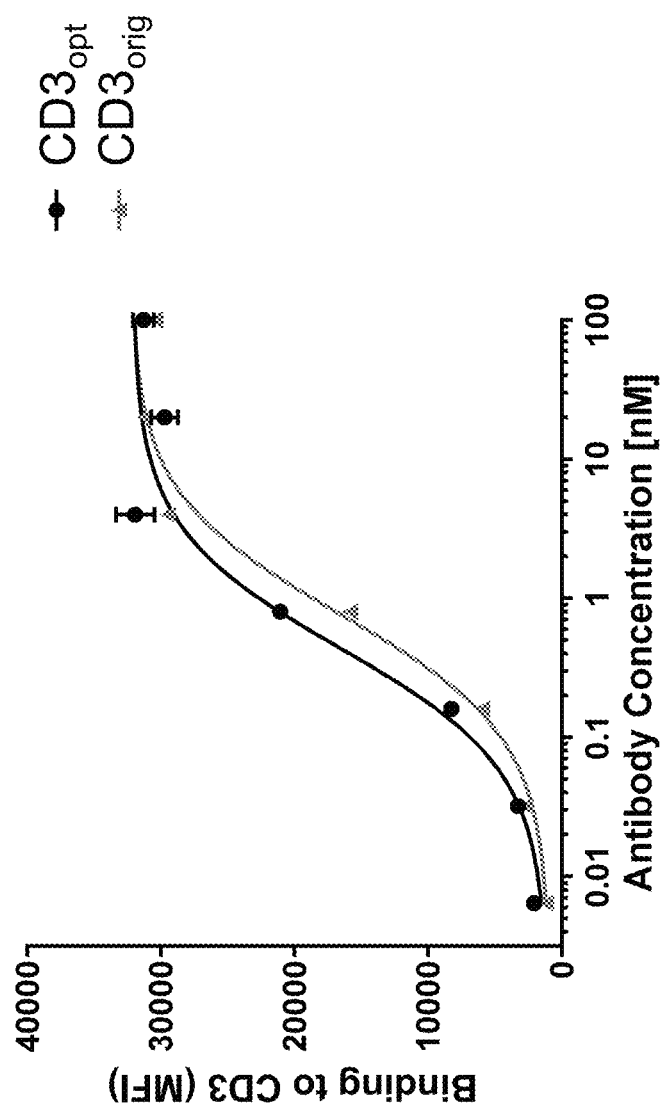
FIG. 3. Binding of original and optimized CD3 binders, $CD3_{orig}$ and $CD3_{opt}$, to Jurkat NFAT cells as measured by flow cytometry (IgG format). Antibodies bound to Jurkat NFAT cells were detected with a fluorescently labeled anti-human Fc specific secondary antibody.

As shown in FIG. 3, the optimized CD3 binder "$CD3_{opt}$" and the original CD3 binder "$CD3_{orig}$" bound comparably well to CD3 on Jurkat cells.

Example 3—Functional Activity of Optimized CD3 Binder

Figure 4:
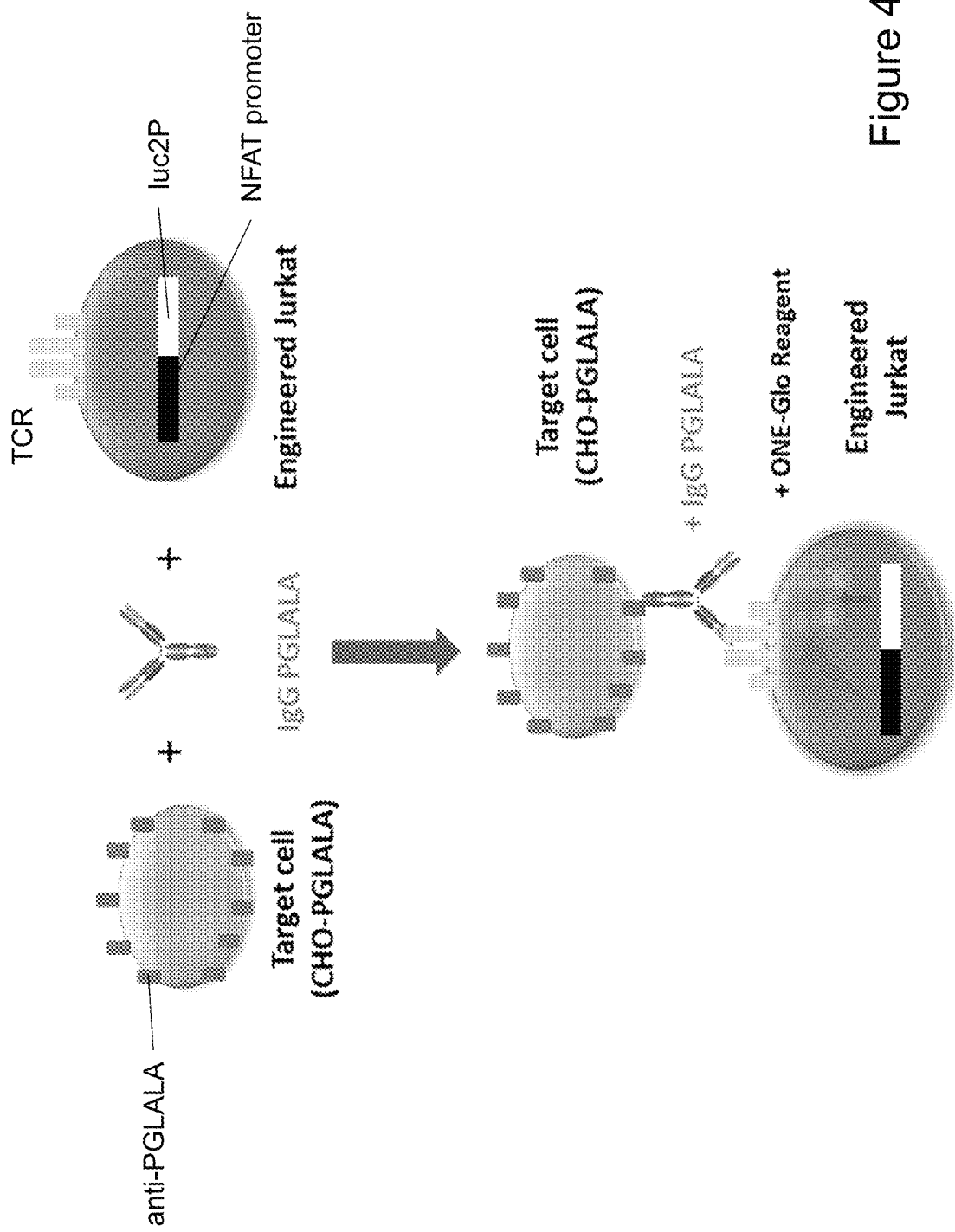
FIG. 4. Schematic illustration of the CD3 activation assay used in Example 3.

The functional activity of the optimized CD3 binder "$CD3_{opt}$" was tested in a Jurkat reporter cell assay and compared to the activity of the original CD3 binder "$CD3_{orig}$". To test the functional activity of the IgGs, anti-PGLALA expressing CHO cells were co-incubated with Jurkat NFAT reporter cells in the presence of increasing concentrations of $CD3_{opt}$ human IgG1 PGLALA or $CD3_{orig}$ human IgG1 PGLALA. Activation of CD3 on the Jurkat NFAT reporter cells upon T cell cross-linking induces the production of luciferase and luminescence can be measured as an activation marker. $CD3_{orig}$ human IgG1 wt was included as negative control which cannot bind to anti-PGLALA expressing CHO cells and therefore cannot be crosslinked on Jurkat NFAT cells. A schematic illustration of the assay is provided in FIG. 4.

Anti-PGLALA expressing CHO cells are CHO-K1 cells engineered to express on their surface an antibody that specifically binds human $IgG_1$ Fc(PGLALA) (see WO 2017/072210, incorporated herein by reference). These cells were cultured in DMEM/F12 medium containing 5% FCS+1% GluMax. The Jurkat NFAT reporter cells are as described in Example 2.

Upon simultaneous binding of the CD3 huIgG1 PGLALA to anti-PGLALA expressed on CHO and CD3 expressed on Jurkat-NFAT reporter cells, the NFAT promoter is activated and leads to expression of active firefly luciferase. The intensity of luminescence signal (obtained upon addition of luciferase substrate) is proportional to the intensity of CD3 activation and signaling.

Jurkat-NFAT reporter cells grow in suspension and were cultured in RPMI1640, 2g/l glucose, 2 g/l $NaHCO_3$, 10% FCS, 25 mM HEPES, 2 mM L-glutamin, 1× NEAA, 1× sodium-pyruvate at 0.1-0.5 mio cells per ml, 200 µg per ml hygromycin. For the assay, CHO cells were harvested and viability determined using ViCell. 30 000 target cells/well were plated in a flat-bottom, white-walled 96-well-plate (Greiner bio-one #655098) in 100 µl medium and 50 µl/well of diluted antibodies or medium (for controls) were added to the CHO cells. Subsequently, Jurkat-NFAT reporter cells were harvested and viability assessed using ViCell. Cells were resuspended at 1.2 mio cells/ml in cell culture medium without hygromycin B and added to CHO cells at 60 000 cells/well (50 µl/well) to obtain a final effector-to-target (E:T) ratio of 2:1 and a final volume of 200 µl per well.

Figure 5:
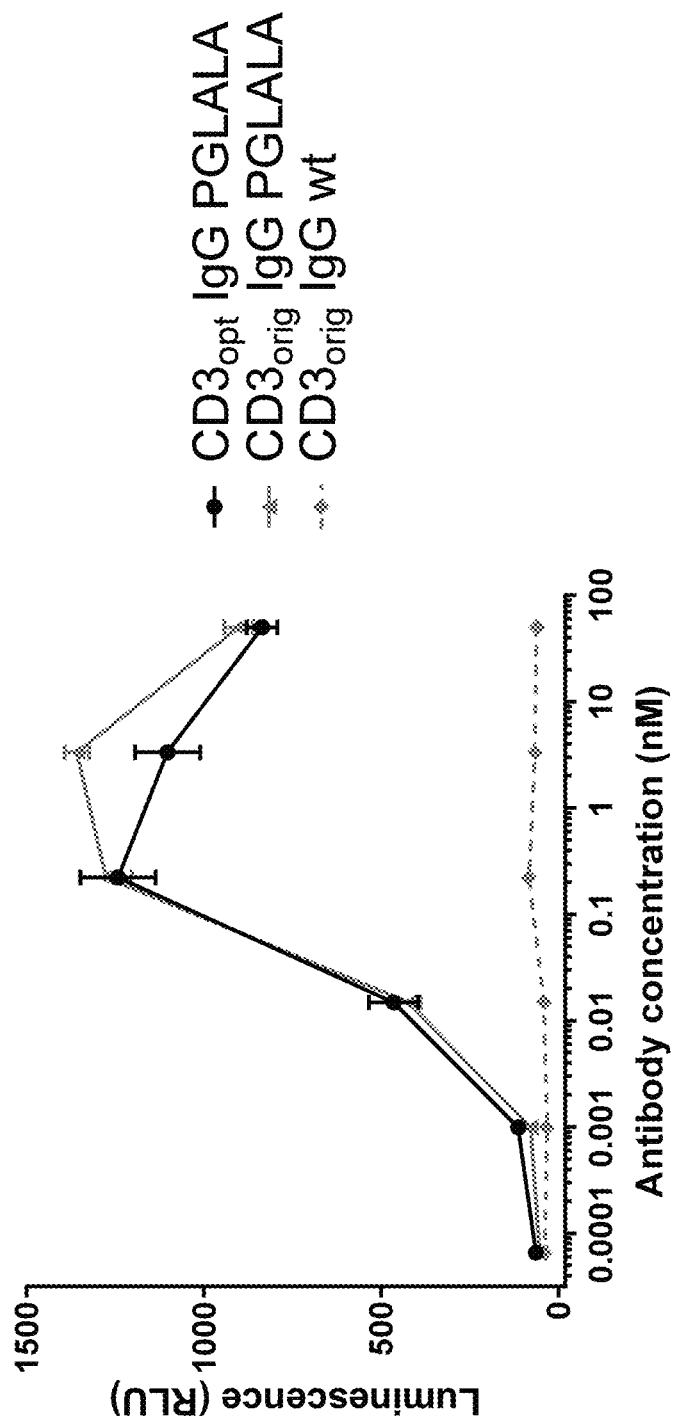
FIG. 5. Jurkat NFAT activation with original and optimized CD3 binders, $CD3_{orig}$ and $CD3_{opt}$ (IgG format). Jurkat NFAT reporter cells were co-incubated with anti-PGLALA expressing CHO (CHO-PGLALA) cells in the presence of $CD3_{orig}$ or $CD3_{opt}$ IgG PGLALA, or $CD3_{opt}$ IgG wt as negative control. CD3 activation was quantified by measuring luminescence after 24 h.

Then, 4 µl of GloSensor (Promega #E1291) was added to each well (2% of final volume). Cells were incubated for 24 h at 37° C. in a humidified incubator. At the end of incubation time, luminescence was detected using a TECAN® Spark 10M device. As shown in FIG. 5, the optimized CD3 binder $CD3_{opt}$ had a similar activity on Jurkat NFAT cells upon crosslinking as $CD3_{orig}$.

Example 4—Generation of T-Cell Bispecific Antibody Comprising Optimized CD3 Binder

TYRP1 TCB

The optimized CD3 binder identified in Example 1 ("$CD3_{opt}$", SEQ ID NOs 7 (VH) and 11 (VL)) was used to generate a T-cell bispecific antibody (TCB) targeting CD3 and TYRP1 ("TYRP1 TCB").

The TYRP1 binder comprised in this TCB was generated by humanization of the TYRP1 binder "TA99" (see GEN-BANK® entries AXQ57811 and AXQ57813 for the heavy and light chain, respectively), and comprises the heavy and light chain variable region sequences shown in SEQ ID NOs 18 and 22, respectively.

Figure 6:
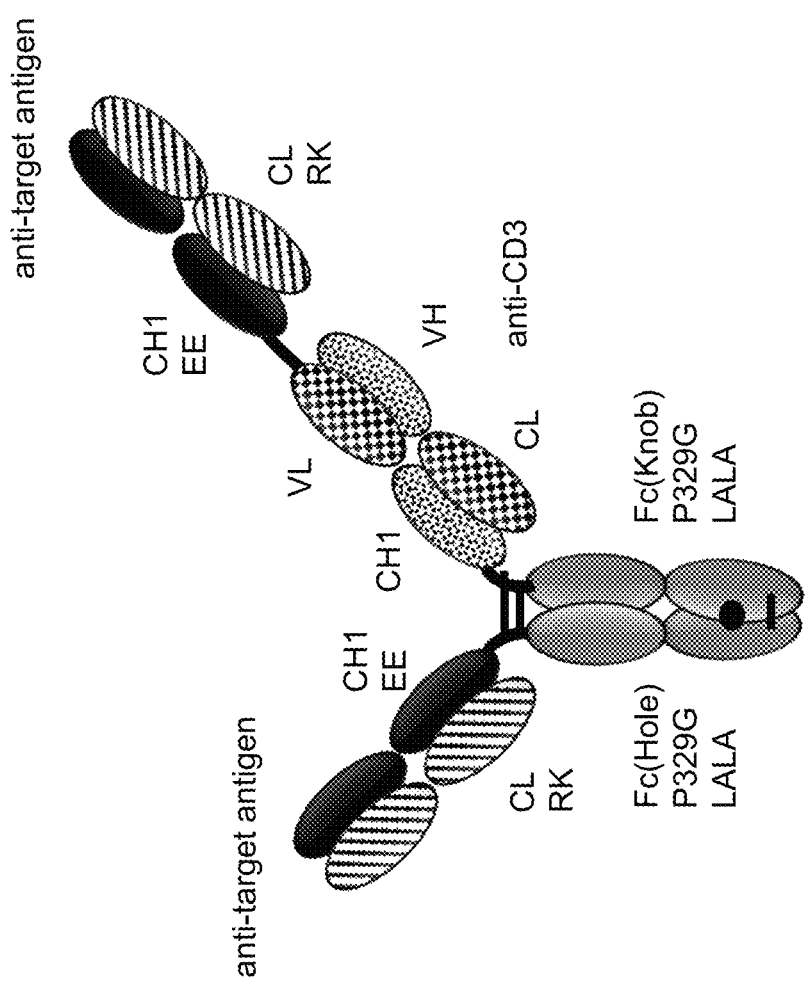
FIG. 6. Schematic illustration of the T-cell bispecific antibody (TCB) molecules prepared in the Examples. All tested TCB antibody molecules were produced as "2+1 IgG CrossFab, inverted" with charge modifications (VH/VL exchange in CD3 binder, charge modifications in target antigen binders, EE=147E, 213E; RK=123R, 124K).

A schematic illustration of the TCB molecule is provided in FIG. 6, and its full sequences are given in SEQ ID NOs 23, 24, 25 and 27.

An analogous molecule with the original CD3 binding sequences was also prepared (SEQ ID NOs 23, 24, 25 and 26).

Bispecific molecules were generated by transient transfection of HEK293 EBNA cells. The cells were transfected with the corresponding expression vectors in a 1:2:1:1 ratio ("vector heavy chain (VH-CH1-VL-CH1-CH2-CH3)": "vector light chain (VL-CL)": "vector heavy chain (VH-CH1-CH2-CH3)": "vector light chain (VH-CL)") Cells were centrifuged and medium was replaced by pre-warmed CD CHO medium (Thermo Fisher, #10743029). Expression vectors were mixed in CD CHO medium, PEI (polyethylenimine, Polysciences, #23966-1) was added, the solution vortexed and incubated for 10 minutes at room temperature. Afterwards, cells (2 mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added. One day after transfection, supplements (Feed, 12% of total volume) were added. Cell supernatants were harvested after 7 days by centrifugation and subsequent filtration (0.2 µm filter).

Proteins were purified from filtered cell culture supernatants by standard methods. In brief, Fc containing proteins were purified from cell culture supernatants by Protein A-affinity chromatography (MabSelect Sure, GE Healthcare: equilibration buffer: 20 mM sodium citrate, 20 mM sodium phosphate, pH 7.5; elution buffer: 20 mM sodium citrate, 100 mM NaCl, 100 mM glycine pH 3.0). Elution was achieved at pH 3.0 followed by immediate pH neutralization of the sample. The protein was concentrated by centrifugation (Millipore Amicon® ULTRA-15 (#UFC903096)), and aggregated protein was separated from monomeric protein by size exclusion chromatography (Superdex 200, GE Healthcare) in 20 mM histidine, 140 mM sodium chloride, pH 6.0.

The concentration of purified proteins was determined by measuring the absorption at 280 nm using the mass extinction coefficient calculated on the basis of the amino acid sequence according to Pace et al. (1995), Protein Science 4, 2411-23. Purity and molecular weight of the proteins were analyzed by CE-SDS in the presence and absence of a reducing agent using a LabChipGXII (Perkin Elmer) (Table 1). Determination of the aggregate content was performed by HPLC chromatography at 25° C. using analytical size-exclusion column (TSKgel G3000 SW XL or UP-SW3000) equilibrated in running buffer (25 mM $K_2HPO_4$, 125 mM NaCl, 200 mM L-arginine monohydrochloride, pH 6.7 or 200 mM $KH_2PO_4$, 250 mM KCl pH 6.2, respectively) (Table 2).

TABLE 1

CE-SDS analyses (non-reduced) of TYRP1 TCBs.

| Molecule | Peak # | Size [kDa] | Purity [%] |
|---|---|---|---|
| TYRP1 TCB $CD3_{opt}$ | 1 | 221 | 100 |
| TYRP1 TCB $CD3_{orig}$ | 1 | 206 | 100 |

TABLE 2

Summary production and purification of TYRP1 TCBs.

| Molecule | Titer [mg/l] | Recovery [%] | Yield [mg/l] | Analytical SEC (HMW/Monomer/LMW) [%] |
|---|---|---|---|---|
| TYRP1 TCB $CD3_{opt}$ | 114 | 20 | 22.8 | 0.5/98.6/0.9 |
| TYRP1 TCB $CD3_{orig}$ | 72 | 12 | 8.7 | 0/97.5/2.5 |

Example 5—Binding of T-Cell Bispecific Antibody Comprising Optimized CD3 Binder to CD3 and TYRP1

Binding to Recombinant CD3

Binding of the TYRP1 TCB to recombinant CD3 was assessed by SPR, using the TCBs with either the optimized (TYRP1 TCB $CD3_{opt}$) or the original (TYRP1 TCB $CD3_{orig}$) CD3 binding sequences.

SPR experiments were performed on a Biacore T200 with HBS-EP as running buffer (0.01 M HEPES pH 7.4, 0.15 M NaCl, 0.05% (v/v) Surfactant P20 (GE Healthcare)). TYRP1 TCB was captured on a CM5 sensorchip surface with an immobilized antibody that specifically binds human $IgG_1$ Fc(PGLALA) (see WO 2017/072210, incorporated herein by reference). Capture antibody was coupled to the sensorchip surface by direct immobilization of around 8700 resonance units (RU) at pH 5.0 using the standard amine coupling kit (GE Healthcare). TCB molecules were captured for 30 s at 5 nM with a flow of 10 μl/min.

The human and cynomolgus antigens (see below) were passed at a concentration of 12.35-3000 nM with a flow of 30 μl/min through the flow cells over 240 s. The dissociation phase was monitored for 240 s and triggered by switching from the sample solution to HBS-EP. The chip surface was regenerated after every cycle using one injection of 10 mM glycine pH 2.0 for 30 s.

The antigens used were heterodimers of either human or cynomolgus CD3 delta and CD3 epsilon ectodomains fused to a human Fc domain with knob-into-hole modifications and a C-terminal AviTag™ tag (see SEQ ID NOs 28 and 29 (human CD3) and SEQ ID NOs 30 and 31 (cynomolgus CD3)).

Bulk refractive index differences were corrected by subtracting the response obtained on the reference flow cell (no TCB captured). The affinity constants were derived from the kinetic rate constants by fitting to a 1:1 Langmuir binding using the BIAeval software (GE Healthcare).

The $K_D$ values for binding to human and cynomolgus CD3 were determined as 50 nM and 20 nM, respectively, for TYRP1 TCB $CD3_{opt}$ and were similar to the ones for TYRP1 TCB $CD3_{orig}$ (50 nM and 40 nM, respectively).

This shows that in unstressed condition both TCBs, comprising either $CD3_{opt}$ or $CD3_{orig}$, bound comparably well to recombinant CD3.

Binding of the TYRP1 TCB to recombinant human CD3 was also assessed after temperature stress for 14 days at 37° C. or 40° C., using the TCBs with either the optimized or the original CD3 binding sequences. The experiment was performed as described in Example 2 above, using the TCB instead of IgG molecules.

Figure 7:
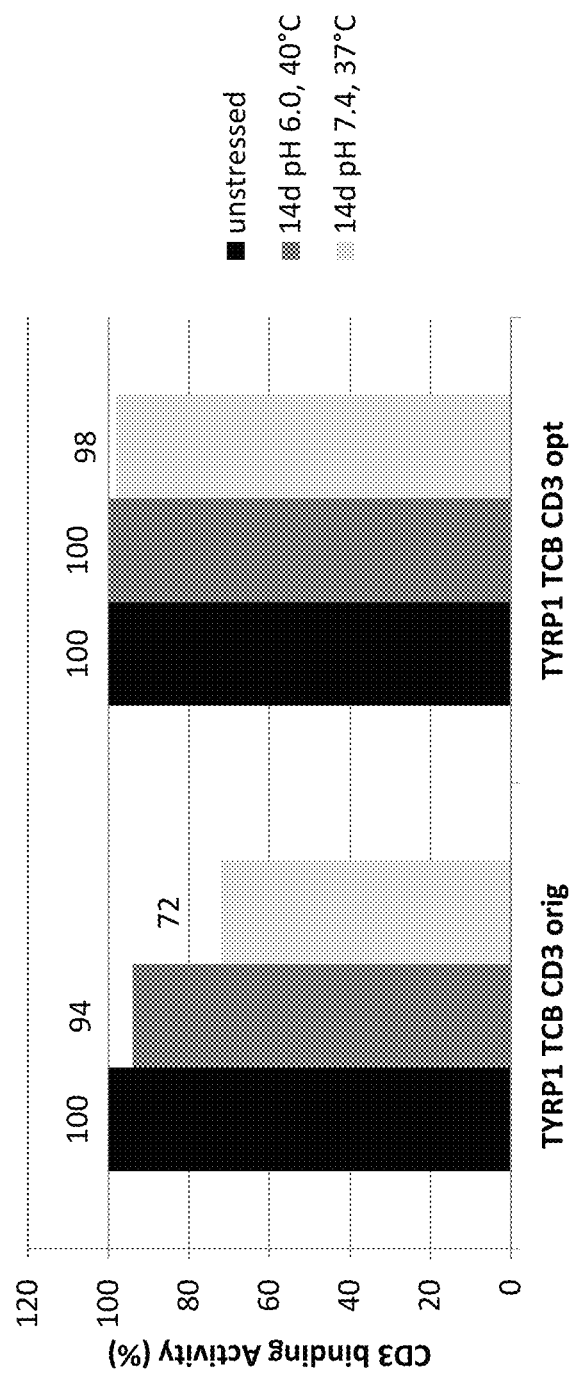
FIG. 7. Relative binding activity of TYRP1 TCBs comprising original or optimized CD3 binders, $CD3_{orig}$ or $CD3_{opt}$, to recombinant CD3 as measured by SPR in unstressed condition, after 14 d at 40° C. pH 6, or after 14 d at 37° C. pH 7.4.

The results of this experiment are shown in FIG. 7.

As can be seen in FIG. 7, the TCB comprising the optimized CD3 binder $CD3_{opt}$ showed strongly improved binding to CD3 after stress (2 weeks at 37° C., pH 7.4) as compared to the TCB comprising the original CD3 binder $CD3_{orig}$. This result confirms that the improved properties of the optimized CD3 binder (see Example 2) are maintained at the TCB level.

Binding to Recombinant TYRP1

Binding to recombinant TYRP1 was assessed by SPR, using TYRP1 Fab fragments prepared by plasmin digestion of corresponding antibody.

SPR experiments were performed on a Biacore T200 with HBS-EP as running buffer (0.01 M HEPES pH 7.4, 0.15 M NaCl, 0.05% (v/v) Surfactant P20 (GE Healthcare)).

An antibody that specifically binds human $IgG_1$ Fc(PGLALA) (see WO 2017/072210, incorporated herein by reference) was directly coupled on a CM5 sensor chip at pH 5.0 using the standard amine coupling kit (GE Healthcare). Antigens (see below) were captured with a flow rate of 10 μl/min for 30 s. A 3-fold dilution series of the TYRP1 Fab fragments was passed on the flow cells at 30 μl/min for 180 s to record the association phase. The dissociation phase was monitored for 180 s or 1200 s and triggered by switching from the sample solution to HBS-EP. The chip surface was regenerated after every cycle using one injection of 10 mM glycine pH 2 for 30 s at 30 μl/min.

The antigens used were monomeric fusions of the human, cynomolgus or mouse TYRP1 extracellular domain (ECD) to a human Fc-domain with knob-into-hole (and PG LALA) modifications and a C-terminal AviTag™ tag (see SEQ ID NOs 32 and 35 (human TYRP1), SEQ ID NOs 33 and 35 (cynomolgus TYRP1) or SEQ ID NOs 34 and 35 (mouse TYRP1)). Bulk refractive index differences were corrected by subtracting the response obtained on the reference flow cell (no antigen captured). The affinity constants ($K_D$) were derived from the kinetic rate constants by fitting to a 1:1 Langmuir binding using the BIAeval software (GE Healthcare).

The $K_D$ values for binding to human, cynomolgus and mouse TYRP1 were determined as 130 pM, 180 pM and 530 pM, respectively, and were similar to the ones for the parental TA99 antibody (90 pM, 120 pM and 310 pM, respectively).

Binding of the TYRP1 TCB to recombinant TYRP1 was also assessed after temperature stress for 14 days at 37° C. or 40° C., using the TCBs with either the optimized or the original CD3 binding sequences.

The experiment was performed as described above for the binding to CD3, using recombinant TYRP1 (Sino Biologicals) as antigen.

Figure 8:
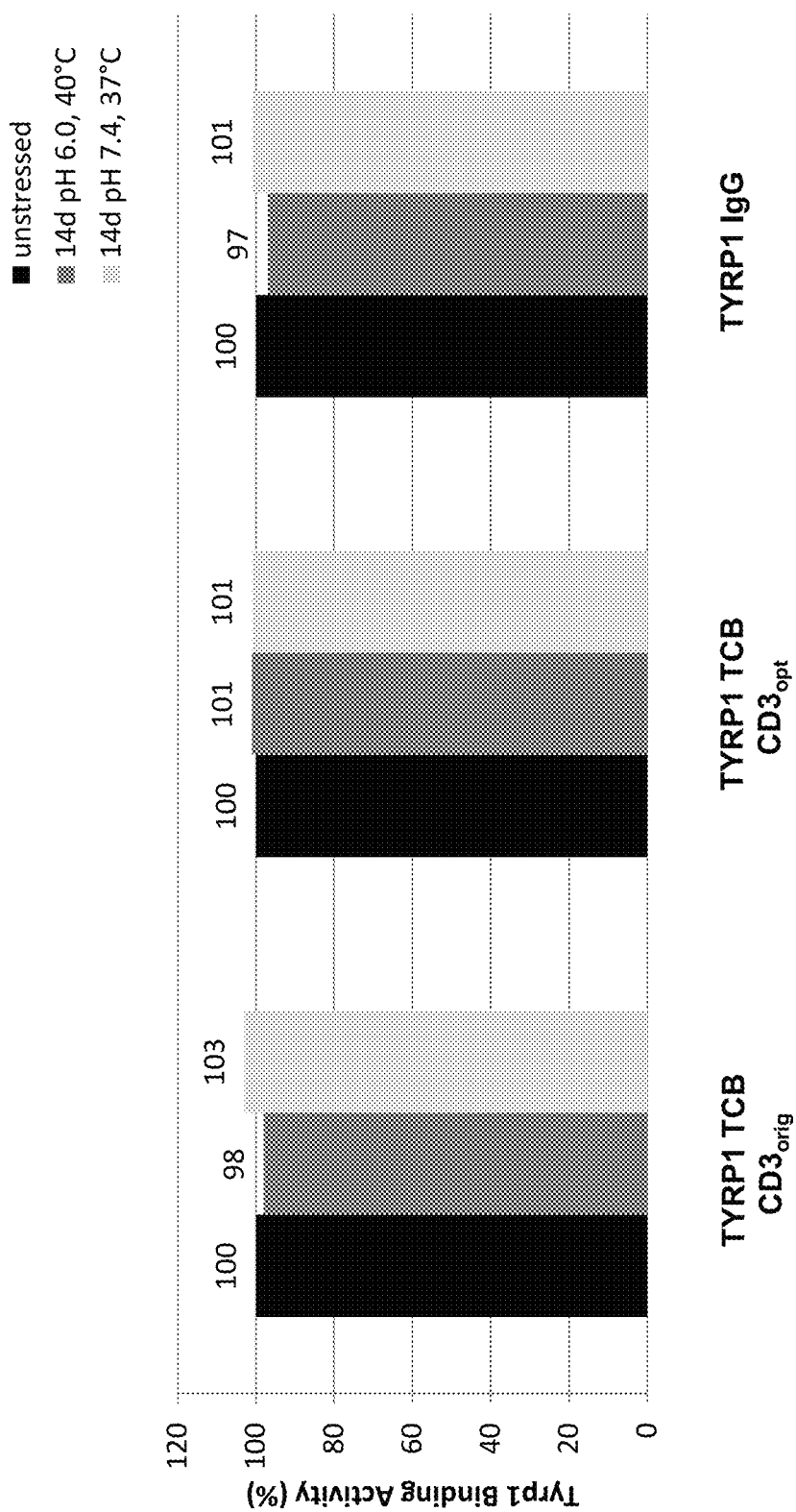
FIG. 8. Relative binding activity of TYRP1 TCBs comprising original or optimized CD3 binders, $CD3_{orig}$ or $CD3_{opt}$, or the corresponding TYRP1 IgG, to recombinant TYRP1 as measured by SPR in unstressed condition, after 14 d at 40° C. pH 6, or after 14 d at 37° C. pH 7.4.

The results of this experiment are shown in FIG. 8. They confirm that the binding to human TYRP1 for both TCBs (as well as for the corresponding TYRP1 binder in IgG format) is not affected by stress conditions.

Binding to CD3 on Jurkat Cells

Binding to CD3 on the human reporter T-cell line Jurkat NFAT was determined by FACS for TYRP1 TCBs comprising the optimized CD3 binder "$CD3_{opt}$" or the original CD3 binder "$CD3_{orig}$", as described above in Example 2.

Figure 9:
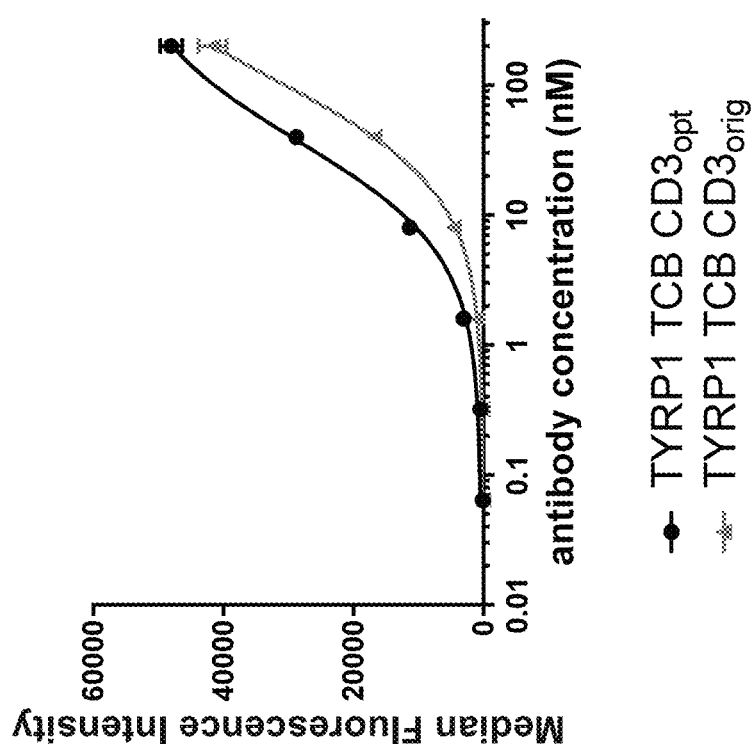
FIG. 9. Binding of TYRP1 TCBs comprising original or optimized CD3 binders, $CD3_{orig}$ or $CD3_{opt}$, to Jurkat NFAT cells as measured by flow cytometry. TCBs bound to Jurkat NFAT cells were detected with a fluorescently labeled anti-human Fc specific secondary antibody.

As shown in FIG. 9, the TCB comprising the optimized CD3 binder "$CD3_{opt}$" binds to CD3 on Jurkat cells at least comparably well to the TCB comprising the original CD3 binder "$CD3_{orig}$".

Example 6—Functional Activity of T-Cell Bispecific Antibody Comprising Optimized CD3 Binder CD3 Activation The TYRP1 TCBs containing either the optimized CD3 binder $CD3_{opt}$ or the original CD3 binder $CD3_{orig}$ (Example 4) were tested in the Jurkat NFAT reporter cell assay (see Example 3) in the presence of TYRP1 positive melanoma cells M150543 (primary melanoma cell line, obtained from the dermatology cell bank of the University of Zurich).

Upon simultaneous binding of TYRP1 TCB to TYRP1 positive target cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. The assay was performed as described in Example 3, using M150543 instead of anti-PGLALA expressing CHO cells.

Figure 10:
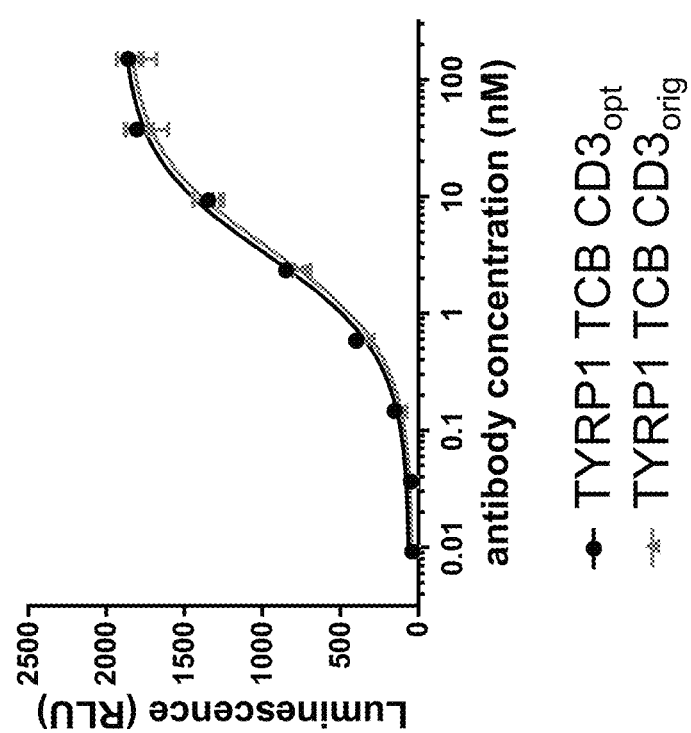
FIG. 10. Jurkat NFAT activation with TYRP1 TCBs comprising original or optimized CD3 binders. Jurkat NFAT reporter cells were co-incubated with the melanoma cell line M150543 in the presence of TYRP1 TCB $CD3_{orig}$ or TYRP1 TCB $CD3_{opt}$. CD3 activation in the presence of the TCBs was quantified by measuring luminescence after 24 h.
Figure 11B:
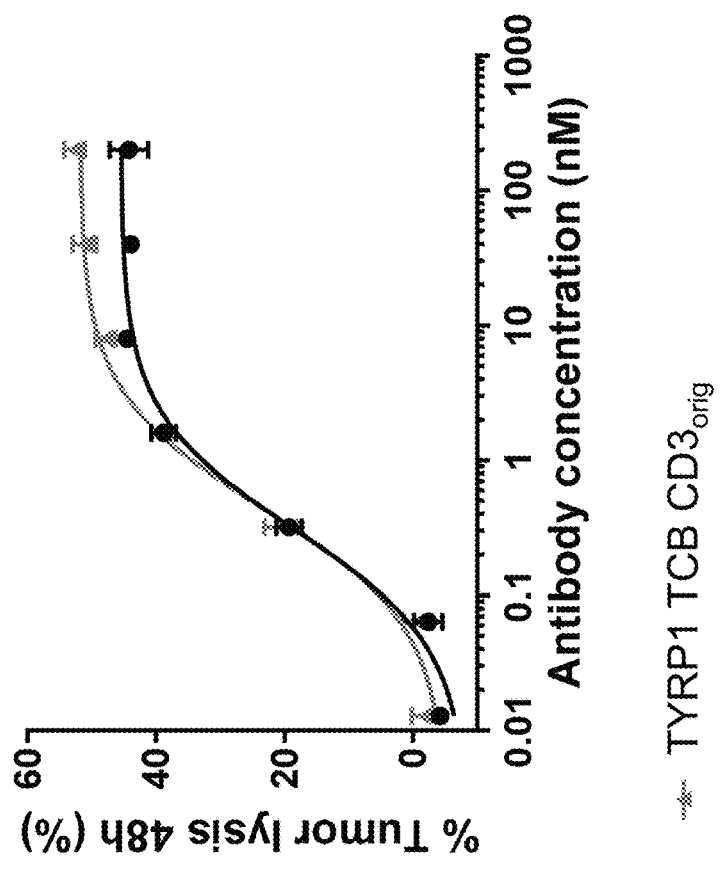
Figure 11A:
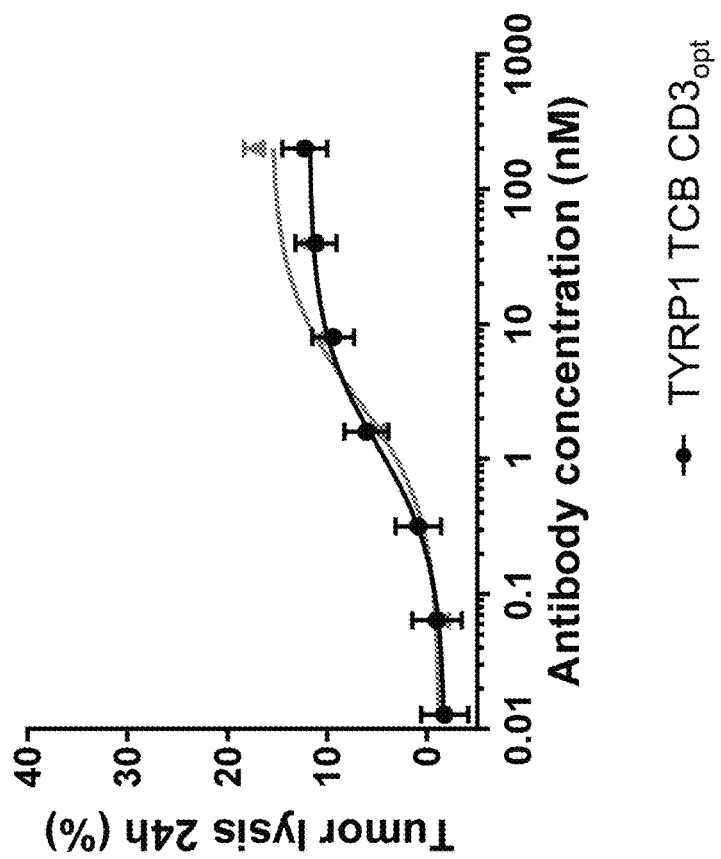
Figure 11C:
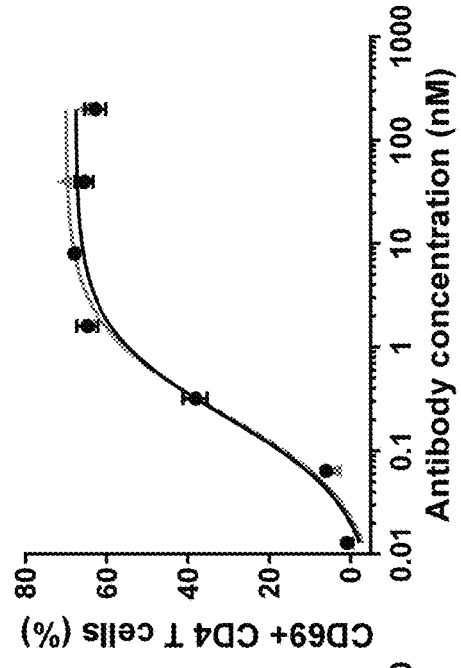
Figure 11D:
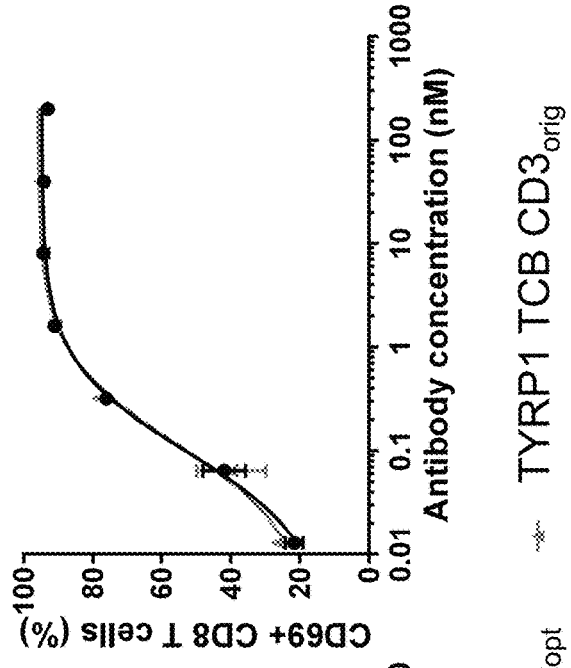
Figure 11E:
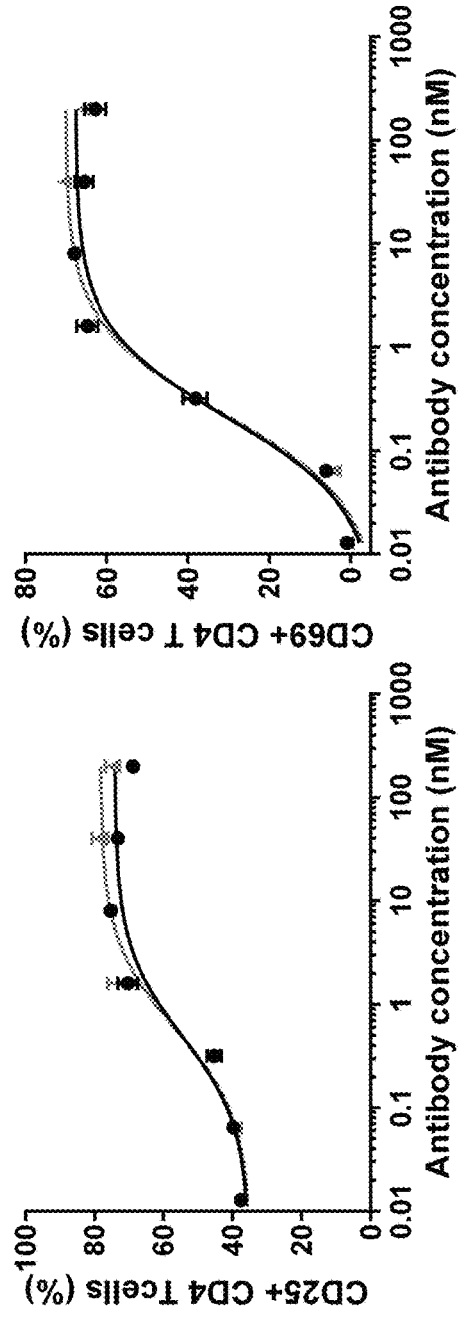
Figure 11F:
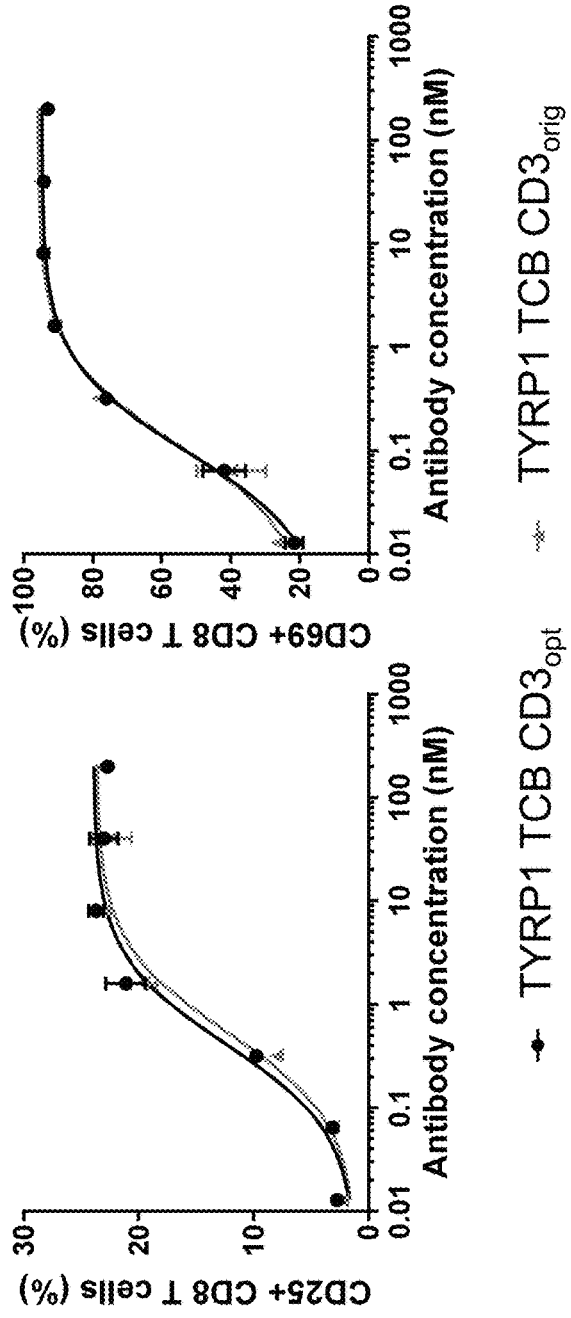
Figure 11G:
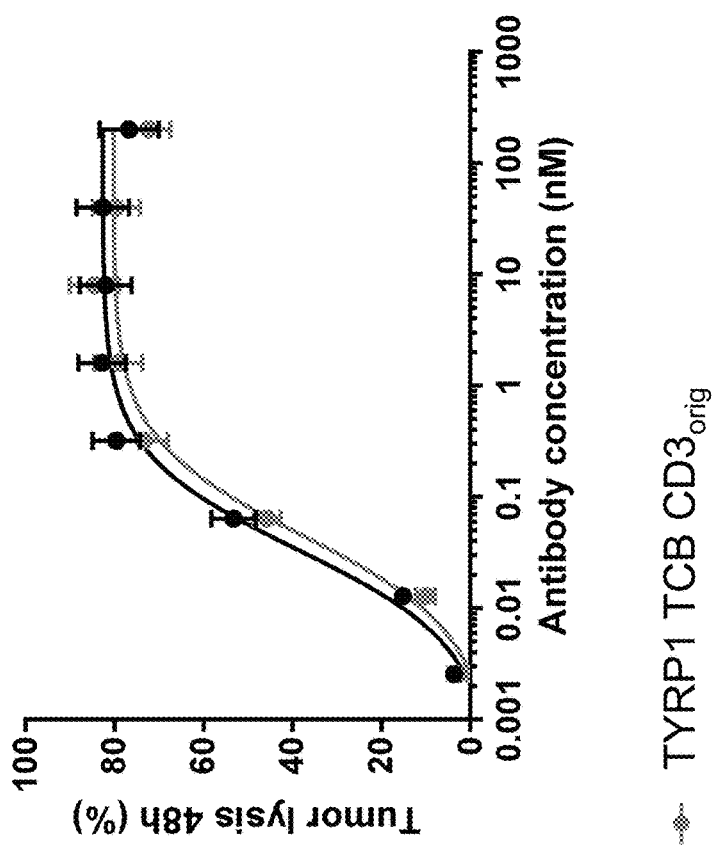
FIGS. 11G-11L: donor 2.
Figure 11H:
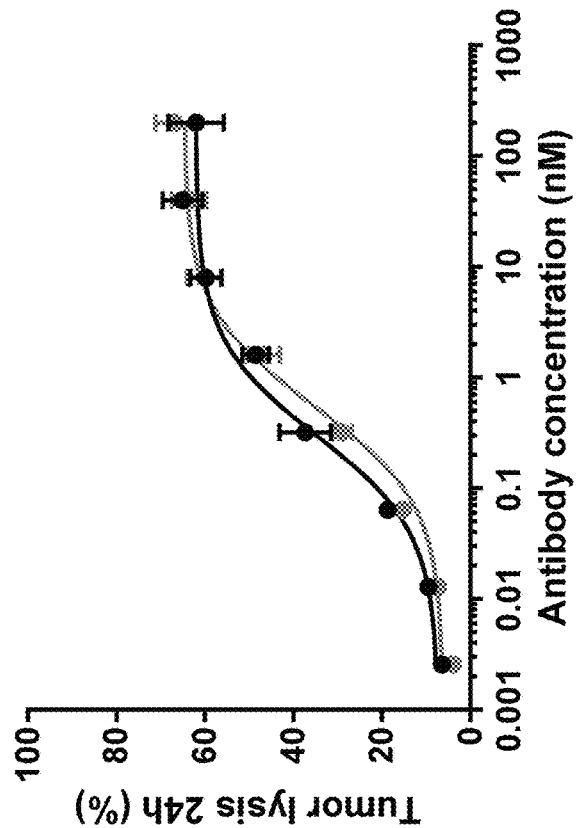
Figure 11I:
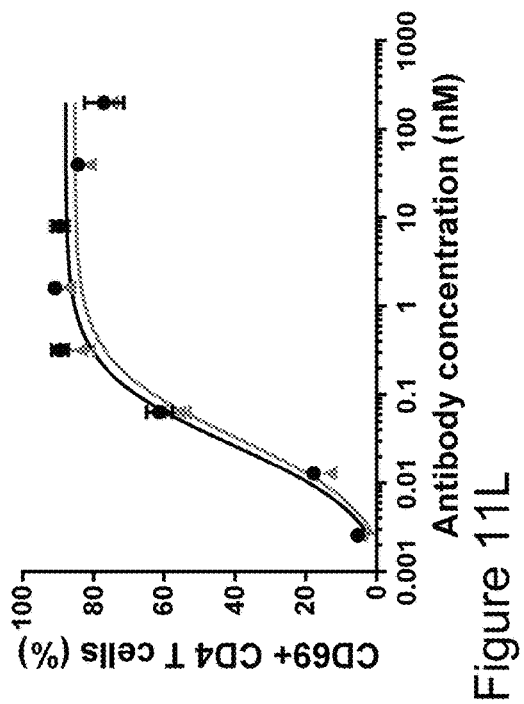
Figure 11J:
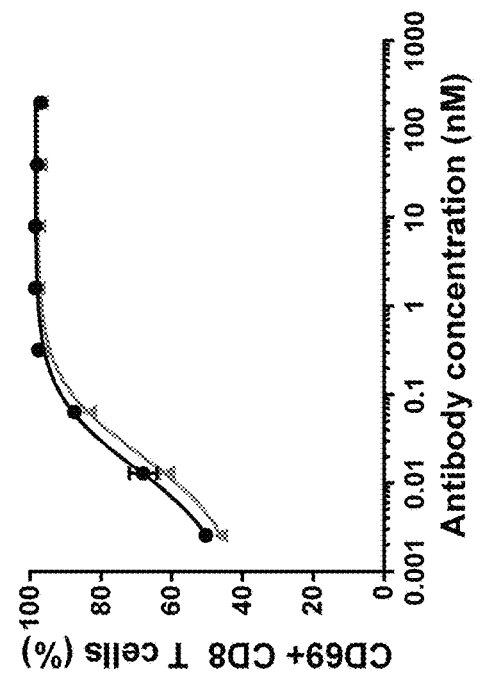
Figure 11K:
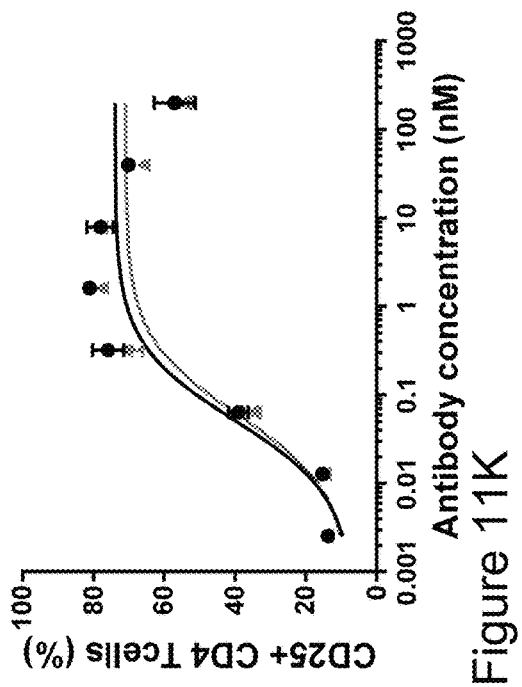
Figure 11L:
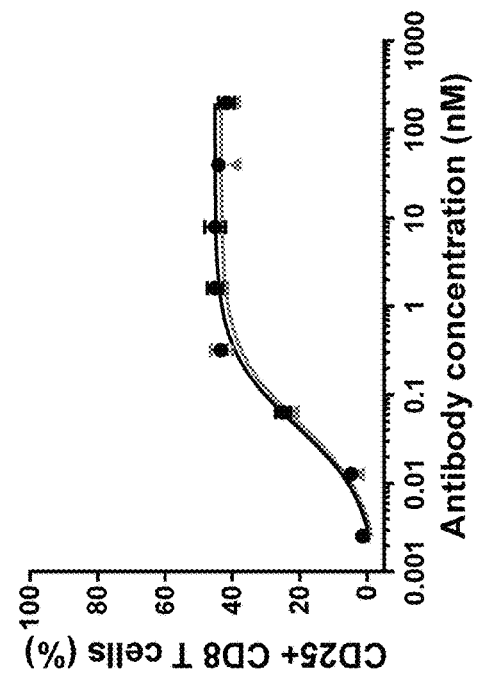
Figure 11N:
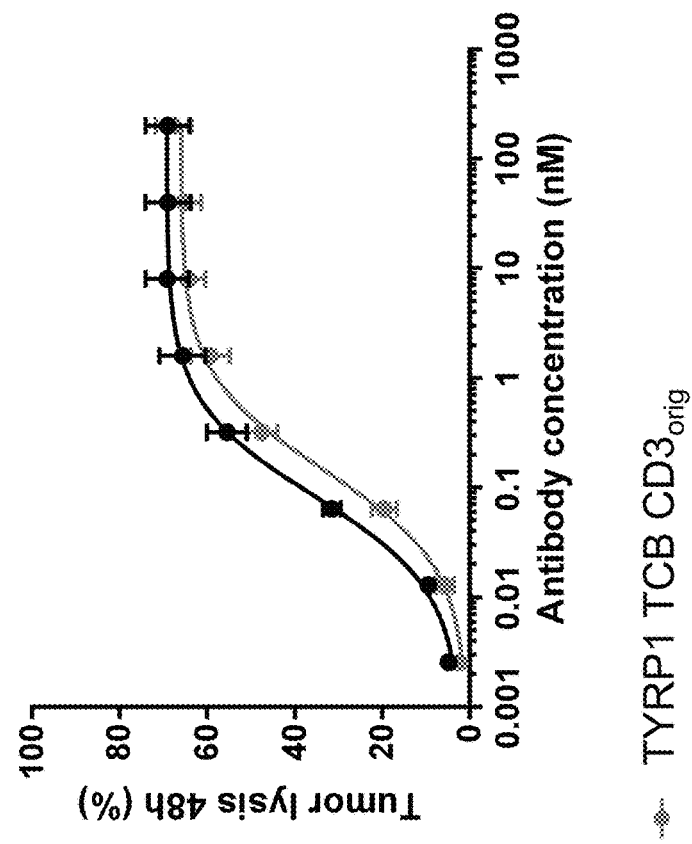
Figure 11M:
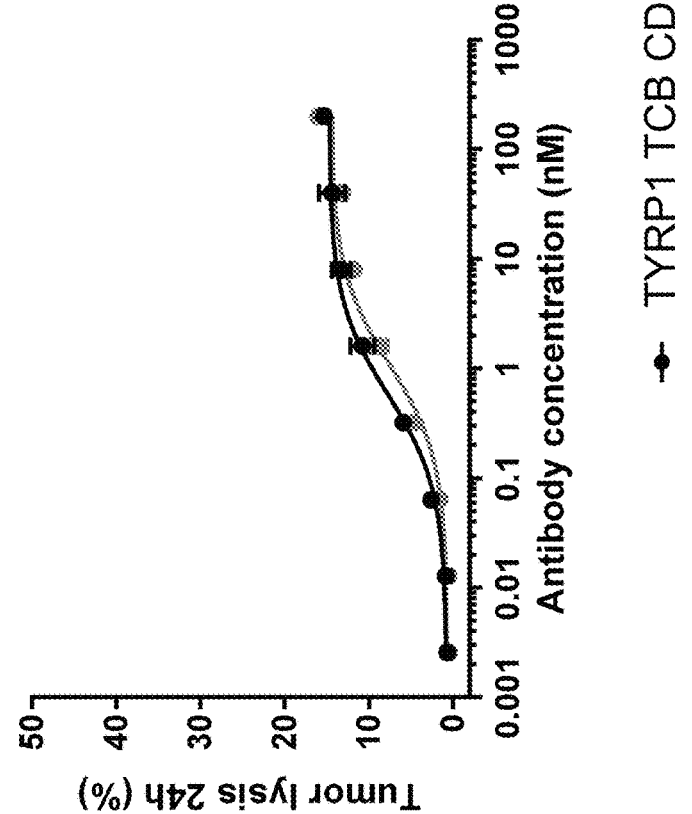

As seen for the IgGs (Example 3) both TCBs containing either $CD3_{opt}$ or $CD3_{orig}$ had a similar functional activity on the Jurkat NFAT reporter cells and induced CD3 activation in a concentration dependent manner (FIG. 10).

Target Cell Killing

In a next step, both TCB molecules were tested in a tumor cell killing assay with freshly isolated human PBMCs from three different donors, co-incubated with the human melanoma cell line M150543. Tumor cell lysis was determined by LDH release after 24 h and 48 h. Activation of CD4 and CD8 T cells was analyzed by upregulation of CD69 and CD25 on both cell subsets after 48 h.

Briefly, target cells were harvested with Trypsin/EDTA, washed, and plated at density of 30 000 cells/well using flat-bottom 96-well plates. Cells were left to adhere overnight. Peripheral blood mononuclear cells (PBMCs) were prepared by Histopaque™ density centrifugation of fresh blood obtained from healthy human donors. Fresh blood was diluted with sterile PBS and layered over Histopaque™ gradient (Sigma #H8889). After centrifugation (450×g, 30 minutes, room temperature), the plasma above the PBMC-containing interphase was discarded and PBMCs transferred into a new Falcon tube subsequently filled with 50 ml of PBS. The mixture was centrifuged (400 x g, 10 minutes, room temperature), the supernatant discarded and the PBMC pellet washed twice with sterile PBS (centrifugation steps 350 x g, 10 minutes). The resulting PBMC population was counted automatically (ViCell) and stored in RPMI1640 medium containing 10% FCS and 1% L-alanyl-L-glutamine (Biochrom #K0302) at 37° C., 5% $CO_2$ in cell incubator until further use (no longer than 24 h). For the killing assay, the antibodies were added at the indicated concentrations in triplicates. PBMCs were added to target cells at final effector-to-target (E:T) ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science #11 644 793 001). Maximal lysis of the target cells (=100%) was achieved by incubation of target cells with 1% TRITON® X-100 detergent. Minimal lysis (=0%) refers to target cells co-incubated with effector cells without bispecific construct.

Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend #300514), CD8 FITC (BioLegend #344704), CD25 BV421 (BioLegend #302630) and CD69 PE (BioLegend #310906) was performed according to the suppliers' indications. Cells were washed twice with 150 μl/well FACS buffer and fixed for 15 min at 4° C. using 100 μl/well fixation buffer (BD #554655). After centrifugation, the samples were resuspended in 200 μl/well FACS buffer. Samples were analyzed at BD FACS Fortessa device.

On all three donors both TCBs, comprising either the optimized or the original CD3 binder, induced T cell activation and tumor cell lysis in a comparable manner (FIG. 11). The EC50 values of tumor cell lysis for all three donors after 48 h are summarized in Table 3.

TABLE 3

Summary of EC50 values of tumor cell killing with TYRP1 TCBs at 48 h.

| PBMC donor | TYRP1 TCB ($CD3_{opt}$) EC50 (95% confidence interval) | TYRP1 TCB ($CD3_{orig}$) EC50 (95% confidence interval) |
|---|---|---|
| Donor 1 | 0.31 nM (0.17 to 0.55) | 0.44 nM (0.28 to 0.70) |
| Donor 2 | 0.03 nM (0.02 to 0.06) | 0.05 nM (0.02 to 0.09) |
| Donor 3 | 0.08 nM (0.07 to 0.1) | 0.14 nM (0.11 to 0.18) |

Example 7—PK Study with T-Cell Bispecific Antibodies in Mice

The pharmacokinetics (PK) of the TYRP1 TCB with different CD3 binders ($CD3_{orig}$ and $CD3_{opt}$) was studied following intravenous bolus administration at 1 mg/kg to human FcRn transgenic (line32, homozygous) and FcRn knock-out mice (Jackson Laboratory strain numbers 003982 and 014565) (n=3/strain/test compound). Serial blood microsamples were taken from human FcRn transgenic (tg) mice up to 672 h (9 samples per mouse from 5 min to 672 h post dose) and up to 96 h in FcRn knockout (ko) mice (8 samples per mouse from 5 min to 96 h post-dose). Serum was prepared and stored frozen until analysis. Mouse serum samples were analysed with a generic ECLIA method specific for human Ig/Fab CH1/kappa domain using Cobas® e411 (Roche) instrument under non-GLP conditions. Pharmacokinetic evaluation was conducted using standard non-compartmental analysis.

The results of this study are shown in Table 4. This indicates that the engineering of the CDRs did not give rise to other sequence liability, that would affect antibody clearance. CD3$_{opt}$ is equally good in as CD3$_{orig}$ in terms of serum half-life, while having the additional benefit of increased CDR stability.

TABLE 4

Clearance data in huFcRn tg mice and FcRn ko mice (ml/day/kg; mean and (CV)).

| Mouse strain | TYRP1 TCB (CD3$_{orig}$) | TYRP1 TCB (CD3$_{opt}$) |
|---|---|---|
| hFcRn tg32 | 8.82 (10.0) | 6.68 (12.5) |
| FcRn ko | 66.4 (16.2) | 65.0 (6.5) |

Example 8—Generation of a Further T-Cell Bispecific Antibody Comprising Optimized CD3 Binder The optimized CD3 binder identified in Example 1 ("CD3$_{opt}$", SEQ ID NOs 7 (VH) and 11 (VL)) was used to generate a T-cell bispecific antibody (TCB) targeting CD3 and EGFRvIII ("EGFRvIII TCB").

The EGFRvIII binder comprised in this TCB (P063.056) was derived from phage display followed by affinity maturation (see below), and comprises the heavy and light chain variable region sequences shown in SEQ ID NOs 88 and 92, respectively.

A schematic illustration of the TCB molecule is provided in FIG. 6, and its full sequences are given in SEQ ID NOs 109, 110, 111 and 27.

An analogous molecule with the original CD3 binding sequences was also prepared (SEQ ID NOs 109, 110, 111 and 26).

Bispecific molecules were generated by transient transfection of HEK293 EBNA cells, purified and analysed as described above in Example 4.

Furthermore, EGFRvIII antibodies derived from phage display were produced in human IgG$_1$ format in an analogous manner (transfecting the HEK EBNA cells with the expression vectors for the IgG heavy and light chains, in a 1:1 ratio), for use as described below.

All IgGs and TCB constructs were purified in comparable quality with a monomer content above 95% as determined by size exclusion chromatography.

Selection of EGFRvIII Antibody

EGFRvIII antibodies were derived from phage display and affinity matured. Antibodies showing high affinity binding and specificity for EGFRvIII (P056.021 (SEQ ID NOs 40 and 44), P056.052 (SEQ ID NOs 48 and 52), P047.019 (SEQ ID NOs 56 and 60), P057.012 (SEQ ID NOs 64 and 68), P057.011 (SEQ ID NOs 72 and 76), P056.027 (SEQ ID NOs 80 and 84)) were tested for binding to EGFRvIII expressed on the cell surface using CHO cells stably expressing EGFRvIII and the EGFRvIII positive human glioblastoma cell line DK-MG. To confirm specificity and to exclude crossreactivity to wild-type EGFR (EGFRwt) the selected antibodies were tested for binding to the EGFRwt positive human tumor cell line MKN-45 (FIG. 12). Cetuximab was included as positive control for binding to EGFRwt and the untargeted DP47 IgG as negative control. All selected antibodies specifically bound to EGFRvIII without crossreactivity to EGFRwt and were considered for further characterization.

Figure 13:
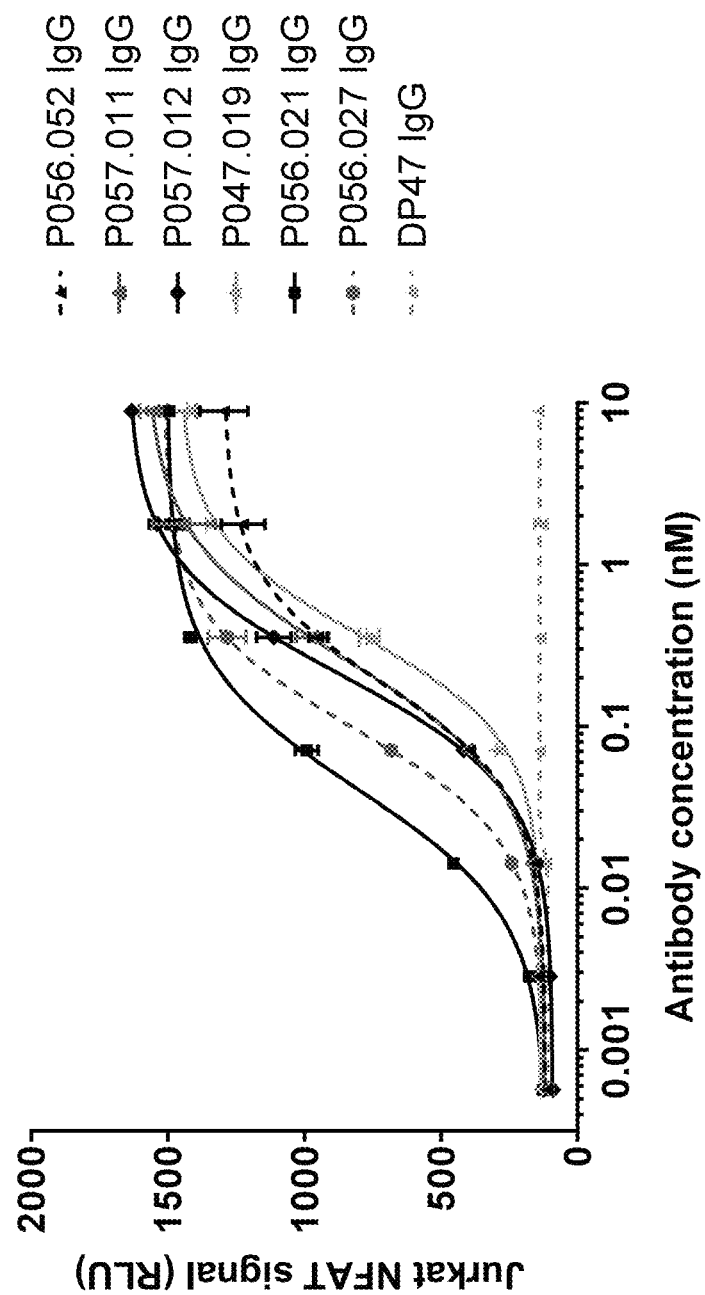
FIG. 13. CAR J activation with EGFRvIII IgG PGLALA. Jurkat NFAT reporter cells expressing anti-PGLALA CAR were co-incubated with EGFRvIII expressing DK-MG cells and EGFRvIII IgG PGLALA antibodies or DP47 IgG PGLALA as negative control. Activation of Jurkat NFAT cells was quantified by measuring luminescence after 22 h.

In a next step, the functional activity of these EGFRvIII antibodies as IgG1 PGLALA (human IgG1 format with P329G L234A L235A ("PGLALA", EU numbering) mutations in the Fc region) was assessed on DK-MG cells co-incubated with Jurkat NFAT reporter cells expressing an anti-PGLALA chimeric antigen receptor (CAR) by measuring luminescence (CAR assay, see PCT application no. PCT/EP2018/086038, incorporated herein by reference in its entirety). DP47 IgG1 PGLALA was included as negative control. All tested EGFRvIII antibodies induced strong activation of the CAR-expressing Jurkat NFAT reporter cells (FIG. 13). All tested EGFRvIII antibodies, except for P047.019 which showed the weakest binding and activation, were selected for conversion into the TCB format (with CD$_{orig}$ as CD3 binder).

Figure 14A:
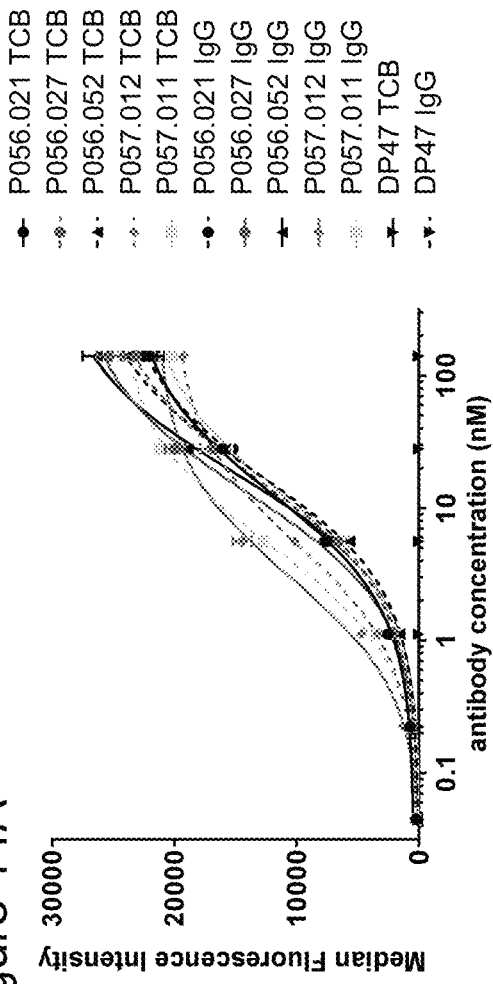
FIGS. 14A-14B. Binding of EGFRvIII IgG PGLALA and corresponding TCBs to EGFRvIII. Specific binding of EGFRvIII binders as IgG PGLALA and converted into TCBs to CHO-EGFRvIII (FIG. 14A) and MKN-45 (FIG. 14B) cells was measured by flow cytometry.
Figure 14B:
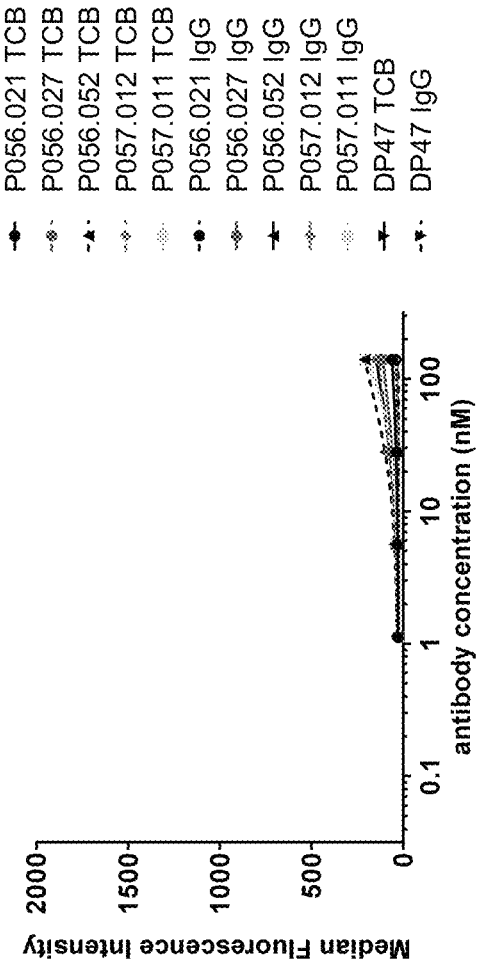

Binding of the selected EGFRvIII antibodies converted into the TCB format to CHO-EGFRvIII cells was compared to binding of the corresponding IgGs (FIG. 14) to confirm that conversion into the TCB format has no impact on the binding capacities of the EGFRvIII antibodies. Most of the tested EGFRvIII clones retained their capacity to bind to EGFRvIII upon conversion into TCB format; only clone P057.011 showed slightly reduced binding to EGFRvIII in the TCB format compared to the corresponding IgG (Table 5).

TABLE 5

Binding of EGFRvIII IgG and TCB to CHO-EGFRvIII (EC50).

| EGFRvIII clone | EC50 IgG (nM) | EC50 TCB (nM) |
|---|---|---|
| P056.021 | 16.5 | 13.0 |
| P056.027 | 13.1 | 15.9 |
| P056.052 | 18.2 | 19.5 |
| P057.012 | 3.0 | 5.5 |
| P057.011 | 5.3 | 12.8 |

Figure 15:
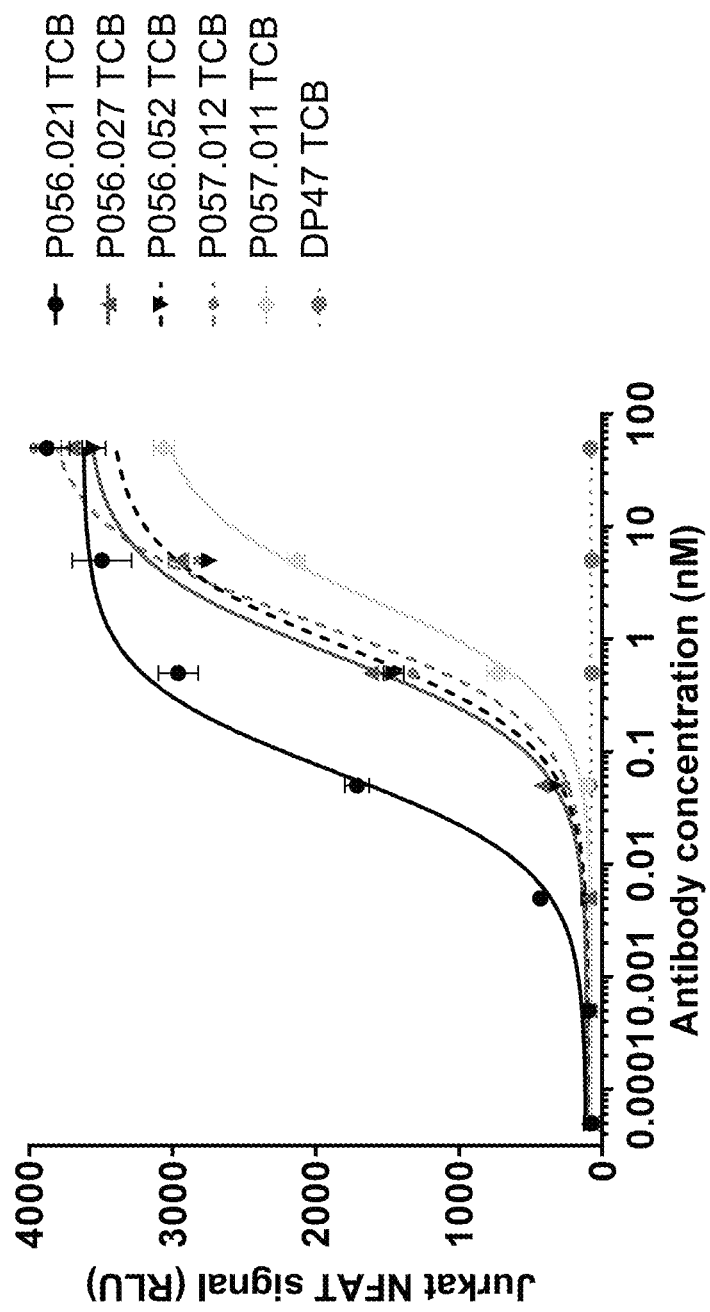
FIG. 15. Jurkat NFAT activation with EGFRvIII TCBs. Jurkat NFAT activation was determined as a marker for CD3 engagement with EGFRvIII TCBs in the presence of EGFRvIII positive DK-MG cells. DP47 TCB was included as negative control.

Subsequently the functional activity of the EGFRvIII TCBs was tested in a Jurkat NFAT reporter cell assay on EGFRvIII positive DK-MG cells (FIG. 15). All tested EGFRvIII TCBs had activity in the Jurkat NFAT reporter cell assay with P056.021 being the most potent one, followed by P056.027, P056.052 and P057.012 which had similar activity, and P057.011 which had the lowest activity. Next, the EGFRvIII TCBs were tested in a tumor cell lysis assay with PBMCs co-cultured with either DK-MG or MKN-45 cells to exclude crossreactivity of the EGFRvIII TCBs to EGFRwt (FIG. 16). In this assay, apart from tumor cell lysis, T cell activation (FIG. 17) and cytokine release (FIG. 18) was measured as additional read-outs. As seen in the reporter cell assay before, EGFRvIII TCB P056.021 had the highest activity on EGFRvIII positive cells without having any activity on EGFRwt positive cells. EGFRvIII TCB P057.011 showed unspecific activity on EGFRwt cells and was therefore excluded. EGFRvIII TCBs P056.027, P056.052 and P057.012 had comparable activity. Based on these results, EGFRvIII binder P056.021 and P057.012 were selected for an additional round of affinity maturation.

No good binders could be derived from P057.012 (results not shown). Affinity and specificity to EGFRvIII of selected EGFRvIII binders derived from P056.021 as determined by SPR is shown in Table 6.

TABLE 6

Affinity and specificity to EGFRvIII of selected EGFRvIII binders as determined by SPR.

| Binder | Specificity (no binding to EGFRwt) | Binding to EGFRvIII (KD [nM]) |
|---|---|---|
| P056.021 (parental) | yes | 35 |
| P063.056 | yes | 10 |

TABLE 6-continued

Affinity and specificity to EGFRvIII of selected
EGFRvIII binders as determined by SPR.

| Binder | Specificity (no binding to EGFRwt) | Binding to EGFRvIII (KD [nM]) |
|---|---|---|
| P064.078 | no | 15 |
| P065.036 | no | 10 |

Figure 20A:
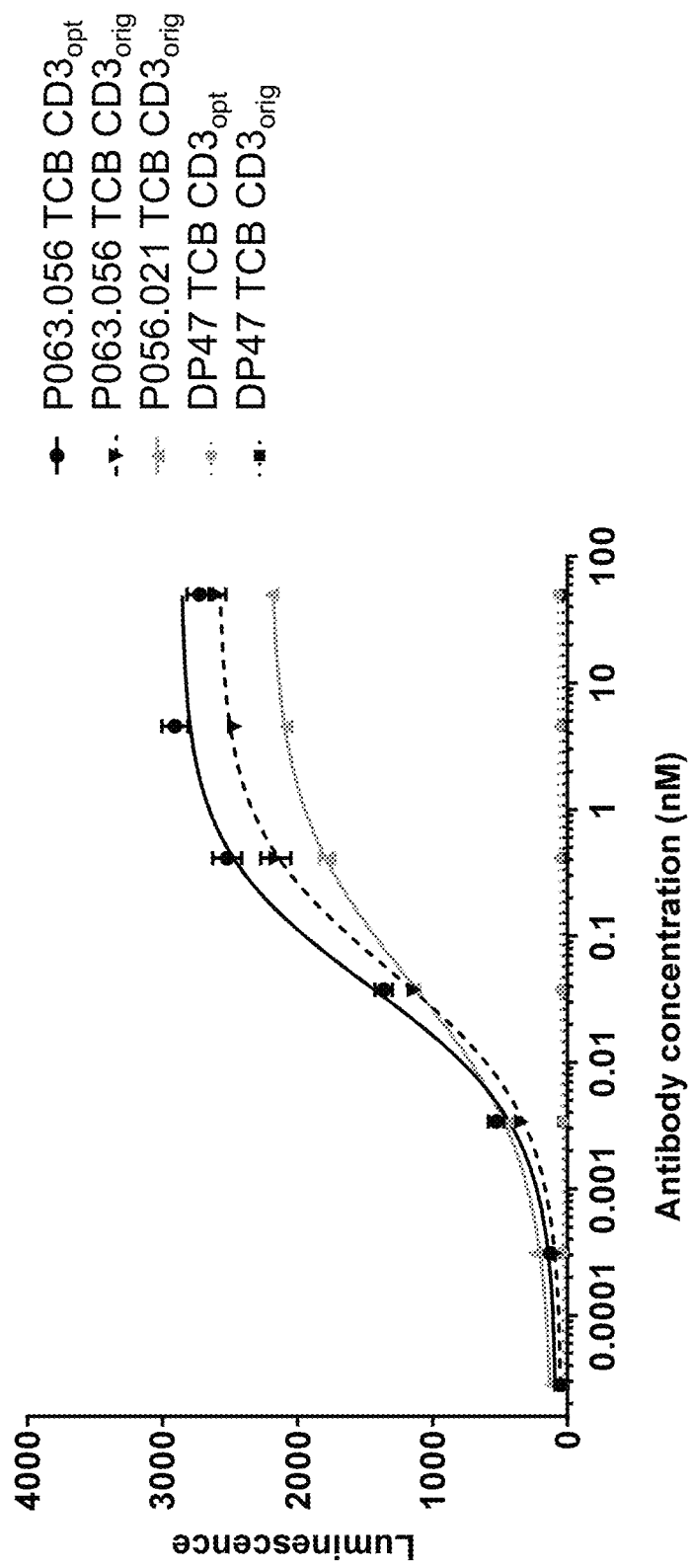
FIGS. 20A-20C. Jurkat NFAT activation by EGFRvIII TCBs. Jurkat NFAT activation was determined as a marker for CD3 engagement with EGFRvIII TCBs in the presence of EGFRvIII positive DK-MG cells (FIG. 20A), U87MG-EGFRvIII cells (FIG. 20B) and MKN-45 cells (FIG. 20C). DP47 TCB was included as negative control.
Figure 20B:
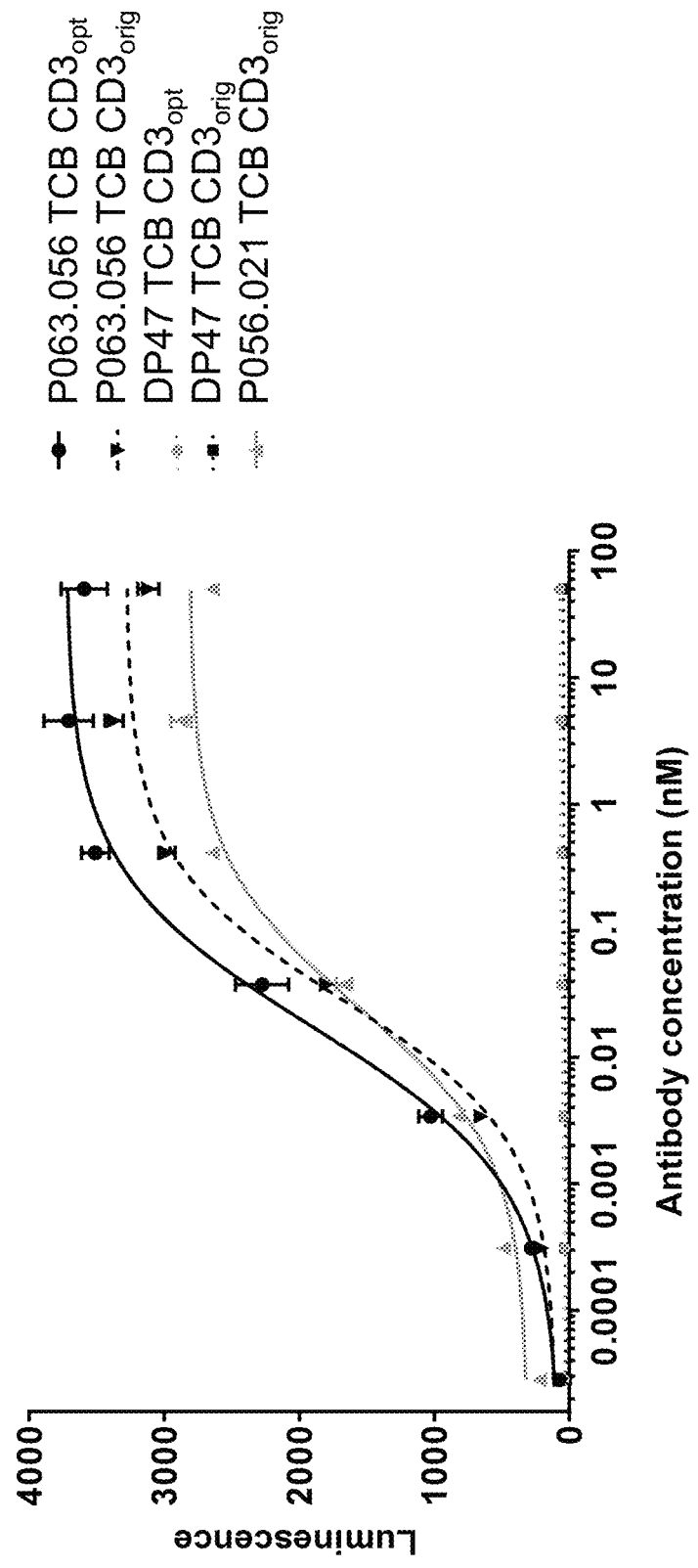
Figure 20C:
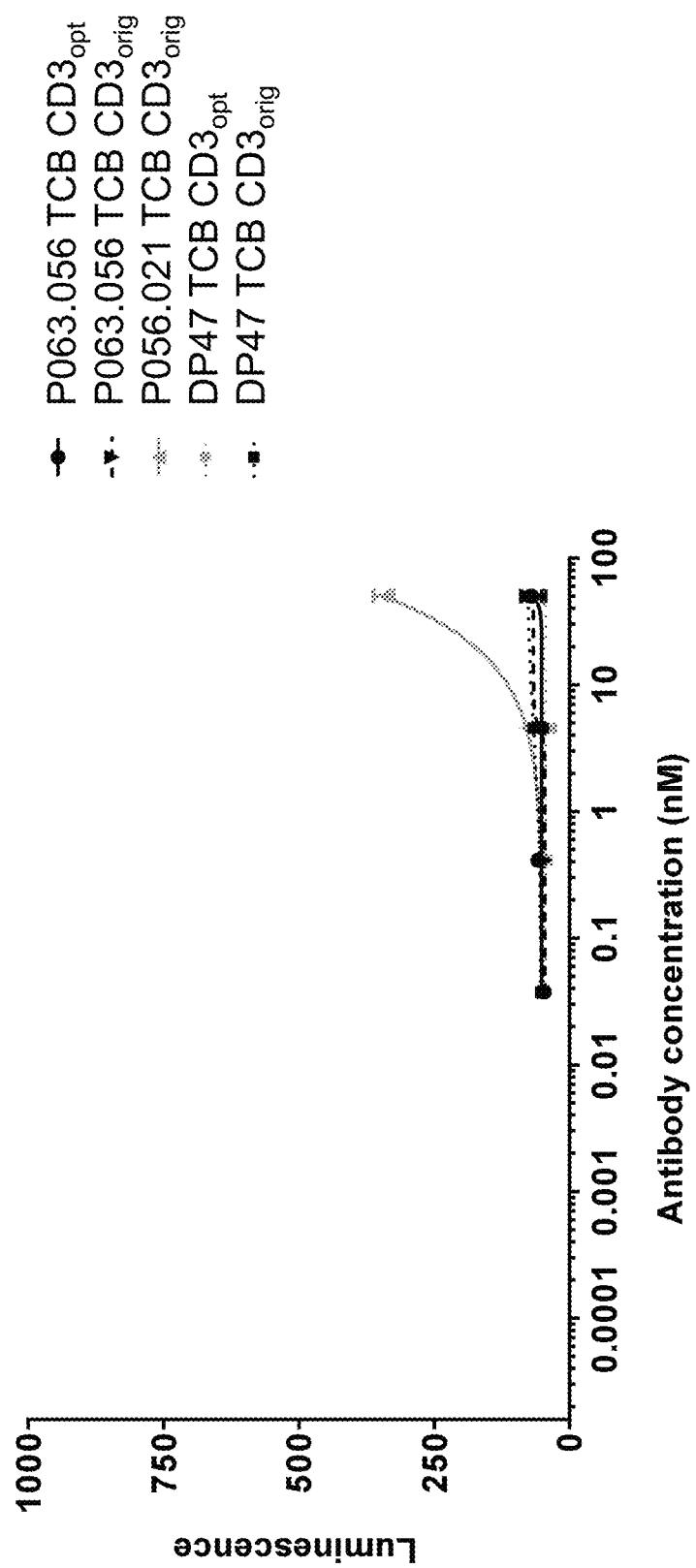

Affinity matured EGFRvIII binders (P063.056 (SEQ ID NOs 88 and 92), P064.078 (SEQ ID NOs 96 and 100), P065.036 (SEQ ID NOs 104 and 108)) were also compared to the parental binder for specific binding to EGFRvIII on U87MG-EGFRvIII and MKN-45 cells (FIG. 19). The best EGFRvIII binder in terms of affinity and specificity for EGFRvIII, P063.056, was selected for conversion into TCB format with either $CD3_{orig}$ or $CD3_{opt\ as\ CD}3$ binder. Functional activity of the EGFRvIII TCB P063.056 (with $CD3_{opt}$ or $CD3_{orig}$) was compared to the parental EGFRvIII TCB P056.021 in the Jurkat NFAT reporter cell assay on U87MG-EGFRvIII, DK-MG and MKN-45 cells (FIG. 20). All three TCBs induce specific Jurkat NFAT activation only in the presence of EGFRvIII positive cells. The EGFRvIII TCB P063.056 had a slightly higher activity than the parental EGFRvIII TCB P056.021.

Methods

Surface Plasmon Resonance

Affinity of EGFRvIII antibodies to EGFRvIII was determined by surface plasmon resonance on Biacore T200 with HBS-EP as running buffer (0.01 M HEPES pH 7.4, 0.15 M NaCl, 0.005% (v/v) Surfactant P20; GE Healthcare) at 25° C. Anti-EGFRvIII PGLALA IgGs were captured for 30 s at 25 nM with an antibody that specifically binds human $IgG_1$ Fc(PGLALA) (see WO 2017/072210, incorporated herein by reference) immobilized on a CM5 chip. The EGFRvIII-ECD avi his antigen (see below, Example 9) was passed at a concentration of 12.4-1000 nM with a flow of 30 µl/min through all flow cells over 200 s. The dissociation phase was monitored for 300 s and triggered by switching from the sample solution to HBS-EP. The chip surface was regenerated after every cycle using two injections of 10 mM glycine pH 2.0 for 30 s. Bulk refractive index differences were corrected by subtracting the response obtained on the reference flow cell. The affinity constants were derived from the kinetic rate constants by fitting to a 1:1 Langmuir binding using the BIAeval software (GE Healthcare).

For specificity determination EGFRvIII and EGFRwt ECD antigens were captured with an anti-his (Penta His, Qiagen) immobilized on a CM5 chip for 40 s at 100 nM. A single injection of anti-EGFRvIII antibodies at 500 nM for 60 s was performed, before regeneration with 10 mM glycine pH 2.0 for 60 s. Response units above 50 were observed for EGFRvIII binding. Responses above 5 response units (RU) were considered positive for EGFRwt binding and IgGs were categorized as specific with response below 5 RU for EGFRwt.

Cell Lines

Jurkat-NFAT reporter cells (GloResponse Jurkat NFAT-RE-luc2P; Promega #CS176501) are a human acute lymphatic leukemia reporter cell line with a NFAT promoter, expressing human CD3. The cells were cultured in RPMI1640, 2g/l glucose, 2 g/l $NaHCO_3$, 10% FCS, 25 mM HEPES, 1% GLUTAMAX® supplement, 1 x NEAA, 1 x sodium-pyruvate at 0.1-0.5 mio cells per ml. A final concentration of 200 µg per ml hygromycin B was added whenever cells were passaged.

Jurkat NFAT cells with PGLALA CAR were generated in house. The original cell line (Jurkat NFAT; Signosis) is a human acute lymphatic leukemia reporter cell line with a NFAT promoter leading to luciferase expression upon activation via human CD3. They were engineered to express a chimeric antigen receptor able to recognize the P293G LALA mutation. When cultured, the cells grow in suspension in RPMI1640 supplemented with 10% FCS and 1% glutamine and maintained between 0.4-1.5 mio cells per ml.

CHO-EGFRvIII cells were generated in house. CHO-K1 cells were stably transduced with EGFRvIII. Cells were cultured in DMEM/F12 medium containing 5% FCS, 1% GLUTAMAX® supplement and 6 µg/ml puromycin.

DK-MG (DSMZ #ACC 277) is a human glioblastoma cell line. DK-MG cells were enriched by cell sorting for EGFRvIII expression. The cells were cultured in RPMI 1860, 10% FCS and 1% GLUTAMAX® supplement.

U87MG-EGFRvIII (ATCC HTB-14) is a human glioblastoma cell line which were stably transduced with EGFRvIII. The cells were cultured in DMEM, 10% FCS and 1% GLUTAMAX® supplement.

MKN-45 (DSMZ ACC 409) is a human gastric adenocarcinoma cells expressing high levels of EGFRwt. The cells were cultured in advanced RPMI1640 containing 2% FCS and 1% GLUTAMAX® supplement.

Target Binding by Flow Cytometry

Cells used for binding experiments were harvested, washed with PBS and resuspended in FACS buffer. The antibody staining was performed in a 96-well round bottom plate. Cells were harvested, counted and 100 000 to 200 000 cells were seeded per well. The plate was centrifuged for 4 min at 400 x g and the supernatant was removed. The test antibodies were diluted in FACS buffer and 20 µl of the antibody solution were added to the cells for 30 min at 4° C. To remove unbound antibody the cells were washed twice with FACS buffer before addition of the diluted secondary antibody PE-conjugated AffiniPure F(ab')2 Fragment goat anti-human IgG Fcg Fragment Specific (Jackson ImmunoResearch, #109-116-170 or #109-116-098). After 30 min incubation on 4° C. unbound secondary antibody was washed away. Before measurement the cells were resuspended in 200 µl FACS buffer and analyzed by flow cytometry using BD Canto II or BD FACS Fortessa device.

CAR J NFAT Reporter Cell Assay with EGFRvIII PGLALA IgGs

The potency of the EGFRvIII PGLALA IgGs to induce T cell activation was assessed using the CAR J NFAT reporter cell assay. The principle of the assay is to co-culture Jurkat-NFAT engineered effector cells with cancer cells expressing the tumor antigen. Only upon simultaneous binding of the IgGs to the CAR via the PGLALA mutation and the target antigen EGFRvIII, the NFAT promoter is activated and leads to increasing luciferase expression in the Jurkat effector cells. Upon addition of an adequate substrate, active Firefly Luciferase leads to emission of luminescence, which can be measured as a signal of CAR-mediated activation. Briefly, target cells were harvested and viability determined. 30 000 target cells/well were plated in a flat-bottom, white-walled 96-well-plate (Greiner bio-one, #655098) in 100 µl medium the day before the assay start. On the next day the medium was removed and 25 µl/well of diluted antibodies or medium (for controls) were added to the target cells. Subsequently, Jurkat-NFAT reporter cells were harvested and viability assessed using ViCell. Cells were resuspended at 1.5 mio cells/ml in cell culture medium and added to tumor cells at 75 000 cells/well (50 µl/well) to obtain a final effector-to-target (E:T) ratio of 2.5:1 and a final volume of 75 µl per well. Then 4 µl of GloSensor (Promega, #E1291) was added to each well (2% of end volume). Cells were incubated for 24 h at 37° C. in a humidified incubator. At the end of incubation time, the plates were adapted to room temperature (about 15 min). Then 25 µl/well of One-Glo Luciferase (Promega, #E6120) was added and the plate was incubated for 15 min in the dark before luminescence was detected using a TECAN® Spark device.

Jurkat NFAT Reporter Cell Assay with EGFRvIII TCB

The capacity of EGFRvIII TCB with either the improved CD3 or the original CD3 binder to induce T cell cross-linking and subsequently T cell activation was assessed using EGFRvIII positive cells and Jurkat-NFAT reporter cells. Upon simultaneous binding of EGFRvIII TCB to EGFRvIII positive target cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. For the assay, target cells were harvested and viability determined. 30 000 target cells/well were plated in a flat-bottom, white-walled 96-well-plate (Greiner bio-one, #655098) in 100 µl medium and 50 µl/well of diluted antibodies or medium (for controls) were added to the target cells. Subsequently, Jurkat-NFAT reporter cells were harvested and viability assessed using ViCell. Cells were resuspended at 1.2 mio cells/ml in cell culture medium without hygromycin B and added to tumor cells at 60 000 cells/well (50 µl/well) to obtain a final effector-to-target (E:T) ratio of 2:1 and a final volume of 200 µl per well. Then 4 µl of GloSensor™ reagent (Promega, #E1291) was added to each well (2% of end volume). Cells were incubated for 24 h at 37° C. in a humidified incubator. At the end of incubation time, luminescence was detected using a TECAN® Spark device.

T-Cell Mediated Tumor Cell Killing

Target cells were harvested with Trypsin/EDTA, washed, and plated at density of 30 000 cells/well using flat-bottom 96-well plates. Cells were left to adhere overnight. Peripheral blood mononuclear cells (PBMCs) were prepared by Histopaque™ density centrifugation of fresh blood obtained from healthy human donors. Fresh blood was diluted with sterile PBS and layered over Histopaque™ gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400 x g, 10 minutes, room temperature), the supernatant discarded and the PBMC pellet washed twice with sterile PBS (centrifugation steps 350 x g, 10 minutes). The resulting PBMC population was counted automatically (ViCell) and stored in RPMI1640 medium containing 10% FCS and 1% GLUTAMAX® supplement at 37° C., 5% $CO_2$ in cell incubator until further use (not longer than 24 h). For the killing assay, the antibody was added at the indicated concentrations in triplicates. PBMCs were added to target cells at final effector to target (E:T) ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% TRITON® X-100 detergent. Minimal lysis (=0%) refers to target cells co-incubated with effector cells without bispecific construct. Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend, #300514), CD8 FITC (BioLegend, #344704), CD25 BV421 (BioLegend, #302630) and CD69 PE (BioLegend, #310906) was performed according to the suppliers' indications. Cells were washed twice with 150 µDwell FACS buffer and fixed for 15 min at 4° C. using 100 µl/well fixation buffer (BD, #554655). After centrifugation, the samples were resuspended in 200 µl/well FACS buffer. Samples were analyzed at BD FACS Fortessa device.

Cytokine secretion in the supernatant was measured by flow cytometry, using the cytometric bead array (CBA) according to the manufacturer's instructions but instead of 50 µl beads and sample only 25 µl of the supernatant and beads were used. The following CBA kits (BD Biosciences) were used: CBA human interferon gamma (IFNγ) Flex Set, CBA human Granzyme 13 Flex Set and CBA human TNF Flex Set. Samples were measured using the BD FACS Canto II or BD FACS Fortessa device and analyses were performed using the Diva Software (BD Biosciences).

Example 9—Binding of T-Cell Bispecific Antibody Comprising Optimized CD3 Binder to CD3 and EGFRvIII Binding to Recombinant CD3

Binding of the EGFRvIII TCB to recombinant CD3 was assessed by SPR, using the TCBs with either the optimized (EGFRvIII TCB $CD3_{opt}$) or the original (EGFRvIII TCB $CD3_{orig}$) CD3 binding sequences, as described for TYRP1 TCB in Example 5 above. Capture antibody was coupled to the sensorchip surface by direct immobilization of around 5200 resonance units (RU) at pH 5.0 using the standard amine coupling kit (GE Healthcare), and TCB molecules were captured for 30 s at 20 nM with a flow of 10 µl/min.

The $K_D$ values for binding to human and cynomolgus CD3 were determined as 30 nM and 20 nM, respectively, for TYRP1 TCB $CD3_{opt}$ and were similar to the ones for TYRP1 TCB $CD3_{orig}$ (40 nM and 30 nM, respectively).

This shows that in unstressed condition both TCBs, comprising either $CD3_{opt}$ or $CD3_{orig}$, bound comparably well to recombinant CD3.

Binding of the EGFRvIII TCB to recombinant human CD3 was also assessed after temperature stress for 14 days at 37° C. or 40° C., using the TCBs with either the optimized or the original CD3 binding sequences. The experiment was performed as described in Example 2 above, using the TCB instead of IgG molecules.

Figure 21:
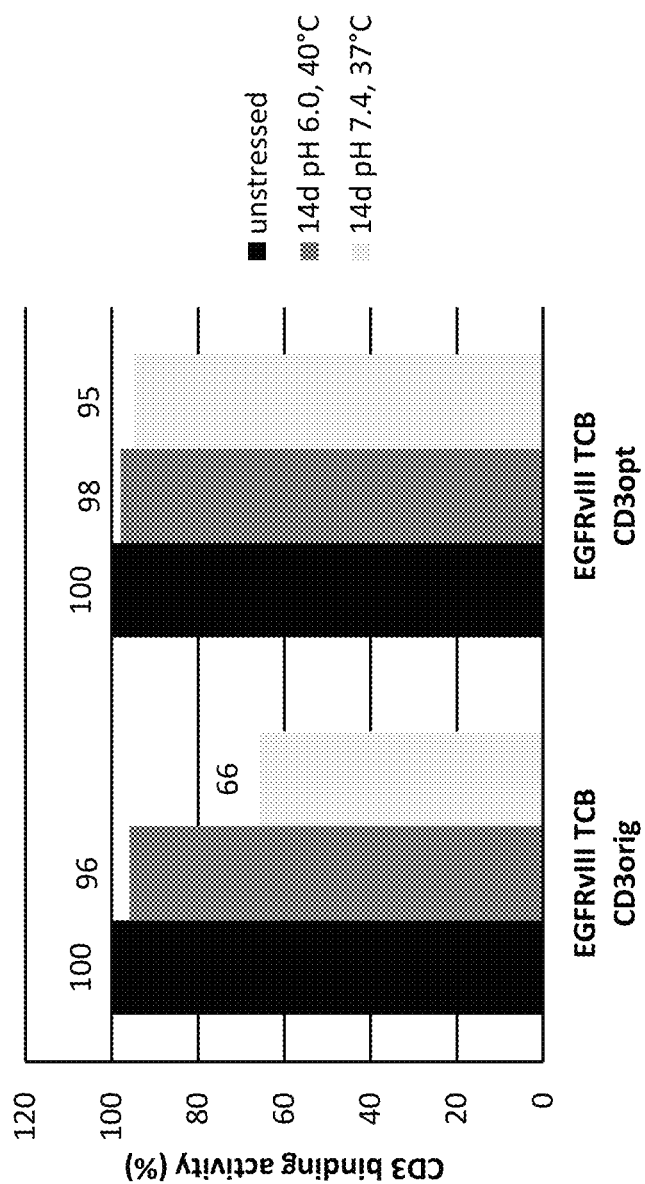
FIG. 21. Relative binding activity of EGFRvIII TCBs comprising original or optimized CD3 binders, $CD3_{orig}$ or $CD3_{opt}$, to recombinant CD3 as measured by SPR in unstressed condition, after 14 d at 40° C. pH 6, or after 14 d at 37° C. pH 7.4.

The results of this experiment are shown in FIG. 21.

As can be seen in FIG. 21, the TCB comprising the optimized CD3 binder $CD3_{opt}$ showed strongly improved binding to CD3 after stress (2 weeks at 37° C., pH 7.4) as compared to the TCB comprising the original CD3 binder $CD3_{orig}$. This result again confirms that the improved properties of the optimized CD3 binder (see Example 2) are maintained at the TCB level.

Binding to Recombinant EGFRvIII

Binding of the EGFRvIII TCBs to recombinant EGFRvIII was assessed by SPR.

SPR experiments were performed on a Biacore T200 with HBS-EP as running buffer (0.01 M HEPES pH 7.4, 0.15 M NaCl, 0.05% (v/v) Surfactant P20 (GE Healthcare)).

An anti-Fc antibody (GE Healthcare) was directly coupled on a CM5 sensor chip at pH 5.0 using the standard amine coupling kit (GE Healthcare). EGFRvIII TCB (5 nM) was captured with a flow rate of 10 µl/min for 30 s. A 3-fold dilution series of the EGFRvIII antigen was passed on the flow cells at 30 µl/min for 200 s to record the association phase. The dissociation phase was monitored for 300 s and triggered by switching from the sample solution to HBS-EP. The chip surface was regenerated after every cycle using one injection of 3 M MgCL2 for 30 s at 20 µl/min.

The antigen used contains the extracellular domain of human EGFRvIII fused to an AviTag™ tag and a His-tag on the C-terminus (EGFRvIII-ECD avi his; SEQ ID NO: 36).

Bulk refractive index differences were corrected by subtracting the response obtained on the reference flow cell (no TCB captured). The affinity constants ($K_D$) were derived from the kinetic rate constants by fitting to a 1:1 Langmuir binding using the BIAeval software (GE Healthcare). The apparent avidity constant $K_D$ was approximated by kinetic analysis via the rate constants using a 1:1 binding fit on this 2:1 interaction.

The $K_D$ values (affinity) for binding to human EGFRvIII were determined as 6 nM for both the EGFRvIII TCB comprising either $CD3_{opt}$ or $CD3_{orig}$.

Binding of the EGFRvIII TCB to recombinant EGFRvIII was also assessed after temperature stress for 14 days at 37° C. or 40° C., using the TCBs with either the optimized or the original CD3 binding sequences. The experiment was performed as described above in Example 5, using EGFRvIII-ECD avi his as antigen (see above).

Figure 22:
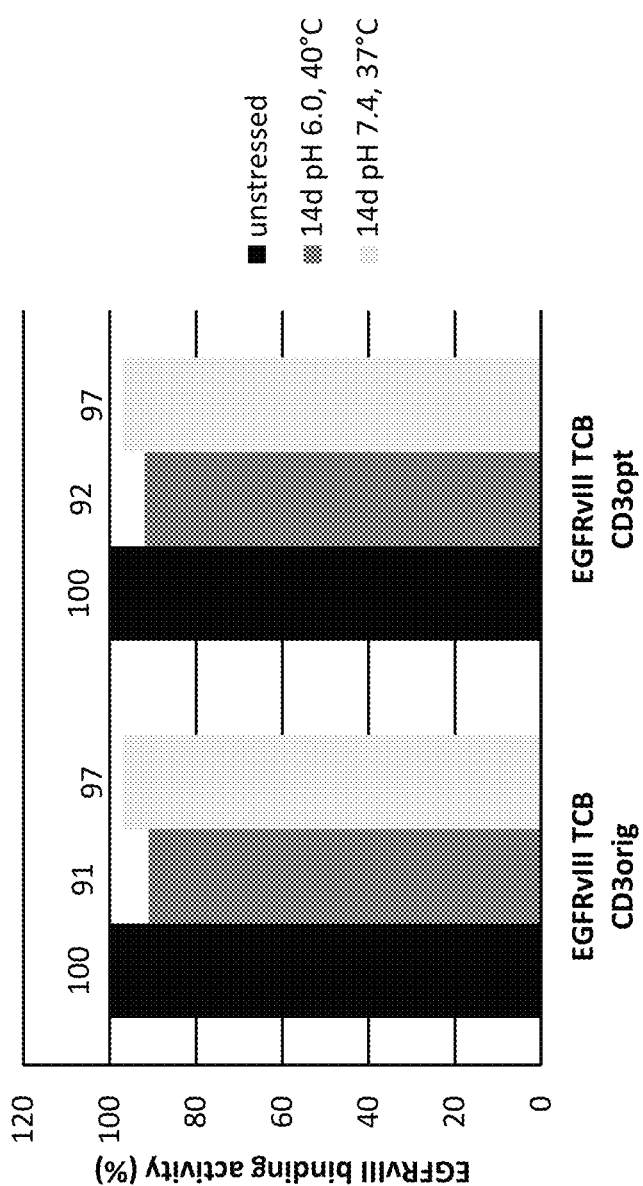
FIG. 22. Relative binding activity of EGFRvIII TCBs comprising original or optimized CD3 binders, $CD3_{orig}$ or $CD3_{opt}$, to recombinant EGFRvIII as measured by SPR in unstressed condition, after 14 d at 40° C. pH 6, or after 14 d at 37° C. pH 7.4.

The results of this experiment are shown in FIG. 22. They confirm that the binding to human EGFRvIII for both TCBs is not affected by stress conditions.

Binding to CD3 on Jurkat Cells

Binding to CD3 on the human reporter T-cell line Jurkat NFAT was determined by FACS for EGFRvIII TCBs comprising the optimized CD3 binder "$CD3_{opt}$," or the original CD3 binder "$CD3_{orig}$", as described above in Example 2.

Figure 23:
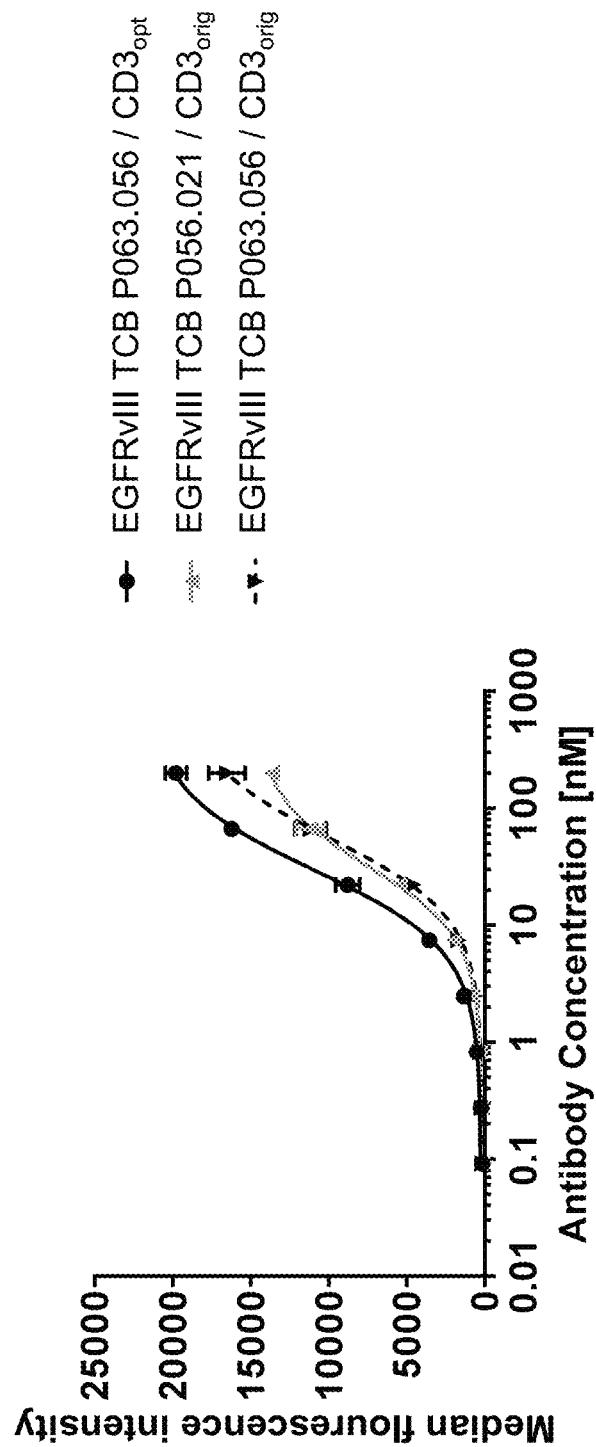
FIG. 23. Binding of EGFRvIII TCBs comprising original or optimized CD3 binders, $CD3_{orig}$ or $CD3_{opt}$, to Jurkat NFAT cells as measured by flow cytometry. TCBs bound to Jurkat NFAT cells were detected with a fluorescently labeled anti-human Fc specific secondary antibody.

As shown in FIG. 23, the TCBs comprising either the optimized CD3 binder "$CD3_{opt}$," or the original CD3 binder "$CD3_{orig}$" bound comparably well to CD3 on Jurkat cells.

Binding to EGFRvIII on U87MG-EGFRvIII Cells

Binding to EGFRvIII on the human glioblastoma cell line U87MG-EGFRvIII was determined by FACS for EGFRvIII TCBs comprising the EGFRvIII binder P063.056 with either $CD3_{opt}$ or $CD3_{orig}$, or the EGFRvIII clone P056.021 with $CD3_{orig}$. The EGFRvIII binder P063.056 was included also in IgG format.

Figure 24:
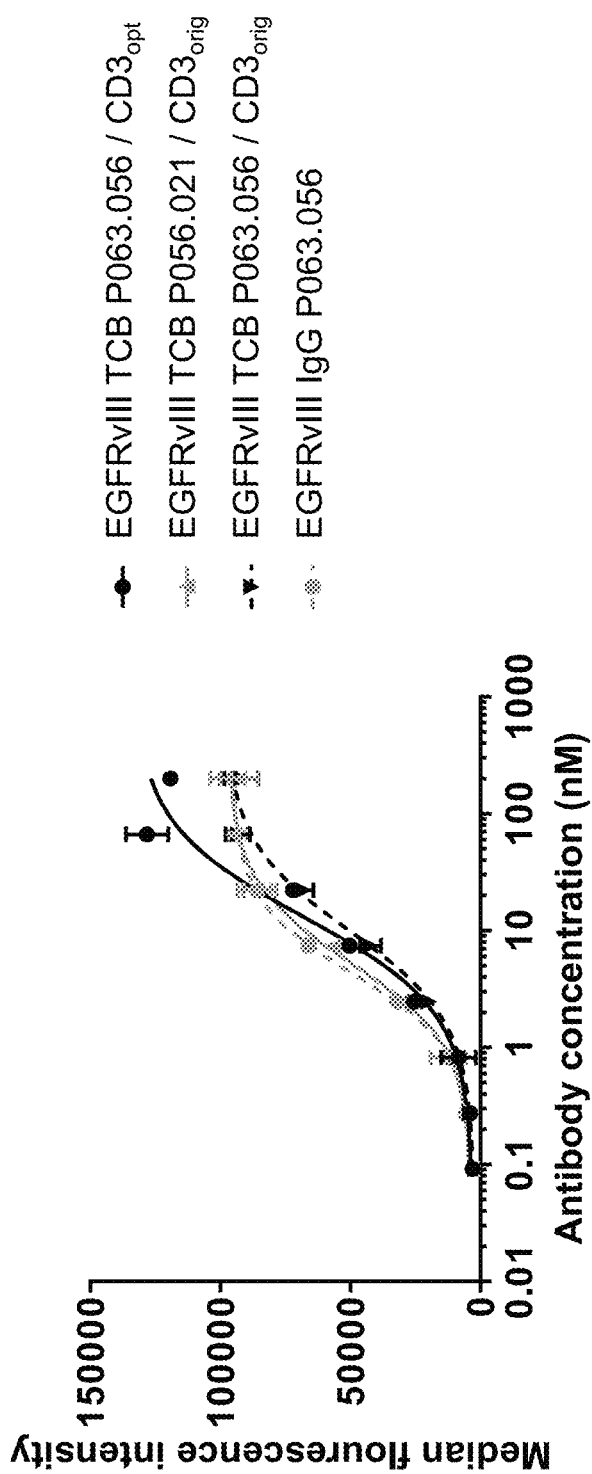
FIG. 24. Binding of EGFRvIII TCBs comprising P063.056 or P056.021 EGFRvIII binder to U87MG-EGFRvIII cells as measured by flow cytometry. TCBs bound to U87MG-EGFRvIII cells were detected with a fluorescently labeled anti-human Fc specific secondary antibody.
Figure 25A:
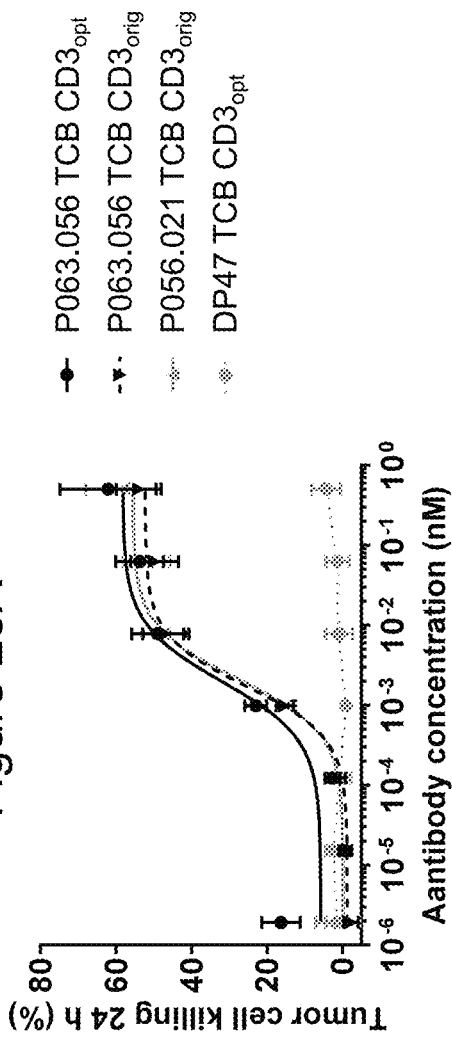
FIGS. 25A-25D. Tumor cell lysis and T cell activation with EGFRvIII TCBs. Induction of specific tumor cell lysis (FIG. 25A, FIG. 25B) and T cell activation (FIG. 25C, FIG. 25D) by EGFRvIII TCBs was determined upon co-culture with freshly isolated PBMCs and U87MG-EGFRvIII cells for 24 h (FIG. 25A, FIG. 25C) or 48 h (FIG. 25B, FIG. 25D). DP47 TCB was included as negative control.
Figure 25B:
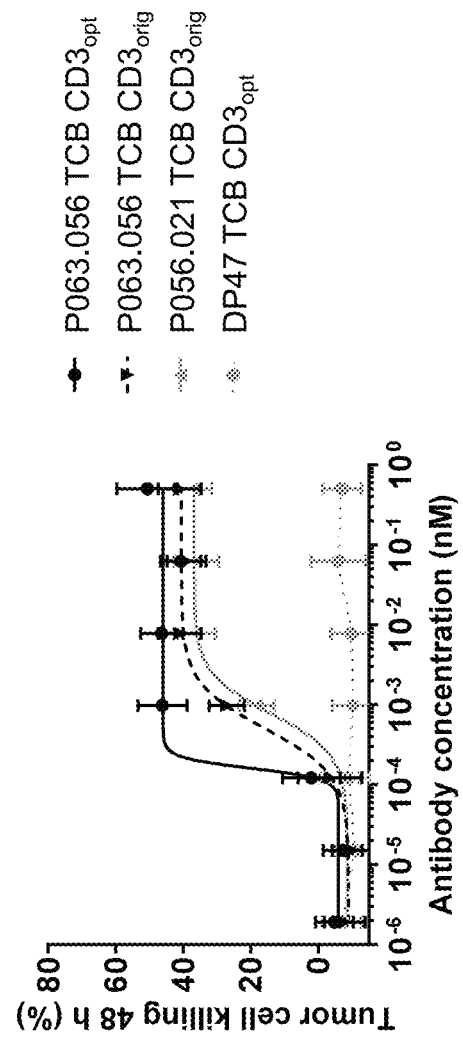
Figure 25C:
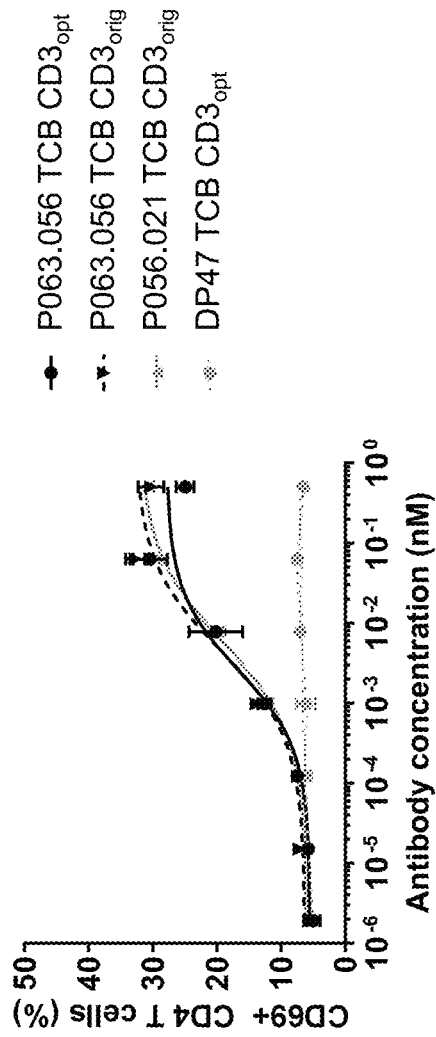
Figure 25D:
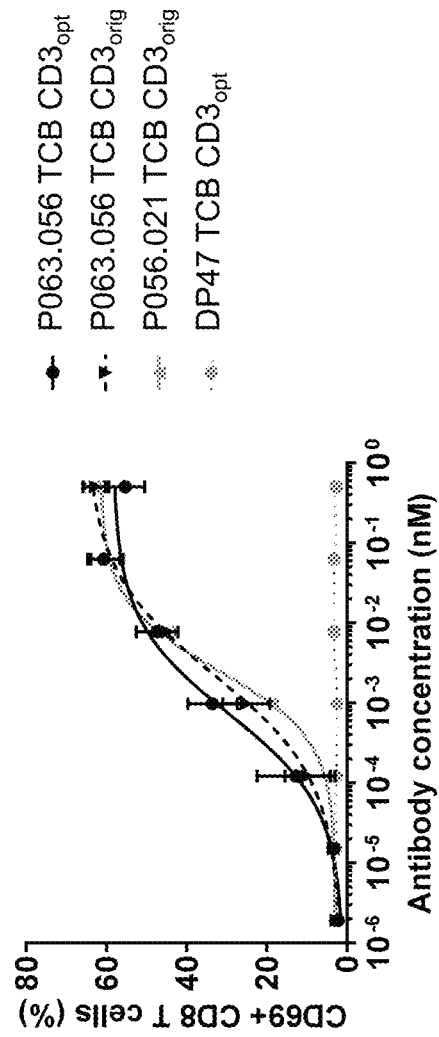

As shown in FIG. 24 all three TCBs bind with high affinity to EGFRvIII expressed on U87MG-EGFRvIII cells and binding is not impaired by the conversion into the TCB format.

Example 10—Functional Activity of T-Cell Bispecific Antibody Comprising Optimized CD3 Binder CD3 Activation The EGFRvIII TCBs containing the selected EGFRvIII binder (P063.056) and either the optimized CD3 binder $CD3_{opt}$ or the original CD3 binder $CD3_{orig}$ were tested in the Jurkat NFAT reporter cell assay in the presence of EGFRvIII positive glioblastoma cells DK-MG, U87MG-huEGFRvIII and EGFRwt positive MKN45 cells as described above in Example 8.

As seen for the IgGs (Example 3) both TCBs containing either $CD3_{opt}$ or $CD3_{orig}$ had a similar functional activity on the Jurkat NFAT reporter cells and induced CD3 activation in a concentration dependent manner (FIG. 20).

Target Cell Killing

The EGFRvIII TCBs containing the selected EGFRvIII binder (P063.056) and either the optimized CD3 binder $CD3_{opt}$ or the original CD3 binder $CD3_{orig}$ were compared to the EGFRvIII TCB containing the parental EGFRvIII binder P056.021 and the CD3 binder $CD3_{orig}$ in a tumor cell killing experiment in the presence of the glioblastoma cell line U87MG-EGFRvIII and PBMCs as described above in Example 8. As seen on the Jurkat NFAT reporter cells, the functional activity of the TCBs with either the $CD3_{opt}$ or $CD3_{orig}$ is similar with regard to induction of tumor cell lysis and activation of CD4 and CD8 T cells as measured by CD69 upregulation (FIG. 25).

Figure 26:
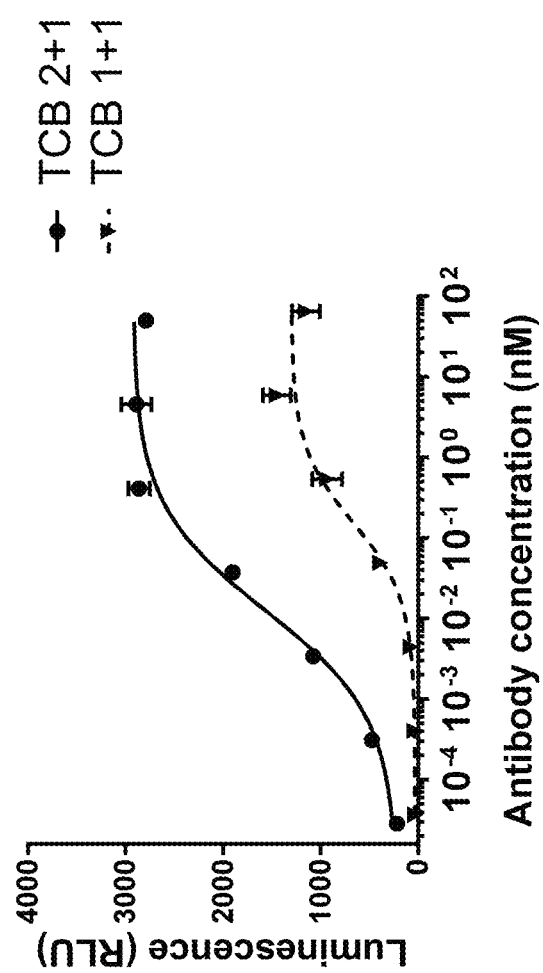
FIG. 26. Jurkat NFAT activation comparing EGFRvIII TCB 2+1 format and 1+1 format. Jurkat NFAT activation was determined as a marker for CD3 engagement with EGFRvIII TCB in the 2+1 inverted format and in the 1+1 head-to-tail format in the presence of EGFRvIII positive U87MG-EGFRvIII cells.
Figure 27A:
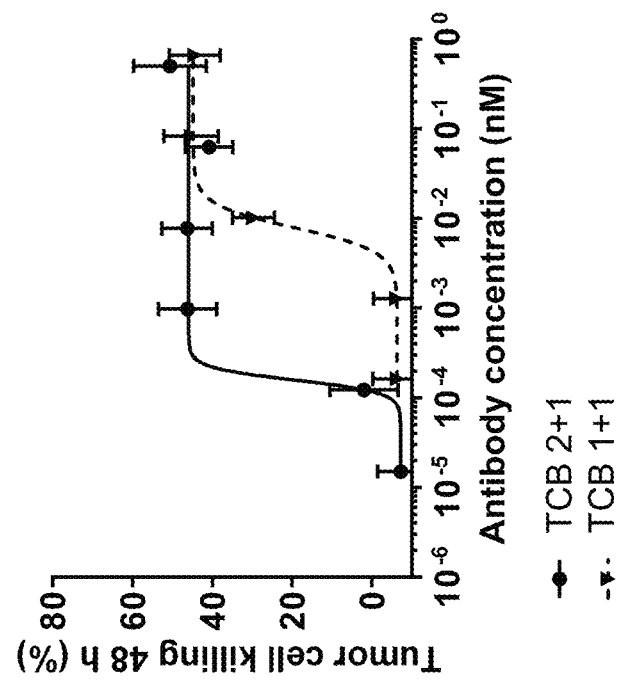
FIGS. 27A-27D. Tumor cell lysis and T cell activation comparing EGFRvIII TCB 2+1 format and 1+1 format. Induction of specific tumor cell lysis (FIG. 27A, FIG. 27B) and T cell activation (FIG. 27C, FIG. 27D) by EGFRvIII TCB in the 2+1 inverted format and in the 1+1 head-to-tail format was determined upon co-culture with freshly isolated PBMCs and U87MG-EGFRvIII cells for 24 h (FIG. 27A, FIG. 27C) or 48 h (FIG. 27B, FIG. 27D).
Figure 27B:
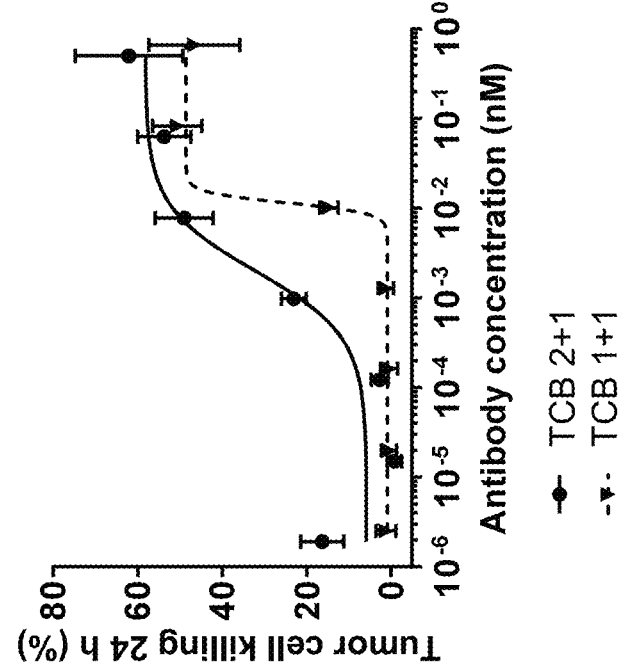
Figure 27C:
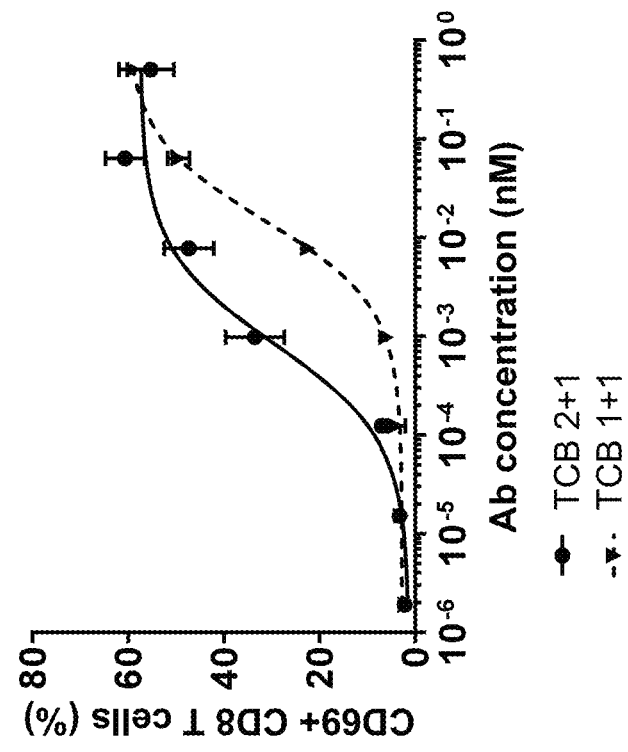
Figure 27D:
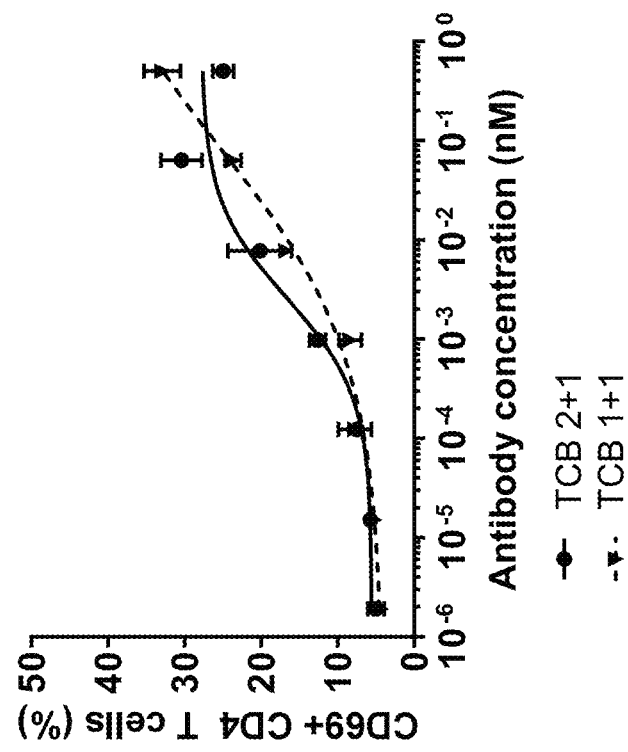
Figure 29A:
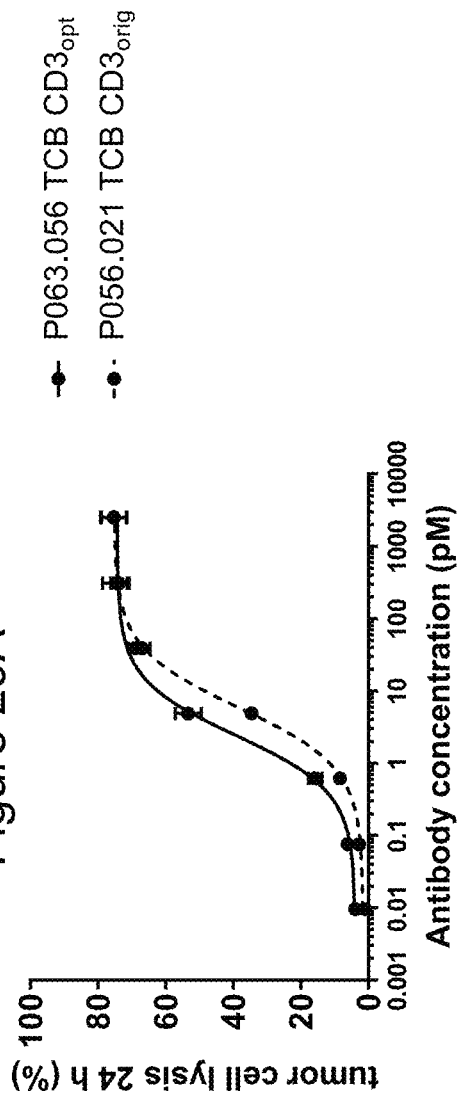
FIGS. 29A-29F. Tumor cell lysis, T cell activation and cytokine release with EGFRvIII TCBs. Induction of tumor cell lysis (FIG. 29A, FIG. 29B), T cell activation (FIG. 29C, FIG. 29D) and release of IFNγ and TNFα (FIG. 29E, FIG. 29F) by EGFRvIII TCBs was determined upon co-culture of U87MG-EGFRvIII cells with PBMCs. Tumor cell lysis was measured after 24 h and 48 h of treatment, T cell activation and cytokine release was measured after 48 h.
Figure 29B:
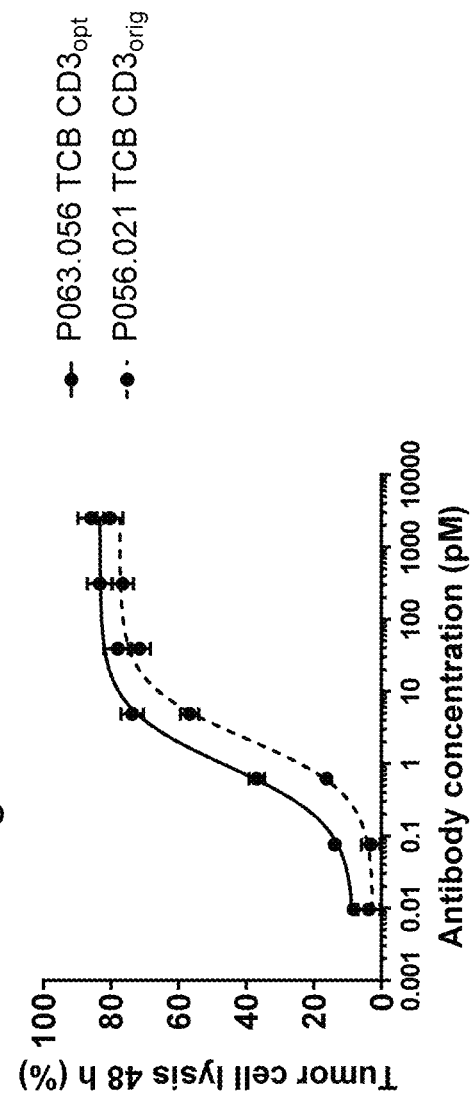
Figure 29C:
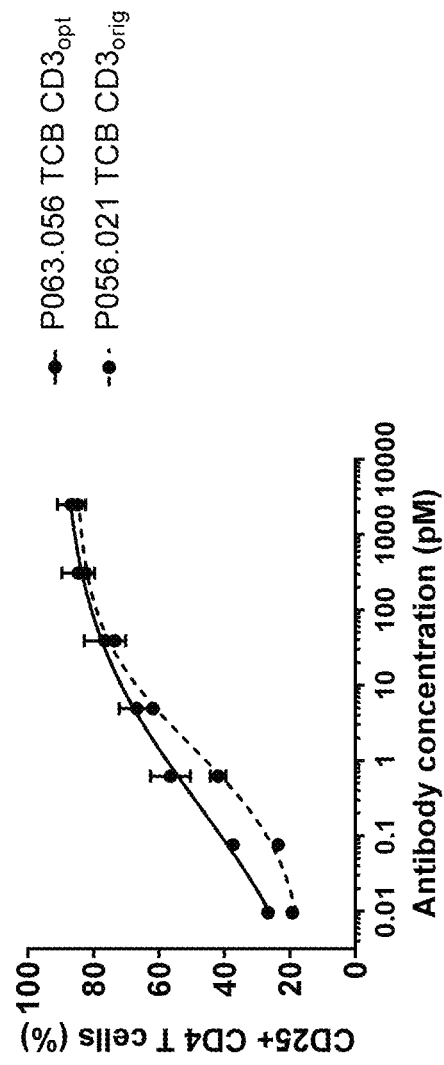
Figure 29D:
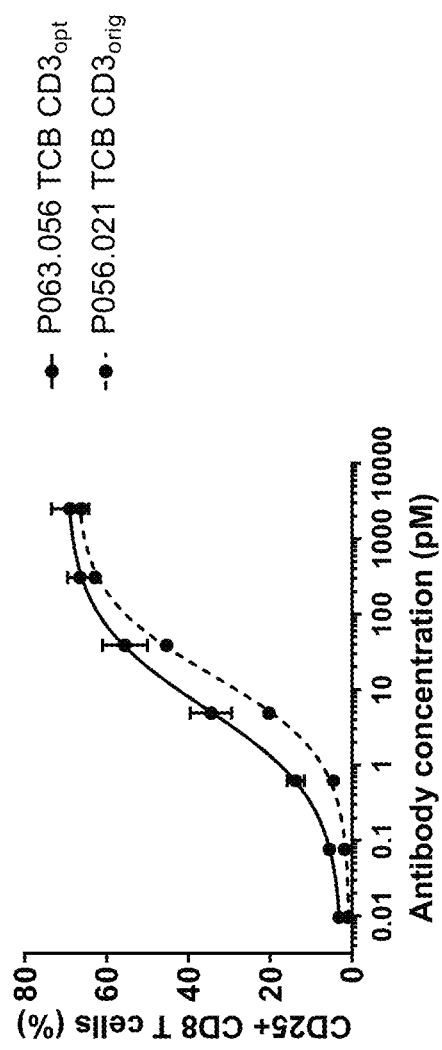
Figure 29E:
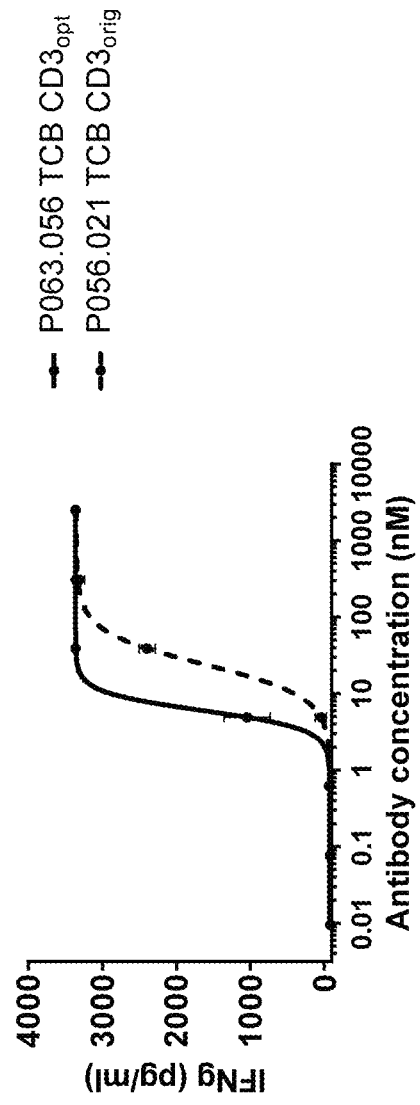
Figure 29F:
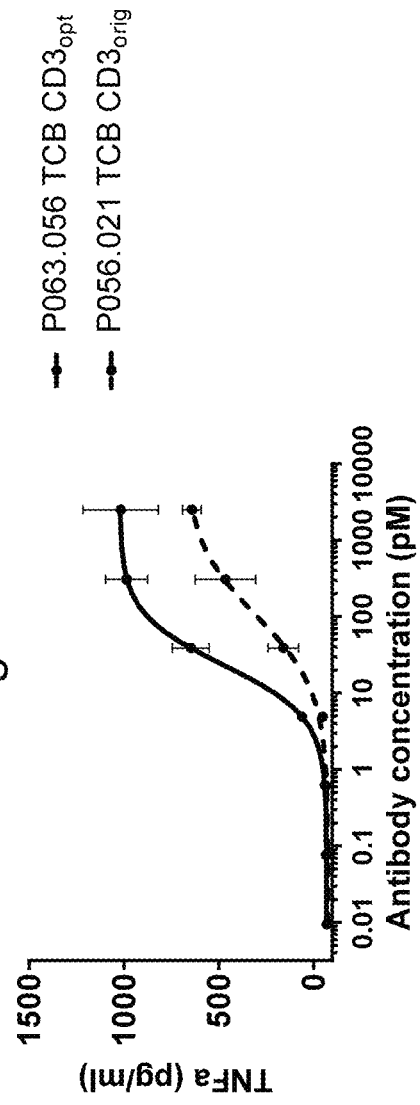

In addition, the functional activity of the EGFRvIII TCB with the EGFRvIII binder P063.056 and the optimized CD3 binder $CD3_{opt}$ in the "2+1 format" (as illustrated in FIG. 6) was compared to an EGFRvIII TCB with the same EGFRvIII and CD3 binder in the "1+1 head-to-tail format" (schematically depicted in FIG. 1G). These two EGFRvIII TCBs were tested in the Jurkat NFAT reporter cell assay and in a tumor cell killing assay with the glioblastoma cell line U87MG-EGFRvIII as described in Example 8. The EGFRvIII TCB in the 2+1 format had a superior functional activity both in CD3 activation measured in the Jurkat NFAT reporter cell assay (FIG. 26) and in the induction of tumor cell killing and T cell activation in the killing assay with PBMCs (FIG. 27).

Example 11—Functional Characterization of T-Cell Bispecific Antibodies Comprising Optimized CD3 Binder T Cell Proliferation and Activation by EGFRvIII TCB Functional activity of the EGFRvIII TCBs containing the selected EGFR binder (P063.056) and either the optimized CD3 binder $CD3_{opt}$ or the original CD3 binder $CD3_{orig}$ was compared to the EGFRvIII TCB containing the parental EGFRvIII binder P056.021 and the CD3 binder $CD3_{orig}$ in a T cell proliferation assay on U87MG-EGFRvIII cells (FIG. 28). All three TCBs induced strong proliferation and activation of CD4 T cells and CD8 T cells. The P063.056 EGFRvIII TCB with $CD3_{opt}$ had a higher activity than the other two EGFRvIII TCBs.

Tumor Cell Lysis by EGFRvIII TCB

Next, the EGFRvIII TCB containing the selected EGFR binder (P063.056) and the optimized CD3 binder $CD3_{opt}$ and the EGFRvIII TCB containing the parental EGFRvIII binder P056.021 and the CD3 binder $CD3_{orig}$ were tested in a tumor cell lysis assay with PBMCs co-cultured with DK-MG cells (FIG. 29). In this assay, apart from tumor cell lysis, T cell activation and cytokine release was measured as additional read-outs. As seen before, the P063.056 EGFRvIII TCB with $CD3_{opt}$ had a higher activity than the P056.021 EGFRvIII TCB with $CD3_{orig}$ with regard to tumor cell lysis, T cell activation and release of IFNγ and TNFα.

T Cell Activation and Tumor Cell Lysis by TYRP1 TCB

The functional property of TYRP1 TCB to induce cytokine release was tested by co-cultivation of the primary melanoma cell line M150543 with PBMCs isolated from a healthy donor. Tumor cell lysis mediated by T cells via TYRP1 TCB was analyzed after 24 h and 48 h of treatment (FIG. 30). Release of IFNγ and TNFα into the supernatant as well as CD4 and CD8 T cell activation was analyzed after 48 h of treatment. TYRP1 TCB was able to induce potent tumor cell lysis already after 24 h. This was accompanied by strong activation of CD4 and CD8 T cells determined by upregulation of CD25 as well as significant release of IFNγ and TNFα.

Methods

PBMC Isolation

Peripheral blood mononuclear cells (PBMCs) were prepared by Histopaque™ density centrifugation of fresh blood obtained from healthy human donors. Fresh blood was diluted with sterile PBS and layered over Histopaque™ gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400 × g, 10 minutes, room temperature), the supernatant discarded and the PBMC pellet washed twice with sterile PBS (centrifugation steps 350 × g, 10 minutes). The resulting PBMC population was counted automatically (ViCell) and stored in RPMI1640 medium containing 10% FCS and 1% GLUTAMAX® supplement at 37° C., 5% $CO_2$ in cell incubator until further use (not longer than 24 h) or frozen and stored in liquid nitrogen until further use. The day before use frozen PBMCs were thawed and cultured overnight in medium at 37° C.

T Cell Proliferation

Briefly, target cells harvested, counted and washed twice with PBS. Cells were resuspended at 5 mio cells per ml in PBS. Cells were stained with the cell proliferation dye EFLUOR® 670 (eBioscience, #65-0840-85) with a final concentration of 5 µM for 10 min at 37° C. To stop the staining reaction, 4 volumes of cold complete cell culture medium were added to the cell suspension and incubated for 5 min at 4° C. and then washed three times with medium. Labeled target cells were counted and adjusted to 0.1 mio cells per ml in RPMI1640, 10% FCS and 1% GLUTAMAX® supplement. 10'000 target cells per well were seeded into a 96 well plate. Then the treatment was added at the indicated concentrations and at the end 100'000 PBMCs isolated from a healthy donor were added per well. The cells were incubated for 5 days at 37° C., then PBMCs were harvested and stained with CD3 BUV395 (BioLegend, #563548), CD4 PE (BioLegend, #300508), CD8 APC (BioLegend, #344722), CD25 PE/Cy7 (BioLegend, #302612). Proliferation was determined by dilution of the EFLUOR® 670 dye in CD4 T cells and CD8 T cells measured by flow cytometry (FACS Fortessa device, BD Bioscience) and activation of CD4 and CD8 T cells by measuring CD25 upregulation.

T Cell Mediated Tumor Cell Killing

Target cells were harvested with trypsin/EDTA, washed, and plated at density of 30 000 cells/well using flat-bottom 96-well plates. Cells were left to adhere overnight. For the killing assay, the antibodies were added at the indicated concentrations in triplicates. PBMCs were added to target cells at final effector to target (E:T) ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% TRITON® X-100 detergent. Minimal lysis (=0%) refers to target cells co-incubated with effector cells without bispecific construct.

T Cell Activation

Activation of CD8 and CD4 T cells upon T cell killing of target cells mediated by the TCB was assessed by flow cytometry using antibodies recognizing the T cell activation markers CD25 (late activation marker) and CD69 (early activation marker). After 48 h incubation, PBMCs were transferred to a round-bottom 96-well plate, centrifuged at 350×g for 5 min and washed twice with FACS buffer. Surface staining for CD4 APC (BioLegend, #300514), CD8 FITC (#344704, BioLegend), CD25 BV421 (BioLegend, #302630) and CD69 PE (BioLegend, #310906) was performed according to the suppliers' indications. Cells were washed twice with 150 µl/well FACS buffer and fixed for 15 min at 4° C. using 100 µl/well fixation buffer (BD, #554655). After centrifugation, the samples were resuspended in 200 µl/well FACS buffer. Samples were analyzed at BD FACS Fortessa device.

Cytokine Secretion

Cytokine secretion in the supernatant was measured by flow cytometry, using the cytometric bead array (CBA) according to the manufacturer's instructions but instead of 50 µl beads and sample only 25 µl of the supernatant and beads were used. The following CBA kits (BD Biosciences) were used: CBA human interferon gamma (IFNγ) Flex Set and CBA human TNF Flex Set. Samples were measured using the BD FACS Canto II or BD FACS Fortessa device and analyses were performed using the Diva Software (BD Biosciences).

Example 13—In Vivo Efficacy of T-Cell Bispecific Antibodies Comprising Optimized CD3 Binder The TYRP1 TCB (comprising the optimized CD3 binder identified in Example 1) was tested for its anti-tumoral efficacy in a xenograft mouse model of a human tumor cell line, the IGR-1 melanoma xenograft model.

IGR-1 cells (human melanoma) were cultured in DMEM medium containing 10% FCS (Sigma). The cells were cultured at 37° C. in a water-saturated atmosphere at 5% $CO_2$. Passage 6 was used for transplantation. Cell viability was 96.7%. $2 \times 10^6$ cells per animal were injected subcutaneously in 100 µl of RPMI cell culture medium (Gibco) into the flank of mice using a 1 ml tuberculin syringe (BD Biosciences, Germany).

Fully humanized NSG female mice (Roche Glycart AG, Switzerland) were maintained under specific-pathogen-free condition with daily cycles of 12 h light/12 h darkness according to committed guidelines (GV-Solas; Felasa; TierschG). The experimental study protocol was reviewed and approved by local government (ZH223/2017). Continuous health monitoring was carried out on a regular basis.

Mice were injected subcutaneously on study day 0 with $2 \times 10^6$ of IGR-1 cells, randomized and weighed. Twenty days after the tumor cell injection (tumor volume >200 $mm^3$), mice were injected i.v. with 10 µg (0.5 mg/kg) TYRP1 TCB twice weekly for five weeks. All mice were injected i.v. with 200 µl of the appropriate solution. The mice in the vehicle group were injected with histidine buffer and the treatment group with the TYRP1 TCB construct. To obtain the proper amount of antibody per 200 µl, the stock solutions were diluted with histidine buffer when necessary. Tumor size was measured with a caliper three times a week and plotted with GrahPad Prism software as volume in $mm^3$+/−SEM. Statistical analysis was performed with JMP12 software.

Figure 31:
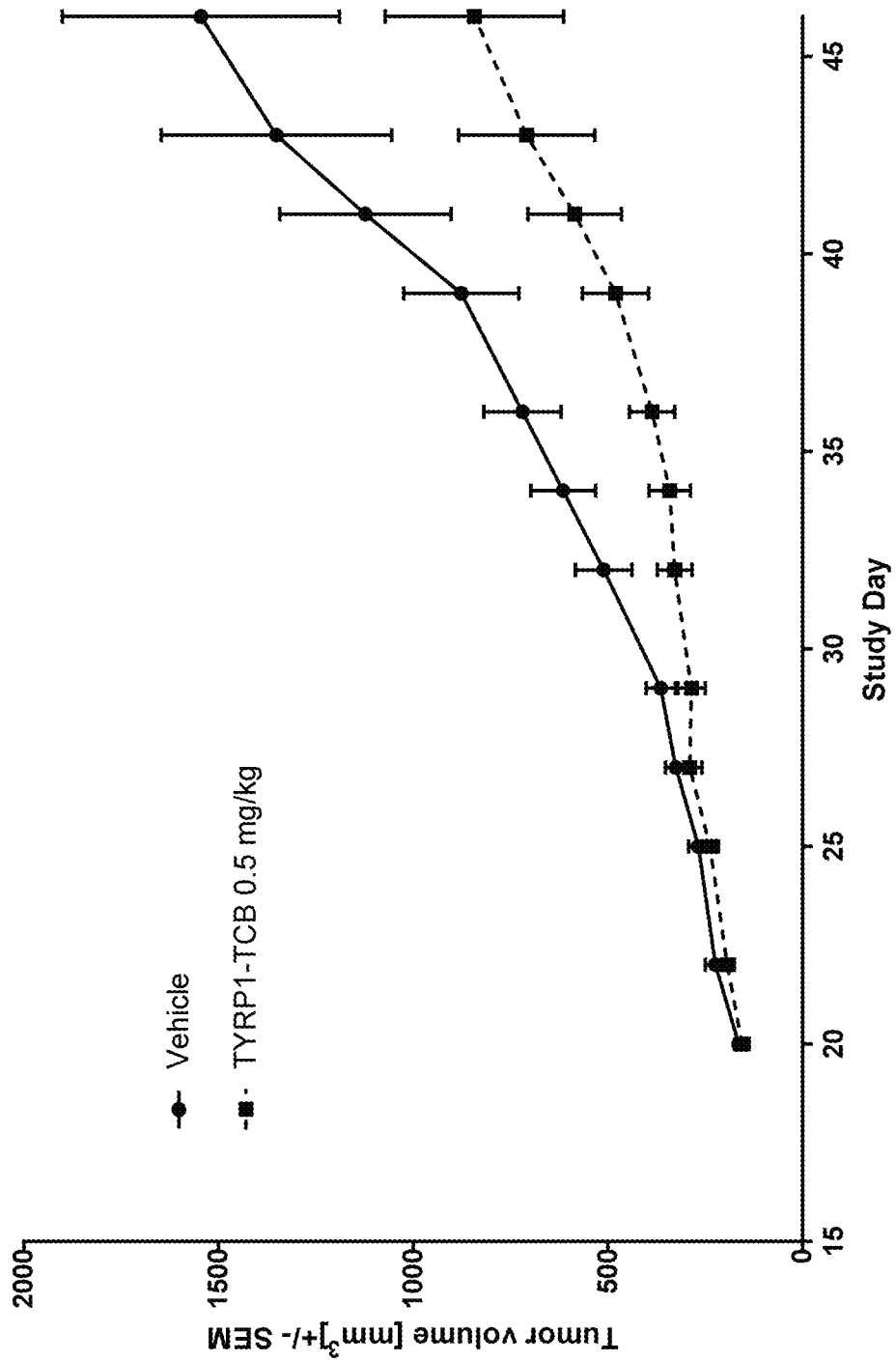
FIG. 31. In vivo efficacy of TYRP-1 TCB. The IGR-1 human melanoma cell line was injected subcutaneously in humanized NSG mice to study tumor growth inhibition in a melanoma subcutaneous xenograft model. Significant tumor growth inhibition (TGI) was observed in the TYRP-1 TCB group (68% TGI, p=0.0058*) compared to vehicle group.

FIG. 31 shows that TYRP1 TCB mediated significant efficacy in terms of tumor growth inhibition compared to the vehicle group (68% TGI, p=0.0058*).

The EGFRvIII TCB (comprising the optimized CD3 binder identified in Example 1) was likewise tested for its anti-tumoral efficacy in a xenograft mouse model of a human tumor cell line, the U87-EGFRvIII glioblastoma xenograft model.

U87 cells (human glioblastoma) were originally obtained from ATCC (Manassas, USA) and stably transfected to express the human EGFRvIII protein (Roche Glycart AG, Switzerland). After expansion the cells were deposited in the Roche Glycart internal cell bank. The U87-EGFRvIII cell line was cultured in DMEM medium containing 10% FCS (Sigma) and 0.5 µg/ml Puromycin (Invitrogen). The cells were cultured at 37° C. in a water-saturated atmosphere at 5% $CO_2$. Passage 8 was used for transplantation. Cell viability was 94.7%. $5 \times 10^5$ cells per animal were injected subcutaneously in 100 µl of RPMI cell culture medium (Gibco) into the flank of mice using a 1 ml tuberculin syringe (BD Biosciences, Germany).

Fully humanized NSG female mice (Roche Glycart AG, Switzerland) were maintained under specific-pathogen-free condition with daily cycles of 12 h light/12 h darkness according to committed guidelines (GV-Solas; Felasa; TierschG). The experimental study protocol was reviewed and approved by local government (ZH223/2017). Continuous health monitoring was carried out on a regular basis.

Mice were injected subcutaneously on study day 0 with $5 \times 10^5$ of U87-EGFRvIII cells, randomized and weighed. Two weeks after the tumor cell injection (tumor volume >200 mm$^3$), mice were injected i.v. with 10 µg (0.5 mg/kg) EGFRvIII TCB twice weekly for three weeks. All mice were injected i.v. with 200 µl of the appropriate solution. The mice in the vehicle group were injected with histidine buffer and the treatment group with the EGFRvIII TCB construct.

To obtain the proper amount of antibody per 200 µl, the stock solutions were diluted with histidine buffer when necessary. Tumor size was measured with a caliper three times a week and plotted with GrahPad Prism software as volume in mm$^3$+/-SEM.

Figure 32:
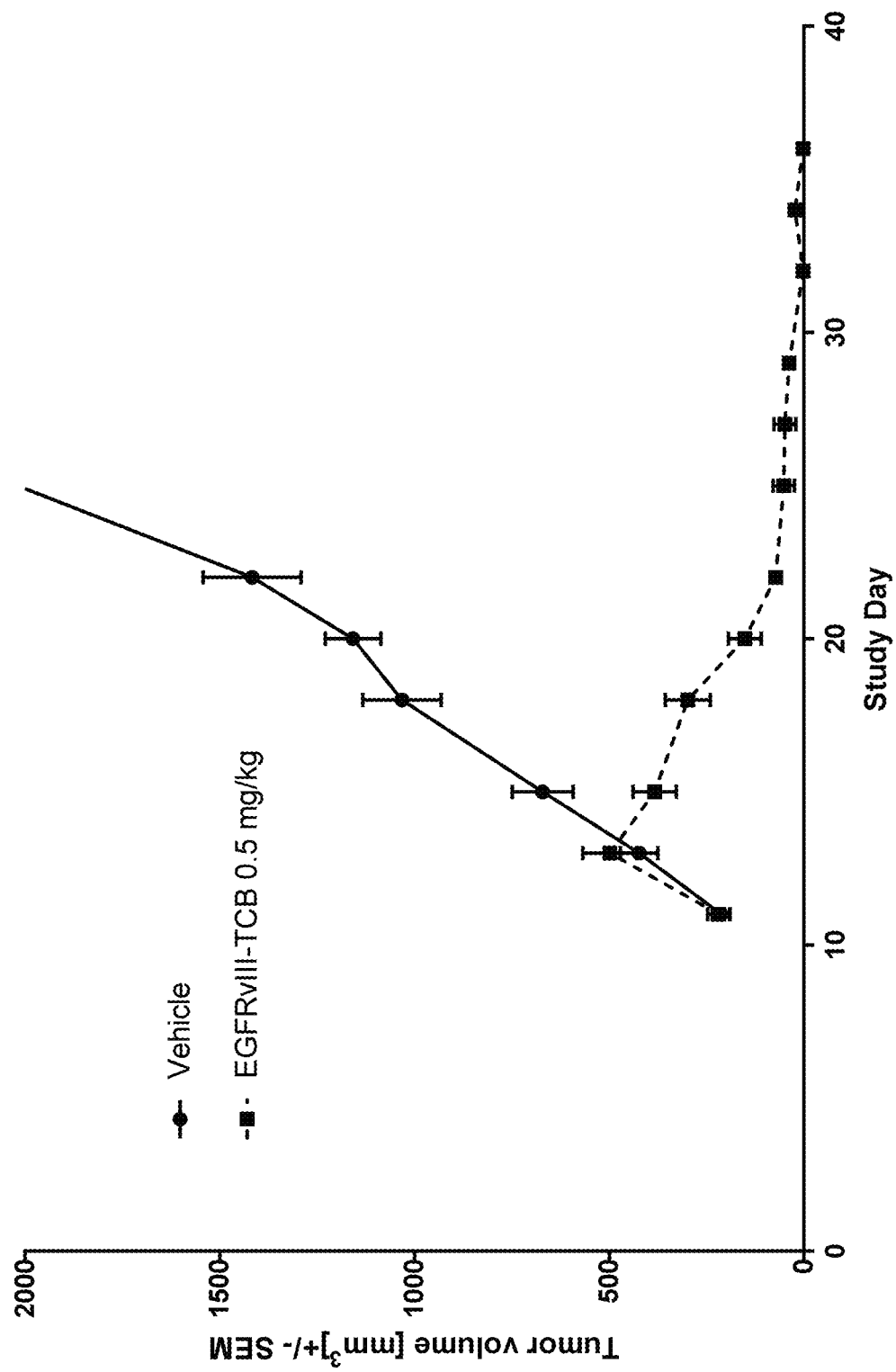
FIG. 32. In vivo efficacy of EGFRvIII TCB. The U87-huEGFRvIII human glioblastoma cell line was injected subcutaneously in humanized NSG mice to study tumor growth inhibition in a glioblastoma subcutaneous xenograft model. Significant tumor control was observed in the EGFRvIII TCB group with all mice achieving complete remission.

FIG. 32 shows that EGFRvIII TCB mediated significant efficacy in terms of tumor growth control with all mice achieving complete remission.

Example 12—PK Study with EGFRvIII TCB in Mice

The pharmacokinetics (PK) of the EGFRvIII TCB comprising the optimized CD3 binder, $CD3_{opt}$, was studied following intravenous bolus administration at 1 mg/kg to human FcRn transgenic (line32, homozygous) and NOD-SCID mice. Serial blood microsamples were taken from human FcRn transgenic (tg) mice and NOD-SCID mice up to 672 h (9 samples per mouse from 5 min to 672 h post dose). Samples of mouse serum treated with EGFRvIII TCB were analyzed using a specific enzyme-linked immunosorbent assay (ELISA) under non-GLP conditions. Capture of EGFRvIII TCB was done with biotinylated EGFRvIII antigen (huEGFRvIII his biotin) on streptavidin-coated microtiter plates (SA-MTP). Bound EGFRvIII TCB was detected with digoxigenin-labeled monoclonal antibody against human $IgG_1$ Fc(PGLALA) (see Example 3) followed by addition of an anti-digoxigenin-POD secondary detection antibody. Signals were generated by addition of peroxidase substrate (ABTS). The calibration range was 2.35 ng/ml to 150 ng/ml with 2.5 ng/ml being the lower limit of quantification (LLOQ).

The results of this study are shown in Table 7. The PK profile of EGFRvIII TCB is within the expected range for both tested mouse strains. This indicates that the engineering of the CDRs of the CD3 binder did not give rise to other sequence liability, that would affect antibody clearance.

TABLE 7

| Clearance data in huFcRn tg mice and NOD-SCID mice (ml/day/kg; mean). | |
|---|---|
| Mouse strain | EGFRvIII TCB ($CD3_{opt}$) |
| hFcRn tg32 | 12.4 |
| NOD-SCID | 10.1 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a TYRP-1-expressing cancer in a human individual having a TYRP-1-expressing cancer, the method comprising administering to the individual an effective amount of a bispecific antibody molecule, wherein the bispecific antibody molecule comprises: (a) a first antigen-binding domain that binds to human CD3 and (b) a second antigen-binding domain that binds to human TYRP-1, wherein the first antigen-binding domain comprises a heavy chain variable region (VH) comprising a heavy chain complementarity determining region (HCDR) 1 comprising the amino acid sequence SYAMN (SEQ ID NO: 2), a HCDR 2 comprising the amino acid sequence RIRSKYNNYATYYADSVKG (SEQ ID NO: 3, and a HCDR 3 comprising the amino acid sequence HTTFPSSYVSYYGY (SEQ ID NO: 5), and a light chain variable region (VL) comprising a light chain complementarity determining region (LCDR) 1 comprising the amino acid sequence GSSTGAVTTSNYAN (SEQ ID NO: 8), a LCDR 2 comprising the amino acid sequence GTNKRAP (SEQ ID NO: 9), and a LCDR 3 comprising the amino acid sequence ALWYSNLWV (SEQ ID NO: 10), and wherein the second antigen-binding domain comprises a VH comprising a HCDR 1 comprising the amino acid sequence DYFLH (SEQ ID NO: 15), a HCDR 2 comprising the amino acid sequence WINPDNG-NTVYAQKFQG (SEQ ID NO: 16), and a HCDR 3 comprising the amino acid sequence RDYTYE-KAALDY (SEQ ID NO: 17), and a VL comprising a LCDR 1 comprising the amino acid sequence RASGNIYNYLA (SEQ ID NO: 19), a LCDR 2 comprising the amino acid sequence DAKTLAD (SEQ ID NO: 20, and a LCDR 3 comprising the amino acid sequence QHFWSLPFT (SEQ ID NO: 21).

2. The method of claim 1, wherein (a) the first antigen-binding domain comprises a VH that is at least 95% identical to the amino acid sequence of SEQ ID NO: 7 and a VL that is at least 95% identical to the amino acid sequence of SEQ ID NO: 11, and/or (b) the second antigen-binding domain comprises a VH that is at least 95% identical to the amino acid sequence of SEQ ID NO: 18 and a VL that is at least 95% identical to the amino acid sequence of SEQ ID NO: 22.

3. The method of claim 1, wherein (a) the first antigen-binding domain comprises a VH comprising the amino acid sequence of SEQ ID NO: 7 and a VL comprising the amino acid sequence of SEQ ID NO: 11, and/or (b) the second antigen-binding domain comprises a VH comprising the amino acid sequence of SEQ ID NO: 18 and a VL comprising the amino acid sequence of SEQ ID NO: 22.

4. The method of claim 1, wherein the bispecific antibody molecule comprises an Fc domain comprising a first subunit and a second subunit.

5. The method of claim 4, wherein each of the first antigen-binding domain and the second antigen-binding domain is a Fab molecule, and wherein:
(i) the second antigen-binding domain is fused at the C-terminus of the Fab heavy chain to the N-terminus of the Fab heavy chain of the first antigen-binding domain, and the first antigen-binding domain is fused at the C-terminus of the Fab heavy chain to the N-terminus of the first subunit of the Fc domain; or
(ii) the first antigen-binding domain is fused at the C-terminus of the Fab heavy chain to the N-terminus of the Fab heavy chain of the second antigen-binding domain, and the second antigen-binding domain is fused at the C-terminus of the Fab heavy chain to the N-terminus of the first subunit of the Fc domain.

6. The method of claim 4, wherein the bispecific antibody molecule further comprises a third antigen-binding domain that binds to TYRP-1, and wherein the second antigen-binding domain and the third antigen-binding domain each comprises (a) a VH comprising a HCDR 1 comprising the amino acid sequence DYFLH (SEQ ID NO: 15), a HCDR 2 comprising the amino acid sequence WINPDNG-NTVYAQKFQG (SEQ ID NO: 16), and a HCDR 3 comprising the amino acid sequence RDYTYEKAALDY (SEQ ID NO: 17), and (b) a VL comprising a LCDR 1 comprising the amino acid sequence RASGNIYNYLA (SEQ ID NO: 19), a LCDR 2 comprising the amino acid sequence DAKTLAD (SEQ ID NO: 20), and a LCDR 3 comprising the amino acid sequence QHFWSLPFT (SEQ ID NO: 21).

7. The method of claim 6, wherein (a) the first antigen-binding domain comprises a VH that is at least 95% identical to the amino acid sequence of SEQ ID NO: 7 and a VL that is at least 95% identical to the amino acid sequence of SEQ ID NO: 11 and/or (b) the second antigen-binding domain and the third antigen-binding domain each comprises a VH that is at least 95% identical to the amino acid sequence of SEQ ID NO: 18 and a VL that is at least 95% identical to the amino acid sequence of SEQ ID NO: 22.

8. The method of claim 7, wherein (a) the first antigen-binding domain comprises a VH comprising the amino acid sequence of SEQ ID NO: 7 and a VL comprising the amino acid sequence of SEQ ID NO: 11; and/or (b) the second antigen-binding domain and the third antigen-binding domain each comprises a VH comprising the amino acid sequence of SEQ ID NO: 18 and a VL comprising the amino acid sequence of SEQ ID NO: 22.

9. The method of claim 6, wherein (a) the first antigen-binding domain is a crossover Fab molecule, wherein the variable domains VL and VH or the constant domains CL and CH1 of the Fab light chain and the Fab heavy chain are replaced by each other and/or (b) each of the second antigen-binding domain and the third antigen-binding domain is a conventional Fab molecule.

10. The method of claim 9, wherein in the constant domain CL of the second antigen-binding domain and/or the third antigen-binding domain, the amino acid at position 124 is substituted independently by lysine (K), arginine (R), or histidine (H), numbered according to Kabat numbering, and the amino acid at position 123 is substituted independently by lysine (K), arginine (R), or histidine (H), numbered according to Kabat numbering, and in the constant domain CH1 of the second antigen-binding domain and/or the third antigen-binding domain, the amino acid at position 147 is substituted independently by glutamic acid (E) or aspartic acid (D), numbered according to Kabat EU index numbering, and the amino acid at position 213 is substituted independently by glutamic acid (E) or aspartic acid (D), numbered according to Kabat EU index numbering.

11. The method of claim 6, wherein each of the first antigen-binding domain, the second antigen-binding domain, and the third antigen-binding domain is a Fab molecule, and wherein the third antigen-binding domain is fused at the C-terminus of the Fab heavy chain to the N-terminus of the second subunit of the Fc domain; and
(i) the second antigen-binding domain is fused at the C-terminus of the Fab heavy chain to the N-terminus of the Fab heavy chain of the first antigen-binding domain, and the first antigen-binding domain is fused at the C-terminus of the Fab heavy chain to the N-terminus of the first subunit of the Fc domain; or
(ii) the first antigen-binding domain is fused at the C-terminus of the Fab heavy chain to the N-terminus of the Fab heavy chain of the second antigen-binding domain, and the second antigen-binding domain is fused at the C-terminus of the Fab heavy chain to the N-terminus of the first subunit of the Fc domain.

12. The method of claim 4, wherein the Fc comprises a modification promoting the association of the first and the second subunit of the Fc domain.

13. The method of claim 4, wherein the Fc domain comprises one or more amino acid substitutions that reduce binding to an Fc receptor and/or effector function.

14. The method of claim 4, wherein the Fc domain is a human Fc domain and/or an IgG Fc domain.

15. The method of claim 1, wherein the TYRP-1-expressing cancer is a skin cancer.

16. The method of claim 15, wherein the skin cancer is melanoma.

* * * * *

UNITED STATES PATENT AND TRADEMARK OFFICE
CERTIFICATE OF CORRECTION

| | | |
|---|---|---|
| PATENT NO. | : 11,672,858 B2 | Page 1 of 1 |
| APPLICATION NO. | : 16/721254 | |
| DATED | : June 13, 2023 | |
| INVENTOR(S) | : Anne Freimoser-Grundschober et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 87 days.

Signed and Sealed this
Twentieth Day of May, 2025

Coke Morgan Stewart
*Acting Director of the United States Patent and Trademark Office*